US012668819B2

(12) United States Patent
Nakanishi et al.

(10) Patent No.: US 12,668,819 B2
(45) Date of Patent: Jun. 30, 2026

(54) CRISPR-AID USING CATALYTICALLY INACTIVE RNA-GUIDED ENDONUCLEASE

(71) Applicant: Novozymes A/S, Bagsvaerd (DK)

(72) Inventors: Takashi Nakanishi, Chiba (JP); Michael David Thomas, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 677 days.

(21) Appl. No.: 17/910,166

(22) PCT Filed: Mar. 10, 2021

(86) PCT No.: PCT/US2021/021670
§ 371 (c)(1),
(2) Date: Sep. 8, 2022

(87) PCT Pub. No.: WO2021/183622
PCT Pub. Date: Sep. 16, 2021

(65) Prior Publication Data
US 2025/0179528 A1      Jun. 5, 2025

(30) Foreign Application Priority Data

Mar. 12, 2020    (EP) .................................... 20162685

(51) Int. Cl.
| | |
|---|---|
| *C07H 21/02* | (2006.01) |
| *C12N 9/22* | (2006.01) |
| *C12N 9/78* | (2006.01) |
| *C12N 15/11* | (2006.01) |
| *C12N 15/75* | (2006.01) |
| *C12N 15/81* | (2006.01) |
| *C12N 15/90* | (2006.01) |

(52) U.S. Cl.
CPC .............. *C12N 15/90* (2013.01); *C12N 9/22* (2013.01); *C12N 9/78* (2013.01); *C12N 15/11* (2013.01); *C12N 15/75* (2013.01); *C12N 15/815* (2013.01); *C12Y 305/04005* (2013.01); *C12N 2310/20* (2017.05); *C12N 2800/101* (2013.01); *C12N 2800/102* (2013.01)

(58) Field of Classification Search
CPC .............................. C12N 2310/20; C12N 9/22
See application file for complete search history.

(56) References Cited

U.S. PATENT DOCUMENTS

| | | | | |
|---|---|---|---|---|
| 10,167,457 | B2 * | 1/2019 | Liu | ............................ A61P 7/04 |
| 11,214,781 | B2 * | 1/2022 | Kim | .......................... C12N 9/22 |
| 2015/0166980 | A1 | 6/2015 | Liu et al. | |
| 2017/0073670 | A1 | 3/2017 | Nishida et al. | |
| 2018/0312828 | A1 | 11/2018 | Liu et al. | |
| 2021/0222140 | A1 | 7/2021 | Choe et al. | |

FOREIGN PATENT DOCUMENTS

| | | | | |
|---|---|---|---|---|
| WO | 2015089406 | A1 | 6/2015 | |
| WO | 201513354 | A1 | 9/2015 | |
| WO | 2019046703 | A1 | 3/2019 | |
| WO | WO-2020030984 | A2 * | 2/2020 | .......... C07K 14/415 |

OTHER PUBLICATIONS

Cho et al. (Genome Research, 24, 132-141, 2014).*
Evanoff_2019 Emerging topics in life sciences 3(5) 483-491.
Komor 2016 Nature 533 420-424.
Li_2018_Nature_biotechnology_36_324-327.
Nishida 2016 Science 353(6305) aaf8729.
Rees_2018_Natures_Review_Genetics_19_770-788.
Rogozin_2007_EBI_Accession_No. A5H718.
WO 2020-030984 A2—EBI Accession No. BHI49189.
Rogozin et al., 2007, GenBank Accession No. ABO15149.1.

* cited by examiner

*Primary Examiner* — Amy Rose Hudson
(74) *Attorney, Agent, or Firm* — Eric J. Fechter

(57) ABSTRACT

The present invention relates to nucleobase editing complexes comprising a) a catalytically inactive RNA-guided endonuclease having a sequence identity of at least 60% to SEQ ID NO: 126 or SEQ ID NO: 155 and b) a nucleobase editing domain, as well as polynucleotides encoding said nucleobase editing complexes, nucleic acid constructs and expression vectors comprising said polynucleotides, host cells comprising said nucleobase editing complexes and/or polynucleotides, and methods for preparing and using said nucleobase editing complexes.

34 Claims, 13 Drawing Sheets

Specification includes a Sequence Listing.

| wA target #1 | | |
|---|---|---|

WT CAGCAGTCCTCTGCTCTAGAAGG (SEQ ID NO: 170)

mut-1 CAGTAGTCCTCTGCTCTAGAAGG (SEQ ID NO: 171)
mut-2 CAGTAGTCCTCTGCTCTAGAAGG (SEQ ID NO: 171)
mut-3 CAGTAGTCCTCTGCTCTAGAAGG (SEQ ID NO: 171)

| wA target #2 | | |
|---|---|---|

WT TCCAACCCACTCCTGGAATCGG (SEQ ID NO: 167)

mut-1 TTTAACCCACTCCTGGAATCGG (SEQ ID NO: 172)
mut-2 TTTAACCCACTCCTGGAATCGG (SEQ ID NO: 172)
mut-3 TTTAACCCACTCCTGGAATCGG (SEQ ID NO: 173)
mut-4 TCTAACCCACTCCTGGAATCGG (SEQ ID NO: 173)
mut-5 TCTAACCCACTCCTGGAATCGG (SEQ ID NO: 173)

| wA target #3 | | |
|---|---|---|

WT CCGATTCCGAGTCAACATGCTGG (SEQ ID NO: 174)

mut-1 CCGATTCCGAGTCAACATACTAG (SEQ ID NO: 175)
mut-2 CCGATTCCGAGTCAACATGCTAG (SEQ ID NO: 176)
mut-3 CCGATTCCGAGTCAACATGCTAG (SEQ ID NO: 176)
mut-4 CCGATTCCGAGTCAACATGCTAG (SEQ ID NO: 176)

| wA target #4 | | |
|---|---|---|

WT CCTACGACGACTATGCTGGGACA (SEQ ID NO: 177)

mut-1 CCTACGACGACTATGCTGAAACA (SEQ ID NO: 178)
mut-2 CCTACGACGACTATGCTGAAACA (SEQ ID NO: 178)
mut-3 CCTACGACGACTATGCTGAGACA (SEQ ID NO: 179)

Fig. 6 pTNA287
14,619 bp

MdwA8

WT    TTTCATCCCTGGCGGTAACCGAGCA    (SEQ ID NO: 180)

mut-1   TTTCATCCCTGGCGGTAACTGAGCA    (SEQ ID NO: 181)

mut-2   TTTCATCCCTGGCGGTAACCAAGCA    (SEQ ID NO: 182)

MdwA13

WT    GAGCTTCTGGAACCTCCTGTACAAA    (SEQ ID NO: 183)

mut-1   GAGCTTCTAGAACCTCCTGTACAAA    (SEQ ID NO: 184)

Fig. 8

MdwA8

| WT | TTTCATCCTGGCGGTAACCGAGCA | (SEQ ID NO: 180) |
|---|---|---|
| mut-1 | TTTTATTTTGGCGGTAACCGAGCA | (SEQ ID NO: 185) |
| mut-2 | TTTTATTTTGGCGGTAACCGAGCA | (SEQ ID NO: 185) |
| mut-3 | TTTCATTTTGGCGGTAACCGAGCA | (SEQ ID NO: 186) |
| mut-4 | TTTCATCTTTGGCGGTAACCGAGCA | (SEQ ID NO: 187) |
| mut-5 | TTTCATCCCTAACAGTAACCGAGCA | (SEQ ID NO: 188) |
| mut-6 | TTTCATCCCTGGCGGTAACTGAGCA | (SEQ ID NO: 189) |
| mut-7 | TTTCATCCCTGGCGGTAACTGAGCA | (SEQ ID NO: 189) |
| mut-8 | TTTCATCCCTGGCGGTAACCAAGCA | (SEQ ID NO: 190) |
| mut-9 | TTTCATCCCTGGCGGTAACCAAGCA | (SEQ ID NO: 190) |
| mut-10 | TTTCATCCCTGGCGGTAACCGAGTA | (SEQ ID NO: 191) |

MdwA2

| WT | CTTTTTGGAGACCAGACCAGCGACA | (SEQ ID NO: 192) |
|---|---|---|
| Mut-1 | CTTTTTGGAGATTAGACCAGCGACA | (SEQ ID NO: 193) |
| Mut-2 | CTTTTTGGAGATTAGACCAGCGACA | (SEQ ID NO: 193) |
| Mut-3 | CTTTTTGGAGATTAGACCAGCGACA | (SEQ ID NO: 193) |
| Mut-4 | CTTTTTGGAGACTAGACCAGCGACA | (SEQ ID NO: 194) |
| Mut-5 | CTTTTTGGAGACTAGACCAGCGACA | (SEQ ID NO: 194) |
| Mut-6 | CTTTTTGGAGACTAGACCAGCGACA | (SEQ ID NO: 194) |
| Mut-7 | CTTTTTGGAGACTAGACTAGCGACA | (SEQ ID NO: 195) |

MdwA3

| WT | GAGCTTCTGGAACCTCCTGTACAAA | (SEQ ID NO: 183) |
|---|---|---|
| Mut-1 | GAGCTTCTAGAACCTCCTGTACAAA | (SEQ ID NO: 184) |
| Mut-2 | GAGCTTCTGAAACCTCCTGTACAAA | (SEQ ID NO: 196) |

Fig. 9

DsRED expression cassette of MDT545
1743 bp

CRISPR-AID USING CATALYTICALLY INACTIVE RNA-GUIDED ENDONUCLEASE

CROSS-REFERENCE TO RELATED APPLICATIONS

This application is a 35 U.S.C. 371 national application of PCT/US2021/021670, filed Mar. 10, 2021, which claims priority or the benefit from European Patent Application No. 20162685.0, filed Mar. 12, 2020. The contents of these applications are fully incorporated herein by reference.

REFERENCE TO A SEQUENCE LISTING

This application contains a Sequence Listing that was submitted as an ASCII text file named New SQ ST25 2.txt (created on Mar. 26, 2026, containing 304,353 bytes) in computer readable form, which is incorporated herein by reference.

FIELD OF THE INVENTION

The present invention relates to nucleobase editing complexes comprising a) a catalytically inactive RNA-guided endonuclease having a sequence identity of at least 60% to SEQ ID NO: 126 or SEQ ID NO: 155 and b) a nucleobase editing domain, as well as polynucleotides encoding said nucleobase editing complexes, nucleic acid constructs and expression vectors comprising said polynucleotides, host cells comprising said nucleobase editing complexes and/or polynucleotides, and methods for preparing and using said nucleobase editing complexes.

BACKGROUND OF THE INVENTION

Introduction of single nucleotide polymorphisms (SNPs), also known as single nucleotide variations, SNVs) into genomes is key for evolution of a given organism. Industrially important microbes are often mutagenized in a laboratory to obtain new or enhanced functions such as stress tolerance, higher expression potential of a molecule of interest, and so forth. However, the existing methods for SNP introduction have notable limitations. Random mutagenesis obtained via UV irradiation or chemical exposure provides highly diversified genotypes, but identification of beneficial SNPs is labor intensive. Site-directed mutagenesis obtained via the CRISPR technology allows introduction of target-specific SNPs and thus seems more promising. Briefly, an RNA-guided endonuclease such as Cas9 or Cpf1 is directed to a locus of interest using a guide-RNA (gRNA) that has a protospacer region complementary to a DNA sequence in the locus of interest. The RNA-guided endonuclease binds and cuts the DNA strand at the target locus, leading to a double-stranded break (DSB) that the cell will attempt to repair using non-homologous end joining (NHEJ) or similar mechanisms. However, if the cell is supplied with repair DNA that encode a desired point mutation and is flanked by sequences homologous to the regions upstream and downstream of the DSB, homology-directed repair (HDR) will result in incorporation of the repair DNA containing the desired mutation in the locus of interest. Although widely applied, this CRISPR-based approach is not suited for large-scale mutagenesis studies since repair DNA would be needed for every single target locus. Moreover, the introductions of DSBs is associated with cytotoxicity. Hence, a method of generating highly diverse mutants in a targetable manner and with easy identification of the resulting SNPs would be very advantageous.

The requirement for repair DNA may be circumvented by using the so-called CRISPR-AID technology (Komor et al., *Nature*, vol. 533, pp. 420-424, 2016; Nishida et al., *Science*, vol. 353, aaf8729, 2016). Herein, a catalytically inactive RNA-guided endonuclease is tethered to a nucleobase editing domain to form a nucleobase editing complex. The nucleobase editing domain is either a cytosine base editor (CBE) that converts C-G base pairs to T-A base pairs or an adenine base editor (ABE) that converts A-T base pairs into G-C base pairs (Rees and Liu, *Nat. Rev. Genetics*, vol. 19, pp. 770-788, 2018). Binding of the catalytically inactive RNA-guided endonuclease to the target locus via base pairing between the gRNA protospacer and its complementary DNA sequence leads to displacement of a small segment of single-stranded DNA in a so-called "R loop", wherein the nucleobases are exposed to deamination by the nucleobase editing domain, resulting in transition mutations and SNP generation. Importantly, since the nucleobase editing complex is adapted to operate only on single-stranded DNA, DSBs do not occur and the associated cytotoxic side-effects are avoided. CRISPR-AID is thus a useful methodology for introducing SNPs into a genome of interest in a scalable and targetable manner.

Catalytically inactive variants of Cas9 and Cpf1 have been widely applied in the CRISPR-AID technology (Nishida et al., vide supra; Li et al., *Nat. Biotech.*, vol. 36, pp. 324-327, 2018). However, further developments of CRISPR-AID systems are still warranted to alter or improve various properties such as editing efficiency or editing window.

WO 2015/133554 describes CRISPR-AID utilizing Cas9d as the catalytically inactive RNA-guided endonuclease and activation-induced cytidine deaminase (AID) as nucleobase editing domain.

SUMMARY OF THE INVENTION

The present inventors have investigated the use of catalytically inactive versions of the RNA-guided endonuclease known as Mad7 isolated from *Eubacterium rectale* in CRISPR-AID base editing. Mad7 has only 31% sequence identity to Cpf1 isolated from *Acidominococcus* sp. and is thus structurally very different from other known RNA-guided endonucleases. However, as illustrated in the Examples disclosed herein, CRISPR-AID base editing utilizing Mad7d-AID provided editing efficiency comparable to Cas9d-AID in microbial host cells transformed with a single plasmid containing Mad7d-AID and gRNA expression cassettes for stable expression of Mad7d-AID components. Moreover, the editing window observed for Mad7d-AID was broader than for Cas9d-AID, illustrating that Mad7d-based CRISPR-AID is more suitable for generating multiple different SNPs of the same target locus, which is highly beneficial for generating SNP libraries and for screening purposes.

In a first aspect, the present invention relates to nucleobase editing complexes comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126; and

3 b) a nucleobase editing domain.

In a second aspect, the present invention relates to polynucleotides encoding nucleobase editing complexes of the first aspect.

In a third aspect, the present invention relates to nucleic acid constructs comprising polynucleotides of the second aspect.

In a fourth aspect, the present invention relates to expression vectors comprising polynucleotides of the second aspect and/or nucleic acid constructs of the third aspect.

In a fifth aspect, the present invention relates to host cells comprising nucleobase editing complexes of the first aspect, polynucleotides of the second aspect, nucleic acid constructs of the third aspect, and/or expression vectors of the fourth aspect.

In a sixth aspect, the present invention relates to methods for modifying at least one nucleobase in a DNA target sequence, the method comprising:

a) providing a nucleobase editing complex of the first aspect complexed with a gRNA that is complementary to and capable of hybridizing to the DNA target sequence; and b) contacting the nucleobase editing complex with the DNA target sequence;

wherein at least one nucleobase in the DNA target sequence is converted to a different nucleobase without introducing a double-strand break in the DNA sequence of interest.

BRIEF DESCRIPTION OF FIGURES

FIG. 6 shows genome sequences of white spore mutants generated by dCas9-AID-UGI.

FIG. 8 shows genome sequences of white spore mutants generated by Mad7d-AID-UGI.

FIG. 9 shows genome sequences of white spore mutants generated by 34° C. incubation.

DEFINITIONS

Figure 1:
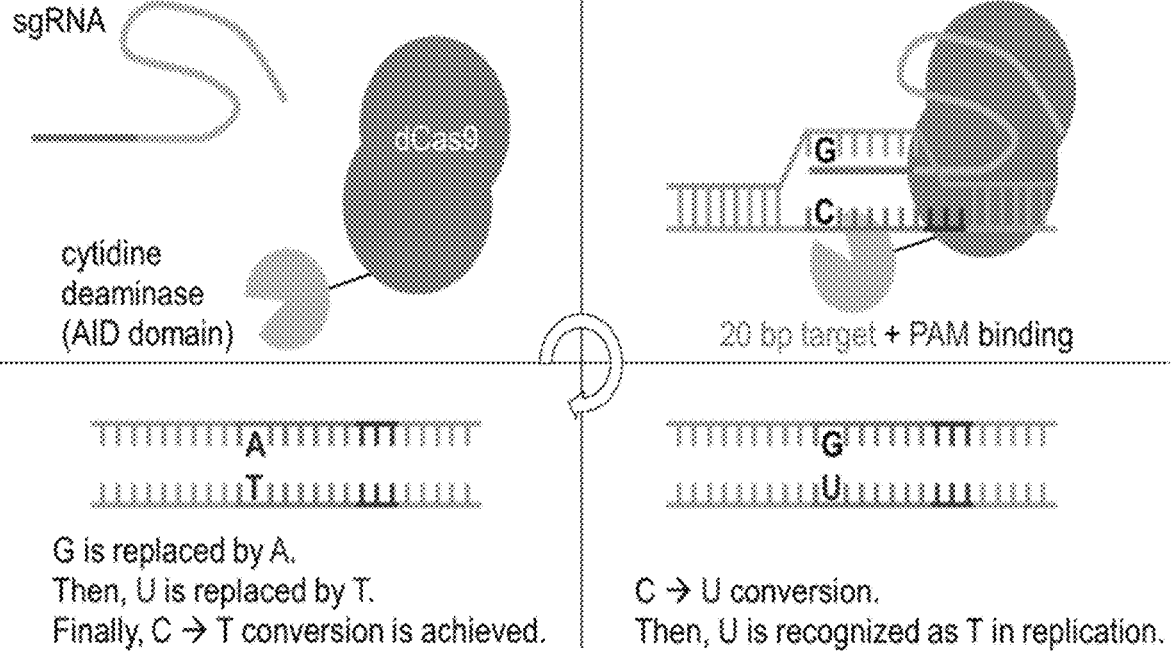
FIG. 1 shows a schematic illustration of CRISPR-AID mode of action.

In accordance with this detailed description, the following definitions apply. Note that the singular forms "a," "an," and "the" include plural references unless the context clearly dictates otherwise.

Reference to "about" a value or parameter herein includes aspects that are directed to that value or parameter per se. For example, description referring to "about X" includes the aspect "X".

Unless defined otherwise or clearly indicated by context, all technical and scientific terms used herein have the same meaning as commonly understood by one of ordinary skill in the art to which this invention belongs.

Catalytically inactive: The term "catalytically inactive" is used to described RNA-guided endonucleases for which endonuclease activity has been disrupted. A catalytically inactive endonuclease can bind to but not introduce any breaks in a target DNA sequence. The terms "catalytically inactive", "nuclease-null" and "dead" (abbreviated "d", e.g., Mad7d) are used interchangeably herein.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon, such as ATG, GTG, or TTG, and ends with a stop codon, such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide of the present invention. Each control sequence may be native (i.e., from the same gene) or heterologous (i.e., from a different gene) to the polynucleotide encoding the polypeptide or native or heterologous to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" means any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fusion polypeptide: The term "fusion polypeptide" is a polypeptide in which one polypeptide is fused at the N-terminus or the C-terminus of a polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3:568-576; Svetina et al., 2000, *J. Biotechnol.* 76:245-251; Rasmussen-Wilson et al., 1997, *Appl. Environ. Microbiol.* 63:3488-3493; Ward et al., 1995, *Biotechnology* 13:498-503; and Contreras et al., 1991, *Biotechnology* 9:378-381; Eaton et al., 1986, *Biochemistry* 25:505-512; Collins-Racie et al., 1995, *Biotechnology* 13:982-987; Carter et al., 1989, *Proteins: Structure, Function, and Genetics* 6:240-248; and Stevens, 2003, *Drug Discovery World* 4:35-48.

Heterologous: The term "heterologous" means, with respect to a host cell, that a polypeptide or nucleic acid does not naturally occur in the host cell. The term "heterologous" means, with respect to a polypeptide or nucleic acid, that a control sequence, e.g., promoter, or domain of a polypeptide or nucleic acid is not naturally associated with the polypeptide or nucleic acid, i.e., the control sequence is from a gene other than the gene encoding the mature polypeptide of SEQ ID NO: 126.

Host cell: The term "host cell" means any microbial or plant cell into which a nucleic acid construct or expression vector comprising a polynucleotide of the present invention has been introduced. Methods for introduction include but are not limited to protoplast fusion, transfection, transformation, electroporation, conjugation, and transduction. In some embodiments, the host cell is an isolated recombinant host cell that is partially or completely separated from at least one other component with, including but not limited to, proteins, nucleic acids, cells, etc.

Isolated: The term "isolated" means a polypeptide, nucleic acid, cell, or other specified material or component that is separated from at least one other material or component with which it is naturally associated as found in nature, including but not limited to, for example, other proteins, nucleic acids, cells, etc. An isolated polypeptide includes, but is not limited to, a culture broth containing the secreted polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

RNA-guided endonuclease: The term "RNA-guided endonuclease" means a polypeptide having endonuclease activity, wherein the endonuclease activity is controlled by one or more gRNA that form a complex with the RNA-guided endonuclease and directs the endonuclease activity to a target DNA sequence that is complementary to and capable of hybridizing to the protospacer region(s) of the one or more gRNA.

Sequence identity: The relatedness between two amino acid sequences or between two nucleotide sequences is described by the parameter "sequence identity".

For purposes of the present invention, the sequence identity between two amino acid sequences is determined as the output of "longest identity" using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-277), preferably version 6.6.0 or later. The parameters used are a gap open penalty of 10, a gap extension penalty of 0.5, and the EBLOSUM62 (EMBOSS version of BLOSUM62) substitution matrix. In order for the Needle program to report the longest identity, the -nobrief option must be specified in the command line. The output of Needle labeled "longest identity" is calculated as follows:

$$\text{(Identical Residues} \times 100)/\text{(Length of Alignment} - \text{Total Number of Gaps in Alignment)}$$

For purposes of the present invention, the sequence identity between two polynucleotide sequences is determined as the output of "longest identity" using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 6.6.0 or later. The parameters used are a gap open penalty of 10, a gap extension penalty of 0.5, and the EDNAFULL (EMBOSS version of NCBI NUC4.4) substitution matrix. In order for the Needle program to report the longest identity, the nobrief option must be specified in the command line. The output of Needle labeled "longest identity" is calculated as follows:

$$\text{(Identical Deoxyribonucleotides} \times 100)/$$
$$\text{(Length of Alignment} - \text{Total Number of Gaps in Alignment)}$$

Conventions for Designations of Variants

For purposes of the present invention, the polypeptide disclosed in SEQ ID NO: 126 is used to determine the corresponding amino acid position in another RNA-guided endonuclease. The amino acid sequence of another RNA-guided endonuclease is aligned with the polypeptide disclosed in SEQ ID NO: 126, and based on the alignment, the amino acid position number corresponding to any amino acid residue in the polypeptide disclosed in SEQ ID NO: 126 is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 5.0.0 or later. The parameters used are gap open penalty of 10, gap extension penalty of 0.5, and the EBLOSUM62 (EMBOSS version of BLOSUM62) substitution matrix.

In describing the variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine(S) with phenylalanine (F), respectively.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195 | 195 195a 195b |
| G | G - K - A |

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Different alterations. Where different alterations can be introduced at a position, the different alterations are separated by a comma, e.g., "Arg170Tyr, Glu" represents a substitution of arginine at position 170 with tyrosine or glutamic acid. Thus, "Tyr167Gly, Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present inventors have investigated the use of catalytically inactive versions of the RNA-guided endonuclease known as Mad7 isolated from *Eubacterium rectale* in CRISPR-AID base editing. Mad7 has only 31% sequence identity to Cpf1 isolated from *Acidominococcus* sp. and is thus structurally very different from other known RNA-guided endonucleases. However, as illustrated in the Examples disclosed herein, CRISPR-AID base editing utilizing Mad7d-AID provided editing efficiency comparable to Cas9d-AID in microbial host cells transformed with a single plasmid containing Mad7d-AID and gRNA expression cassettes for stable expression of Mad7d-AID components. Moreover, the editing window observed for Mad7d-AID was broader than for Cas9d-AID, illustrating that Mad7d-based CRISPR-AID is more suitable for generating multiple different SNPs of the same target locus, which is highly beneficial for generating SNP libraries and for screening purposes.

Nucleobase Editing Complexes

In a first aspect, the present invention relates to a nucleobase editing complex comprising, consisting essentially of, or consisting of:

a) a catalytically inactive RNA-guided endonuclease having a sequence identity of at least 60%, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain.

In an embodiment, the nucleobase editing complex comprises, consists essentially of, or consists of:

a) a catalytically inactive RNA-guided endonuclease having a sequence identity of at least 60%, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126; and b) a nucleobase editing domain.

The catalytically inactive RNA-guided endonuclease may be any catalytically inactive RNA-guided endonuclease having at least 60% sequence identity to SEQ ID NO: 126 or SEQ ID NO: 155. In a preferred aspect, the catalytically inactive RNA-guided endonuclease comprises an alteration of an amino acid at a position corresponding to position 877 of SEQ ID NO: 126. In an embodiment, the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the variant comprises or consists of the substitution D877A of SEQ ID NO: 126. In a preferred embodiment, the catalytically inactive RNA-guided endonuclease comprises, consists essentially of, or consists of SEQ ID NO: 126. In another preferred embodiment, the catalytically inactive RNA-guided endonuclease comprises, consists essentially of, or consists of SEQ ID NO: 155. In one embodiment the catalytically inactive RNA-guided endonuclease is encoded by a polynucleotide having a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 156. Preferably the polynucleotide encoding the catalytically inactive RNA-guided endonuclease comprises or consists of the polynucleotide of SEQ ID NO: 156.

The nucleobase editing domain may be either a cytosine base editor (CBE) that converts C-G base pairs to T-A base pairs or an adenine base editor (ABE) that converts A-T base pairs into G-C base pairs. Collectively, CBEs and ABEs can mediate all four possible transition mutations (C to T, A to G, T to C, and G to A) of DNA nucleobases (Rees and Liu, vide supra).

In an aspect, the nucleobase editing domain is a cytosine base editor (CBE). CBEs convert C-G base pairs to T-A base pairs by deaminating the exocyclic amine a target cytosine

9

10

(C) to generate uracil (U), which is read as thymine (T) by polymerase enzymes. Suitable CBEs include members of the APOBEC/AID family, in particular cytidine deaminase 1 (CDA1, such as PmCDA1 obtained from *Petromyzon marinus* encoded by the polynucleotide with SEQ ID NO: 127; Nishida et al., vide supra) and APOBEC1 (Harris et al., *Mol. Cell.*, vol. 10, pp. 1247-1253, 2002), but also APOBEC2, APOBEC3, APOBEC4, and APOBEC5 (Knisbacher et al., *Trends Genet.*, vol. 32, pp. 553-563, 2000).

In a preferred embodiment, the nucleobase editing domain is a cytosine base editor of the APOBEC/AID family.

In a preferred embodiment, the nucleobase editing domain is APOBEC1 or a homolog or variant thereof.

In a preferred embodiment, the nucleobase editing domain is CDA1 or a homolog or variant thereof; most preferably the nucleobase editing domain is PmCDA1 obtained from *Petromyzon marinus*.

In a preferred embodiment, the nucleobase editing domain comprises or consists of a polypeptide having a sequence identity of at least 80%, such as, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.

In an aspect, the nucleobase editing domain is an adenine base editor (ABE). Similar to CBEs, ABEs convert A-T base pairs into G-C base pairs by deaminating the exocyclic amine of a target adenine (A) to generate inosine (I). In the context of a polymerase active site, I has a preference for base pairing with cytosine (C), which is then read or replicated as guanine (G). Suitable ABEs are based on tRNA adenosine deaminase (TadA) from *E. coli* (Gaudelli et al., *Nature*, vol. 551, p. 464-471, 2017) and include TadA, TadA* (a A106V and/or D108N variant of TadA), TadA homodimers, and TadA-TadA* heterodimers.

In a preferred embodiment, the nucleobase editing domain is an adenine base editor based on tRNA adenosine deaminase (TadA).

In a preferred embodiment, the nucleobase editing domain is selected from the group consisting of TadA, TadA*, TadA homodimer, and TadA-TadA* heterodimer; most preferably the nucleobase editing domain is a TadA-TadA* heterodimer.

A challenge for the use of nucleobase editing domains in eukaryotic cells, in particular mammalian cells, is the need to circumvent the DNA repair processes that are initiated upon formation of the A-U and I-T intermediates, in particular the base excision repair process that is activated by the U-G mismatch generated from the deamination of C to U by CBEs. The repair of U-G mismatches is initiated by uracil N-glycosylase (UNG), and this enzyme may be inhibited by uracil DNA glycosylase inhibitor (UGI), a DNA mimetic derived from the PBS bacteriophage (Mol et al., *Cell*, vol. 82, pp. 701-708, 1995).

In an embodiment, the nucleobase editing domain is a cytosine base editor (CBE), and the nucleobase editing complex further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.

The catalytically inactive RNA-guided endonuclease and the nucleobase editing domain may be linked in various ways to form a nucleobase editing complex of the invention. In one embodiment, the RNA-guided endonuclease and the nucleobase editing domain are fused end-to-end, i.e., without an intervening polypeptide sequence. In another embodiment, the catalytically inactive RNA-guided endonuclease and the nucleobase editing domain are connected via an intervening polypeptide (i.e., a linker polypeptide). By arranging the catalytically inactive RNA-guided endonuclease and nucleobase editing domain end-to-end or connecting these via a linker polypeptide, one can express the nucleobase editing complex as a single fusion polypeptide. The length and amino acid composition of the linker polypeptide will depend on the size and the three-dimensional structure of the catalytically inactive RNA-guided endonuclease and the nucleobase editing domain, and the linker polypeptide should in general be of sufficient length and flexibility to prevent steric occlusion of the binding and/or active site(s) of the catalytically inactive RNA-guided endonuclease and the nucleobase editing domain when these are linked together.

Thus, in an aspect, the nucleobase editing complex is a fusion polypeptide comprising a catalytically inactive RNA-guided endonuclease and a nucleobase editing domain. Techniques for producing fusion polypeptide are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779).

In an embodiment, the catalytically inactive RNA-guided endonuclease and the nucleobase editing domain are fused end-to-end, i.e., with no intervening linker polypeptide.

In another embodiment, the catalytically inactive RNA-guided endonuclease and the nucleobase editing domain are separated by a linker polypeptide. Preferably, the catalytically inactive RNA-guided endonuclease, the linker polypeptide, and the nucleobase editing domain are encoded in frame and are expressed as a single polypeptide.

Preferably, the linker polypeptide comprises at least 10 amino acid residues, such as, e.g., at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 350, at least 400, at least 500, at least 600, at least 700, at least 800, at least 900, at least 1000, or more, amino acid resides. More preferably, the linker polypeptide comprises at least 75 amino acid residues, such as, e.g., at least 80, at least 85, at least 90, at least 95, at least 100, at least 105, at least 110, at least 115, at least 120, or at least 125 amino acid residues. Even more preferably, the linker polypeptide comprises 80-120 amino acid residues, such as, e.g., 85-115 amino acid residues, 90-110 amino acid residues, or 95-105 amino acid residues.

In a preferred embodiment, the linker comprises or consists of 16 amino acid residues.

In a preferred embodiment, the linker comprises or consists of 32 amino acid residues.

In a preferred embodiment, the linker comprises or consists of 100 amino acid residues.

In a preferred embodiment, the linker comprises or consists of 105 amino acid residues.

In an embodiment, the linker polypeptide has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 130. Preferably, the linker polypeptide comprises or consists of the polypeptide of SEQ ID NO: 130. In one embodiment the linker polypeptide is encoded by a polynucleotide having a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 129. Preferably the polynucleotide encoding the linker polypeptide comprises or consists of the polynucleotide of SEQ ID NO: 129.

Another option for constructing a nucleobase editing complex of the invention is to express the catalytically inactive RNA-guided endonuclease and the nucleobase editing domain as two separate polypeptides and then subsequently connect these via chemical conjugation methods utilizing biocompatible, and preferably biorthogonal, small molecule reactions. Typically, the polypeptides are modified post-translationally by installing the required small molecule functionalities, which optionally may be attached to the polypeptide via a linker. A suitable conjugation method is the Cu(I)-catalyzed azide-alkyne cycloaddition (CuAAC; Rostovtsev et al., *Angew. Chem. Int. Ed*, vol. 41, pp. 2596-2599, 2002; Tornøe et al., *J. Org. Chem*, vol. 67, pp. 3057-3064, 2002).

In an embodiment, the nucleobase editing complex of the invention comprises:
a) a catalytically inactive RNA-guided endonuclease having a sequence identity of at least 60%, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126; and
b) a nucleobase editing domain comprising a polypeptide having a sequence identity of at least 80%, such as, e.g., at least 85%, at least 90%, at least 91%, at least 92%, at least 93%, at least 94%, at least 95%, at least 96%, at least 97%, at least 98%, at least 99%, or 100%, to SEQ ID NO: 128.

In an embodiment, the nucleobase editing complex of the invention comprises:
a) a catalytically inactive RNA-guided endonuclease having a sequence identity of at least 60%, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126;
b) a nucleobase editing domain comprising a polypeptide having a sequence identity of at least 80%, such as, e.g., at least 85%, at least 90%, at least 91%, at least 92%, at least 93%, at least 94%, at least 95%, at least 96%, at least 97%, at least 98%, at least 99%, or 100%, to SEQ ID NO: 128; and
c) an uracil DNA glycosylase inhibitor comprising a polypeptide having a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132.

In an embodiment, the nucleobase editing complex of the invention comprises:

a) a catalytically inactive RNA-guided endonuclease having a sequence identity of at least 60%, such as e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126;
b) a nucleobase editing domain comprising a polypeptide having a sequence identity of at least 80%, such as, e.g., at least 85%, at least 90%, at least 91%, at least 92%, at least 93%, at least 94%, at least 95%, at least 96%, at least 97%, at least 98%, at least 99%, or 100%, to SEQ ID NO: 128; and
c) an uracil DNA glycosylase inhibitor comprising a polypeptide having a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132,
wherein the catalytically inactive RNA-guided endonuclease and the nucleobase editing domain is separated by a linker polypeptide comprising at least 50 amino acids; preferably at least 100 amino acids.

Guide-RNA

The gRNA constitutes the re-programmable part of the CRISPR system that allows targeting of the RNA-guided endonuclease to a specific locus of interest. In most natural systems, including *S. pyogenes*, the gRNA is a complex of two RNA polynucleotides, a first RNA (crRNA or protospacer) containing about 20 nucleotides that determine the specificity of the RNA-guided endonuclease and a second RNA (tracrRNA or scaffold) which hybridizes to the first RNA to form an RNA complex that interacts with RNA-guided endonuclease (see Jinek et al., 2012, A programmable dual-RNA-guided DNA endonuclease in adaptive bacterial immunity, Science 337: 816-821). The terms crRNA and tracrRNA are used interchangeably with the terms tracr-mate RNA and tracr RNA herein.

Since the discovery of the CRISPR-Cas9 system, single polynucleotide gRNAs have been developed and successfully applied just as effectively as natural two-part gRNA complex.

In a preferred embodiment, the gRNA is a single gRNA or RNA complex comprising a first RNA comprising 20 or more nucleotides that are at least 85% complementary to and capable of hybridizing to the one or more DNA target sequence; preferably the 20 or more nucleotides are at least 90%, 95%, 97%, 98%, 99% or even 100% complementary to and capable of hybridizing to the one or more DNA target sequence.

In a particularly preferred embodiment, the gRNA is a single gRNA or RNA complex comprising a first RNA comprising 21 nucleotides that are at least 85% complementary to and capable of hybridizing to the one or more DNA target sequence; preferably the 21 are at least 90%, 95%, 97%, 98%, 99% or even 100% complementary to and capable of hybridizing to the one or more DNA target sequence.

In another preferred embodiment, the gRNA comprises the first and second RNAs in the form of a single polynucleotide, wherein the tracr mate sequence and the tracr sequence form a stem-loop structure when hybridized with each other.

DNA Target Sequence

The DNA target sequence may be found anywhere, including in vivo (e.g., inside a cell or a living organism, including as part of the genome of said cell or organism), ex vivo, or in vitro. The DNA target sequence should be complementary to and capable of hybridizing to a gRNA suitable for directing the binding of the catalytically inactive RNA-guided endonucleases of the invention to the DNA target sequence.

Preferably, the DNA target sequence is at least 20 nucleotides in length in order to allow its hybridization to the corresponding at least 20 nucleotide sequence of the gRNA. The DNA target sequence can be located anywhere in the genome but will often be within a coding sequence or open reading frame.

In a preferred embodiment, the DNA target sequence comprises a polynucleotide comprising 20 or more nucleotides that are at least 85% complementary to and capable of hybridizing to the gRNA; preferably the 20 or more nucleotides are at least 90%, 95%, 97%, 98%, 99% or even 100% complementary to and capable of hybridizing to the gRNA.

In a particularly preferred embodiment, the DNA target sequence comprises a polynucleotide comprising 21 nucleotides that are at least 85% complementary to and capable of hybridizing to the gRNA; preferably the 21 nucleotides are at least 90%, 95%, 97%, 98%, 99% or even 100% complementary to and capable of hybridizing to the gRNA.

The DNA target sequence should be flanked by a functional protospacer adjacent motif (PAM) that is recognized by the RNA-guided endonuclease of the invention. For an overview of PAM sequences, see, for example, Shah et al., 2013, Protospacer recognition motifs, RNA Biol. 10(5): 891-899. Preferably, the PAM sequence is 5'-TTTN-3' or 5'-CTTN-3'. More preferably, the PAM sequence is 5'-TTTN-3'. Most preferably, the PAM sequence is 5'-TTTC-3' or 5'-TTTG-3'.

In a preferred embodiment, the DNA target sequence is located at the 3' end of the PAM sequence. Most preferably, the DNA target sequence is located directly adjacent to the 3' end of the PAM sequence.

Preferably, the DNA target sequence is comprised in an open reading frame encoding a polypeptide or in a promoter region. Also preferably, the DNA target sequence encode one or more enzyme selected from the group consisting of hydrolase, isomerase, ligase, lyase, oxidoreductase, or a transferase; preferably the one or more enzyme is an alpha-amylase, alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucano-transferase, glucoamylase, invertase, laccase, lipase, mannosidase, mutanase, oxidase, pectinolytic enzyme, peroxidase, phosphodiesterase, phytase, polyphenoloxidase, proteolytic enzyme, ribonuclease, transglutaminase, and xylanase.

Preferably, the DNA target sequence encodes a fluorescent protein (e.g., green fluorescent protein), a fragment or a variant thereof.

Polynucleotides

The present invention also relates to isolated polynucleotides encoding a nucleobase editing complex of the present invention, as described herein.

The techniques used to isolate or clone a polynucleotide are known in the art and include isolation from genomic DNA or cDNA, or a combination thereof. The cloning of the polynucleotides from genomic DNA can be affected, e.g., by using the polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

Nucleic Acid Constructs

The present invention also relates to nucleic acid constructs comprising a polynucleotide encoding a nucleobase editing complex of the present invention, wherein the polynucleotide is operably linked to one or more control sequences that direct the expression of the coding sequence in a suitable host cell under conditions compatible with the control sequences.

The polynucleotide may be manipulated in a variety of ways to provide for expression of the nucleobase editing complex. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the polynucleotide of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13:97-107), *E. coli* lac operon, *E. coli* trc promoter (Egon et al., 1988, *Gene* 69:301-315), *Streptomyces coelicolor* agarase gene (dagA), and prokaryotic beta-lactamase gene (Villa-Kamaroff et al., 1978, *Proc. Natl. Acad. Sci. USA* 75:3727-3731), as well as the tac promoter (DeBoer et al., 1983, *Proc. Natl. Acad. Sci. USA* 80:21-25). Further promoters are described in "Useful proteins from recombinant bacteria" in Gilbert et al., 1980, *Scientific American* 242:74-94; and in Sambrook et al., 1989, supra. Examples of tandem promoters are disclosed in WO 99/43835.

Examples of suitable promoters for directing transcription of the polynucleotide of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V,

*Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8:423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *J. Bacteriol.* 177:3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15:5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is heterologous to the coding sequence. A heterologous signal peptide coding sequence may be required where the coding sequence does not naturally contain a signal peptide coding sequence. Alternatively, a heterologous signal peptide coding sequence may simply replace the natural signal peptide coding sequence to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiol. Rev.* 57:109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide encoding a nucleobase editing complex of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Res.* 15:9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide encoding a nucleobase editing complex of the present invention operably linked to one or more control sequences that direct the expression of the nucleobase editing complex. A construct or vector comprising a polynucleotide is introduced into a host cell so that the construct or vector is maintained as a chromosomal integrant or as a self-replicating extra-chromosomal vector as described earlier.

In some embodiments, at least one of the one or more control sequences is heterologous to the polynucleotide encoding the nucleobase editing complex. In some embodiments, at least one of the one or more control sequences is heterologous to the host cell.

In some embodiments, the recombinant host cell comprises at least two copies, e.g., three, four, or five, of the polynucleotide of the present invention.

The host cell may be any cell, e.g., a prokaryotic cell or a eukaryotic cell.

The host cell may be any mammalian cell, microbial cell, or plant cell.

Preferably, the mammalian host cell is a mouse, rat, monkey, or human cell.

Preferably, the microbial cell is a prokaryotic cell (e.g., bacterial cell) or a fungal cell (e.g., a filamentous fungal cell or a yest cell).

The host cell may be any microbial or plant cell, e.g., a prokaryotic cell or a fungal cell.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus,*

*Bacillus lentus, Bacillus licheniformis, Bacillus megaterium, Bacillus pumilus, Bacillus stearothermophilus, Bacillus subtilis*, and *Bacillus thuringiensis* cells. Most preferably the bacterial host cell is a *Bacillus licheniformis* cell.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168:111-115), competent cell transformation (see, e.g., Young and Spizizen, 1961, *J. Bacteriol.* 81:823-829, or Dubnau and Davidoff-Abelson, 1971, *J. Mol. Biol.* 56:209-221), electroporation (see, e.g., Shigekawa and Dower, 1988, *Biotechniques* 6:742-751), or conjugation (see, e.g., Koehler and Thorne, 1987, *J. Bacteriol.* 169:5271-5278). The introduction of DNA into an *E. coli* cell may be effected by protoplast transformation (see, e.g., Hanahan, 1983, *J. Mol. Biol.* 166:557-580) or electroporation (see, e.g., Dower et al., 1988, *Nucleic Acids Res.* 16:6127-6145). The introduction of DNA into a *Streptomyces* cell may be effected by protoplast transformation, electroporation (see, e.g., Gong et al., 2004, *Folia Microbiol. (Praha)* 49:399-405), conjugation (see, e.g., Mazodier et al., 1989, *J. Bacteriol.* 171:3583-3585), or transduction (see, e.g., Burke et al., 2001, *Proc. Natl. Acad. Sci.* USA 98:6289-6294). The introduction of DNA into a *Pseudomonas* cell may be effected by electroporation (see, e.g., Choi et al., 2006, *J. Microbiol. Methods* 64:391-397) or conjugation (see, e.g., Pinedo and Smets, 2005, *Appl. Environ. Microbiol.* 71:51-57). The introduction of DNA into a *Streptococcus* cell may be effected by natural competence (see, e.g., Perry and Kuramitsu, 1981, *Infect. Immun.* 32:1295-1297), protoplast transformation (see, e.g., Catt and Jollick, 1991, *Microbios* 68:189-207), electroporation (see, e.g., Buckley et al., 1999, *Appl. Environ. Microbiol.* 65:3800-3804), or conjugation (see, e.g., Clewell, 1981, *Microbiol. Rev.* 45:409-436). However, any method known in the art for introducing DNA into a host cell can be used.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Pichia pastoris* (also known as *Khomagataella phaffii*), *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell. Most preferably the yeast host cell is a *Pichia pastoris* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolismis obligately aerobic. In contrast, vegetative growth by yeasts such as *Saccharomyces cerevisiae* is by budding of a unicellular thallus and carbon catabolismmay be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell. More preferably the filamentous fungal host cell is an *Aspergillus niger, Aspergillus oryzae,* or *Trichoderma reesei* cell. Most preferably the filamentous fungal host cell is an *Aspergillus niger* or *Aspergillus oryzae* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81:1470-1474, and Christensen et al., 1988, *Bio/Technology* 6:1419-1422. Suitable methods for transforming *Fusarium* species are described by Malardier et al., 1989, *Gene* 78:147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153:163; and Hinnen et al., 1978, *Proc. Natl. Acad. Sci. USA* 75:1920.

EXAMPLES

Materials and Methods

Unless otherwise stated, DNA manipulations and transformations were performed using standard methods of molecular biology as described in Sambrook et al. (1989) *Molecular cloning: A laboratory manual,* Cold Spring Harbor lab., Cold Spring Harbor, NY; Ausubel, F. M. et al. (eds.)

"*Current protocols in Molecular Biology*", John Wiley and Sons, 1995; Harwood, C. R., and Cutting, S. M. (eds.) "Molecular Biological Methods for *Bacillus*". John Wiley and Sons, 1990.

Purchased Material (*E. coli* and Kits)

*E. coli* DH5α (Toyobo) and Stellar (TakaRa) are used for plasmid construction and amplification. Amplified plasmids are recovered with Qiagen Plasmid Kit (Qiagen). Ligation is done with either NEBuilder HiFi DNA Assembly Cloning kit (New England Biolabs, Inc.) or In-Fusion kit (Clontech Laboratories, Inc.) according to the manufactory instructions. Polymerase Chain Reaction (PCR) is carried out with either PrimeSTAR GXL DNA polymerase kit (TaKaRa). QIAquick™ Gel Extraction Kit (Qiagen) is used for either the purification of PCR fragments or extraction of DNA fragment from agarose gel.

Enzymes

Enzymes for DNA manipulations (e.g. restriction endonucleases, ligases etc.) are obtain-able from New England Biolabs, Inc. and were used according to the manufacturer's instructions.

Plasmids pBluescript II SK-(Stratagene #212206).

The CRISPR-Cas9 plasmids described in examples contains U6-2 promoter from Magnaporthe *oryzae, Aspergillus fumigatus* tRNA Gly promoter, *A. fumigatus* tef1 promoter and hph marker gene. Details are described in the example section.

The sequence for Po AMG harboring the amyloglucosidase from *Penicillium oxalicum* is described in WO2011/127802.

The pAT3530 CRISPR-ma7d-AID-UGI plasmid is described in Example 7.

Microbial Strains

The expression host strain *Aspergillus niger* M1364 was isolated by Novozymes and is a derivative of *Aspergillus niger* NN049184 which was isolated from soil as described in Example 14 of WO 2012/160093. M1364 is a strain which produces the glucoamylase from *Penicillium oxalicum* (Po AMG).

The expression host strain *Aspergillus oryzae* JaL355 is described in Example 10 of WO 2005/070962.

*Bacillus subtilis* PP3724: This strain is a donor strain for conjugation of *Bacillus* strains as described in WO 1996/029418.

*Bacillus licheniformis* SJ1904: This strain is described in WO 2008/066931.

Medium

COVE trace metals solution was composed of 0.04 g of NaB4O7·10H2O, 0.4 g of CuSO4·5H2O, 1.2 g of FeSO4·7H2O, 0.7 g of MnSO4·H2O, 0.8 g of Na2MoO2·2H2O, 10 g of ZnSO4·7H2O, and deionized water to 1 liter.

50× COVE salts solution was composed of 26 g of KCl, 26 g of MgSO4·7H2O, 76 g of KH2PO4, 50 ml of COVE trace metals solution, and deionized water to 1 liter.

COVE medium was composed of 342.3 g of sucrose, 20 ml of 50× COVE salts solution, 10 ml of 1 M acetamide, 10 ml of 1.5 M CsCl2, 25 g of Noble agar, and deionized water to 1 liter.

COVE-N-Gly plates were composed of 218 g of sorbitol, 10 g of glycerol, 2.02 g of KNO3, 50 ml of COVE salts solution, 25 g of Noble agar, and deionized water to 1 liter.

COVE-N (tf) was composed of 342.3 g of sucrose, 3 g of NaNO3, 20 ml of COVE salts solution, 30 g of Noble agar, and deionized water to 1 liter.

COVE-N top agarose was composed of 342.3 g of sucrose, 3 g of NaNO3, 20 ml of COVE salts solution, 10 g of low melt agarose, and deionized water to 1 liter.

COVE-N was composed of 30 g of sucrose, 3 g of NaNO3, 20 ml of COVE salts solution, 30 g of Noble agar, and deionized water to 1 liter.

STC buffer was composed of 0.8 M sorbitol, 25 mM Tris pH 8, and 25 mM CaCl2.

STPC buffer was composed of 40% PEG 4000 in STC buffer.

LB medium was composed of 10 g of tryptone, 5 g of yeast extract, 5 g of sodium chloride, and deionized water to 1 liter.

LB plus ampicilin plates were composed of 10 g of tryptone, 5 g of yeast extract, 5 g of sodium chloride, 15 g of Bacto agar, ampicillin at 100 μg per ml, and deionized water to 1 liter.

YPG medium was composed of 10 g of yeast extract, 20 g of Bacto peptone, 20 g of glucose, and deionized water to 1 liter.

SOC medium was composed of 20 g of tryptone, 5 g of yeast extract, 0.5 g of NaCl, 10 ml of 250 mM KCl, and deionized water to 1 liter.

TAE buffer was composed of 4.84 g of Tris Base, 1.14 ml of Glacial acetic acid, 2 ml of 0.5 M EDTA pH 8.0, and deionized water to 1 liter.

*Bacillus* strains were grown on LB agar (10 g/l Tryptone, 5 g/l yeast extract, 5 g/l NaCl, 15 g/l agar) plates, on Difco Tryptose Blood Agar Base plates, or in LB liquid medium (10 g/l Tryptone, 5 g/l yeast extract, 5 g/l NaCl).

To select for erythromycin resistance, agar media were supplemented with 1 μg/ml erythromycin and 25 μg/ml lincomycin, and liquid media were supplemented with 5 μg/ml erythromycin. To select for tetracycline resistance, agar and liquid media were supplemented with 15 μg/ml tetracycline. To select for erythromycin resistance and tetracycline resistance simultaneously, agar and liquid media were supplemented with 2 μg/ml erythromycin and 15 μg/ml tetracycline.

Spizizen I and Spizizen II media were used for preparation and transformation of competent *Bacillus subtilis* cells.

Spizizen I medium consists of 1× Spizizen salts (6 g/l KH2P04, 14 g/l K2HP04, 2 g/l (NH4) 2S04, 1 g/l sodium citrate dihydrate, 0.2 g/l MgS04·7H20, pH 7.0), 0.5% glucose, 0.1% yeast extract, and 0.02% casein hydrolysate.

Spizizen II medium consists of Spizizen I medium supplemented with 0.5 mM CaCl2, and 2.5 mM MgCl2.

Conjugation donor strains were supplemented with 100 μg/ml D-alanine.

Transformation of *Aspergillus niger*

Transformation of *Aspergillus* species can be achieved using the general methods for yeast transformation. The preferred procedure for the invention is described below.

*A. niger* host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLU-CANEX™, Novozymes A/S, Bagsværd, Denmark) at a final concentration of 20 mg per ml. The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ proto-plasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove or Cove-N top agarose, the reaction was poured onto Cove or Cove-N (tf) agar plates and the plates were incubated at 32° C. for 5 days.

Transformation of *Aspergillus oryzae*

*Aspergillus* transformation was done as described by Christensen et al.; *Biotechnology* 1988 6 1419-1422. In short, *A. oryzae* mycelia were grown in a rich nutrient broth. The mycelia were separated from the broth by filtration. The enzyme preparation Glucanex® (Novozymes) was added to the mycelia in osmotically stabilizing buffer such as 1.2 M MgSO4 buffered to pH 5.0 with sodium phosphate. The suspension was incubated for 60 minutes at 37 degrees C. with agitation. The protoplast was filtered through mira-cloth to remove mycelial debris. The protoplast was harvested and washed twice with STC (1.2 M sorbitol, 10 mM CaCl2, 10 mM Tris-HCl pH 7.5). The protoplasts were finally re-suspended in 200-1000 microl STC.

For transformation, 1 μg CRISPR-AID-UGI plasmid (pAT3532-3537) was added to 100 μl protoplast suspension and then 200 μl PEG solution (60% PEG 4000, 10 mM CaCl2, 10 mM Tris-HCl pH 7.5) was added and the mixture is incubated for 20 minutes at room temperature. The protoplast was harvested and washed twice with 1.2 M sorbitol. The protoplast was finally re-suspended 200 μl 1.2 M sorbitol. Transformants containing the pyrG gene were selected for its ability to grow on minimal plates without addition of 10 mM uridine (Cove D. J. 1966. *Biochem. Biophys. Acta.* 113:51-56) containing 1.0 M sucrose as carbon source, 10 mM NaNO4 as nitrogen source. After 5-7 days of growth at 37 degrees C., stable transformants appeared as vigorously growing and sporulating colonies. Transformants were purified one through conidiophores.

Transformation and Conjugation of *Bacillus* Cells

Competent cells of *Bacillus subtilis* strains prepared and transformed according to the method described in Yasbin et al. (1973): Transformation and transfection in lysogenic strains of *Bacillus subtilis* 168. *J. Bacteriol.* 113, 540-548.

Conjugation of *Bacillus licheniformis* was performed essentially as described in WO 1996/029418.

PCR Amplifications in Examples

Polymerase Chain Reaction (PCR) was carried out with PrimeSTAR GXL DNA polymerase (TaKaRa) as follows.

| Component | Volume | Final Concentration |
|---|---|---|
| 5x PrimeSTAR GXL Buffer | 10 μl | 1x |
| 2.5 mM dNTPs | 4 μl | 0.2 mM each |
| 5 pmol/μl Primer #1 | 2 μl | 0.2 μM |
| 5 pmol/μl Primer #2 | 2 μl | 0.2 μM |
| Template DNA | X μl | |
| Genomic DNA | 10-200 ng/50 μl | |
| or Plasmid DNA | 1-50 ng/50 μl | |
| PCR grade water | Y μl | |
| PrimeSTAR GXL polymerase (1.25 U/μl) | 1 μl | 1.25 U/50 μl |
| Total reaction volume | 50 μl | |

| 3-step cycle: |
|---|
| Pre-denaturation: 98° C., 2 min. |
| Denaturation: 98° C., 15 sec. |
| Annealing: Tm-[5-10] ° C., 15 sec. |
| Extension: 68° C., 1 min./kb |
| 25-30 cycles |

For Examples 9 to 11, Polymerase Chain Reaction (PCR) was carried out with SapphireAmp Fast PCR Master Mix (Takara Bio) as follows.

| Primer ID | Sequence | Expected PCR fragment size |
|---|---|---|
| 1202334 | TTGCACCGTCTAATGG (SEQ ID NO: 165) | 757 bp |
| 1228373 | GATGATGCCTTCCTTCAGTT (SEQ ID NO: 166) | |

| Component | Volume | Final Concentration |
|---|---|---|
| 2x SapphireAmp Fast PCR Master Mix | 10 µl | 1x |
| 50 pmol/µl Primer 1202334 | 0.08 µl | 0.2 µM |
| 50 pmol/µl Primer 1228373 | 0.08 µl | 0.2 µM |
| Culture broth | 1 µl | |
| PCR grade water | 8.84 µl | |
| Total reaction volume | 20 µl | |

Pre-denaturation: 95° C., 3 min.
30 cycles of
    Denaturation: 95° C., 15 sec.
    Annealing: 58° C., 15 sec.
    Extension: 72° C., 15 sec.

*A. fumigatus* tRNAgly(GCC) 1-6, and Cas9. The *M. oryzae* U6-2 promoter and terminator were identified by searching the gene annotations of the *M. grisea* strain 70-15 (MG8) genome sequence database from the Joint Genome Institute (JGI). The *A. fumigatus* tRNAgly(GCC) 1-6 gene sequence was identified ((chr4: 3650153-3650223 (+)) by searching the gene annotations of the *A. fumigatus* strain 293 genome sequence database from the JGI.

The amplified fragments were assembled and ligated into the 5.5-kb NheI fragment from pHiTe132 (a derivative of pHiTe50 which is described in WO 2015/025055) using NEBuilder HiFi DNA Assembly Cloning Kit according to the instruction, to create pHiTe277. Plasmid preparation was carried out in *E. coli* DH5α.

TABLE 1a

Primers for U6 promoter-tRNA, dCas9 and hph genes

| Fragment | Primers used (5'→3'), forward and reverse | PCR product (bp) |
|---|---|---|
| Fragment 1: from *M. oryzae* U6-2 promoter to dCas9 (D10A) | HTJP-889: ctagaaagtataggaacttcgctagctctgctcgaggccatctg (SEQ ID NO: 1) <br> HTJP-890: gttcgttccaatggccagcccgatgctatacttc (SEQ ID NO: 2) | 1850 |
| Fragment 2: from dCas9 (D10A) to dCas9 (D840A) | HTJP-891: agtatagcatcgggctggccattggaacgaactcgg (SEQ ID NO: 3) <br> HTJP-892: gattgcgggacgatagcgtcaacatcgtagtccgacaaccg (SEQ ID NO: 4) | 2524 |
| Fragment 3: from dCas9 (D840A) to hph marker | HTJP-893: tcggactacgatgttgacgctatcgtcccgcaatccttcct (SEQ ID NO: 5) <br> HTJP-894: ggtagagtaataacgcctaggacacgcaaaacgaggtacatt (SEQ ID NO: 6) | 1852 |
| Fragment 4: hph marker | HTJP-895: gtcctaggcgttattactctaccgcaagg (SEQ ID NO: 7) <br> HTJP-896: taggaacttcaatcgatctagtcctaggctacgccaggaccgag-caagc (SEQ ID NO: 8) | 2131 |

Final extension: 72° C., 3 min.
PART A: *Aspergillus niger.*

Example 1. Construction of the Plasmids which Harbors the Expression Cassette of dCas9-AID Complex and sgRNAs Targeting PKS Gene Construction of dCas9 Expression Plasmid The purpose of this experiment is first to prepare the plasmid to express a catalytically inactive (="dead") Cas9 (i.e. dCas9 which include D10A and D840A substitutions to Cas9) in *A. niger* strains.

The fragments of U6-2 promoter (from *Magnaporthe oryzae*) fused to *Aspergillus* fumigatus tRNA Gly and tef1 promoter-dCas9 followed by hph selective maker were amplified by PCR with primer pairs (Table 1a) using pSMai289 plasmid DNA as template.

Figure 2:
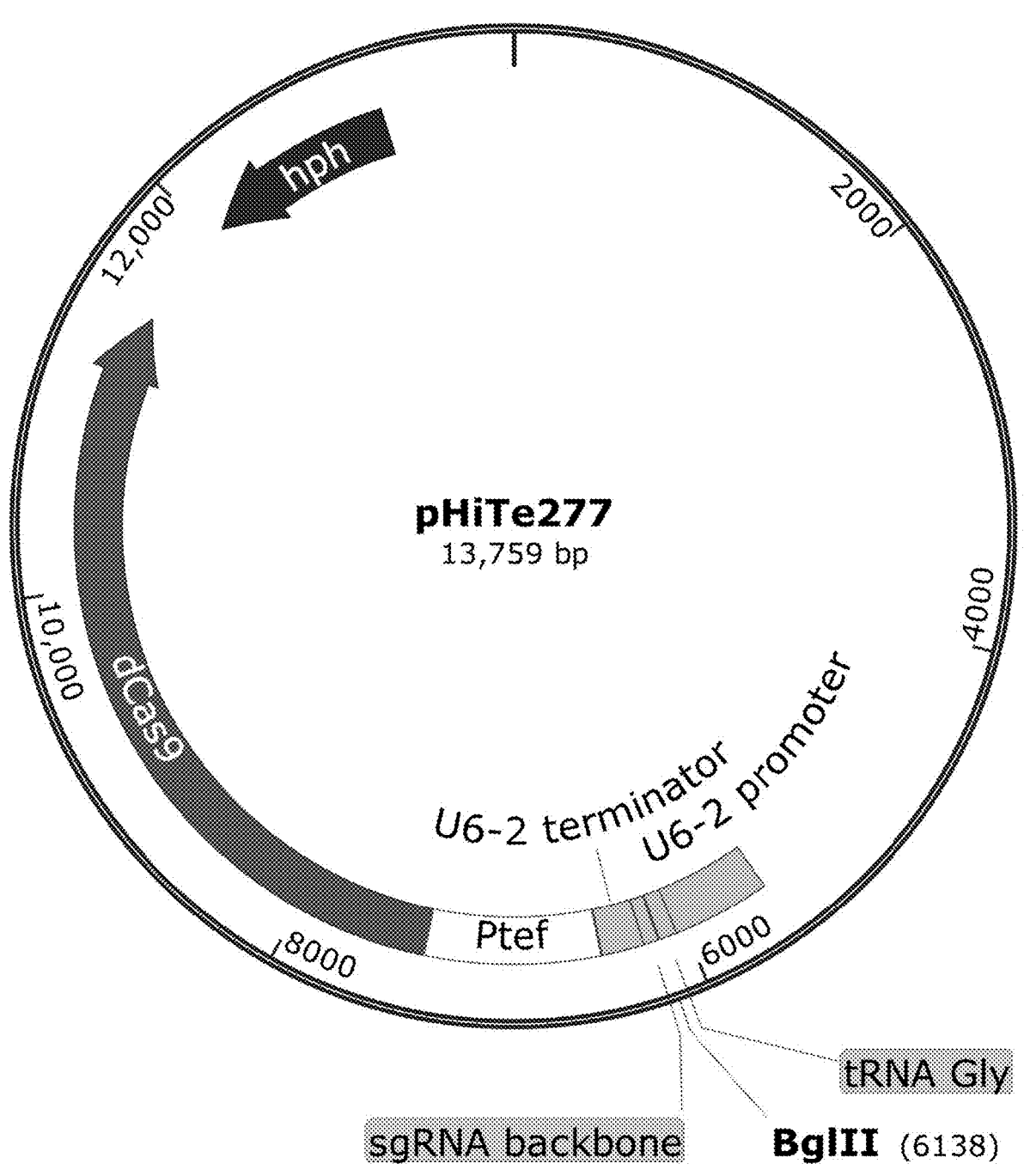
FIG. 2 shows a schematic drawing of the plasmid pHite277.

The CRISPR-Cas9 plasmid pSMai289 contains the sequences for the *M. oryzae* U6-2 promoter and terminator, The resulting plasmid pHiTe277 contains the following elements in order (FIG. 2):
    *M. oryzae* U6-2 promoter (SEQ ID NO:9)
    *A. fumigatus* tRNA Gly (SEQ ID NO: 10)
    Cas9 sgRNA backbone (SEQ ID NO:11)
    *M. oryzae* U6-2 terminator (SEQ ID NO:12)
    *A. nidulans* tef1 promoter (SEQ ID NO:13)
    dCas9_coding (SEQ ID NO: 14)
    dCas9_protein (SEQ ID NO: 15)
    hph selection marker (SEQ ID NO:16)
Construction of dCas9-AID Expression Plasmids with sgRNA Expression Cassettes Targeting PKS Gene.

The purpose of this experiment is to prepare plasmid DNAs for testing the effect of AID mutational activity when linked to dead Cas9 as a control for Mad7d-AID. The PKS (or also called wA) gene was used as a model target of dCas9-AID. The PKS knocked-out mutant would show white colored spore phenotype, which is good indicator to select for expected mutants.

27 28

Figure 3:
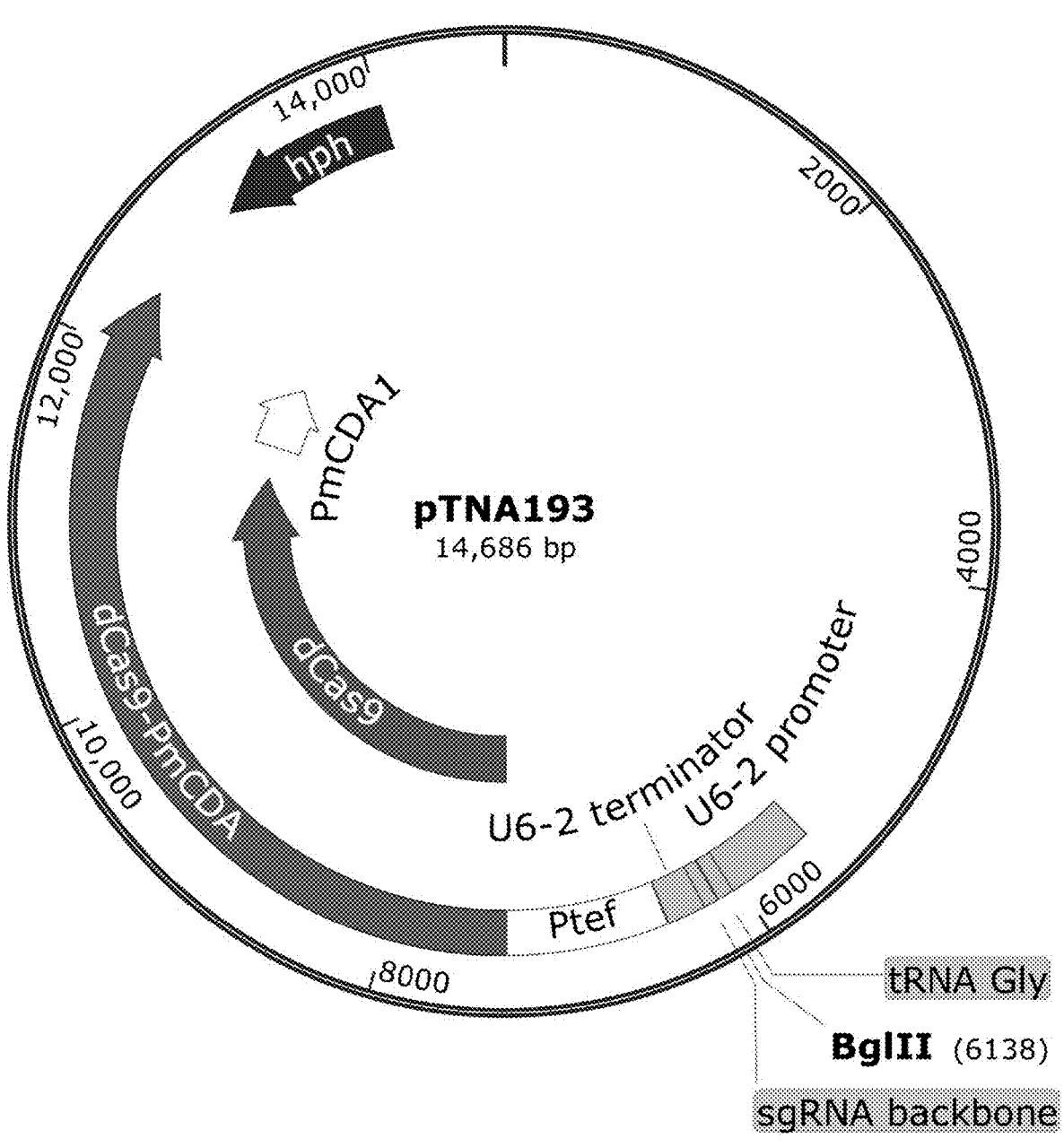
FIG. 3 shows a schematic drawing of the plasmid pTNA193.

To fuse *Petromyzon marinus*-derived cytidine deaminase to C-terminus of dCas9 gene, codon-optimized deaminase gene was ordered as synthetic DNA (GeneArt—ThermoFisher Scientific). To prepare DNA fragments for cloning, dCas9 gene and vector region of pHite277 were independently PCR amplified. The vector fragment, dCas9 fragment and deaminase gene fragment were conjugated by NEB HiFi cloning kit, resulting in construction of pTNA 193 (dCas9-AID, sgRNA empty). The pairs of primers were described in Table 1b. FIG. 3 shows the schematic drawing of pTNA193.

TABLE 1b

Primers used for construction of dCas9-AID with empty sgRNA vectors

| Primer name | Sequence 5' → 3' | SEQ ID NO: |
|---|---|---|
| IF_U6cas9_fwd | ttttctctgctgtctgcctcg | 17 |
| IF_dCasCDA_rev | gtcgcccccagttgactaag | 18 |
| IF_CDA3UTR_fwd | gcggacattcgatttatgccgttatg | 19 |
| IF_U63UTR_rev | agacagcagagaaaagccagatgg | 20 |
| CDAinsert_fwd | caactgggggcgacagcag | 21 |
| CDAinsert_rev | aaatcgaatgtccgcttatccggag | 22 | the target C should locate at 2nd to 5th position when numbered from PAM distal end (K. Nishida et al., (2016) Science).

TABLE 2

Protospacer sequences for disruption of PKS gene. Potential target "C" is underlined.

| Plasmid (target number) | Protospacer (5' → 3'), potential target C is underlined | Protospacer adjacent motif (PAM) sequence |
|---|---|---|
| pTNA197 (wA1) | CAGCAGTCCTCTGCTCTAGA (SEQ ID NO: 23) sense strand | agg |
| pTNA198 (wA2) | TCCAACCCACTCCCTGGAAT (SEQ ID NO: 24) sense strand | cgg |
| pTNA199 (wA3) | CCAGCATGTTGACTCGGAAT (SEQ ID NO: 25) antisense strand | cgg |
| pTNA200 (wA4) | TGTCCCAGCATAGTCGTCGT (SEQ ID NO: 26) antisense strand | agg |

TABLE 3

The oligo DNAs for the construction of pTNA197-200. Sequence which matches protospacers is shown in capital.

| Primer name | Sequence 5' → 3' | SEQ ID NO: |
|---|---|---|
| wA_sense_1 | ttcgattcacggatgatgcaCAGCAGTCCTCTGCTCTAGAgttttagagctagaaatagc | 27 |
| wA_sense_1_rev | gctatttctagctctaaaacTCTAGAGCAGAGGACTGCTGtgcatcatccgtgaatcgaa | 28 |
| wA_sense_2 | ttcgattcacggatgatgcaTCCAACCCACTCCCTGGAATgttttagagctagaaatagc | 29 |
| wA_sense_2_rev | gctatttctagctctaaaacATTCCAGGGAGTGGGTTGGAtgcatcatccgtgaatcgaa | 30 |
| wA_anti_1 | ttcgattcacggatgatgcaCCAGCATGTTGACTCGGAATgttttagagctagaaatagc | 31 |
| wA_anti_1_rev | gctatttctagctctaaaacATTCCGAGTCAACATGCTGGtgcatcatccgtgaatcgaa | 32 |
| wA_anti_2 | ttcgattcacggatgatgcaTGTCCCAGCATAGTCGTCGtgttttagagctagaaatagc | 33 |
| wA_anti_2_rev | gctatttctagctctaaaacACGACGACTATGCTGGGACAtgcatcatccgtgaatcgaa | 34 |

Four different protospacers were designed to target the PKS gene as shown in Table 2. Pairs of oligo DNAs including each of protospacers were ordered and cloned into BglII site of pTNA193 by NEBuilder HiFi cloning kit, resulting in construction of pTNA197 to 200 (dCas9-AID, wA target #1 to #4, respectively). Oligo DNAs used for construction of those plasmids are shown in Table 3. To inactivate the PKS gene, protospacers were selected by following criteria: (1) stop codon (TAG, TAA, or TGA) should be introduced by C to T nucleotide conversion, (2)

Protospacer cloning to pTNA193 was carried out as follows. The backbone plasmid pTNA 193 was digested by BglII at 37° C. for 1 hour. The digested fragment was then gel purified by using QIAquick Gel Extraction kit (QIAGEN). The purified DNA fragment was mixed with each pair of oligo DNAs shown in Table 3 and protospacer sequences were cloned into the vectors by NEBuilder HiFi DNA Assembly kit. Two micro-liter of the reaction mixture were transformed into DH5a chemically competent *E. coli* cells. Transformants were spread onto LB plus ampicillin plates and incubated at 37° C. overnight. Plasmid DNA was purified from several transformants using a QIAGEN mini-prep kit. The plasmid DNA was screened for proper ligation by restriction enzyme digestion followed by 1.0% agarose gel electrophoresis with TAE buffer. Commercial sequence service was used to determine the actual DNA sequences.

The representative plasmid pTNA193 contains the following elements in order (FIG. 3):

M. oryzae U6-2 promoter (SEQ ID NO:9)
A. fumigatus tRNA Gly (SEQ ID NO: 10)
Cas9 sgRNA backbone (SEQ ID NO:11)
M. oryzae U6-2 terminator (SEQ ID NO: 12)
A. nidulans tef1 promoter (SEQ ID NO:13)
dCas9-AID_coding (SEQ ID NO:35)
dCas9-AID_protein (SEQ ID NO:36)
hph selection marker (SEQ ID NO: 16)

The target PKS (wA) gene sequence can also be found in the Sequence Listing (SEQ ID NO: 37).

Example 2. Transformation of CRISPR-AID Plasmids for the PKS Gene Inactivation The PKS inactivation in Aspergillus niger strain M1364

The purpose of this experiment is to demonstrate that dCas9-AID can introduce target specific C to T conversion in A. niger genome, and to assess the efficiency of mutational effect. To this end, the A. niger strain M1364 was transformed with dCas9-AID plasmids targeting endogeneous PKS gene (described in Example 1). The dCas9-AID and sgRNA expression cassette was site-specifically integrated into A. niger genome together with a hygromycin resistance gene. After isolation and spore maturation, the spore color of transformants was checked since PKS gene inactivation should lead to white colored spore phenotype. Clones which showed the expected phenotype were further analysed by target locus sequencing.

TABLE 4

Summary of PKS-targeting dCas9-AID transformation

| DNA | Description | | Colony count | Iso-lation | White spore | Hit rate (%) |
|-----|-------------|---|------|------|------|------|
| pTNA193 | no sgRNA | dCas9-AID | 350 | 12 | 0 | 0% |
| pTNA197 | wA1 | dCas9-AID | 180 | 12 | 0 | 0% |
| pTNA198 | wA2 | dCas9-AID | 90 | 12 | 1 | 8% |
| pTNA199 | wA3 | dCas9-AID | 40 | 12 | 1 | 8% |
| pTNA200 | wA4 | dCas9-AID | 30 | 12 | 0 | 0% |

Table 4 shows the summary of PKS-targeting experiments. As a result, we got white spored clones at 8% efficiency by using pTNA198 or 199, which possesses wA2 or wA3 sgRNA and dCas9-AID expression cassettes, respectively. To see if the PKS gene of those white clones was mutated as expected, genome DNA was isolated and target locus was PCR-amplified. The primers are shown as follows:

```
For wA2 target:
SEQ ID NO: 38:
Primer pks_seq_f2: 5' tcatatcggttctgccaagg 3'

SEQ ID NO: 39:
Primer pks_R: 5' gttgttgacgaaagttcgcc 3'
```

```
-continued
For wA3 target:
SEQ ID NO: 40:
Primer pks_F: 5' actgcgactgggaatctgcg 3'

SEQ ID NO: 41:
Primer pks_seq_r3: 5' cttgtaattcttggaaatgcagg 3'
```

Figure 4:
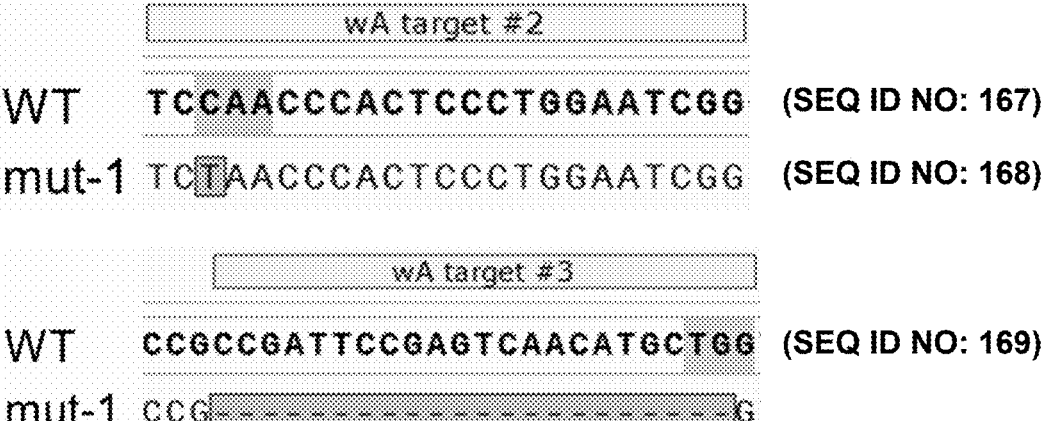
FIG. 4 shows genome sequences of white spore mutants generated by dCas9-AID.

The amplicon was then gel purified by QIAquick Gel Extraction Kit (Qiagen) and sent to commercial sequence service to determine the mutation patterns at targeted region. The black spored clone which was isolated from pTNA193 (no sgRNA) treatment showed no mutation at that genomic region, whereas the white spored clones showed C to T mutation at the expected position (FIG. 4). The mutant generated by pTNA199 (wA3 target) had 17 bp deletion at the sgRNA targeted site (FIG. 4). This might be because of cellular error-prone DNA repair such as base excision repair, other than the mechanism presented in FIG. 1. Anyways, these data showed that CRISPR-Cas9-AID can work in A. niger strain.

Example 3. Improvement of Mutation Efficiency by Adding UGI Domain

Construction of dCas9-AID-UGI Expression Plasmid

We showed that dCas9-AID system introduced targeted mutation at around 8% efficiency, as described in Example 2. However, this is not practical enough. Recent reports suggested that addition of UGI (uracil glycosylase inhibitor) to C-terminus of dCas9-AID improves the mutation efficiency in vivo (Rees H. A. and Liu D. R. Nature Reviews Genetics 19, 770-788 (2018)). Thus, this experiment aims to prepare plasmid DNAs which harbour dCas9-AID-UGI coding sequence and sgRNA expression cassettes. The target gene is same as what described in Example 2.

Figure 5:
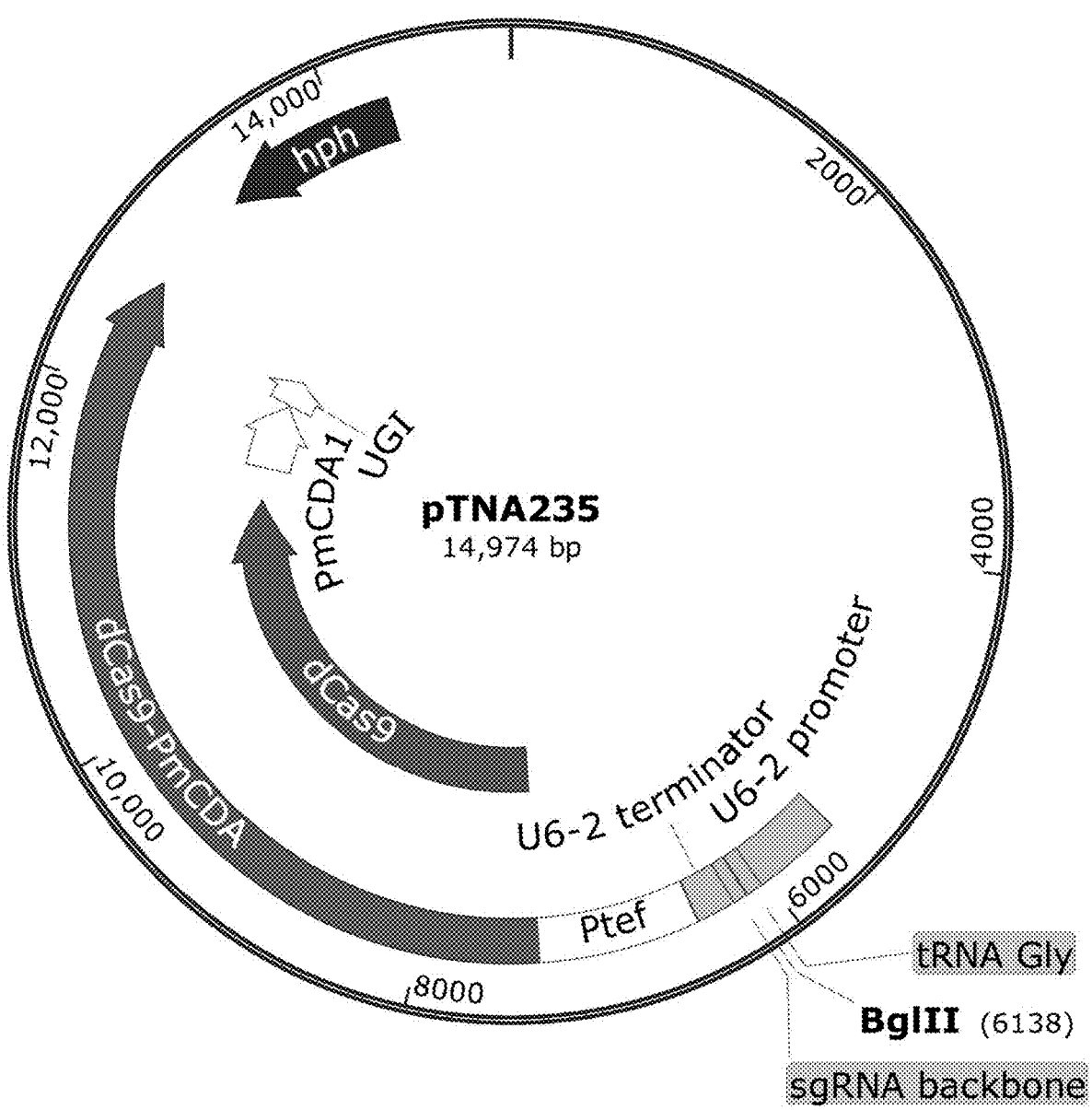
FIG. 5 shows a schematic drawing of the plasmid pTNA235.

To fuse UGI gene derived from bacteriophage to C-terminus of dCas9-AID, codon-optimized UGI gene was ordered as synthetic DNA (GeneArt—ThermoFisher Scientific), see SEQ ID NO: 131. To prepare DNA fragments for cloning, pTNA193 was first digested by XbaI and BmtI restriction enzymes and dCas9-AID encoding fragment was gel-purified. The vector part was next PCR amplified with adding BsrGI restriction site to the 5' end of 3'UTR for dCas9-AID. This PCR fragment was then digested by BsrGI and BmtI. Finally, UGI gene was PCR amplified with adding XbaI and BsrGI restriction sites to its 5' and 3' end, respectively. This UGI fragment was also digested by XbaI and BsrGI. Digested DNA fragments described above were conjugated by NEB HiFi cloning kit, resulting in construction of pTNA235 (dCas9-AID-UGI, sgRNA empty). The pairs of primers to were described in Table 5. FIG. 5 shows the schematic drawing of pTNA235.

TABLE 5

| Primers used for construction of dCas9-AID-UGI with empty sgRNA vectors | | | |
| --- | --- | --- | --- |
| Primer name | Sequence 5' → 3' | Purpose | SEQ ID NO: |
| BsrGI-3UTR-fwd | gtctaatgtacagcggacattcgatttatgc | vector fragment | 42 |
| NheI-FRT-rev | agcagagctagcgaagttcctatactttctag | vector fragment | 43 |
| Ex-UGItop-fwd | atgatctctagaggctccggaaccaacctg | UGI fragment | 44 |
| UGIend-rev | aaatcgaatgtccgctgtacattag | UGI fragment | 45 |

The sgRNA target sequences were same as what described in Example 1. Four different target protospacers were selected (see Table 2). To target these regions by dCas9-AID-UGI, pTNA235 was digested by BglII and protospacer sequences were introduced there (see Table 3), resulting in construction of pTNA240-243 (targeting wA1 to wA4, respectively).

The representative plasmid pTNA235 contains the following elements in order (FIG. 5):

*M. oryzae* U6-2 promoter (SEQ ID NO:9)

*A. fumigatus* tRNA Gly (SEQ ID NO: 10)

Cas9 sgRNA backbone (SEQ ID NO:11)

*M. oryzae* U6-2 terminator (SEQ ID NO: 12)

*A. nidulans* tef1 promoter (SEQ ID NO:13)

dCas9-AID-UGI_coding (SEQ ID NO:46)

dCas9-AID-UGI_protein (SEQ ID NO:47)

hph selection marker (SEQ ID NO:16)

The PKS Inactivation in *Aspergillus niger* Strain M1364

The purpose of this experiment is to demonstrate the addition of UGI domain to dCas9-AID improves the mutation efficiency. To this end, as described in Example 2, the *A. niger* strain M1364 was transformed with pTNA235 and 240-243. After isolation and spore maturation, the spore color of transformants was checked since PKS gene inactivation should lead to white colored spore phenotype. Clones which showed the expected phenotype were further analysed by target locus sequencing.

TABLE 6

| Summary of PKS-targeting dCas9-AID-UGI transformation | | | | | |
| --- | --- | --- | --- | --- | --- |
| DNA | | Description | Colony count | Iso- lation | White spore | Hit rate (%) |
| pTNA235 | no sgRNA | dCas9-AID-UGI | 20 | 20 | 0 | 0% |
| pTNA240 | wA1 | dCas9-AID-UGI | 8 | 8 | 2 | 25% |
| pTNA241 | wA2 | dCas9-AID-UGI | 12 | 12 | 5 | 42% |
| pTNA242 | wA3 | dCas9-AID-UGI | 12 | 12 | 4 | 33% |
| pTNA243 | wA4 | dCas9-AID-UGI | 12 | 12 | 3 | 25% |

Table 6 shows the summary of PKS-targeting experiments. As a result, we got white spored clones at 25-42% efficiency, which was clearly higher than the efficiency without UGI (see Example 2). To see if the PKS gene of those white clones was mutated as expected, genome DNA was isolated and target locus was PCR-amplified. The primers are shown as follows:

For wA1 target:
SEQ ID NO: 40:
Primer pks_F: 5' actgcgactgggaatctgcg 3'

SEQ ID NO: 48:
Primer pks_seq_r1: 5' atttgcaagagtggtttgtg 3'

For wA2 target:
SEQ ID NO: 38:
Primer pks_seq_f2: 5' tcatatcggttctgccaagg 3'

SEQ ID NO: 39:
Primer pks_R: 5' gttgttgacgaaagttcgcc 3'

For wA3 target:
SEQ ID NO: 40:
Primer pks_F: 5' actgcgactgggaatctgcg 3'

SEQ ID NO: 41:
Primer pks_seq_r3: 5' cttgtaattcttggaaatgcagg 3'

For wA4 target:
SEQ ID NO: 40:
Primer pks_F: 5' actgcgactgggaatctgcg 3'

SEQ ID NO: 48:
Primer pks_seq_r1: 5' atttgcaagagtggtttgtg 3'

The amplicon was then gel purified by QIAquick Gel Extraction Kit (Qiagen) and sent to commercial sequence service to determine the mutation patterns at targeted region. The black spored clone which was isolated from pTNA235 (no sgRNA) treatment showed no mutation at that genomic region, whereas the white spored clones showed C to T mutation at the expected position (FIG. 6). Thus, these data showed that the addition of UGI domain to dCas9-AID actually improved the mutational efficiency.

Example 4. Construction of Mad7d

Finding Putative Catalytic Residue of Mad7 for Endonuclease Activity

The catalytic site responsible for endonuclease activity in Mad7 was identified via sequence alignments with homologous sequences surrounding the active site of the otherwise distant relative FnCpf1, which can be catalytically inactivated by introducing a particular substitution (D917A) in its RuvC-like domain (Zetsche et al., 2015, *Cell* 163, 759-771). The corresponding conserved region was identified in Mad7 by a multiple alignment with the related *Lachnospiraceae bacterium* Cpf1 (LbCpf1) and *Francisella tularensis* Cpf1 (FnCpf1) using the MUSCLE algorithm. The alignment revealed position 877 to be relevant for the endonuclease activity of Mad7, and substitution of the native Asp with Ala (D877A) resulted in a catalytically inactive version of Mad7 (Mad7d), see the polypeptide with SEQ ID NO: 125 encoded by the polynucleotide with SEQ ID NO: 124.

The coding DNA and amino acid sequences of Mad7 nuclease can be found in SEQ ID NO: 49 and SEQ ID: 50, respectively. The amino acid sequences used for multiple alignment described above can be found in SEQ ID NO:51 to 53.

Construction of Mad7d-AID-UGI Expression Plasmid

Figure 7:
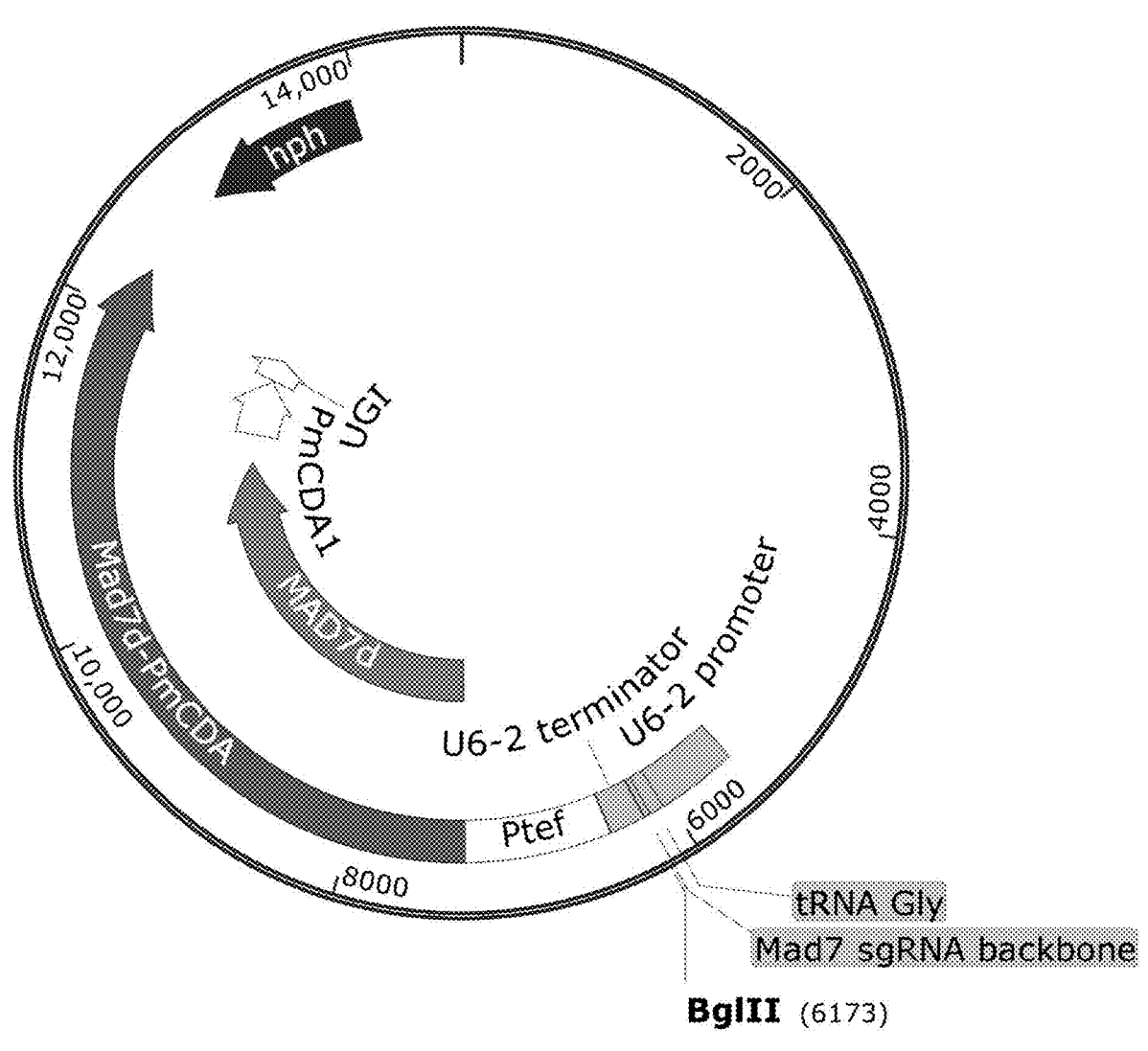
FIG. 7 shows a schematic drawing of the plasmid pTNA287.

To replace dCas9 part with Mad7d in the plasmid pTNA235, Mad7d gene was ordered as synthetic DNA (GeneArt—ThermoFisher Scientific). To replace dCas part with Mad7d in pTNA235, DNA sequences on pTNA235 except for dCas9 were PCR-amplified and gel purified. Mad7d gene was cloned into that fragment by NEBuilder HiFi DNA Assembly Cloning kit (New England Biolabs, Inc.), resulting in construction of pTNA261 (Mad7d-AID-UGI, Cas9 sgRNA expression). To replace Cas9 sgRNA expression cassette with that of Mad7, pTNA261 was digested by BglII and PmlI. Mad7 sgRNA coding sequences were introduced into that site by cloning synthetic oligo DNAs with NEBuilder HiFi DNA Assembly Cloning kit, resulting in construction of pTNA287 (Mad7d-AID-UGI, Mad7 sgRNA expression (empty)). The pairs of primers to were described in Table 7. FIG. 7 shows the schematic drawing of pTNA287.

stop codon when C to T mutation is introduced by Mad7d-AID. Target position of C is numbered from PAM proximal end. These protospacer sequences were cloned into BglII digested site of pTNA287, resulting in construction of pTNA296-307 and pTNA324-330 using the oligo DNAs shown in Table 9.

TABLE 8

Protospacer sequences for disruption of PKS gene. Potential target "C" is underlined.

| Plasmid (target number) | Protospacer (5' → 3'), potential target C is underlined | Protospacer adjacent motif (PAM) sequence (5' → 3') |
|---|---|---|
| pTNA296 MdwA1 | TTGGAGACCAGACCAGCGACA (SEQ ID NO: 63) sense strand | cttt |
| pTNA297 MdwA2 | GAGACCAGACCAGCGACATCG (SEQ ID NO: 64) sense strand | tttg |

TABLE 7

Primers used for construction of Mad7d-AID-UGI with empty sgRNA vectors

| Primer name | Sequence 5' → 3' | SEQ ID NO: |
|---|---|---|
| IF-Ptef-rev | ggtgaaggttgtgttatgttttgtgg | 54 |
| IF-nls-fwd | agcagggctgaccccaagaag | 55 |
| IF-PtfMd7-fwd | aacacaaccttcaccatgaacaacggcacaaacaac | 56 |
| IF-nlsMd7-rev | ggggtcagccctgctaggcaagtacctcttgttctg | 57 |
| sg-site_fwd | ttcgattcacggatgatgcagtcaaaagacctttttaatttctactcttgtagatagatc ttttttttggctcttgggttcgaactgc | 58 |
| sg-site_rev | tttggcttcggaaagcacacgtgaagggtaggaacaaagatggaatgattggca ggggtgacccaaatggtggggcataaaaaaaaagatgaccaaaacatgggc cttgggcagttcgaacccaagagcc | 59 |

The representative plasmid pTNA287 contains the following elements in order:
*M. oryzae* U6-2 promoter (SEQ ID NO:9)
*A. fumigatus* tRNA Gly (SEQ ID NO: 10)
Mad7 sgRNA backbone (SEQ ID NO:60)
*M. oryzae* U6-2 terminator (SEQ ID NO:12)
*A. nidulans* tef1 promoter (SEQ ID NO:13)
Mad7d-AID-UGI_coding (SEQ ID NO:61)
Mad7d-AID-UGI_protein (SEQ ID NO:62)
hph selection marker (SEQ ID NO:16)

Example 5. Transformation of Mad7d-AID Plasmids for the PKS Gene Inactivation The PKS Inactivation by Mad7d-AID in *A. niger* Strain M1364

The purpose of this experiment is to demonstrate that Mad7d-AID can introduce target specific C to T conversion in *A. niger* genome, and to assess the efficiency of mutational effect, as shown in Example 2 for the case of dCas9-AID. Since nobody has reported the activity of Mad7d linked deaminase, we first aimed to clarify the target position of cytidine as a substrate for AID. To this end, 19 target sequences with varied target positions on PKS locus were designed (Table 8), each of which would form premature TABLE 8-continued Protospacer sequences for disruption of PKS gene. Potential target "C" is underlined.

| Plasmid (target number) | Protospacer (5' → 3'), potential target C is underlined | Protospacer adjacent motif (PAM) sequence (5' → 3') |
|---|---|---|
| pTNA298 MdwA3 | TTCCAGCAATGCTTCCATGCA (SEQ ID NO: 65) sense strand | cttt |
| pTNA299 MdwA4 | CAGCAATGCTTCCATGCAATT (SEQ ID NO: 66) sense strand | tttc |
| pTNA300 MdwA5 | CATGCAATTCGTCAAGAGATC (SEQ ID NO: 67) sense strand | cttc |
| pTNA301 MdwA6 | TCGAGTTCGAGAACTGGTGGA (SEQ ID NO: 68) sense strand | tttt |
| pTNA302 MdwA7 | CGATCTCGAGTAGCGCCACTC (SEQ ID NO: 69) sense strand | tttt |

TABLE 8-continued

Protospacer sequences for disruption of PKS gene.
Potential target "C" is underlined.

| Plasmid (target number) | Protospacer (5' → 3'), potential target C is underlined | Protospacer adjacent motif (PAM) sequence (5' → 3') |
|---|---|---|
| pTNA303 MdwA8 | ATCCCTGGCGGTAACCGAGCA (SEQ ID NO: 70) sense strand | tttc |
| pTNA304 MdwA9 | AGGAAAGCGGCGAACTTTCGT (SEQ ID NO: 71) sense strand | cttc |
| pTNA305 MdwA10 | ACTGCATCGCAAGAAGCCAGG (SEQ ID NO: 72) sense strand | tttg |
| pTNA306 MdwA11 | GCCCTGTCGTGGTACAAGTGG (SEQ ID NO: 73) sense strand | ctta |
| pTNA307 MdwA12 | TGGCCGGCGTGCTCAGTTGCT (SEQ ID NO: 74) sense strand | tttg |
| pTNA324 MdwA13 | TACAGGAGGTTCCAGAAGCTC (SEQ ID NO: 75) antisense strand | tttg |

TABLE 8-continued

Protospacer sequences for disruption of PKS gene.
Potential target "C" is underlined.

| Plasmid (target number) | Protospacer (5' → 3'), potential target C is underlined | Protospacer adjacent motif (PAM) sequence (5' → 3') |
|---|---|---|
| pTNA325 MdwA14 | TCCAGATCGAATTGCAAGCCA (SEQ ID NO: 76) antisense strand | tttc |
| pTNA326 MdwA15 | CTGAAGCTGGCCGATTCCAGG (SEQ ID NO: 77) antisense strand | tttc |
| pTNA327 MdwA16 | ACACCCAGAGCAGTCCAGTAA (SEQ ID NO: 78) antisense strand | cttc |
| pTNA328 MdwA17 | GGGCCGAGACACTCCCAGTTA (SEQ ID NO: 79) antisense strand | cttg |
| pTNA329 MdwA18 | AGATCCCACTTGTAGGCTGGG (SEQ ID NO: 80) antisense strand | cttg |
| pTNA330 MdwA19 | TTCTCCGCCCAATCCGCTGTC (SEQ ID NO: 81) antisense strand | cttc |

TABLE 9

The oligo DNAs for the construction of pTNA296-307 and 324-330. Sequence which matches protospacers is shown in capital.

| Primer name | Sequence 5' → 3' | SEQ ID NO: |
|---|---|---|
| 296-C9-sense | taatttctactcttgtagatTTGGAGACCAGACCAGCGACAttttttttggctcttgggttc | 82 |
| 296-C9-anti | gaacccaagagccaaaaaaaTGTCGCTGGTCTGGTCTCCAatctacaagagtagaaatta | 83 |
| 297-C6-sense | taatttctactcttgtagatGAGACCAGACCAGCGACATCGtttttttttggctcttgggttc | 84 |
| 297-C6-anti | gaacccaagagccaaaaaaaCGATGTCGCTGGTCTGGTCTCatctacaagagtagaaatta | 85 |
| 298-C4_7-sense | taatttctactcttgtagatTTCCAGCAATGCTTCCATGCAttttttttggctcttgggttc | 86 |
| 298-C4_7-anti | gaacccaagagccaaaaaaaTGCATGGAAGCATTGCTGGAAatctacaagagtagaaatta | 87 |
| 299-C1_4-sense | taatttctactcttgtagatCAGCAATGCTTCCATGCAATTtttttttttggctcttgggttc | 88 |
| 299-C1_4-anti | gaacccaagagccaaaaaaaAATTGCATGGAAGCATTGCTGatctacaagagtagaaatta | 89 |
| 300-C13-sense | taatttctactcttgtagatCATGCAATTCGTCAAGAGATCtttttttttggctcttgggttc | 90 |
| 300-C13-anti | gaacccaagagccaaaaaaaGATCTCTTGACGAATTGCATGatctacaagagtagaaatta | 91 |

TABLE 9-continued

The oligo DNAs for the construction of pTNA296-307 and 324-330. Sequence which matches protospacers is shown in capital.

| Primer name | Sequence 5' → 3' | SEQ ID NO: |
|---|---|---|
| 301-C2_8-sense | taatttctactcttgtagatTCGAGTTCGAGAACTGGTGGAttttttttggctcttgggttc | 92 |
| 301-C2_8-anti | gaacccaagagccaaaaaaaTCCACCAGTTCTCGAACTCGAatctacaagagtagaaatta | 93 |
| 302-C21-sense | taatttctactcttgtagatCGATCTCGAGTAGCGCCACTCttttttttggctcttgggtc | 94 |
| 302-C21-anti | gaacccaagagccaaaaaaaGAGTGGCGCTACTCGAGATCGatctacaagagtagaaatta | 95 |
| 303-C16-sense | taatttctactcttgtagatATCCCTGGCGGTAACCGAGCAttttttttggctcttgggttc | 96 |
| 303-C16-anti | gaacccaagagccaaaaaaaTGCTCGGTTACCGCCAGGGATatctacaagagtagaaatta | 97 |
| 304-C11-sense | taatttctactcttgtagatAGGAAAGCGGCGAACTTTCGTttttttttggctcttgggtc | 98 |
| 304-C11-anti | gaacccaagagccaaaaaaaACGAAAGTTCGCCGCTTTCCTatctacaagagtagaaatta | 99 |
| 305-C18-sense | taatttctactcttgtagatACTGCATCGCAAGAAGCCAGGttttttttggctcttgggttc | 100 |
| 305-C18-anti | gaacccaagagccaaaaaaaCCTGGCTTCTTGCGATGCAGTatctacaagagtagaaatta | 101 |
| 306-C15-sense | taatttctactcttgtagatGCCCTGTCGTGGTACAAGTGGttttttttggctcttgggttc | 102 |
| 306-C15-anti | gaacccaagagccaaaaaaaCCACTTGTACCACGACAGGGCatctacaagagtagaaatta | 103 |
| 307-C14-sense | taatttctactcttgtagatTGGCCGGCGTGCTCAGTTGCTttttttttggctcttgggttc | 104 |
| 307-C14-anti | gaacccaagagccaaaaaaaAGCAACTGAGCACGCCGGCCAatctacaagagtagaaatta | 105 |
| 324-C12,13-sense | taatttctactcttgtagatTACAGGAGGTTCCAGAAGCTCttttttttggctcttgggtc | 106 |
| 324-C12,13-anti | gaacccaagagccaaaaaaaGAGCTTCTGGAACCTCCTGTAatctacaagagtagaaatta | 107 |
| 325-C2,3-sense | taatttctactcttgtagatTCCAGATCGAATTGCAAGCCAttttttttggctcttgggtc | 108 |
| 325-C2,3-anti | gaacccaagagccaaaaaaaTGGCTTGCAATTCGATCTGGAatctacaagagtagaaatta | 109 |
| 326-C17,18-sense | taatttctactcttgtagatCTGAAGCTGGCCGATTCCAGGttttttttggctcttgggttc | 110 |
| 326-C17,18-anti | gaacccaagagccaaaaaaaCCTGGAATCGGCCAGCTTCAGatctacaagagtagaaatta | 111 |
| 327-C15,16-sense | taatttctactcttgtagatACACCCAGAGCAGTCCAGTAAttttttttggctcttgggtc | 112 |
| 327-C15,16-anti | gaacccaagagccaaaaaaaTTACTGGACTGCTCTGGGTGTatctacaagagtagaaatta | 113 |

TABLE 9-continued

The oligo DNAs for the construction of pTNA296-307 and 324-330. Sequence which matches protospacers is shown in capital.

| Primer name | Sequence 5' → 3' | SEQ ID NO: |
|---|---|---|
| 328-C15, 16-2-sense | taatttctactcttgtagatGGGCCGAGACACTCCCAGTTAtttttttggctcttggg ttc | 114 |
| 328-C15, 16-2-anti | gaacccaagagccaaaaaaaTAACTGGGAGTGTCTCGGCCCatctacaa gagtagaaatta | 115 |
| 329-C6,7-sense | taatttctactcttgtagatAGATCCCACTTGTAGGCTGGGtttttttggctcttgggt tc | 116 |
| 329-C6, 7-anti | gaacccaagagccaaaaaaaCCCAGCCTACAAGTGGGATCTatctacaa gagtagaaatta | 117 |
| 330-C9, 10-sense | taatttctactcttgtagatTTCTCCGCCCAATCCGCTGTCtttttttggctcttgggt tc | 118 |
| 330-C9, 10-anti | gaacccaagagccaaaaaaaGACAGCGGATTGGGCGGAGAAatctacaa gagtagaaatta | 119 |

Next, as described in Example 2, the *A. niger* strain M1364 was transformed those plasmid DNAs. The Mad7d-AID and sgRNA expression cassette was site-specifically integrated into *A. niger* genome together with a hygromycin resistance gene. After isolation and spore maturation, the spore color of transformants was checked. Clones which showed the expected phenotype (white spore colour) were further analysed by target locus sequencing.

For MdwA8 target:
SEQ ID NO: 120:
Primer pks_seq_f5: 5' ttcttcaacatgtcgcctcgg 3'

SEQ ID NO: 121:
Primer pks_seq_r6: 5' gtgttacagttgccagtgg 3'

TABLE 10

Summary of PKS-targeting Mad7d-AID transformation

| DNA | Description | | Colony count | Isolation | White spore | Hit rate (%) |
|---|---|---|---|---|---|---|
| pTNA287 | no sgRNA | Mad7d-AID-UGI | >200 | 12 | 0 | 0% |
| pTNA296 | MdwA1 | Mad7d-AID-UGI | >200 | 12 | 0 | 0% |
| pTNA297 | MdwA2 | Mad7d-AID-UGI | >200 | 12 | 0 | 0% |
| pTNA298 | MdwA3 | Mad7d-AID-UGI | >200 | 12 | 0 | 0% |
| pTNA299 | MdwA4 | Mad7d-AID-UGI | >200 | 12 | 0 | 0% |
| pTNA300 | MdwA5 | Mad7d-AID-UGI | >200 | 12 | 0 | 0% |
| pTNA301 | MdwA6 | Mad7d-AID-UGI | >200 | 12 | 0 | 0% |
| pTNA302 | MdwA7 | Mad7d-AID-UGI | >200 | 12 | 0 | 0% |
| pTNA303 | MdwA8 | Mad7d-AID-UGI | >200 | 12 | 2 | 17% |
| pTNA304 | MdwA9 | Mad7d-AID-UGI | >200 | 12 | 0 | 0% |
| pTNA305 | MdwA10 | Mad7d-AID-UGI | >200 | 12 | 0 | 0% |
| pTNA306 | MdwA11 | Mad7d-AID-UGI | >200 | 12 | 0 | 0% |
| pTNA307 | MdwA12 | Mad7d-AID-UGI | >200 | 12 | 0 | 0% |
| pTNA324 | MdwA13 | Mad7d-AID-UGI | >200 | 12 | 1 | 8% |
| pTNA325 | MdwA14 | Mad7d-AID-UGI | >200 | 12 | 0 | 0% |
| pTNA326 | MdwA15 | Mad7d-AID-UGI | >200 | 12 | 0 | 0% |
| pTNA327 | MdwA16 | Mad7d-AID-UGI | >200 | 12 | 0 | 0% |
| pTNA328 | MdwA17 | Mad7d-AID-UGI | >200 | 12 | 0 | 0% |
| pTNA329 | MdwA18 | Mad7d-AID-UGI | >200 | 12 | 0 | 0% |
| pTNA330 | MdwA19 | Mad7d-AID-UGI | >200 | 12 | 0 | 0% |

As shown in Table 10, white spore mutants were obtained at 8 to 17% efficiency with effective sgRNAs. To see if the PKS gene of those white clones was mutated as expected, genome DNA was isolated and target locus was PCR-amplified. The primers are shown as follows:

-continued
For MdwA13 target:
SEQ ID NO: 122:
Primer pks_seq_f4: 5' ggtacttgatgaattcgtcg 3'

SEQ ID NO: 121:
Primer pks_seq_r6: 5' gtgttacagttgccagtgg 3'

The amplicon was then gel purified by QIAquick Gel Extraction Kit (Qiagen) and sequenced to determine the mutation patterns at targeted region. The black spored clone which was isolated from pTNA287 (no sgRNA) treatment showed no mutation at read genomic region, whereas mutants had mutations at C16, G17 (antisense) by pTNA303, and C13 by pTNA324 as expected (FIG. 8). This suggests that the primary target window of Mad7d-AID is C13 to C17, and that Mad7d-AID system can introduce C to T mutations in industrially important microbes such as *A. niger.*

Example 6. Investigation of Optimum Temperature for Mad7d-AID Activity

The PKS Inactivation by Mad7d-AID with Various Incubation Temperatures

The purpose of this experiment is to investigate the optimum temperature for Mad7d-AID activity. To this end, pTNA303 was transformed into M1364 host strain, and transformants were incubated at 25, 30, or 34° C. until spore maturation. The procedure described in Example 5 was followed in this experiment except for incubation temperature. The results are summarized in Table 11.

TABLE 11

Summary of pTNA303 transformation at various temperatures

| DNA | sgRNA | Incubation temperature | Colony count | Iso-lation | White spore | Hit rate (%) |
|---|---|---|---|---|---|---|
| pTNA303 | MdwA8 | 34° C. | 50 | 12 | 8 | 67% |
| pTNA303 | MdwA8 | 30° C. | 120 | 12 | 2 | 17% |
| pTNA303 | MdwA8 | 25° C. | 220 | 12 | 0 | 0% |

As shown in Table 11, white spore mutants were obtained at 0 to 67% efficiency with a clear trend that higher temperature gives better efficiency. To see if the PKS gene of those white clones was mutated as expected, genome DNA was isolated and target locus was PCR-amplified. The primers are shown as follows:

```
SEQ ID NO: 120:
Primer pks_seq_f5: 5' ttcttcaacatgtcgcctcgg 3'

SEQ ID NO: 121:
Primer pks_seq_r6: 5' gtgttacagttgccagtgg 3'
```

The amplicon was then gel purified by QIAquick Gel Extraction Kit (Qiagen) and sent to commercial sequence service to determine the mutation patterns at targeted region. Interestingly, the white spore mutants had C to T or G to A mutations across sgRNA targeted sequences, as shown in FIG. 9. G to A mutations may be introduced by antisense C to T mutations.

Next, to see if this efficiency improvement is general to other sgRNAs or not, we tested 13 sgRNAs for 34° C. incubation, as listed in Table 12.

TABLE 12

Summary of re-visiting PKS-targeting sgRNAs for 34° C. incubation

| DNA | | Description | Colony count | Isolation | White spore | Hit rate (%) |
|---|---|---|---|---|---|---|
| pTNA287 | no sgRNA | Mad7d-AID-UGI | 50-100 | 12 | 0 | 0% |
| pTNA296 | MdwA1 | Mad7d-AID-UGI | 50-100 | 12 | 1 | 8% |
| pTNA297 | MdwA2 | Mad7d-AID-UGI | 50-100 | 12 | 7 | 58% |
| pTNA298 | MdwA3 | Mad7d-AID-UGI | 50-100 | 12 | 0 | 0% |
| pTNA299 | MdwA4 | Mad7d-AID-UGI | 50-100 | 12 | 1 | 8% |
| pTNA300 | MdwA5 | Mad7d-AID-UGI | 50-100 | 12 | 1 | 8% |
| pTNA301 | MdwA6 | Mad7d-AID-UGI | 50-100 | 12 | 1 | 8% |
| pTNA302 | MdwA7 | Mad7d-AID-UGI | 50-100 | 12 | 0 | 0% |
| pTNA303 | MdwA8 | Mad7d-AID-UGI | 50-100 | 12 | 7 | 58% |
| pTNA304 | MdwA9 | Mad7d-AID-UGI | 50-100 | 12 | 0 | 0% |
| pTNA324 | MdwA13 | Mad7d-AID-UGI | 50-100 | 12 | 2 | 17% |
| pTNA325 | MdwA14 | Mad7d-AID-UGI | 50-100 | 12 | 3 | 25% |
| pTNA326 | MdwA15 | Mad7d-AID-UGI | 50-100 | 12 | 0 | 0% |
| pTNA327 | MdwA16 | Mad7d-AID-UGI | 50-100 | 12 | 0 | 0% |

As shown in Table 12, white spore mutants were obtained at 0 to 58% efficiency. When compared to Table 10, editing efficiency was clearly improved with some of sgRNAs like MdwA2, MdwA8, MdwA13, and MdwA14. To see if the PKS gene of those white clones was mutated as expected, genome DNA was isolated and target locus was PCR-amplified. The primers are shown as follows:

```
For MdwA1-6:
SEQ ID NO: 123:
Primer MS-test-wA3: 5' tgaattcaactctttacaatcg 3'

SEQ ID NO: 41:
Primer pks_seq_r3: 5' cttgtaattcttggaaatgcagg 3'

For MdwA8-14:
SEQ ID NO: 122:
Primer pks_seq_f4: 5' ggtacttgatgaattcgtcg 3'

SEQ ID NO: 121:
Primer pks_seq_r6: 5' gtgttacagttgccagtgg 3'
```

The amplicon was then gel purified by QIAquick Gel Extraction Kit (Qiagen) sequenced to determine the mutation patterns at targeted region. Some representative genotypes are also shown in FIG. 9.

These data suggest that Mad7d-AID provides at least two beneficial effects:

1) Mad7d-AID may be able to target both sense and antisense strands simultaneously. In general, sgRNA should form tight heteroduplex with targeting strand of the genome DNA due to its complementarity, which makes non-targeting strand free and targetable by AID, vice versa, targeting strand cannot be targeted because of duplex formation. As described in Example 3, dCas9-AID introduced mutations to either sense or antisense strand dependent on sgRNA targeting strand. But, as shown in FIG. 9, pTNA303 transformants had C to T and/or G to A mutations at the protospacer region despite targeting only sense strand by MdwA8 sgRNA. Although the mechanism is not yet completely clear, this effect seems to be mediated by Mad7d-AID deamination of both strands.

2) Mad7d-AID may be able to target cytidines at any position of protospacer region. as shown in FIG. 9, pTNA303 transformants had C to T and/or G to A mutations across the protospacer region (21 bp-long), which is well distinct from dCad9-AID whose target range is limited to 4 bp window within protospacer (20 bp-long), as described in Example 3. This is clearly beneficial when making mutant library, since Mad7d-AID creates larger variety of mutations from a single sgRNA than dCas9-AID.

Taken together, the Mad7d-AID system has beneficial and hitherto undescribed features especially when creating mutant library for screening purposes, which is key for development of industrially important strains.

PART B: *Aspergillus oryzae.*

Example 7. Construction of pAT3530 Mad7d-AID-UGI Expression Plasmid for *A. Oryzae*

Figure 10:
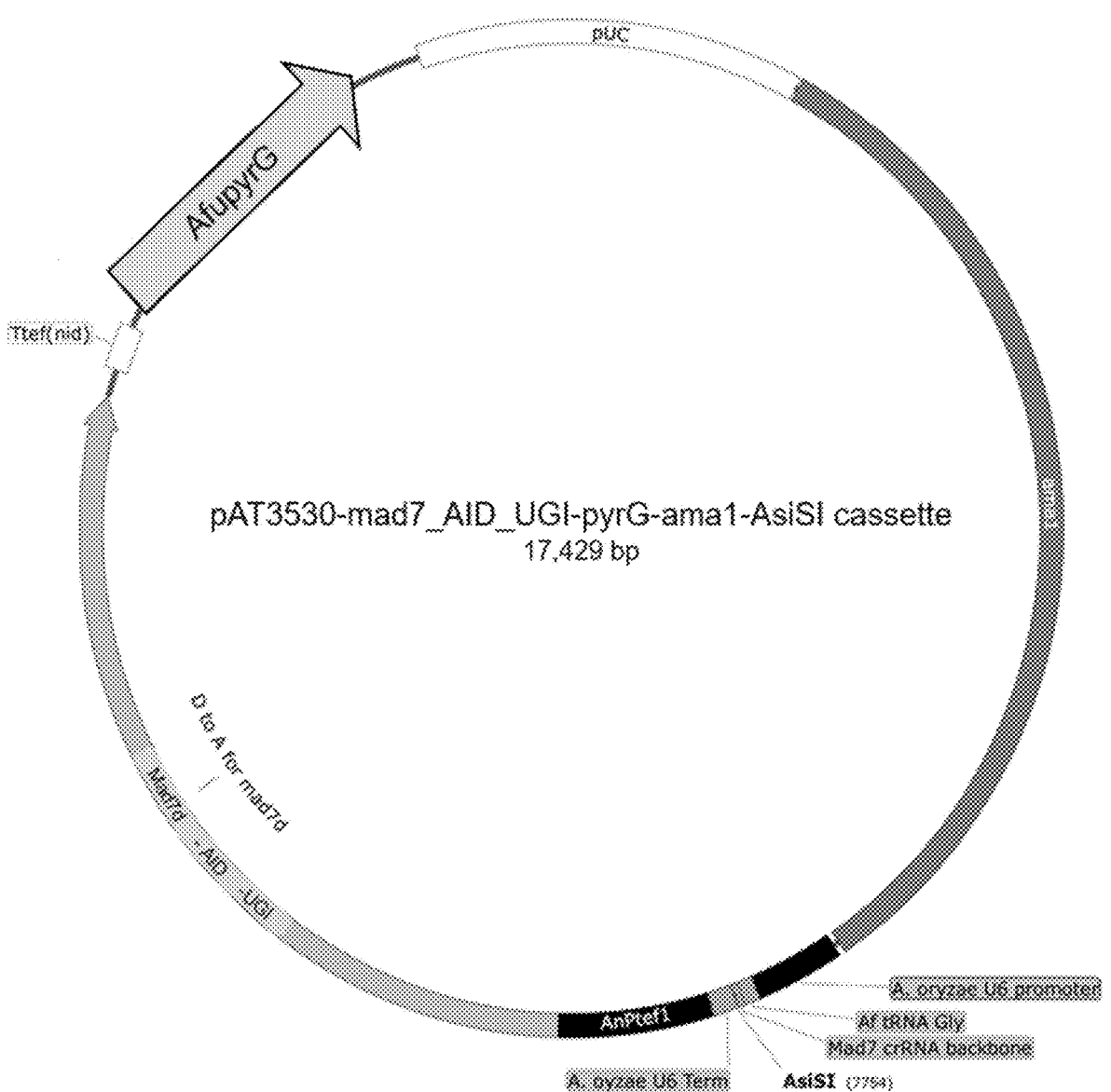
FIG. 10 shows a schematic drawing of the plasmid pAT3530.

Plasmid pAT3530 (FIG. 10, SEQ ID NO: 133) is a vector ready for cloning of protospacer sequences into the single AsiSI restriction site.

Plasmid pAT3530 contains the following elements:

| Position in SEQ ID NO: 133 | Element |
|---|---|
| 15.845-1.343 | pUC plasmid |
| 1.359-1.358 | Linker sequence |
| 1.359-7.079 | Ama1 sequence for replication in *A. oryzae* |
| 7.080-7.115 | Linker sequence |
| 7.116-7.623 | *A. oryzae* U6 promoter |
| 7.624-7.714 | *A. fumigatus* tRNA (Gly) |
| 7.715-7.749 | Mad7 crRNA |
| 7.750-7.757 | AsiSl restriction site (used for cloning of protoscers) |
| 7.758-7.895 | *A. oryzae* U6 terminator |
| 7.896-7.903 | Linker sequence |
| 7.904-8.789 | *A. nidulans* Tef1 promoter |
| 8.790-13.817 | Mad7d-AID-UGI gene (taken from pTNA287 in Example 4) |
| 13.818-13.823 | Linker sequence |
| 13.824-14.228 | *A. nidulans* Tef1 terminator |
| 14.229-14.405 | Linker sequence |
| 14.406-15.844 | *A. fumigatus* pyrG gene |

The *A. oryzae* target wA gene sequence can be found in the Sequence Listing as SEQ ID NO: 134.

Example 8. Transformation of Mad7d-AID-UGI Plasmids for the wA Gene Inactivation in *A. oryzae* Strain JaL355

The purpose of this experiment is to demonstrate that Mad7d-AID-UGI can introduce target specific C to T conversion in the *A. oryzae* genome, and to assess the efficiency of mutational effect, as shown in Example 5 for the case of Mad7d-AID. To our knowledge, nobody has reported the activity of Mad7d-linked deaminase, so we first aimed to clarify the target position of cytidine as a substrate for AID. To this end, six target sequences with varied target positions on PKS locus were designed (Table 13), each of which would form premature stop codon when C to T mutation is introduced by Mad7d-AID. Target position of C is numbered from PAM proximal end. These protospacer sequences (Table 14) were cloned into AsiSI digested site of pAT3530, resulting in construction of pAT3532-pAT3537.

TABLE 13

Protospacer sequences for disruption of wA gene in *A. oryzae*. Potential target "C" is underlined.

| Plasmid (target number) | Protospacer (5' → 3'), potential target C is underlined | Protospacer adjacent motif (PAM) sequence (5' → 3') |
|---|---|---|
| pAT3532 | ACGCTTTGCGCCAAGAGATC (SEQ ID NO: 135) sense strand | TTTC |
| pAT3533 | CGCCAAGAGATCGCGAGGCT (SEQ ID NO: 136) sense strand | TTTC |
| pAT3534 | AAGCACTGCGACACAAAGCT (SEQ ID NO: 137) sense strand | TTTC |
| pAT3535 | CATTCTGCCCAAGTTACTCC (SEQ ID NO: 138) sense strand | TTTC |
| pAT3536 | CGGAAGCCGGTCTGTTCCAA (SEQ ID NO: 139) antisense strand | TTTC |
| pAT3537 | TACCTAGTGAACCCCAATAG (SEQ ID NO: 140) antisense strand | TTTA |

TABLE 14

The oligo DNAs for the construction of pAT3532-3537. Sequence which matches protospacers is shown in capital.

| Primer name | Sequence 5' → 3' | SEQ ID NO: |
|---|---|---|
| oAT3941 | aatttctactcttgtagatACGCTTTGCGCCAAGAGATCtttttttttttgagcatttatcagc | 141 |
| oAT3942 | aatttctactcttgtagatCGCCAAGAGATCGCGAGGCTtttttttttttgagcattttatcagc | 142 |

TABLE 14-continued

The oligo DNAs for the construction of pAT3532-3537. Sequence which matches
protospacers is shown in capital.

| Primer name | Sequence 5' → 3' | SEQ ID NO: |
|---|---|---|
| oAT3943 | aatttctactcttgtagatAAGCACTGCGACACAAAGCTtttttttttttgagcatttat cagc | 143 |
| oAT3944 | aatttctactcttgtagatCATTCTGCCCAAGTTACTCCttttttttttttgagcatttatc agc | 144 |
| oAT3945 | aatttctactcttgtagatCGGAAGCCGGTCTGTTCCAttttttttttttgagcatttat cagc | 145 |
| oAT3946 | aatttctactcttgtagatTACCTAGTGAACCCCAATAGttttttttttttgagcatttatc agc | 146 |

Next, the plasmids pAT3530 and pAT3532-pAT3537, was transformed into *A. oryzae* strain JaL355 as described in methods for *A. oryzae* transformation. The plasmids containing the Mad7d-AID-UGI and sgRNA expression cassettes was maintained as replicative plasmid by the pyrG gene on the plasmids. Thereafter all colonies having white spore colour and a corresponding number of green spore colour colonies from each transformation was spore isolated on non-selective plates (containing uridine) so the replicative plasmids were lost. All re-isolated transformants were further analysed by target locus sequencing.

TABLE 15

Summary of wA-targeting Mad7d-AID-
UGI *A. oryzae* transformation

| DNA | | Description | Colony count | White spore isolated | Green spore isolated |
|---|---|---|---|---|---|
| pAT3530 | no sgRNA | Mad7d-AID-UGI | >200 | 0 | 0 |
| pAT3532 | sgRNA | Mad7d-AID-UGI | >200 | 1 | 1 |
| pAT3533 | sgRNA | Mad7d-AID-UGI | >200 | 3 | 3 |
| pAT3534 | sgRNA | Mad7d-AID-UGI | >200 | 1 | 1 |
| pAT3535 | sgRNA | Mad7d-AID-UGI | >200 | 1 | 1 |
| pAT3536 | sgRNA | Mad7d-AID-UGI | >200 | 5 | 5 |
| pAT3537 | sgRNA | Mad7d-AID-UGI | >200 | 3 | 3 |

As shown in Table 15, white spore mutants were obtained with effective sgRNAs. To see if the PKS gene of those white clones was mutated as expected, genome DNA was isolated and target locus was PCR-amplified as following for the 6 targets:

For pAT3532 and pAT3533 target: PCR amplification was done with oAT3912: 5' TCCAAGTTCTTTGCATGC 3' (SEQ ID NO: 147) and oAT3613: 5' TATCTCAGGT-TAGGCTCG 3' (SEQ ID NO: 148) resulting in an amplicon on 500 bp.

For pAT3534 target: PCR amplification was done with oJaL188: 5' CCATGGTCCTTAC-CATGC 3' (SEQ ID NO: 149) and oAT3616 5' TATTTATCTCCCGATAGTCATC 3' (SEQ ID NO: 150) resulting in an amplicon on 812 bp.

For pAT3535 amplification target: PCR was done with oAT919: 5' CTGGCTGTCAAGGCTTCC 3' (SEQ ID NO: 151) and oAT1040: 5' TTTGTGGTGCAGCTTGAAT 3' (SEQ ID NO: 152) resulting in an amplicon on 733 bp.

For pAT3536 target: PCR amplification was done with oJaL188 and oAT967: 5' GCGAACACGAACCCTAC 3' (SEQ ID NO: 153) resulting in an amplicon on 2033 bp.

For pAT3537 target: PCR amplification was done with oJaL188 and oAT3618: 5' TCAAAGCAGCAAACTCC 3' (SEQ ID NO: 154) resulting in an amplicon on 2312 bp.

The amplicon was then gel purified by QIAquick Gel Extraction Kit (Qiagen) and sequenced using the primers for the PCR amplification to determine the mutation patterns at targeted region. All isolated green spore colonies showed no mutation at the target region or any of the sequenced amplicon. For white spore colonies from pAT3532, pAT3533, pAT3534, and pAT3535, none of them had mutations at the target site or in the rest of the amplicon. With respect to white spore colonies from pAT3536, one colony had the expected C17 mutation leading to a stop codon, and another colony had a silent mutation at C8 indicating that another mutation had happened elsewhere in the wA gene. With respect to white spore colonies from pAT3537, two colonies had the same expected C15 mutation leading to a stop codon.

The examples generated in *A. oryzae* supports the findings in *A. niger* and suggests that the primary target window of Mad7d-AID-UGI is C8 to C17, and that the Mad7d-AID-UGI system also can introduce C to T mutations in *A. oryzae*.

PART C: *Bacillus licheniformis*

Example 9: Construction of a Plasmid for
Expression of MAD7d-AID-UGI in *Bacillus
licheniformis*

Plasmid pMDT452 was constructed for expression of MAD7d-AID-UGI in *Bacillus*. Plasmid pMDT452 comprises the MAD7d-AID-UGI coding sequence flanked upstream by promoter PamyL4199 (U.S. Pat. No. 6,100, 063) and downstream by the aprH transcription terminator of *Bacillus clausii* in mobilizable plasmid vector pBC16 (Bernhard et al. (1978): Bacteriocin and Antibiotic Resistance Plasmids in *Bacillus cereus* and *Bacillus subtilis*. *J. Bacteriol*. 133, 897-903). Plasmid pMDT452 was introduced into conjugation donor strain *Bacillus subtilis* PP3724 by transformation, resulting in strain PP3724/pMDT452.

Figure 11:
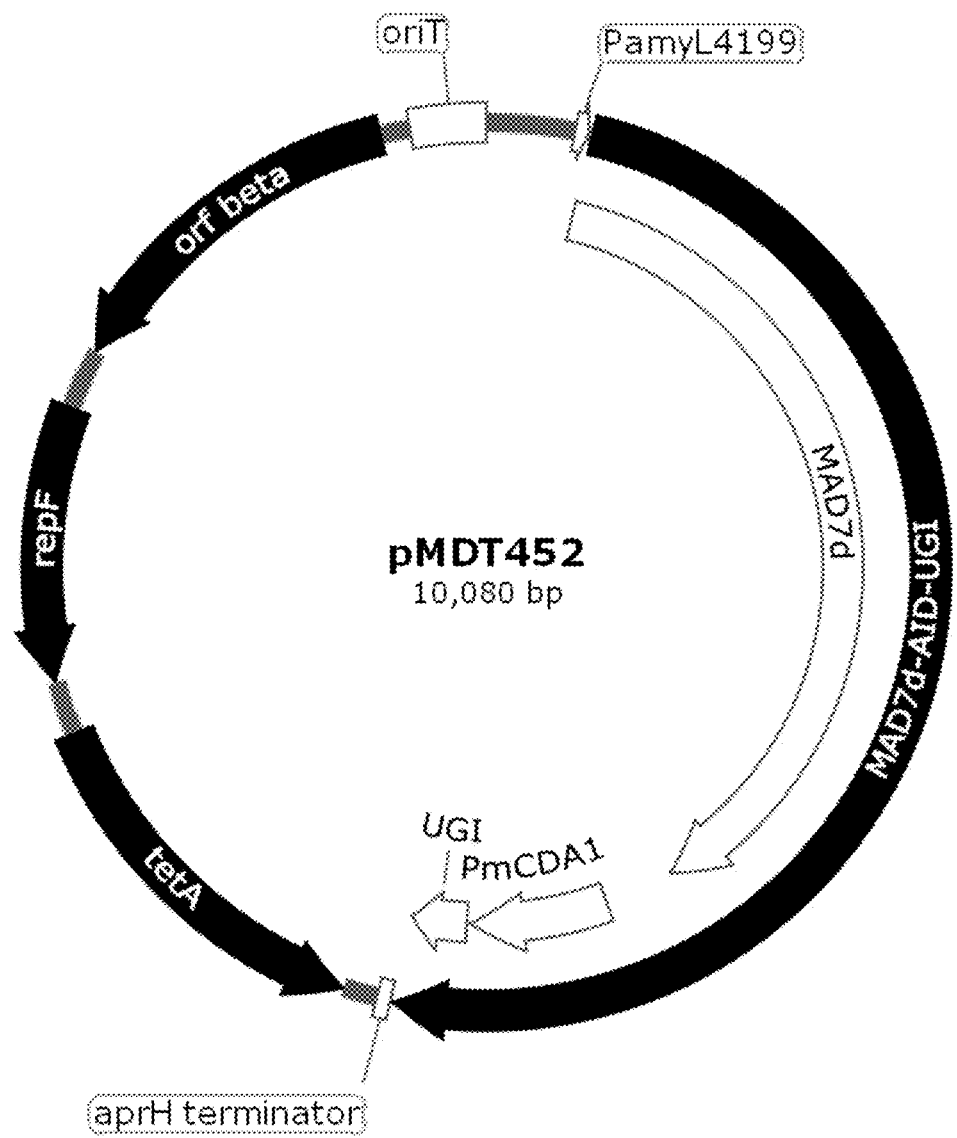
FIG. 11 shows a schematic drawing of the plasmid pMDT452.

A map of pMDT452 is shown in FIG. 11, the DNA sequence of the MAD7d-AID-UGI coding region is shown in SEQ ID NO: 158, and the corresponding amino acid sequence is shown in SEQ ID NO: 159.

Example 10. Construction of Plasmids for
Expression of sgRNAs Targeting a DsRED Gene in
*Bacillus licheniformis*

Plasmids pMDT454 and pMDT455 were constructed for expression of sgRNAs targeting the DsRED gene of *Bacillus*

*licheniformis* strain MDT545. Each plasmid comprises an sgRNA cassette with the sgRNA expressed from the PamyQsc promoter (Pr*short "consensus" amyQ*; U.S. Pat. No. 6,255,076) in a plasmid vector based on temperature sensitive pAMβ1-derived plasmid pWT (Bidnenko et al. (1998): In vivo relations between pAMβ1-encoded type I topoisomerase and plasmid replication. *Mol. Microbiol.* 28, 1005-1016) and comprising the origin of transfer oriT of plasmid pUB110 (Selinger, L. B., McGregor, N. F., Khachatourians, G. G. and Hynes, M. F. (1990). Mobilization of closely related plasmids pUB110 and pBC16 by *Bacillus* plasmid pXO503 requires trans-acting open reading frame β. *J. Bacteriol.*, 172, 3290-3297) for mobilization by conjugation. Two protospacers with different target positions within the DsRED coding sequence were designed (Table 16), each of which could form a premature stop codon when a C to T mutation is introduced by MAD7d-AID. Plasmids pMDT454 and pMDT455 were introduced into conjugation donor strain *Bacillus subtilis* PP3724 by transformation, resulting in strains PP3724/pMDT454 and PP3724/pMDT455 respectively.

Figure 12:
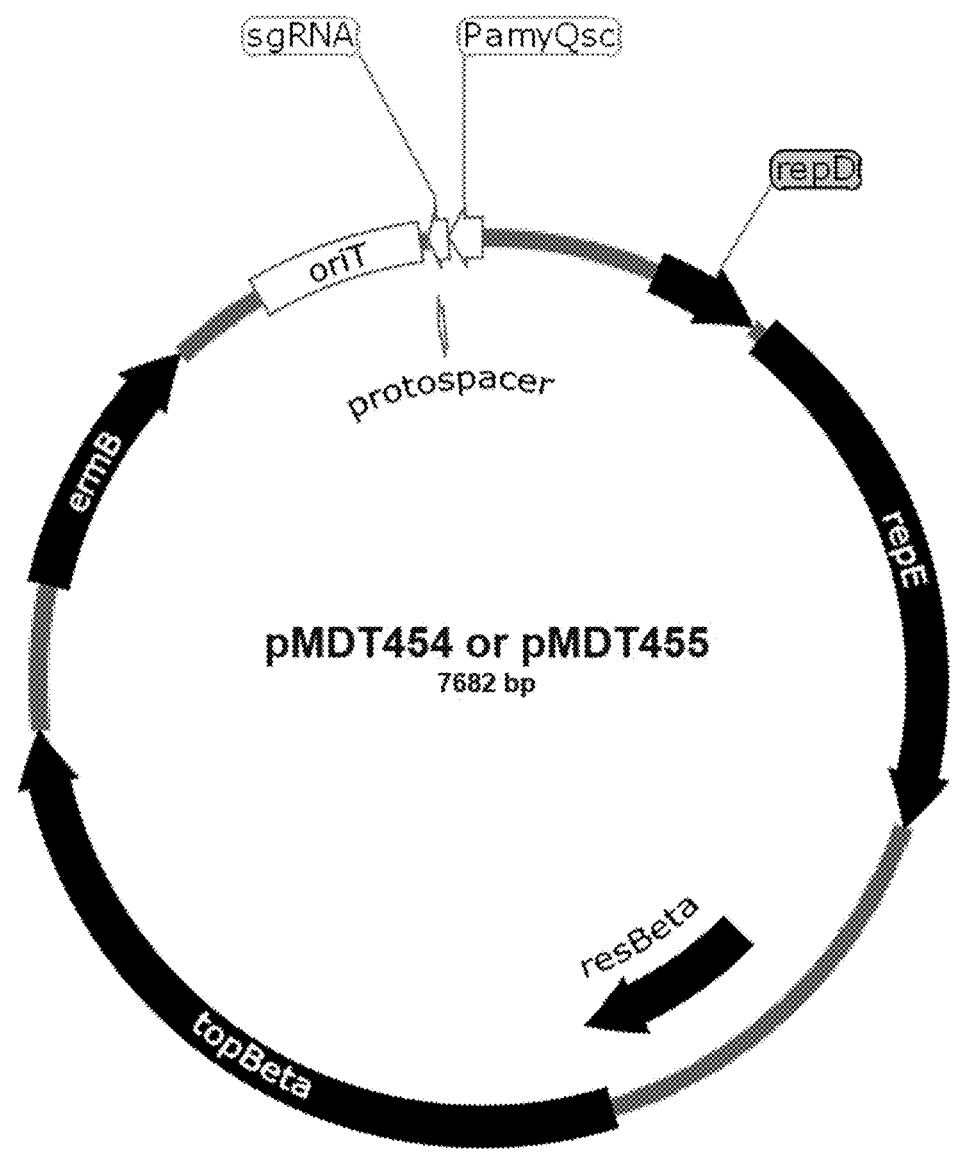
FIG. 12 shows a schematic drawing of the plasmid pMDT454/pMDT455.

A map representing the structure of sgRNA plasmids pMDT454 and pMDT455 is shown in FIG. 12. As an example of the sgRNA plasmids, the DNA sequence of pMDT454 is shown in SEQ ID NO: 160.

TABLE 16

| Protospacer sequences for disruption of DsRED gene. Potential target C's are underlined. | | |
|---|---|---|
| Plasmid (proto-spacer number) | Protospacer (5' → 3'), potential target C's are underlined | Protospacer adjacent motif (PAM) sequence (5' → 3') |
| pMDT454 (PS1-AID) | AGTCCGCAGTTTCAGTATGGG (SEQ ID NO: 161) sense strand | CTTA |
| pMDT455 (PS2-AID) | AGATGTCCCAAGCAAACGGCA (SEQ ID NO: 162) antisense strand | CTTA |

Example 11. Introduction of MAD7d-AID-UGI Plasmid and sgRNA Plasmids for DsRED Gene Inactivation into *Bacillus licheniformis*

Figure 13:
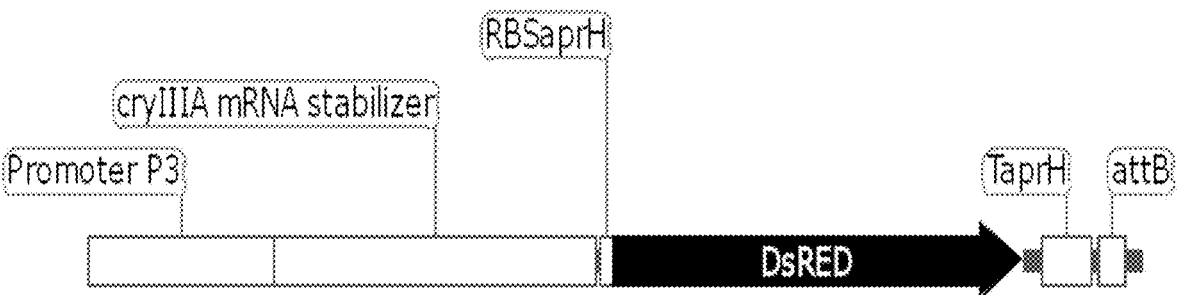
FIG. 13 shows a schematic drawing of the DsRed expression cassette of strain MDT545.

*Bacillus licheniformis* MDT545 is a derivative of *Bacillus licheniformis* SJ1904 comprising a DsRED expression cassette inserted at the amyL locus of the chromosome and a GFP expression cassette inserted at the xylA locus of the chromosome. A map of the inserted DsRED expression cassette is shown in FIG. 13, and the corresponding DNA sequence is shown in SEQ ID NO: 163; the DNA sequence of the DsRED coding region is shown in SEQ ID NO: 164.

Using conjugation donor strain PP3724/pMDT452, plasmid pMDT452 was introduced by conjugation into *Bacillus licheniformis* MDT545, selecting for resistance to erythromycin at 34° C. The resulting strain was designated MDT545/pMDT452.

Using conjugation donor strains PP3724/pMDT454 and PP3724/pMDT455, sgRNA plasmids pMDT454 and pMDT455 were respectively introduced by conjugation into *Bacillus* licheniformis MDT545/pMDT452, selecting for resistance to both erythromycin and tetracycline at 34° C.

Colonies of strain MDT545 appear red, due to expression of DsRED. Disruption of the DsRED results in a strain that appears green, due to expression of GFP. However, binding of MAD7d to the DsRED gene can also result in gene silencing, resulting in reduction of DsRED expression and a green appearance of colonies. Colonies that appear green due to silencing of the DsRED gene will appear red again if either of the plasmids is lost, whereas colonies that appear green due to mutation of the DsRED gene will remain green even if one of the plasmids is lost. Therefore, in order to distinguish colonies in which the DsRED gene has been mutated from those in which the DsRED gene has merely been silenced, transconjugants must be re-moved from antibiotic selection in order to allow one or both of the plasmids to be lost.

After 2 days' incubation at 34° C., the selective plates from the sgRNA plasmid conjugations were flooded with 2 ml LB broth, and a sterile spreader was used to suspend transconjugant colonies into the broth. Fresh LB broth supplemented with 2 µg/ml erythromycin and 15 µg/ml tetracycline was then inoculated with the resulting cell suspension from each conjugation and incubated at 34° C. with shaking at 250 rpm. After overnight incubation, fresh LB broth without antibiotic was inoculated with each culture and incubated at 50° C. with shaking at 250 rpm to promote loss of the temperature-sensitive sgRNA plasmids.

After overnight incubation, dilutions of the LB cultures were plated on LB agar and incubated at 34° C. Green colonies were picked, and the DsRED coding region was amplified by PCR from 16 green colonies per conjugation. The PCRs were treated with the ExoSAP-IT PCR Product Cleanup kit (Applied Biosystems) and sequenced to determine the mutation patterns at the targeted region. As can be seen in Table 17, sequencing results indicated that one of the expected nonsense mutations had occurred in the targeted protospacer region of each green strain, which confirms that the nucleobase editing complex of the invention also works efficiently in bacterial cells. The examples generated in *B. licheniformis* supports the findings in *A. oryzae* and *A. niger* and suggests that the Mad7d-AID-UGI system also can introduce C to T mutations in *B. licheniformis*.

TABLE 17

| Summary of results of dsRED-targeting MAD7d-AID-UGI *B. licheniformis* conjugations | | | | |
|---|---|---|---|---|
| sgRNA plasmid | Protospacer | Approximate frequency of green colonies | Expected mutation(s) | Mutations observed in green transconjugants |
| pMDT454 | PS1-AID | 0.5% | C190T (Q64*) or C196T (Q66*) | C190T in 15 of 16; C196T in 1 of 16; |
| pMDT455 | PS2-AID | 1% | G173A or G174A (W58*) | G173A in 6 of 16; G174A in 10 of 16; |

LIST OF EMBODIMENTS

1. A nucleobase editing complex comprising, consisting essentially of, or consisting of:
   a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and
   b) a nucleobase editing domain.
2. The nucleobase editing complex according to embodiment 1, wherein the catalytically inactive RNA-guided endonuclease comprises an alteration of an amino acid at a position corresponding to position 877 of SEQ ID NO: 126; preferably the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val; most preferably the amino acid at a position corresponding to position 877 of SEQ ID NO: 126 is substituted with Ala.
3. The nucleobase editing domain according to any of the preceding embodiments, wherein the catalytically inactive RNA-guided endonuclease comprises, consists essentially of, or consists of SEQ ID NO: 126 or SEQ ID NO: 155.
4. The nucleobase editing complex according to any of the preceding embodiments, wherein the nucleobase editing domain is a cytosine base editor (CBE).
5. The nucleobase editing complex according to embodiment 4, wherein the nucleobase editing domain is a cytosine base editor of the APOBEC1/AID family; preferably the nucleobase editing domain is APOBEC1 or CDA1, in particular PmCDA1.
6. The nucleobase editing complex according to embodiment 4, wherein the nucleobase editing domain comprises or consists of a polypeptide having a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.
7. The nucleobase editing complex according to any of embodiments 4-6, which further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.
8. The nucleobase editing complex according to any of embodiments 1-2, wherein the nucleobase editing domain is an adenine base editor (ABE).; preferably the nucleobase editing domain is selected from the group consisting of TadA, TadA*, TadA homodimer, and TadA-TadA* heterodimer; most preferably the nucleobase editing domain is a TadA-TadA* heterodimer.
9. The nucleobase editing complex according to any of the preceding embodiments, wherein the catalytically inactive RNA-guided endonuclease and the nucleobase editing domain are fused end-to-end or connected via a linker polypeptide; preferably the catalytically inactive RNA-guided endonuclease, the linker polypeptide, and the nucle-obase editing domain are encoded in frame and are expressed as a single polypeptide.
10. The nucleobase editing complex according to embodiment 9, wherein the linker polypeptide comprises at least 10 amino acid residues; preferably the linker polypeptide comprises at least 50 amino acid residues; most preferably the linker polypeptide comprises at least 100 amino acid residues.
11. The nucleobase editing complex according to any of embodiments 10-11, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.
12. A polynucleotide encoding a nucleobase editing complex comprising, consisting essentially of, or consisting of:
   a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and
   b) a nucleobase editing domain.
13. The polynucleotide according to embodiment 12, wherein the catalytically inactive RNA-guided endonuclease and the nucleobase editing domain are encoded in frame and are expressed as a single polypeptide.
14. The polynucleotide of according to any of embodiments 12-13, which further comprises a third polynucleotide encoding a linker polypeptide, wherein the third polynucleotide is positioned between the 3' end of the first polynucleotide and the 5' end of the second polynucleotide, and wherein the first polynucleotide, the second polypeptide, and the third polypeptide are encoded in frame and expressed as a single polypeptide.
15. The polynucleotide according to any of embodiments 12-14, wherein the catalytically inactive RNA-guided endonuclease comprises an alteration of an amino acid at a position corresponding to position 877 of SEQ ID NO: 126; preferably the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val; most preferably the amino acid at a position corresponding to position 877 of SEQ ID NO: 126 is substituted with Ala.
16. The polynucleotide according to any of embodiments 12-15, wherein the catalytically inactive RNA-guided endonuclease comprises, consists essentially of, or consists of SEQ ID NO: 126 or SEQ ID NO: 155.
17. The polynucleotide according to any of embodiments 12-16, wherein the nucleobase editing domain is a cytosine base editor (CBE).
18. The polynucleotide according to embodiment 17, wherein the nucleobase editing domain is a cytosine base editor of the APOBEC1/AID family; preferably the nucleobase editing domain is APOBEC1 or CDA1, in particular PmCDA1.
19. The polynucleotide according to embodiment 17, wherein the nucleobase editing domain comprises or consists of a polypeptide having a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.

20. The polynucleotide according to any of embodiment 12-19, which further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.

21. The polynucleotide according to any of embodiments 12-16, wherein the nucleobase editing domain is an adenine base editor (ABE).; preferably the nucleobase editing domain is selected from the group consisting of TadA, TadA*, TadA homodimer, and TadA-TadA* heterodimer; most preferably the nucleobase editing domain is a TadA-TadA* heterodimer.

22. The polynucleotide according to any of embodiments 14-21, wherein the linker polypeptide comprises at least 10 amino acid residues; preferably the linker polypeptide comprises at least 50 amino acid residues; most preferably the linker polypeptide comprises at least 100 amino acid residues.

23. The polynucleotide according to any of embodiments 14-22, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.

24. A nucleic acid construct comprising a polynucleotide encoding a nucleobase editing complex comprising, consisting essentially of, or consisting of:
   a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and
   b) a nucleobase editing domain.

25. The nucleic acid construct according to embodiment 24, wherein the catalytically inactive RNA-guided endonuclease and the nucleobase editing domain are encoded in frame and are expressed as a single polypeptide.

26. The nucleic acid construct according to any of embodiments 24-25, which further comprises a third polynucleotide encoding a linker polypeptide, wherein the third polynucleotide is positioned between the 3' end of the first polynucleotide and the 5' end of the second polynucleotide, and wherein the first polynucleotide, the second polypeptide, and the third polypeptide are encoded in frame and expressed as a single polypeptide.

27. The nucleic acid construct according to any of embodiments 24-26, wherein the catalytically inactive RNA-guided endonuclease comprises an alteration of an amino acid at a position corresponding to position 877 of SEQ ID NO: 126; preferably the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val; most preferably the amino acid at a position corresponding to position 877 of SEQ ID NO: 126 is substituted with Ala.

28. The nucleic acid construct according to any of embodiments 24-27, wherein the catalytically inactive RNA-guided endonuclease comprises, consists essentially of, or consists of SEQ ID NO: 126 or SEQ ID NO: 155.

29. The nucleic acid construct according to any of embodiments 24-28, wherein the nucleobase editing domain is a cytosine base editor (CBE).

30. The nucleic acid construct according to embodiment 29, wherein the nucleobase editing domain is a cytosine base editor of the APOBEC1/AID family; preferably the nucleobase editing domain is APOBEC1 or CDA1, in particular PmCDA1.

31. The nucleic acid construct according to embodiment 29-30, wherein the nucleobase editing domain comprises or consists of a polypeptide having a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.

32. The nucleic acid construct according to any of embodiment 24-31, which further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.

33. The nucleic acid construct according to any of embodiments 24-28, wherein the nucleobase editing domain is an adenine base editor (ABE); preferably the nucleobase editing domain is selected from the group consisting of TadA, TadA*, TadA homodimer, and TadA-TadA* heterodimer; most preferably the nucleobase editing domain is a TadA-TadA* heterodimer.

34. The nucleic acid construct according to any of embodiments 26-33, wherein the linker polypeptide comprises at least 10 amino acid residues; preferably the linker polypeptide comprises at least 50 amino acid residues; most preferably the linker polypeptide comprises at least 100 amino acid residues.

35. The nucleic acid construct according to any of embodiments 26-34, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.

36. An expression vector comprising:
   I) a polynucleotide encoding a nucleobase editing complex comprising, consisting essentially of, or consisting of:
      a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and
      b) a nucleobase editing domain; OR
   II) a nucleic acid construct comprising a polynucleotide encoding a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain.

37. The expression vector according to embodiment 36, wherein the catalytically inactive RNA-guided endonuclease and the nucleobase editing domain are encoded in frame and are expressed as a single polypeptide.

38. The expression vector according to any of embodiments 36-37, which further comprises a third polynucleotide encoding a linker polypeptide, wherein the third polynucleotide is positioned between the 3' end of the first polynucleotide and the 5' end of the second polynucleotide, and wherein the first polynucleotide, the second polypeptide, and the third polypeptide are encoded in frame and expressed as a single polypeptide.

39. The expression vector according to any of embodiments 36-38, wherein the catalytically inactive RNA-guided endonuclease comprises an alteration of an amino acid at a position corresponding to position 877 of SEQ ID NO: 126; preferably the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val; most preferably the amino acid at a position corresponding to position 877 of SEQ ID NO: 126 is substituted with Ala.

40. The expression vector according to any of embodiments 36-39, wherein the catalytically inactive RNA-guided endonuclease comprises, consists essentially of, or consists of SEQ ID NO: 126 or SEQ ID NO: 155.

41. The expression vector according to any of embodiments 36-40, wherein the nucleobase editing domain is a cytosine base editor (CBE).

42. The expression vector according to embodiment 41, wherein the nucleobase editing domain is a cytosine base editor of the APOBEC1/AID family; preferably the nucleobase editing domain is APOBEC1 or CDA1, in particular PmCDA1.

43. The expression vector according to embodiment 41-42, wherein the nucleobase editing domain comprises or consists of a polypeptide having a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.

44. The expression vector according to any of embodiment 36-43, which further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.

45. The expression vector according to any of embodiments 36-40, wherein the nucleobase editing domain is an adenine base editor (ABE); preferably the nucleobase editing domain is selected from the group consisting of TadA, TadA*, TadA homodimer, and TadA-TadA* heterodimer; most preferably the nucleobase editing domain is a TadA-TadA* heterodimer.

46. The expression vector according to any of embodiments 38-45, wherein the linker polypeptide comprises at least 10 amino acid residues; preferably the linker polypeptide comprises at least 50 amino acid residues; most preferably the linker polypeptide comprises at least 100 amino acid residues.

47. The expression vector according to any of embodiments 38-46, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.

48. A host cell comprising:

I) a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain;

II) a polynucleotide encoding a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain;

III) a nucleic acid construct comprising a polynucleotide encoding a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain; AND/OR IV) an expression vector comprising:

A) a polynucleotide encoding a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and b) a nucleobase editing domain; OR B) a nucleic acid construct comprising a polynucleotide encoding a nucleobase editing complex comprising, consisting essentially of, or consisting of:

a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID
NO: 126 or SEQ ID NO: 155; and b) a nucleobase editing domain.

49. The host cell of embodiment 48, which is a prokaryotic
or eukaryotic host cell.

50. The host cell according to any of embodiments 48-49,
which is a bacterial host cell; preferably the bacterial host
cell is a *Bacillus, Escherichia, Lactobacillus, Lactococcus
Streptococcus*, or *Streptomyces* cell; more preferably the
bacterial host cell is selected from the group consisting of
*Bacillus alkalophilus, Bacillus altitudinis, Bacillus
amyloliquefaciens, B. amyloliquefaciens* subsp. *plantarum,
Bacillus brevis, Bacillus circulans, Bacillus clausii, Bacillus
coagulans, Bacillus firmus, Bacillus lautus, Bacillus lentus,
Bacillus licheniformis, Bacillus megaterium, Bacillus meth-
ylotrophicus, Bacillus pumilus, Bacillus safensis, Bacillus
stearothermophilus, Bacillus subtilis, Bacillus thuringiensis,
Escherichia coli, Lactobacillus acidophilus, Lactobacillus
amylovorus, Lactobacillus brevis, Lactobacillus (para)
casei, Lactobacillus cellobiosus, Lactobacillus crispatus,
Lactobacillus curvatus, Lactobacillus delbrueckii* subsp.
*bulgaricus, L. delbrueckii* subsp. *lactis, Lactobacillus fer-
mentum, Lactobacillus gallinarum, Lactobacillus gasseri,
Lactobacillus helveticus, Lactobacillus johnsonii, Lactoba-
cillus plantarum, Lactobacillus reuteri, Lactobacillus rham-
nosus, Lactobacillus salivarius, Lactococcus chungangen-
sis, Lactococcus formosensis, Lactococcus fujiensis,
Lactococcus garvieae, Lactococcus lactis, Lactococcus pis-
cium, Lactococcus plantarum, Lactococcus raffinolactis,
Lactococcus taiwanensi, Streptococcus equisimilis, Strepto-
coccus pyogenes, Streptococcus uberis, Streptococcus equi*
subsp. *zooepidemicus, Streptomyces achromogenes, Strep-
tomyces avermitilis, Streptomyces coelicolor, Streptomyces
griseus*, and *Streptomyces lividans*; most preferably the
bacterial host cell is *Bacillus licheniformis*.

51. The host cell according to any of embodiments 48-49,
which is a filamentous fungal host cell; preferably the fungal
host cell is a *Acremonium, Aspergillus, Aureobasidium,
Bjerkandera, Ceriporiopsis, Chrysosporium, Coprinus,
Coriolus, Cryptococcus, Filibasidium, Fusarium, Humicola,
Magnaporthe, Mucor, Myceliophthora, Neocallimastix,
Neurospora, Paecilomyces, Penicillium, Phanerochaete,
Phlebia, Piromyces, Pleurotus, Schizophyllum, Talaromy-
ces, Thermoascus, Thielavia, Tolypocladium, Trametes*, or
*Trichoderma* cell; more preferably the filamentous fungal
host cell is selected from the group consisting of *Aspergillus
awamori, Aspergillus foetidus, Aspergillus fumigatus,
Aspergillus japonicus, Aspergillus nidulans, Aspergillus
niger, Aspergillus oryzae, Bjerkandera adusta, Ceriporiop-
sis aneirina, Ceriporiopsis caregiea, Ceriporiopsis gilves-
cens, Ceriporiopsis pannocinta, Ceriporiopsis rivulosa,
Ceriporiopsis subrufa, Ceriporiopsis subvermispora,
Chrysosporium inops, Chrysosporium keratinophilum,
Chrysosporium lucknowense, Chrysosporium merdarium,
Chrysosporium pannicola, Chrysosporium queenslandicum,
Chrysosporium tropicum, Chrysosporium zonatum, Copri-
nus cinereus, Coriolus hirsutus, Fusarium bactridioides,
Fusarium cerealis, Fusarium crookwellense, Fusarium cul-
morum, Fusarium graminearum, Fusarium graminum,
Fusarium heterosporum, Fusarium negundi, Fusarium
oxysporum, Fusarium reticulatum, Fusarium roseum,
Fusarium sambucinum, Fusarium sarcochroum, Fusarium
sporotrichioides, Fusarium sulphureum, Fusarium torulo-
sum, Fusarium trichothecioides, Fusarium venenatum,
Humicola insolens, Humicola lanuginosa, Mucor miehei,
Myceliophthora thermophila, Neurospora crassa, Penicil-
lium purpurogenum, Phanerochaete chrysosporium, Phle-
bia radiata, Pleurotus eryngii, Thielavia terrestris, Trametes
villosa, Trametes versicolor, Trichoderma harzianum,
Trichoderma koningii, Trichoderma longibrachiatum,
Trichoderma reesei*, and *Trichoderma viride* cell; most preferably the filamentous fungal host cell is a *Aspergillus niger,
Aspergillus oryzae*, or *Trichoderma reesei* cell.

52. The host cell according to any of embodiments 48-49,
which is a yeast host cell; preferably the yeast host cell is a
*Candida, Hansenula, Kluyveromyces, Pichia, Saccharomy-
ces, Schizosaccharomyces*, and *Yarrowia* cell; more prefer-
ably the yeast host cell is selected from the group consisting
of *Kluyveromyces lactis, Pichia pastoris, Saccharomyces
carlsbergensis, Saccharomyces cerevisiae, Saccharomyces
diastaticus, Saccharomyces douglasii, Saccharomyces
kluyveri, Saccharomyces norbensis, Saccharomyces ovifor-
mis*, and *Yarrowia lipolytica* cell; most preferably the yeast
host cell is *Pichia pastoris*.

53. The host cell according to any of embodiments 48-49,
which is a mammalian host cell; preferably the mammalian
host cell is a mouse, rat, or human cell.

54. The host cell according to any of embodiments 48-53,
wherein the catalytically inactive RNA-guided endonu-
clease and the nucleobase editing domain are encoded in
frame and are expressed as a single polypeptide.

55. The host cell according to any of embodiments 48-54,
wherein the catalytically inactive RNA-guided endonu-
clease and the nucleobase editing domain are fused end-to-
end or connected via a linker polypeptide; preferably the
catalytically inactive RNA-guided endonuclease, the linker
polypeptide, and the nucleobase editing domain are encoded
in frame and are expressed as a single polypeptide.

56. The host cell according to any of embodiments 48-55,
wherein the catalytically inactive RNA-guided endonu-
clease comprises an alteration of an amino acid at a position
corresponding to position 877 of SEQ ID NO: 126; prefer-
ably the amino acid at a position corresponding to position
877 of SEQ ID NO: 126 is substituted with Ala, Arg, Asn,
Asp, Cys, Gln, Glu, Gly, His, Ile, Leu, Lys, Met, Phe, Pro,
Ser, Thr, Trp, Tyr, or Val; most preferably the amino acid at
a position corresponding to position 877 of SEQ ID NO: 126
is substituted with Ala.

57. The host cell according to any of embodiments 48-56,
wherein the catalytically inactive RNA-guided endonu-
clease comprises, consists essentially of, or consists of SEQ
ID NO: 126 or SEQ ID NO: 155.

58. The host cell according to any of embodiments 48-57,
wherein the nucleobase editing domain is a cytosine base
editor (CBE).

59. The host cell according to embodiment 58, wherein the
nucleobase editing domain is a cytosine base editor of the
APOBEC1/AID family; preferably the nucleobase editing
domain is APOBEC1 or CDA1, in particular PmCDA1.

60. The host cell according to embodiment 58-59, wherein
the nucleobase editing domain comprises or consists of a
polypeptide having a sequence identity of at least 80%, e.g.,
at least 85%, at least 90%, at least 91%, at least 92%, at least
93%, at least 94%, at least 95%, at least 96%, at least 97%,
at least 98%, at least 99%, or 100%, to SEQ ID NO: 128;
preferably the nuclease editing domain comprises, consists
essentially of, or consists of SEQ ID NO: 128.

61. The host cell according to any of embodiment 48-60,
wherein the nucleobase editing complex further comprises
an uracil DNA glycosylase inhibitor (UGI). Preferably, the
uracil DNA glycosylase inhibitor has a sequence identity of
at least 80%, such as e.g., at least 85%, at least 90%, at least
91%, at least 92%, at least 93%, at least 94%, at least 95%,
at least 96%, at least 97%, at least 98%, at least 99%, or
100%, to SEQ ID NO: 132. Most preferably, the uracil DNA
glycosylase inhibitor comprises, consists essentially of, or
consists of SEQ ID NO: 132.

62. The host cell according to any of embodiments 48-57,
wherein the nucleobase editing domain is an adenine base
editor (ABE).; preferably the nucleobase editing domain is
selected from the group consisting of TadA, TadA*, TadA homodimer, and TadA-TadA* heterodimer; most preferably the nucleobase editing domain is a TadA-TadA* heterodimer.

63. The host cell according to any of embodiments 55-62, wherein the linker polypeptide comprises at least 10 amino acid residues; preferably the linker polypeptide comprises at least 50 amino acid residues; most preferably the linker polypeptide comprises at least 100 amino acid residues.

64. The host cell according to any of embodiments 55-63, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.

65. A method for modifying at least one nucleobase in a DNA target sequence, the method comprising:
    I) providing a nucleobase editing complex comprising, consisting essentially of, or consisting of:
    a) a catalytically inactive RNA-guided endonuclease having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO: 126 or SEQ ID NO: 155; and
    b) a nucleobase editing domain;
    wherein the nucleobase editing complex is complexed with a gRNA that is complementary to and capable of hybridizing to the DNA target sequence; and
    II) contacting the nucleobase editing complex with the DNA target sequence;
    wherein at least one nucleobase in the DNA target sequence is converted to a different nucleobase without introducing a double-strand break in the DNA sequence of interest.

66. The method according to embodiment 65, wherein the catalytically inactive RNA-guided endonuclease comprises an alteration of an amino acid at a position corresponding to position 877 of SEQ ID NO: 126; preferably the amino acid at a position corresponding to position 877 of SEQ ID NO: 126 is substituted with Ala, Arg, Asn, Asp, Cys, Gln, Glu, Gly, His, Ile, Leu, Lys, Met, Phe, Pro, Ser, Thr, Trp, Tyr, or Val; most preferably the amino acid at a position corresponding to position 877 of SEQ ID NO: 126 is substituted with Ala.

67. The method according to any of embodiments 65-66, wherein the catalytically inactive RNA-guided endonuclease comprises, consists essentially of, or consists of SEQ ID NO: 126 or SEQ ID NO: 155.

68. The method according to any of embodiments 65-67, wherein the nucleobase editing domain is a cytosine base editor (CBE).

69. The method according to embodiment 68, wherein the nucleobase editing domain is a cytosine base editor of the APOBEC1/AID family; preferably the nucleobase editing domain is APOBEC1 or CDA1, in particular PmCDA1.

70. The method according to embodiment 68-69, wherein the nucleobase editing domain comprises or consists of a polypeptide having a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 128; preferably the nuclease editing domain comprises, consists essentially of, or consists of SEQ ID NO: 128.

71. The method according to any of embodiments 68-70, which further comprises an uracil DNA glycosylase inhibitor (UGI). Preferably, the uracil DNA glycosylase inhibitor has a sequence identity of at least 80%, such as e.g., at least 85%, at least 90%, at least 91%, at least 92%, at least 93%, at least 94%, at least 95%, at least 96%, at least 97%, at least 98%, at least 99%, or 100%, to SEQ ID NO: 132. Most preferably, the uracil DNA glycosylase inhibitor comprises, consists essentially of, or consists of SEQ ID NO: 132.

72. The method according to any of embodiments 65-67, wherein the nucleobase editing domain is an adenine base editor (ABE).; preferably the nucleobase editing domain is selected from the group consisting of TadA, TadA*, TadA homodimer, and TadA-TadA* heterodimer; most preferably the nucleobase editing domain is a TadA-TadA* heterodimer.

73. The method according to any of embodiments 65-72, wherein the catalytically inactive RNA-guided endonuclease and the nucleobase editing domain are fused end-to-end or connected via a linker polypeptide; preferably the catalytically inactive RNA-guided endonuclease, the linker polypeptide, and the nucleobase editing domain are encoded in frame and are expressed as a single polypeptide.

74. The method according to embodiment 73, wherein the linker polypeptide comprises at least 10 amino acid residues; preferably the linker polypeptide comprises at least 50 amino acid residues; most preferably the linker polypeptide comprises at least 100 amino acid residues.

75. The method according to any of embodiments 73-74, wherein the linker polypeptide has a sequence identity of at least 80%, e.g., at least 85%, at least 90%, at least 91%, at least 92%, at least 93%, at least 94%, at least 95%, at least 96%, at least 97%, at least 98%, at least 99%, or 100%, to SEQ ID NO: 130; preferably the linker polypeptide comprises, consists essentially of, or consists of SEQ ID NO: 130.

76. The method according to any of embodiments 65-75, wherein the DNA target sequence comprises a polynucleotide comprising 21 nucleotides that are at least 85% complementary to and capable of hybridizing to the gRNA; preferably the 21 nucleotides are at least 90%, 95%, 97%, 98%, 99% or even 100% complementary to and capable of hybridizing to the gRNA.

77. The method according to any of embodiments 65-76, wherein the DNA target sequence is flanked by a functional protospacer adjacent motif (PAM) that is recognized by the catalytically inactive RNA-guided endonuclease; preferably the PAM sequence is 5'-TTTN-3' or 5'-CTTN-3'; more preferably the PAM sequence is 5'-TTTN-3'; most preferably the PAM sequence is 5'-TTTC-3' or 5'-TTTG-3'.

78. The method according to embodiment 77, wherein the DNA target sequence is located at the 3' end of the PAM sequence; preferably the DNA target sequence is located directly adjacent to the 3' end of the PAM sequence.

79. The method according to any of embodiments 65-78, wherein the DNA target sequence is comprised in an open reading frame encoding a polypeptide or in a promoter region; preferably the DNA target sequence encode one or more enzyme selected from the group consisting of hydrolase, isomerase, ligase, lyase, oxidoreductase, or a transferase; preferably the one or more enzyme is an alpha-amylase, alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucano-transferase, glucoamylase, invertase, laccase, lipase, mannosidase, mutanase, oxidase, pectinolytic enzyme, peroxidase, phosphodiesterase, phytase, polyphenoloxidase, proteolytic enzyme, ribonuclease, transglutaminase, and xylanase.

The invention claimed is:

1. A nucleobase editing complex comprising:
   a) a catalytically inactive RNA-guided endonuclease having a sequence identity of at least 90% to SEQ ID NO: 126; and
   b) a nucleobase editing domain;
   wherein the catalytically inactive RNA-guided endonuclease and the nucleobase editing domain are fused end-to-end or connected via a linker polypeptide.

2. The nucleobase editing complex according to claim 1, wherein the catalytically inactive RNA-guided endonuclease comprises an alteration of an amino acid at a position corresponding to position 877 of SEQ ID NO: 126.

3. The nucleobase editing complex according to claim 1, wherein the amino acid at a position corresponding to position 877 of SEQ ID NO: 126 is Ala.

4. The nucleobase editing domain according to claim 1, wherein the catalytically inactive RNA-guided endonuclease comprises SEQ ID NO: 126.

5. The nucleobase editing complex according to claim 1, wherein the nucleobase editing domain is a cytosine base editor (CBE).

6. The nucleobase editing complex according to claim 5, wherein the nucleobase editing domain is a cytosine base editor of the APOBEC1/AID family.

7. The nucleobase editing complex according to claim 5, wherein the nucleobase editing domain is PmCDA1.

8. The nucleobase editing complex according to claim 5, wherein the nucleobase editing domain comprises or consists of a polypeptide having a sequence identity of at least 90% to SEQ ID NO: 128.

9. The nucleobase editing complex according to claim 5, wherein the nuclease editing domain comprises SEQ ID NO: 128.

10. The nucleobase editing complex according to claim 5, which further comprises an uracil DNA glycosylase inhibitor (UGI).

11. The nucleobase editing complex according to claim 10, wherein the uracil DNA glycosylase inhibitor has a sequence identity of at least 90% to SEQ ID NO: 132.

12. The nucleobase editing complex according to claim 10, the uracil DNA glycosylase inhibitor comprises SEQ ID NO: 132.

13. The nucleobase editing complex according to claim 1, wherein the nucleobase editing domain is an adenine base editor (ABE).

14. The nucleobase editing complex according to claim 1, wherein the nucleobase editing domain is selected from the group consisting of TadA, TadA*, TadA homodimer, and TadA-TadA* heterodimer.

15. The nucleobase editing complex according to claim 1, wherein the nucleobase editing domain is a TadA-TadA* heterodimer.

16. The nucleobase editing complex according to claim 1, wherein the catalytically inactive RNA-guided endonuclease, the linker polypeptide, and the nucleobase editing domain are encoded in frame and are expressed as a single polypeptide.

17. The nucleobase editing complex according to claim 16, wherein the linker polypeptide comprises at least 10 amino acid residues.

18. The nucleobase editing complex according to claim 16, wherein the linker polypeptide comprises at least 50 amino acid residues.

19. The nucleobase editing complex according to claim 16, wherein the linker polypeptide has a sequence identity at least 90% to SEQ ID NO: 130.

20. The nucleobase editing complex according to claim 16, wherein the linker polypeptide comprises SEQ ID NO: 130.

21. A polynucleotide encoding a nucleobase editing complex according to claim 1.

22. A host cell comprising the polynucleotide according to claim 21.

23. The host cell according to claim 22, which is a bacterial host cell.

24. The host cell according to claim 23, wherein the bacterial host cell is *Bacillus licheniformis*.

25. The host cell according to claim 22, which is a filamentous fungal host cell.

26. The host cell according to claim 25, wherein the filamentous fungal host cell is a *Aspergillus niger, Aspergillus oryzae*, or *Trichoderma reesei* cell.

27. The host cell according to claim 22, which is a yeast host cell.

28. The host cell according to claim 27, wherein the yeast host cell is *Pichia pastoris*.

29. The host cell according to claim 22, which is a mammalian host cell.

30. A method for modifying at least one nucleobase in a DNA target sequence, the method comprising:
   a) providing a nucleobase editing complex according to claim 1 complexed with a gRNA that is complementary to and capable of hybridizing to the DNA target sequence; and
   b) contacting the nucleobase editing complex with the DNA target sequence;
   wherein at least one nucleobase in the DNA target sequence is converted to a different nucleobase without introducing a double-strand break in the DNA sequence of interest.

31. The nucleobase editing complex according to claim 1, wherein the catalytically inactive RNA-guided endonuclease has a sequence identity of at least 95% to SEQ ID NO: 126.

32. The nucleobase editing complex according to claim 5, wherein the nucleobase editing domain comprises or consists of a polypeptide having a sequence identity of at least 95% to SEQ ID NO: 128.

33. The nucleobase editing complex according to claim 10, wherein the uracil DNA glycosylase inhibitor has a sequence identity of at least 95% to SEQ ID NO: 132.

34. The nucleobase editing complex according to claim 16, wherein the linker polypeptide has a sequence identity of at least 95% to SEQ ID NO: 130.

* * * * *

SEQUENCE LISTING

<160> NUMBER OF SEQ ID NOS: 196

<210> SEQ ID NO 1
<211> LENGTH: 44
<212> TYPE: DNA
<213> ORGANISM: Artificial Sequence
<220> FEATURE:
<223> OTHER INFORMATION: Primer HTJP-889

<400> SEQUENCE: 1
ctagaaagta taggaacttc gctagctctg ctcgaggcca tctg                      44

<210> SEQ ID NO 2
<211> LENGTH: 34
<212> TYPE: DNA
<213> ORGANISM: Artificial Sequence
<220> FEATURE:
<223> OTHER INFORMATION: Primer HTJP-890

<400> SEQUENCE: 2
gttcgttcca atggccagcc cgatgctata cttc                                 34

<210> SEQ ID NO 3
<211> LENGTH: 36
<212> TYPE: DNA
<213> ORGANISM: Artificial Sequence
<220> FEATURE:
<223> OTHER INFORMATION: Primer HTJP-891

<400> SEQUENCE: 3
agtatagcat cgggctggcc attggaacga actcgg                               36

<210> SEQ ID NO 4
<211> LENGTH: 41
<212> TYPE: DNA
<213> ORGANISM: Artificial Sequence
<220> FEATURE:
<223> OTHER INFORMATION: Primer HTJP-892

<400> SEQUENCE: 4
gattgcggga cgatagcgtc aacatcgtag tccgacaacc g                         41

<210> SEQ ID NO 5
<211> LENGTH: 41
<212> TYPE: DNA
<213> ORGANISM: Artificial Sequence
<220> FEATURE:
<223> OTHER INFORMATION: Primer HTJP-893

<400> SEQUENCE: 5
tcggactacg atgttgacgc tatcgtcccg caatccttcc t                         41

<210> SEQ ID NO 6
<211> LENGTH: 42
<212> TYPE: DNA
<213> ORGANISM: Artificial Sequence
<220> FEATURE:
<223> OTHER INFORMATION: Primer HTJP-894

<400> SEQUENCE: 6
ggtagagtaa taacgcctag gacacgcaaa acgaggtaca tt                        42

<210> SEQ ID NO 7
<211> LENGTH: 29
<212> TYPE: DNA
<213> ORGANISM: Artificial Sequence

```
<220> FEATURE:
<223> OTHER INFORMATION: Primer HTJP-895

<400> SEQUENCE: 7
gtcctaggcg ttattactct accgcaagg                                              29

<210> SEQ ID NO 8
<211> LENGTH: 49
<212> TYPE: DNA
<213> ORGANISM: Artificial Sequence
<220> FEATURE:
<223> OTHER INFORMATION: Primer HTJP-896

<400> SEQUENCE: 8
taggaacttc aatcgatcta gtcctaggct acgccaggac cgagcaagc                        49

<210> SEQ ID NO 9
<211> LENGTH: 500
<212> TYPE: DNA
<213> ORGANISM: Magnaporthe oryzae

<400> SEQUENCE: 9
tctgctcgag gccatctggc ttttctctgc tgtctgcctc gggaatggga tggaatacca           60
cgtacggtat ttggcctccg gtgccatccg aagcgagatg ctttgagctt gaaacccccct         120 cggcctgcac aggtgtctca tcgtgcattt aatccaacgg cggcgagtca aaacatcagc          180
taattgacca ggtttctgga ttgtgaatgc caacttttg ggtcttgagg agttgcgggg           240
tgggaaaaaa gtaaagaaat ttactgagga ttttatcatt gcgactataa aataaagcgg          300
cattgcaaat ccttgcgttg ctactatgta aaatggactg tagttgtgct gctgaaaata          360
gtttggcgat tgtggattgt ggattgtgga ttgtggatta tggcaagttg tcaaggggca          420
agttgacgaa aatgattgtg tggtgtctgc cagcaaattg agaacgtggg tatatatttc          480
atcttttcat gattcccttc                                                      500

<210> SEQ ID NO 10
<211> LENGTH: 91
<212> TYPE: DNA
<213> ORGANISM: Aspergillus fumigatus

<400> SEQUENCE: 10
ggcttgcttg tcaagcaatg gcatcattgg tctagtggta gaattcgtcg ttgccatcga           60
cgaggcccgt gttcgattca cggatgatgc a                                          91

<210> SEQ ID NO 11
<211> LENGTH: 78
<212> TYPE: DNA
<213> ORGANISM: Artificial Sequence
<220> FEATURE:
<223> OTHER INFORMATION: Cas9 sgRNA backbone

<400> SEQUENCE: 11
gttttagagc tagaaatagc aagttaaaat aaggctagtc cgttatcaac ttgaaaaagt           60
ggcaccgagt cggtgctt                                                         78

<210> SEQ ID NO 12
<211> LENGTH: 215
<212> TYPE: DNA
<213> ORGANISM: Magnaporthe oryzae

<400> SEQUENCE: 12
```

```
ttttttttggc tcttgggttc gaactgccca aggcccatgt tttggtcatc tttttttta      60 tgccccacca tttgggtcac ccctgccaat cattccatct ttgttcctac ccttcacgtg     120
tgctttccga agccaaagtt cccattcaac aactctcctt gcgttttttt tttcttgaag     180
cttgtcaccc gtcgatagtt tctgccattt gcaat                                215

<210> SEQ ID NO 13
<211> LENGTH: 886
<212> TYPE: DNA
<213> ORGANISM: Aspergillus nidulans

<400> SEQUENCE: 13
cgagacagca gaatcaccgc ccaagttaag cctttgtgct gatcatgctc tcgaacgggc      60
caagttcggg aaaagcaaag gagcgtttag tgaggggcaa tttgactcac ctcccaggca     120
acagatgagg ggggcaaaaa gaaagaaatt ttcgtgagtc aatatggatt ccgagcatca     180
ttttcttgcg gtctatcttg ctacgtatgt tgatcttgac gctgtggatc aagcaacgcc     240
actcgctcgc tccatcgcag gctggtcgca gacaaattaa aaggcggcaa actcgtacag     300
ccgcggggtt gtccgctgca aagtacagag tgataaaagc cgccatgcga ccatcaacgc     360
gttgatgccc agctttttcg atccgagaat ccaccgtaga ggcgatagca agtaaagaaa     420
agctaaacaa aaaaaaattt ctgcccctaa gccatgaaaa cgagatgggg tggagcagaa     480
ccaaggaaag agtcgcgctg ggctgccgtt ccggaaggtg ttgtaaaggc tcgacgccca     540
aggtgggagt ctaggagaag aatttgcatc gggagtgggg cgggttaccc ctccatatcc     600
aatgacagat atctaccagc caagggtttg agcccgcccg cttagtcgtc gtcctcgctt     660 gccccctccat aaaaggattt cccctccccc tcccacaaaa ttttctttcc cttcctctcc     720
ttgtccgctt cagtacgtat atcttccctt ccctcgcttc tctcctccat ccttctttca     780
tccatctcct gctaacttct ctgctcagca cctctacgca ttactagccg tagtatctga     840
gcacttctcc cttttatatt ccacaaaaca taacacaacc ttcacc                    886

<210> SEQ ID NO 14
<211> LENGTH: 4131
<212> TYPE: DNA
<213> ORGANISM: Artificial Sequence
<220> FEATURE:
<223> OTHER INFORMATION: dCas9_coding

<400> SEQUENCE: 14
atggacaaga agtatagcat cgggctggcc attggaacga actcggttgg ttgggctgtg      60
attacggacg aatacaaggt gccatccaag aagtttaagg tcctgggaaa caccgaccgt     120
cactcaatca gaagaatct cattggagcc ctgctcttcg atagtgggga gaccgccgaa     180
gctactcgac tgaagcgaac ggctcgccgg cgttatacac gacgcaagaa tcgcatctgc     240
tacctccagg agattttcag caacgaaatg gctaaggttg atgactcatt ctttcatcga     300
ctcgaagaaa gtttcttggt cgaggaggat aagaagcacg agcgccatcc gatctttggt     360
aacattgtgg atgaggttgc ctatcacgaa aagtacccaa ctatctatca tcttcgtaag     420
aagctggtcg atagcacgga caaggctgat ttgcgactta tctacctggc actcgcgcac     480
atgattaagt ccgcggcca ttttcttatc gagggtgacc tgaaccccga taattctgac     540
gttgataagc tcttcatcca gttggtccaa acctacaatc agctgtttga ggaaaaccct     600
attaatgcat ctggcgtgga cgccaaggct atccttcgg cgcgcctgtc taagtcgcgg     660
cgtttggaga accttatcgc acaactcccc ggcgaaaaga agaacggcct cttcggtaat     720
```

-continued

```
ttgattgcgt tgtcacttgg tctgactcct aacttcaaga gtaattttga cctggcagag    780
gatgcgaagc tccagttgtc taaggatacg tatgatgacg atctcgacaa cttgcttgcc    840
caaatcggtg accagtacgc tgatcttttc ctggccgcta agaatctctc agatgcaatc    900
ctgctcagtg acattttgcg ggtcaacacc gagattacta aggccccect gtcagctagt    960 atgatcaagc ggtatgatga gcaccatcag gacctcacct tgcttaaggc cctcgtgcgt   1020
cagcaattgc ctgagaagta caaggaaatc ttctttgacc aatccaagaa cggatacgca   1080
gggtatattg atggcggtgc gagccaggag gaattctaca agtttatcaa gccgattttg   1140
gagaagatgg acggcactga ggaactgctc gtcaagctga atcgcgaaga tttgcttcgt   1200
aagcaacgaa cgttcgacaa cggctccatc ccgcaccaga ttcatctggg cgagctccac   1260 gccatcctte gacgccagga agatttctac ccatttctga aggacaaccg tgagaagatc   1320
gaaaagattc ttacattccg aatcccctac tatgtgggac ctttggcccg tgggaattcc   1380
cgatttgctt ggatgacccg aaagagcgag gaaaccatca ctccgtggaa cttcgaggaa   1440
gtcgtggaca agggtgcatc cgcgcagagc ttcattgagc ggatgaccaa ttttgataag   1500
aaccttccga atgaaaaggt cctgccaaag cattcgctgc tctacgagta tttcaccgtg   1560
tataacgaac tgactaaggt caagtacgtg acggagggaa tgcggaagcc agccttcctc   1620 tcagggggaac aaaagaaggc tatcgtcgat ttgcttttta agaccaatcg taaagtgact   1680
gttaagcagc tgaaggagga ttatttcaag aagattgaat gtttcgactc cgtcgagatc   1740
agcggcgtgg aagatcgctt taacgcttcc ctcggtacct accacgacct gctcaagatc   1800
attaaggaca aggatttcct cgataacgag gaaaatgagg acatcttgga agatattgtc   1860
ctcacgttga cactttttga ggaccgcgaa atgatcgagg aacggctcaa gacatatgcc   1920
catttgttcg acgataaggt gatgaagcag ctgaagcggc gtcgatacac cggatggggt   1980
cgccttagcc ggaagctgat caacggcatt cgagataagc aatctggtaa gactatcttg   2040
gatttcctta agtcggacgg cttcgccaac cgcaatttta tgcagcttat tcacgacgat   2100
tccctgacgt tcaaggagga catccagaag gcacaagtct caggacaagg ggattccctg   2160
cacgagcata tcgccaacct ggctggatcc ccggcgatca agaaggggat tcttcagacc   2220
gtcaaggttg tcgacgagct ggtcaaggtg atgggccgtc ataagccaga aaacatcgtg   2280
attgagatgg cccgagaaaa tcagaccact caaaagggtc agaagaacag ccgcgagcgg   2340
atgaagcgga tcgaggaagg cattaaggaa cttggttctc agatcctgaa ggagcaccct   2400
gttgaaaaca cacagctcca aaatgagaag ctgtatctct actatttgca aaatggacgc   2460
gacatgtacg tcgatcagga gctcgacatt aaccggttgt cggactacga tgttgacgct   2520
atcgtcccgc aatccttcct taaggacgat agcattgata acaaggtgct gactcgctca   2580
gataagaacc ggggcaagtc cgacaatgtt ccaagcgagg aagtggttaa gaagatgaag   2640
aactactggc gccaattgct taatgccaag ctcatcacac agcgcaagtt tgacaacttg   2700
accaaggccg agcggggagg gctgagtgaa ctcgataagg ctggcttcat caagcgtcaa   2760
ctcgtggaga cgcgacagat cacaaagcac gttgctcaga ttctggactc ccggatgaac   2820
acaaagtacg acgagaatga taagctcatc cgtgaagtta aggtcattac cctcaagtct   2880
aagttggtgt cggatttccg caaggacttc caatttttata aggttcggga gatcaacaat   2940
tatcaccatg cacatgatgc gtacctcaac gcagtcgtgg gaactgcgct catcaagaag   3000
tatcccaagt tggagtccga attcgtctac ggggattata aggtttacga cgtccgcaag   3060
```

-continued

```
atgatcgcca agagtgagca ggaaattggc aaggccacgg ctaagtattt cttttactcc     3120
aacatcatga atttctttaa gacggagatc acactcgcca atggagaaat ccgtaagcga     3180
cctttgattg agaccaacgg cgagactggt gaaatcgttt gggataaggg cgcgacttc     3240 gctaccgtgc ggaaggttct gagcatgccg caagtcaata tcgtcaagaa aaccgaggtg     3300
cagacaggcg gtttctctaa ggaatcgatt cttccaaagc gtaactctga caagctgatc     3360
gctcgaaaga aggattggga ccccaagaag tatggagggt tcgattctcc tacagtggca     3420
tactcggttc tcgttgtcgc gaaggttgag aagggaaagt ctaagaagct gaagtcggtc     3480
aaggaactgc tcgggatcac cattatggag cgctccagct tcgaaaagaa tcccatcgac     3540
tttctcgagg ccaagggcta taaggaagtc aagaaggatc ttatcattaa gctgcctaag     3600
tactctttgt tcgagcttga aaacggtcga aagcgaatgc tcgcatcggc aggagagttg     3660
cagaagggga atgaattggc acttccctca aagtacgtga acttcctgta tctcgcgtcc     3720
cactacgaga agctgaaggg tagccctgag gacaacgaac agaagcaact ttttgttgag     3780
caacacaagc attatctgga tgagatcatt gaacagattt cagagttcag taagcgcgtc     3840
atcctcgccg atgctaatct cgacaaggtg ttgtcggcct acaacaagca ccgtgacaag     3900
ccgatccgag agcaggctga aaatatcatt catctgttca ccctcactaa cttgggagca     3960
ccagcagcgt tcaagtattt tgatacgaca atcgaccgta agcgatacac gtccacaaag     4020
gaggtgcttg atgcgaccct gattcatcaa tccatcactg ggctctatga aacccgtatc     4080
gaccttagtc aactgggggg cgaccctccc aagaagaagc gcaaggtctg a             4131
```

<210> SEQ ID NO 15
<211> LENGTH: 1376
<212> TYPE: PRT
<213> ORGANISM: Artificial Sequence
<220> FEATURE:
<223> OTHER INFORMATION: dCas9_protein

<400> SEQUENCE: 15

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

-continued

```
Asp Asn Ser Asp Val Asp Lys Leu Phe Ile Gln Leu Val Gln Thr Tyr
            180             185             190

Asn Gln Leu Phe Glu Glu Asn Pro Ile Asn Ala Ser Gly Val Asp Ala
            195             200         205

Lys Ala Ile Leu Ser Ala Arg Leu Ser Lys Ser Arg Arg Leu Glu Asn
        210             215             220

Leu Ile Ala Gln Leu Pro Gly Glu Lys Lys Asn Gly Leu Phe Gly Asn
225             230             235             240

Leu Ile Ala Leu Ser Leu Gly Leu Thr Pro Asn Phe Lys Ser Asn Phe
            245             250             255

Asp Leu Ala Glu Asp Ala Lys Leu Gln Leu Ser Lys Asp Thr Tyr Asp
            260             265             270

Asp Asp Leu Asp Asn Leu Leu Ala Gln Ile Gly Asp Gln Tyr Ala Asp
            275             280             285

Leu Phe Leu Ala Ala Lys Asn Leu Ser Asp Ala Ile Leu Leu Ser Asp
        290             295             300

Ile Leu Arg Val Asn Thr Glu Ile Thr Lys Ala Pro Leu Ser Ala Ser
305             310             315             320

Met Ile Lys Arg Tyr Asp Glu His His Gln Asp Leu Thr Leu Leu Lys
            325             330             335

Ala Leu Val Arg Gln Gln Leu Pro Glu Lys Tyr Lys Glu Ile Phe Phe
            340             345             350

Asp Gln Ser Lys Asn Gly Tyr Ala Gly Tyr Ile Asp Gly Gly Ala Ser
            355             360             365

Gln Glu Glu Phe Tyr Lys Phe Ile Lys Pro Ile Leu Glu Lys Met Asp
        370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
        450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
        530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
```

-continued

```
                595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
                995                 1000                 1005

Val Tyr  Gly Asp Tyr Lys Val  Tyr Asp Val Arg Lys  Met Ile Ala
    1010                 1015                 1020
```

-continued

```
Lys Ser Glu Gln Glu Ile Gly   Lys Ala Thr Ala Lys   Tyr Phe Phe
    1025              1030              1035

Tyr Ser Asn Ile Met Asn Phe   Phe Lys Thr Glu Ile   Thr Leu Ala
    1040              1045              1050

Asn Gly Glu Ile Arg Lys Arg   Pro Leu Ile Glu Thr   Asn Gly Glu
    1055              1060              1065

Thr Gly Glu Ile Val Trp Asp   Lys Gly Arg Asp Phe   Ala Thr Val
    1070              1075              1080

Arg Lys Val Leu Ser Met Pro   Gln Val Asn Ile Val   Lys Lys Thr
    1085              1090              1095

Glu Val Gln Thr Gly Gly Phe   Ser Lys Glu Ser Ile   Leu Pro Lys
    1100              1105              1110

Arg Asn Ser Asp Lys Leu Ile   Ala Arg Lys Lys Asp   Trp Asp Pro
    1115              1120              1125

Lys Lys Tyr Gly Gly Phe Asp   Ser Pro Thr Val Ala   Tyr Ser Val
    1130              1135              1140

Leu Val Val Ala Lys Val Glu   Lys Gly Lys Ser Lys   Lys Leu Lys
    1145              1150              1155

Ser Val Lys Glu Leu Leu Gly   Ile Thr Ile Met Glu   Arg Ser Ser
    1160              1165              1170

Phe Glu Lys Asn Pro Ile Asp   Phe Leu Glu Ala Lys   Gly Tyr Lys
    1175              1180              1185

Glu Val Lys Lys Asp Leu Ile   Ile Lys Leu Pro Lys   Tyr Ser Leu
    1190              1195              1200

Phe Glu Leu Glu Asn Gly Arg   Lys Arg Met Leu Ala   Ser Ala Gly
    1205              1210              1215

Glu Leu Gln Lys Gly Asn Glu   Leu Ala Leu Pro Ser   Lys Tyr Val
    1220              1225              1230

Asn Phe Leu Tyr Leu Ala Ser   His Tyr Glu Lys Leu   Lys Gly Ser
    1235              1240              1245

Pro Glu Asp Asn Glu Gln Lys   Gln Leu Phe Val Glu   Gln His Lys
    1250              1255              1260

His Tyr Leu Asp Glu Ile Ile   Glu Gln Ile Ser Glu   Phe Ser Lys
    1265              1270              1275

Arg Val Ile Leu Ala Asp Ala   Asn Leu Asp Lys Val   Leu Ser Ala
    1280              1285              1290

Tyr Asn Lys His Arg Asp Lys   Pro Ile Arg Glu Gln   Ala Glu Asn
    1295              1300              1305

Ile Ile His Leu Phe Thr Leu   Thr Asn Leu Gly Ala   Pro Ala Ala
    1310              1315              1320

Phe Lys Tyr Phe Asp Thr Thr   Ile Asp Arg Lys Arg   Tyr Thr Ser
    1325              1330              1335

Thr Lys Glu Val Leu Asp Ala   Thr Leu Ile His Gln   Ser Ile Thr
    1340              1345              1350

Gly Leu Tyr Glu Thr Arg Ile   Asp Leu Ser Gln Leu   Gly Gly Asp
    1355              1360              1365

Pro Pro Lys Lys Lys Arg Lys   Val
    1370              1375
```

<210> SEQ ID NO 16
<211> LENGTH: 1023
<212> TYPE: DNA
<213> ORGANISM: Artificial Sequence
<220> FEATURE:

-continued

<223> OTHER INFORMATION: hph selection marker

<400> SEQUENCE: 16

```
atgtcgcctg aactcaccgc gacgtctgtc gagaagtttc tgatcgaaaa gttcgacagc      60
gtctccgacc tgatgcagct ctcggagggc gaagaatctc gtgctttcag cttcgatgta     120
ggagggcgtg gatatgtcct gcgggtaaat agctgcgccg atggtttcta caaagatcgt     180
tatgtttatc ggcactttgc atcggccgcg ctcccgattc cggaagtgct tgacattggg     240
gaattcagcg agagcctgac ctattgcatc tcccgccgtg cacagggtgt cacgttgcaa     300
gacctgcctg aaaccgaact gcccgctgtt ctgcagccgg tcgcggaggc catggatgcg     360
atcgctgcgg ccgatcttag ccagacgagc gggttcggcc cattcggacc gcaaggaatc     420
ggtcaataca ctacatggcg tgatttcata tgcgcgattg ctgatcccca tgtgtatcac     480
tggcaaactg tgatggacga caccgtcagt gcgtccgtcg cgcaggctct cgatgagctg     540
atgctttggg ccgaggactg ccccgaagtc cggcacctcg tgcacgcgga tttcggctcc     600
aacaatgtcc tgacggacaa tggccgcata acagcggtca ttgactggag cgaggcgatg     660 ttcgggggatt cccaatacga ggtcgccaac atcttcttct ggaggccgtg gttggcttgt     720
atggagcagc agacgcgcta cttcgagcgg aggcatccgg agcttgcagg atcgccgcgg     780
ctccgggcgt atatgctccg cattggtctt gaccaactct atcagagctt ggttgacggc     840
aattccgatg atgcagcttg ggcgcagggt cgatgcgacg caatcgtccg atccggagcc     900
gggactgtcg ggcgtacaca aatcgcccgc agaagcgcgg ccgtctggac cgatggctgt     960
gtagaagtac tcgccgatag tggaaaccga cgccccagca ctcgtccgag ggcaaaggaa    1020
tag                                                                  1023
```

<210> SEQ ID NO 17
<211> LENGTH: 21
<212> TYPE: DNA
<213> ORGANISM: Artificial Sequence
<220> FEATURE:
<223> OTHER INFORMATION: Primer IF_U6cas9_fwd

<400> SEQUENCE: 17

```
ttttctctgc tgtctgcctc g                                                 21
```

<210> SEQ ID NO 18
<211> LENGTH: 21
<212> TYPE: DNA
<213> ORGANISM: Artificial Sequence
<220> FEATURE:
<223> OTHER INFORMATION: Primer IF_dCasCDA_rev

<400> SEQUENCE: 18

```
gtcgccccc agttgactaa g                                                  21
```

<210> SEQ ID NO 19
<211> LENGTH: 26
<212> TYPE: DNA
<213> ORGANISM: Artificial Sequence
<220> FEATURE:
<223> OTHER INFORMATION: Primer IF_CDA3UTR_fwd

<400> SEQUENCE: 19

```
gcggacattc gatttatgcc gttatg                                            26
```

<210> SEQ ID NO 20
<211> LENGTH: 24

-continued

```
<212> TYPE: DNA
<213> ORGANISM: Artificial Sequence
<220> FEATURE:
<223> OTHER INFORMATION: Primer IF_U63UTR_rev

<400> SEQUENCE: 20
agacagcaga gaaaagccag atgg                                          24

<210> SEQ ID NO 21
<211> LENGTH: 20
<212> TYPE: DNA
<213> ORGANISM: Artificial Sequence
<220> FEATURE:
<223> OTHER INFORMATION: Primer CDAinsert_fwd

<400> SEQUENCE: 21
caactggggg gcgacagcag                                               20

<210> SEQ ID NO 22
<211> LENGTH: 25
<212> TYPE: DNA
<213> ORGANISM: Artificial Sequence
<220> FEATURE:
<223> OTHER INFORMATION: Primer CDAinsert_rev

<400> SEQUENCE: 22
aaatcgaatg tccgcttatc cggag                                         25

<210> SEQ ID NO 23
<211> LENGTH: 20
<212> TYPE: DNA
<213> ORGANISM: Artificial Sequence
<220> FEATURE:
<223> OTHER INFORMATION: Protospacer for pTNA197

<400> SEQUENCE: 23
cagcagtcct ctgctctaga                                               20

<210> SEQ ID NO 24
<211> LENGTH: 20
<212> TYPE: DNA
<213> ORGANISM: Artificial Sequence
<220> FEATURE:
<223> OTHER INFORMATION: Protospacer for pTNA198

<400> SEQUENCE: 24
tccaacccac tccctggaat                                               20

<210> SEQ ID NO 25
<211> LENGTH: 20
<212> TYPE: DNA
<213> ORGANISM: Artificial Sequence
<220> FEATURE:
<223> OTHER INFORMATION: Protospacer for pTNA199

<400> SEQUENCE: 25
ccagcatgtt gactcggaat                                               20

<210> SEQ ID NO 26
<211> LENGTH: 20
<212> TYPE: DNA
<213> ORGANISM: Artificial Sequence
<220> FEATURE:
<223> OTHER INFORMATION: Protospacer for pTNA200

<400> SEQUENCE: 26
```

-continued

```
tgtcccagca tagtcgtcgt                                                20

<210> SEQ ID NO 27
<211> LENGTH: 60
<212> TYPE: DNA
<213> ORGANISM: Artificial Sequence
<220> FEATURE:
<223> OTHER INFORMATION: Primer wA_sense_1

<400> SEQUENCE: 27
ttcgattcac ggatgatgca cagcagtcct ctgctctaga gttttagagc tagaaatagc      60

<210> SEQ ID NO 28
<211> LENGTH: 60
<212> TYPE: DNA
<213> ORGANISM: Artificial Sequence
<220> FEATURE:
<223> OTHER INFORMATION: Primer wA_sense_1_rev

<400> SEQUENCE: 28
gctatttcta gctctaaaac tctagagcag aggactgctg tgcatcatcc gtgaatcgaa      60

<210> SEQ ID NO 29
<211> LENGTH: 60
<212> TYPE: DNA
<213> ORGANISM: Artificial Sequence
<220> FEATURE:
<223> OTHER INFORMATION: Primer wA_sense_2

<400> SEQUENCE: 29
ttcgattcac ggatgatgca tccaacccac tccctggaat gttttagagc tagaaatagc      60

<210> SEQ ID NO 30
<211> LENGTH: 60
<212> TYPE: DNA
<213> ORGANISM: Artificial Sequence
<220> FEATURE:
<223> OTHER INFORMATION: Primer wA_sense_2_rev

<400> SEQUENCE: 30
gctatttcta gctctaaaac attccaggga gtgggttgga tgcatcatcc gtgaatcgaa      60

<210> SEQ ID NO 31
<211> LENGTH: 60
<212> TYPE: DNA
<213> ORGANISM: Artificial Sequence
<220> FEATURE:
<223> OTHER INFORMATION: Primer wA_anti_1

<400> SEQUENCE: 31
ttcgattcac ggatgatgca ccagcatgtt gactcggaat gttttagagc tagaaatagc      60

<210> SEQ ID NO 32
<211> LENGTH: 60
<212> TYPE: DNA
<213> ORGANISM: Artificial Sequence
<220> FEATURE:
<223> OTHER INFORMATION: Primer wA_anti_1_rev

<400> SEQUENCE: 32
gctatttcta gctctaaaac attccgagtc aacatgctgg tgcatcatcc gtgaatcgaa      60

<210> SEQ ID NO 33
<211> LENGTH: 60
<212> TYPE: DNA
<213> ORGANISM: Artificial Sequence
```

```
<220> FEATURE:
<223> OTHER INFORMATION: Primer wA_anti_2

<400> SEQUENCE: 33
ttcgattcac ggatgatgca tgtcccagca tagtcgtcgt gttttagagc tagaaatagc       60

<210> SEQ ID NO 34
<211> LENGTH: 60
<212> TYPE: DNA
<213> ORGANISM: Artificial Sequence
<220> FEATURE:
<223> OTHER INFORMATION: Primer wA_anti_2_rev

<400> SEQUENCE: 34
gctatttcta gctctaaaac acgacgacta tgctgggaca tgcatcatcc gtgaatcgaa       60

<210> SEQ ID NO 35
<211> LENGTH: 5055
<212> TYPE: DNA
<213> ORGANISM: Artificial Sequence
<220> FEATURE:
<223> OTHER INFORMATION: dCas9-AID_coding

<400> SEQUENCE: 35
atggacaaga agtatagcat cgggctggcc attggaacga actcggttgg ttgggctgtg     60
attacggacg aatacaaggt gccatccaag aagtttaagg tcctgggaaa caccgaccgt    120
cactcaatca agaagaatct cattggagcc ctgctcttcg atagtgggga gaccgccgaa    180
gctactcgac tgaagcgaac ggctcgccgg cgttatacac gacgcaagaa tcgcatctgc    240
tacctccagg agattttcag caacgaaatg gctaaggttg atgactcatt ctttcatcga    300
ctcgaagaaa gtttcttggt cgaggaggat aagaagcacg agcgccatcc gatctttggt    360
aacattgtgg atgaggttgc ctatcacgaa aagtacccaa ctatctatca tcttcgtaag    420
aagctggtcg atagcacgga caaggctgat ttgcgactta tctacctggc actcgcgcac    480
atgattaagt ccgcggcca ttttcttatc gagggtgacc tgaaccccga taattctgac    540
gttgataagc tcttcatcca gttggtccaa acctacaatc agctgtttga ggaaaaccct    600
attaatgcat ctggcgtgga cgccaaggct atcctttcgg cgcgcctgtc taagtcgcgg    660
cgtttggaga accttatcgc acaactcccc ggcgaaaaga gaacggcct cttcggtaat    720 ttgattgcgt tgtcacttgg tctgactcct aacttcaaga gtaattttga cctggcagag    780
gatgcgaagc tccagttgtc taaggatacg tatgatgacg atctcgacaa cttgcttgcc    840
caaatcggtg accagtacgc tgatcttttc ctggccgcta gaatctctc agatgcaatc    900 ctgctcagtg acattttgcg ggtcaacacc gagattacta aggccccct gtcagctagt    960 atgatcaagc ggtatgatga gcaccatcag gacctcacct tgcttaaggc cctcgtgcgt   1020
cagcaattgc ctgagaagta caaggaaatc ttctttgacc aatccaagaa cggatacgca   1080
gggtatattg atggcggtgc gagccaggag gaattctaca agtttatcaa gccgattttg   1140
gagaagatgg acggcactga ggaactgctc gtcaagctga tcgcgaaga tttgcttcgt   1200 aagcaacgaa cgttcgacaa cggctccatc ccgcaccaga ttcatctggg cgagctccac   1260
gccatccttc gacgccagga agatttctac ccatttctga aggacaaccg tgagaagatc   1320
gaaaagattc ttacattccg aatcccctac tatgtgggac cttggcccg tgggaattcc   1380 cgatttgctt ggatgacccg aaaagagcag gaaaccatca ctccgtggaa cttcgaggaa   1440
gtcgtggaca agggtgcatc cgcgcagagc ttcattgagc ggatgaccaa ttttgataag   1500
```

-continued

```
aaccttccga atgaaaaggt cctgccaaag cattcgctgc tctacgagta tttcaccgtg    1560
tataacgaac tgactaaggt caagtacgtg acggagggaa tgcggaagcc agccttcctc    1620
tcaggggaac aaaagaaggc tatcgtcgat ttgctttta agaccaatcg taaagtgact    1680
gttaagcagc tgaaggagga ttatttcaag aagattgaat gtttcgactc cgtcgagatc    1740
agcggcgtgg aagatcgctt taacgcttcc ctcggtacct accacgacct gctcaagatc    1800
attaaggaca aggatttcct cgataacgag gaaaatgagg acatcttgga agatattgtc    1860
ctcacgttga cactttttga ggaccgcgaa atgatcgagg aacggctcaa gacatatgcc    1920
catttgttcg acgataaggt gatgaagcag ctgaagcggc gtcgatacac cggatggggt    1980
cgccttagcc ggaagctgat caacggcatt cgagataagc aatctggtaa gactatcttg    2040
gatttcctta agtcggacgg cttcgccaac cgcaatttta tgcagcttat tcacgacgat    2100
tccctgacgt tcaaggagga catccagaag gcacaagtct caggacaagg ggattccctg    2160
cacgagcata tcgccaacct ggctggatcc ccggcgatca agaaggggat tcttcagacc    2220
gtcaaggttg tcgacgagct ggtcaaggtg atgggccgtc ataagccaga aaacatcgtg    2280
attgagatgg cccgagaaaa tcagaccact caaaagggtc agaagaacag ccgcgagcgg    2340
atgaagcgga tcgaggaagg cattaaggaa cttggttctc agatcctgaa ggagcaccct    2400
gttgaaaaca cacagctcca aaatgagaag ctgtatctct actatttgca aaatggacgc    2460
gacatgtacg tcgatcagga gctcgacatt aaccggttgt cggactacga tgttgacgct    2520
atcgtcccgc aatccttcct taaggacgat agcattgata acaaggtgct gactcgctca    2580
gataagaacc ggggcaagtc cgacaatgtt ccaagcgagg aagtggttaa gaagatgaag    2640
aactactggc gccaattgct taatgccaag ctcatcacac agcgcaagtt tgacaacttg    2700
accaaggccg agcggggagg gctgagtgaa ctcgataagg ctggcttcat caagcgtcaa    2760
ctcgtggaga cgcgacagat cacaaagcac gttgctcaga ttctggactc ccggatgaac    2820
acaaagtacg acgagaatga taagctcatc cgtgaagtta aggtcattac cctcaagtct    2880
aagttggtgt cggatttccg caaggacttc caattttata aggttcggga gatcaacaat    2940
tatcaccatg cacatgatgc gtacctcaac gcagtcgtgg gaactgcgct catcaagaag    3000
tatcccaagt tggagtccga attcgtctac ggggattata aggtttacga cgtccgcaag    3060
atgatcgcca agagtgagca ggaaattggc aaggccacgg ctaagtattt cttttactcc    3120
aacatcatga atttctttaa gacggagatc acactcgcca atggagaaat ccgtaagcga    3180
cctttgattg agaccaacgg cgagactggt gaaatcgttt gggataaggg cgcgacttc    3240 gctaccgtgc ggaaggttct gagcatgccg caagtcaata tcgtcaagaa aaccgaggtg    3300
cagacaggcg gtttctctaa ggaatcgatt cttccaaagc gtaactctga caagctgatc    3360
gctcgaaaga aggattggga ccccaagaag tatggagggt tcgattctcc tacagtggca    3420
tactcggttc tcgttgtcgc gaaggttgag aagggaaagt ctaagaagct gaagtcggtc    3480
aaggaactgc tcgggatcac cattatggag cgctccagct tcgaaaagaa tcccatcgac    3540
tttctcgagg ccaagggcta taaggaagtc aagaaggatc ttatcattaa gctgcctaag    3600
tactctttgt tcgagcttga aaacggtcga aagcgaatgc tcgcatcggc aggagagttg    3660
cagaagggga atgaattggc acttccctca aagtacgtga acttcctgta tctcgcgtcc    3720
cactacgaga agctgaaggg tagccctgag gacaacgaac agaagcaact ttttgttgag    3780
caacacaagc attatctgga tgagatcatt gaacagattt cagagttcag taagcgcgtc    3840
atcctcgccg atgctaatct cgacaaggtg ttgtcggcct acaacaagca ccgtgacaag    3900
```

```
ccgatccgag agcaggctga aaatatcatt catctgttca ccctcactaa cttgggagca    3960
ccagcagcgt tcaagtattt tgatacgaca atcgaccgta agcgatacac gtccacaaag    4020
gaggtgcttg atgcgaccct gattcatcaa tccatcactg ggctctatga aacccgtatc    4080
gaccttagtc aactgggggg cgacagcagg gctgacccca agaagaagag gaaggtgggt    4140
ggaggaggtt ctggaggtgg aggttctgca gagtatgtgc gggccctctt tgactttaat    4200
gggaatgatg aagaagacct tccctttaag aaaggagaca tcctgagaat ccgggataag    4260
cctgaagagc agtggtggaa tgcagaggac agcgaaggaa agaggggggat gattcctgtc    4320 ccttacgtgg agaagtattc cggagactat aaggaccacg acggagacta caaggatcat    4380
gatattgatt acaaagacga tgacgataag tctaggatga ccgacgctga gtacgtgaga    4440
atccatgaga agttggacat ctacacgttt aagaaacagt ttttcaacaa caaaaaatcc    4500
gtgtcgcata gatgctacgt tctctttgaa ttaaaacgac ggggtgaacg tagagcgtgt    4560
ttttggggct atgctgtgaa taaaccacag agcgggacag aacgtggcat tcacgccgaa    4620
atctttagca ttagaaaagt cgaagaatac ctgcgcgaca accccggaca attcacgata    4680
aattggtact catcctggag tccttgtgca gattgcgctg aaaaaatctt agaatggtat    4740
aaccaggagc tgcggggggaa cggccacact ttgaaaatct gggcttgcaa actctattac    4800
gagaaaaatg cgaggaatca aattgggctg tggaacctca gagataacgg ggttgggttg    4860
aatgtaatgg taagtgaaca ctaccaatgt tgcaggaaaa tattcatcca atcgtcgcac    4920
aatcaattga atgagaatag atggcttgag aagactttga agcgagctga aaaacgacgg    4980
agcgagttgt ccattatgat tcaggtaaaa atactccaca ccactaagag tcctgctgtt    5040
tctagaggct ccgga                                                    5055
```

<210> SEQ ID NO 36
<211> LENGTH: 1685
<212> TYPE: PRT
<213> ORGANISM: Artificial Sequence
<220> FEATURE:
<223> OTHER INFORMATION: dCas9-AID_protein

<400> SEQUENCE: 36

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
```

-continued

```
145             150             155             160

Met Ile Lys Phe Arg Gly His Phe Leu Ile Glu Gly Asp Leu Asn Pro
            165             170             175

Asp Asn Ser Asp Val Asp Lys Leu Phe Ile Gln Leu Val Gln Thr Tyr
            180             185             190

Asn Gln Leu Phe Glu Glu Asn Pro Ile Asn Ala Ser Gly Val Asp Ala
            195             200             205

Lys Ala Ile Leu Ser Ala Arg Leu Ser Lys Ser Arg Arg Leu Glu Asn
            210             215             220

Leu Ile Ala Gln Leu Pro Gly Glu Lys Lys Asn Gly Leu Phe Gly Asn
225             230             235             240

Leu Ile Ala Leu Ser Leu Gly Leu Thr Pro Asn Phe Lys Ser Asn Phe
            245             250             255

Asp Leu Ala Glu Asp Ala Lys Leu Gln Leu Ser Lys Asp Thr Tyr Asp
            260             265             270

Asp Asp Leu Asp Asn Leu Leu Ala Gln Ile Gly Asp Gln Tyr Ala Asp
            275             280             285

Leu Phe Leu Ala Ala Lys Asn Leu Ser Asp Ala Ile Leu Leu Ser Asp
            290             295             300

Ile Leu Arg Val Asn Thr Glu Ile Thr Lys Ala Pro Leu Ser Ala Ser
305             310             315             320

Met Ile Lys Arg Tyr Asp Glu His His Gln Asp Leu Thr Leu Leu Lys
            325             330             335

Ala Leu Val Arg Gln Gln Leu Pro Glu Lys Tyr Lys Glu Ile Phe Phe
            340             345             350

Asp Gln Ser Lys Asn Gly Tyr Ala Gly Tyr Ile Asp Gly Gly Ala Ser
            355             360             365

Gln Glu Glu Phe Tyr Lys Phe Ile Lys Pro Ile Leu Glu Lys Met Asp
            370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
            450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
            530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575
```

Ser Val Glu Ile Ser Gly Val Glu Asp Arg Phe Asn Ala Ser Leu Gly
                580                     585                     590

Thr Tyr His Asp Leu Leu Lys Ile Ile Lys Asp Lys Asp Phe Leu Asp
            595                     600                     605

Asn Glu Glu Asn Glu Asp Ile Leu Glu Asp Ile Val Leu Thr Leu Thr
            610                     615                     620

Leu Phe Glu Asp Arg Glu Met Ile Glu Glu Arg Leu Lys Thr Tyr Ala
625                     630                     635                     640

His Leu Phe Asp Asp Lys Val Met Lys Gln Leu Lys Arg Arg Arg Tyr
                645                     650                     655

Thr Gly Trp Gly Arg Leu Ser Arg Lys Leu Ile Asn Gly Ile Arg Asp
            660                     665                     670

Lys Gln Ser Gly Lys Thr Ile Leu Asp Phe Leu Lys Ser Asp Gly Phe
            675                     680                     685

Ala Asn Arg Asn Phe Met Gln Leu Ile His Asp Asp Ser Leu Thr Phe
            690                     695                     700

Lys Glu Asp Ile Gln Lys Ala Gln Val Ser Gly Gln Gly Asp Ser Leu
705                     710                     715                     720

His Glu His Ile Ala Asn Leu Ala Gly Ser Pro Ala Ile Lys Lys Gly
                725                     730                     735

Ile Leu Gln Thr Val Lys Val Val Asp Glu Leu Val Lys Val Met Gly
                740                     745                     750

Arg His Lys Pro Glu Asn Ile Val Ile Glu Met Ala Arg Glu Asn Gln
            755                     760                     765

Thr Thr Gln Lys Gly Gln Lys Asn Ser Arg Glu Arg Met Lys Arg Ile
770                     775                     780

Glu Glu Gly Ile Lys Glu Leu Gly Ser Gln Ile Leu Lys Glu His Pro
785                     790                     795                     800

Val Glu Asn Thr Gln Leu Gln Asn Glu Lys Leu Tyr Leu Tyr Tyr Leu
                805                     810                     815

Gln Asn Gly Arg Asp Met Tyr Val Asp Gln Glu Leu Asp Ile Asn Arg
                820                     825                     830

Leu Ser Asp Tyr Asp Val Asp Ala Ile Val Pro Gln Ser Phe Leu Lys
            835                     840                     845

Asp Asp Ser Ile Asp Asn Lys Val Leu Thr Arg Ser Asp Lys Asn Arg
            850                     855                     860

Gly Lys Ser Asp Asn Val Pro Ser Glu Glu Val Val Lys Lys Met Lys
865                     870                     875                     880

Asn Tyr Trp Arg Gln Leu Leu Asn Ala Lys Leu Ile Thr Gln Arg Lys
                885                     890                     895

Phe Asp Asn Leu Thr Lys Ala Glu Arg Gly Gly Leu Ser Glu Leu Asp
            900                     905                     910

Lys Ala Gly Phe Ile Lys Arg Gln Leu Val Glu Thr Arg Gln Ile Thr
            915                     920                     925

Lys His Val Ala Gln Ile Leu Asp Ser Arg Met Asn Thr Lys Tyr Asp
            930                     935                     940

Glu Asn Asp Lys Leu Ile Arg Glu Val Lys Val Ile Thr Leu Lys Ser
945                     950                     955                     960

Lys Leu Val Ser Asp Phe Arg Lys Asp Phe Gln Phe Tyr Lys Val Arg
                965                     970                     975

Glu Ile Asn Asn Tyr His His Ala His Asp Ala Tyr Leu Asn Ala Val
                980                     985                     990

-continued

```
Val Gly Thr Ala Leu Ile Lys Lys  Tyr Pro Lys Leu Glu  Ser Glu Phe
        995              1000              1005

Val Tyr  Gly Asp Tyr Lys Val  Tyr Asp Val Arg Lys  Met Ile Ala
    1010              1015              1020

Lys Ser  Glu Gln Glu Ile Gly  Lys Ala Thr Ala Lys  Tyr Phe Phe
    1025              1030              1035

Tyr Ser  Asn Ile Met Asn Phe  Phe Lys Thr Glu Ile  Thr Leu Ala
    1040              1045              1050

Asn Gly  Glu Ile Arg Lys Arg  Pro Leu Ile Glu Thr  Asn Gly Glu
    1055              1060              1065

Thr Gly  Glu Ile Val Trp Asp  Lys Gly Arg Asp Phe  Ala Thr Val
    1070              1075              1080

Arg Lys  Val Leu Ser Met Pro  Gln Val Asn Ile Val  Lys Lys Thr
    1085              1090              1095

Glu Val  Gln Thr Gly Gly Phe  Ser Lys Glu Ser Ile  Leu Pro Lys
    1100              1105              1110

Arg Asn  Ser Asp Lys Leu Ile  Ala Arg Lys Lys Asp  Trp Asp Pro
    1115              1120              1125

Lys Lys  Tyr Gly Gly Phe Asp  Ser Pro Thr Val Ala  Tyr Ser Val
    1130              1135              1140

Leu Val  Val Ala Lys Val Glu  Lys Gly Lys Ser Lys  Lys Leu Lys
    1145              1150              1155

Ser Val  Lys Glu Leu Leu Gly  Ile Thr Ile Met Glu  Arg Ser Ser
    1160              1165              1170

Phe Glu  Lys Asn Pro Ile Asp  Phe Leu Glu Ala Lys  Gly Tyr Lys
    1175              1180              1185

Glu Val  Lys Lys Asp Leu Ile  Ile Lys Leu Pro Lys  Tyr Ser Leu
    1190              1195              1200

Phe Glu  Leu Glu Asn Gly Arg  Lys Arg Met Leu Ala  Ser Ala Gly
    1205              1210              1215

Glu Leu  Gln Lys Gly Asn Glu  Leu Ala Leu Pro Ser  Lys Tyr Val
    1220              1225              1230

Asn Phe  Leu Tyr Leu Ala Ser  His Tyr Glu Lys Leu  Lys Gly Ser
    1235              1240              1245

Pro Glu  Asp Asn Glu Gln Lys  Gln Leu Phe Val Glu  Gln His Lys
    1250              1255              1260

His Tyr  Leu Asp Glu Ile Ile  Glu Gln Ile Ser Glu  Phe Ser Lys
    1265              1270              1275

Arg Val  Ile Leu Ala Asp Ala  Asn Leu Asp Lys Val  Leu Ser Ala
    1280              1285              1290

Tyr Asn  Lys His Arg Asp Lys  Pro Ile Arg Glu Gln  Ala Glu Asn
    1295              1300              1305

Ile Ile  His Leu Phe Thr Leu  Thr Asn Leu Gly Ala  Pro Ala Ala
    1310              1315              1320

Phe Lys  Tyr Phe Asp Thr Thr  Ile Asp Arg Lys Arg  Tyr Thr Ser
    1325              1330              1335

Thr Lys  Glu Val Leu Asp Ala  Thr Leu Ile His Gln  Ser Ile Thr
    1340              1345              1350

Gly Leu  Tyr Glu Thr Arg Ile  Asp Leu Ser Gln Leu  Gly Gly Asp
    1355              1360              1365

Ser Arg  Ala Asp Pro Lys Lys  Lys Arg Lys Val Gly  Gly Gly Gly
    1370              1375              1380

Ser Gly  Gly Gly Gly Ser Ala  Glu Tyr Val Arg Ala  Leu Phe Asp
```

-continued

```
         1385                1390                1395

Phe Asn  Gly Asn Asp Glu Glu  Asp Leu Pro Phe Lys  Lys Gly Asp
    1400                1405                1410

Ile Leu  Arg Ile Arg Asp Lys  Pro Glu Glu Gln Trp  Trp Asn Ala
    1415                1420                1425

Glu Asp  Ser Glu Gly Lys Arg  Gly Met Ile Pro Val  Pro Tyr Val
    1430                1435                1440

Glu Lys  Tyr Ser Gly Asp Tyr  Lys Asp His Asp Gly  Asp Tyr Lys
    1445                1450                1455

Asp His  Asp Ile Asp Tyr Lys  Asp Asp Asp Lys  Ser Arg Met
    1460                1465                1470

Thr Asp  Ala Glu Tyr Val Arg  Ile His Glu Lys Leu  Asp Ile Tyr
    1475                1480                1485

Thr Phe  Lys Lys Gln Phe Phe  Asn Asn Lys Lys Ser  Val Ser His
    1490                1495                1500

Arg Cys  Tyr Val Leu Phe Glu  Leu Lys Arg Arg Gly  Glu Arg Arg
    1505                1510                1515

Ala Cys  Phe Trp Gly Tyr Ala  Val Asn Lys Pro Gln  Ser Gly Thr
    1520                1525                1530

Glu Arg  Gly Ile His Ala Glu  Ile Phe Ser Ile Arg  Lys Val Glu
    1535                1540                1545

Glu Tyr  Leu Arg Asp Asn Pro  Gly Gln Phe Thr Ile  Asn Trp Tyr
    1550                1555                1560

Ser Ser  Trp Ser Pro Cys Ala  Asp Cys Ala Glu Lys  Ile Leu Glu
    1565                1570                1575

Trp Tyr  Asn Gln Glu Leu Arg  Gly Asn Gly His Thr  Leu Lys Ile
    1580                1585                1590

Trp Ala  Cys Lys Leu Tyr Tyr  Glu Lys Asn Ala Arg  Asn Gln Ile
    1595                1600                1605

Gly Leu  Trp Asn Leu Arg Asp  Asn Gly Val Gly Leu  Asn Val Met
    1610                1615                1620

Val Ser  Glu His Tyr Gln Cys  Cys Arg Lys Ile Phe  Ile Gln Ser
    1625                1630                1635

Ser His  Asn Gln Leu Asn Glu  Asn Arg Trp Leu Glu  Lys Thr Leu
    1640                1645                1650

Lys Arg  Ala Glu Lys Arg Arg  Ser Glu Leu Ser Ile  Met Ile Gln
    1655                1660                1665

Val Lys  Ile Leu His Thr Thr  Lys Ser Pro Ala Val  Ser Arg Gly
    1670                1675                1680

Ser Gly
    1685
```

<210> SEQ ID NO 37
<211> LENGTH: 6680
<212> TYPE: DNA
<213> ORGANISM: Artificial Sequence
<220> FEATURE:
<223> OTHER INFORMATION: PKS (wA) gene locus

<400> SEQUENCE: 37

```
atggagggtc catctcgtgt gtaccttttt ggagaccaga ccagcgacat cgaagctggc        60
ctgcgccgtc tgctccaagc gaagaatagt accattgtcc agtccttttt ccagcaatgc       120
ttccatgcaa ttcgtcaaga gatcgcgaag ctccgccgt ctcatcggaa gctcttccca       180
cgcttcacga gcatcgttga tctcctttcc aggagtcgtg aatcaggtcc tagccctgtc       240
```

-continued

```
ctggagagtg cattgacatg catctaccaa ttgggttgtt tcattcagta agtcaatgag      300
ttaccatcta tacttgacaa gtctgaccag ccttcagctt ttacggggat cttggacatg      360
actaccctac accctccaac agccatcttg ttggcctgtg cactggtgtt ctgagctgca      420
cggctgtaag ttgcgccaga aatgttggag agcttattcc agctgcagtg gaatcggttg      480
taattgcact gcgactggga atctgcgttt ttcgagttcg agaactggtg gactccgccg      540
attccgagtc aacatgctgg tcagcgttgg tttctggaat cagtgaagca gaggctagcc      600
acctgatcga cgagtacagt agtaagaagg tgtgctcttc caactttaaa cccccgcatt      660
gtgggatgct gacagatgca ggctactccg ccttcttcga aaccgtatat cagcgcggta      720
agctctaatg gcgttactgt cagcgcacca cctacggtac ttgatgaatt cgtcgagacc      780
tgcatttcca agaattacaa gccagtgaag gcccctattc atggcccgta ccatgcgcca      840
catctgtatg atgataagga tatcgaccgc atcctgcagc agtcctctgc tctagaagga      900
ctgaccggct gttcacccgt tattcccatc atctccagta acactggaaa gccgatcaag      960
gccaagtcca tcaaagatct cttcaaggtc gcactggagg agatactcct acgacgacta     1020
tgctgggaca aggtcacgga gtcctgcaca tcagtctgca agaccggcac aaaccactct     1080
tgcaaattgt ttccgatctc gagtagcgcc actcaaagtt tgttcacagt cctcaagaag     1140
gccggtgtga gcatcagctt ggagactggg gtaggagaga tcgcgacgaa cccagaaatg     1200
cggaacctta ctggcaaggc agaaaattca aagattgcta tcattggtat gtctggaaga     1260
tttcctgact cggatggtac ggagagcttc tggaacctcc tgtacaaagg actcgacgta     1320
catcgcaaag tccccgcaga ccgttgggac gttgatgccc acgtcgacat gaccgggtca     1380
aagagaaaca caagcaaagt ggcttacggt tgctggatca acgaacccgg cctgtttgac     1440
ccccgattct tcaacatgtc gcctcgggaa gcactccaag cagatcctgc acaacgtctt     1500
gcgttgctta cagcgtacga ggctctcgag atggctggct tcatcccgga tagctctcca     1560
tcgacgcaga gggaccgtgt gggtattttc tacggaatga ccagtgacga ctaccgtgag     1620
atcaacagcg gccaggacat tgatacctat ttcatccctg gcggtaaccg agcatttacg     1680
ccgggtcgga taaactacta cttcaaattt agcggcccca gtgtgagcgt tgacacagcg     1740
tgctcgtcta gtcttgctgc tatccacatg gcttgcaatt cgatctggag aaatgactgc     1800
gatgccgcca tcactggagg tgtgaacatt ctgaccagcc ctgacaacca cgccggtctg     1860
gatcggggcc atttcctgtc caccactggc aactgtaaca cctttgatga cggcgccgac     1920
ggctactgta gagcggacgg agttggaagc atcgttttga agcggcttga agatgccgag     1980
gccgacaacg acccgatcct ggccgtcatc aacggtgctt acaccaacca ctcggcggag     2040
gccgtgtcaa tcactcgtcc ccatgttggc gcgcaagcat tcatcttcaa caagctgctc     2100
aatgatgcga atatcgaccc taaggacgtg agctacgtgg aaatgcatgg cactggaact     2160
caagcaggtg atgcagtcga aatgcagtcc gttcttgacg tcttcgcacc agactaccgc     2220
cggggtcccg gtcaatcgct tcatatcggt tctgccaagg caaacattgg acacggtgaa     2280
tccgcatcag gagtgactgc tcttgtcaag gtcctcctaa tgatgagaga gaacatgatt     2340
cctcctcatt gtggtatcaa gaccaagatc aattccaatt tcccgacaga cttggcgaag     2400
cgcaatgttc atatcgcctt ccaacccact ccctggaatc ggccagcttc aggaaagcgg     2460
cgaactttcg tcaacaactt ttctgctgct ggtggtaaca ctgctcttct actggaagat     2520
gctcccatac cggaacgcca agggcaggac cccaggtcgt tccatttggt ctccgtgtca     2580
```

-continued

```
gcaagatccc agtctgcatt gaagaacaac gtcgaagctc tggtgaagta cattgactct    2640
cagggcaagt cctttggtgt gaaagagact gaattccttc caaacctggc gtacacgacc    2700
accgcacgcc gtatccacca tcccttccgt gtcattgcgg ttggagcgaa cctacaatca    2760
ctgcgtgact cgctgcatgg tgctttgcac cgtgagacat ataccccagt tccctcaacg    2820
gctcctggta ttggtttcgt cttcaccggc caaggagccc aatactccgg aatgggcaag    2880
gaactctacc gcagttgttt ccaattccga accaccattg agcattttga ctgcatcgca    2940
agaagccagg gccttccttc tatccttcct cttgtcgatg gaagcgtggc tgtcgaagaa    3000
cttagccctg tcgtggtaca agtgggaact acctgtgtac aaatggctct agtaaattac    3060
tggactgctc tgggtgtgaa gccggccttt atcatcggac acagtcttgg agactatgca    3120
gcccttaaca cggccggtgt tctatccacc agcgatacaa tctatctttg tggccggcgt    3180
gctcagttgc tgacgaagga atgcaagatt gggacacatt cgatgctggc catcaaggcg    3240
tccctggcag aggtcaaaca tttcctcaga gacgagctcc acgaagtctc ttgtgttaac    3300
gcacctgcgg agaccgtcgt cagcggcctt gtcgctgata tcgacgagtt ggctcagaaa    3360
tgctccacag agggtttgaa gtcaaccaag ctcaaggttc cttacgcgtt ccattcctct    3420
caggttgatc ctatcttgga ggccttcgaa gatattgccc aaggtgtcac cttccacaag    3480
ccgacaacac ctttcgtctc agccctgttc ggggaagtga tcaccgatgc taactgggag    3540
tgtctcggcc ccaagtacct gcgcgatcat tgcagaaaga cggtcaactt ccttggcggc    3600
gtggaggcta cgaggcatgc gaagctgacc aatgacaaga ctctgtgggt tgagatcggc    3660
tcacatacca tttgctctgg aatgatcaaa gcaactcttg accgcaagt tacaacggtt    3720 gcatctctac gccgcgaaga agataccctgg aaggtccttt cgaacagtct tgcgagcctt    3780
catctggcgg gtattgatat caactggaag caatatcacc aggactttag ctcctctctc    3840
caggtcctcc gcctcccagc ctacaagtgg gatctcaaga actactggat tccctatacc    3900
aacaacttct gcctgagcaa gggcgctcca gttgcgacag tagcggcagg gccacagcat    3960
gagtacctga caaccgcggc tcagaaggtc attgagactc gaagtgatgg agcaacagct    4020
acagtcgtga tagagaacga cattgctgat cccgagctca accgcgtcat tcaaggccat    4080
aaggtcaacg gtactgcttt gtgtccctca gtaagttacc gctcttgccc aacgactgcg    4140
ttaagattcg tactaatcag gatatagtca ctatatgccg acatctctca aacgcttgca    4200
gagtatctca tcaaaaagta caagcctgag tacgacggac ttggactgga tgtgtgtgag    4260
gtcacagtgc cacgaccact gattgcgaaa ggcggacagc agctctttag agtatctgcg    4320
acagcggatt gggcggagaa gaagacaacc cttcagatat attcagtcac tgcggagggg    4380
aagaagacgg ctgaccacgc aacttgcact gtccgattct ttgactgcgc tgctgcggag    4440
gcggaatgga aacgagtttc ctaccttgtc aagaggagca ttgaccgact gcatgatatc    4500
gccgaaaatg gtgacgctca ccgtcttggt agaggcatgg tttacaaact cttcgctgcc    4560
ttggttgatt atgacgacaa cttcaagtcc attcgcgagg ttattcttga cagtgaacag    4620
cacgaagcga ctgcacgcgt caagttccaa gcaccacaag gcaatttcca ccgaaacccg    4680
ttctggattg acagttttgg acacctgtct gggttcatca tgaacgcaag cgatgcaacc    4740
gactccaaga accaggtctt tgtcaatcac ggatgggact ccatgcgttg tttgaagaag    4800
ttctcgcctg atgtcaccta caggacttat gttagaatgc agccttggaa agactccatc    4860
tgggctggtg atgtctacgt tttcgatggg gatgatatcg ttgcggtgta tggtgcagtc    4920
aaggtgagtt cggcccgcgc tcagttgcat aagattcaag gtgctaatca ttggtgtcac    4980
```

-continued

```
agttccaagc cttatcacgc aagattctcg atacggtcct acctccagtt ggggcttcga    5040
agggccccgc cagaccagcc gctagcgctc agaaggcggc ccctgctgct gctgccagca    5100
agagtcgtgc tagcgccccg gccccggcga agcctgctgc taagcccagc gccccaagct    5160
tggtcaaacg ggcacttacc atcctcgcag aggaagtggg tctgtctgaa tccgagatta    5220
cggatgatct ggtcttcgca gactacggtg tggactccct tctttcgttg acggtcacgg    5280
gcaggtatcg tgaagagctg gatatcgatc tcgaatcctc catcttcatc gaccagccga    5340
ccgtgaaaga cttcaagcag ttcttggccc caatgagcca gggagaagcc agcgatgggt    5400
ccaccagtga cccagagtct agtagctcct tcaatggtgg ctcttcaaca gacgagtcca    5460
gtgctgggtc ccctgtcagc tcaccaccaa atgagaaggt tacgcaggtc gagcagcatg    5520
ctacgataaa ggagattcgc gccattttgg ccgatgagat tggtgttacg gaggaggagc    5580
tgaaggacga tgagaacttg ggagagatgg ggatggactc tctgctttcg cttacggtgc    5640
ttggtaggat ccgtgagaca ttggatctgg atctaccggg cgagttcttc atcgagaatc    5700
aaactctgaa tgacgtggag gatgcattgg gcctcaaacc caaggcagct cctgcgcctg    5760
cgcctgcgcc tgctcccgta cccgcacccg tgtccgcgcc catattgaag gagcctgtcc    5820
ccaacgcaaa ctctaccatc atggcccggg cgagcccgca ccctcgatca acctccattc    5880
tgttgcaagg aaacccgaaa accgcgacca agacctgtt cctgttccct gatgggtctg    5940
gctccgcaac atcgtatgca accattcccg gagtgtcccc ggacgtgtgt gtctacggat    6000
tgaactgccc gtacatgaag actccagaga agctcaagta tccccttgct gagatgacat    6060 tccctatct ggccgagatc cgccgcagac agcccaaggg cccgtacaac ttcggtggat    6120
ggtctgcagg tggtatttgc gcctatgatg ccgctcgcta cctaatcctt gaagagggcg    6180
aacaggttga ccgattgctt cttcttgact cgcccttccc cattggctta gagaagttgc    6240
ccactcggct gtacggcttc atcaactcaa tgggtctctt tggtgaaggc aacaaggctc    6300
ccccggcctg gttgctccct catttcctgg ccttcattga ttccctcgat acctacaagg    6360 ccgtcccccct cccctttgac gatccgaagt gggccaagaa gatgccaaag acattcatgg    6420
tctgggccaa ggacggtatc tgcagcaagc cggatgaccc gtggcccgag ccggacccgg    6480
acggcaagcc ggacacgaga gagatggtct ggctcctcaa gaaccggacc gacatgggac    6540
ccaacaagtg ggacacactc gtcgggcccc aaaacgtcgg tggaatcact gtgatagagg    6600
gtgcgaatca tttcaccatg actttgggac ccaaggctaa agaattgggc tcgttcattg    6660
gcaacgccat ggccaattaa                                               6680
```

<210> SEQ ID NO 38
<211> LENGTH: 20
<212> TYPE: DNA
<213> ORGANISM: Artificial Sequence
<220> FEATURE:
<223> OTHER INFORMATION: Primer pks_seq_f2

<400> SEQUENCE: 38

```
tcatatcggt tctgccaagg                                                20
```

<210> SEQ ID NO 39
<211> LENGTH: 20
<212> TYPE: DNA
<213> ORGANISM: Artificial Sequence
<220> FEATURE:
<223> OTHER INFORMATION: Primer pks_R -continued

<400> SEQUENCE: 39
gttgttgacg aaagttcgcc                                                    20

<210> SEQ ID NO 40
<211> LENGTH: 20
<212> TYPE: DNA
<213> ORGANISM: Artificial Sequence
<220> FEATURE:
<223> OTHER INFORMATION: Primer pks_F

<400> SEQUENCE: 40
actgcgactg ggaatctgcg                                                    20

<210> SEQ ID NO 41
<211> LENGTH: 23
<212> TYPE: DNA
<213> ORGANISM: Artificial Sequence
<220> FEATURE:
<223> OTHER INFORMATION: Primer pks_seq_r3

<400> SEQUENCE: 41
cttgtaattc ttggaaatgc agg                                                23

<210> SEQ ID NO 42
<211> LENGTH: 31
<212> TYPE: DNA
<213> ORGANISM: Artificial Sequence
<220> FEATURE:
<223> OTHER INFORMATION: Primer BsrGI-3UTR-fwd

<400> SEQUENCE: 42
gtctaatgta cagcggacat cgatttatg c                                        31

<210> SEQ ID NO 43
<211> LENGTH: 32
<212> TYPE: DNA
<213> ORGANISM: Artificial Sequence
<220> FEATURE:
<223> OTHER INFORMATION: Primer NheI-FRT-rev

<400> SEQUENCE: 43
agcagagcta gcgaagttcc tatactttct ag                                      32

<210> SEQ ID NO 44
<211> LENGTH: 30
<212> TYPE: DNA
<213> ORGANISM: Artificial Sequence
<220> FEATURE:
<223> OTHER INFORMATION: Primer Ex-UGItop-fwd

<400> SEQUENCE: 44
atgatctcta gaggctccgg aaccaacctg                                         30

<210> SEQ ID NO 45
<211> LENGTH: 25
<212> TYPE: DNA
<213> ORGANISM: Artificial Sequence
<220> FEATURE:
<223> OTHER INFORMATION: Primer UGIend-rev

<400> SEQUENCE: 45
aaatcgaatg tccgctgtac attag                                              25

<210> SEQ ID NO 46
<211> LENGTH: 5340

-continued

<212> TYPE: DNA
<213> ORGANISM: Artificial Sequence
<220> FEATURE:
<223> OTHER INFORMATION: dCas9-AID-UGI_coding

<400> SEQUENCE: 46

```
atggacaaga agtatagcat cgggctggcc attggaacga actcggttgg ttgggctgtg       60
attacggacg aatacaaggt gccatccaag aagtttaagg tcctgggaaa caccgaccgt      120
cactcaatca agaagaatct cattggagcc ctgctcttcg atagtgggga gaccgccgaa      180
gctactcgac tgaagcgaac ggctcgccgg cgttatacac gacgcaagaa tcgcatctgc      240
tacctccagg agattttcag caacgaaatg gctaaggttg atgactcatt ctttcatcga      300
ctcgaagaaa gtttcttggt cgaggaggat aagaagcacg agcgccatcc gatctttggt      360
aacattgtgg atgaggttgc ctatcacgaa aagtacccaa ctatctatca tcttcgtaag      420
aagctggtcg atagcacgga caaggctgat ttgcgactta tctacctggc actcgcgcac      480
atgattaagt ccgcggcca ttttcttatc gagggtgacc tgaaccccga taattctgac      540
gttgataagc tcttcatcca gttggtccaa acctacaatc agctgtttga ggaaaaccct      600
attaatgcat ctggcgtgga cgccaaggct atcctttcgg cgcgcctgtc taagtcgcgg      660
cgtttggaga accttatcgc acaactcccc ggcgaaaaga agaacggcct cttcggtaat      720
ttgattgcgt tgtcacttgg tctgactcct aacttcaaga gtaattttga cctggcagag      780
gatgcgaagc tccagttgtc taaggatacg tatgatgacg atctcgacaa cttgcttgcc      840
caaatcggtg accagtacgc tgatcttttc ctggccgcta agaatctctc agatgcaatc      900
ctgctcagtg acattttgcg ggtcaacacc gagattacta aggcccccct gtcagctagt      960
atgatcaagc ggtatgatga gcaccatcag gacctcacct tgcttaaggc cctcgtgcgt     1020
cagcaattgc ctgagaagta caaggaaatc ttctttgacc aatccaagaa cggatacgca     1080
gggtatattg atggcggtgc gagccaggag gaattctaca agtttatcaa gccgattttg     1140
gagaagatgg acggcactga ggaactgctc gtcaagctga atcgcgaaga tttgcttcgt     1200
aagcaacgaa cgttcgacaa cggctccatc ccgcaccaga ttcatctggg cgagctccac     1260
gccatccttc gacgccagga agatttctac ccatttctga aggacaaccg tgagaagatc     1320
gaaaagattc ttacattccg aatccctac tatgtgggac ctttggcccg tgggaattcc     1380
cgatttgctt ggatgacccg aaagagcgag gaaaccatca ctccgtggaa cttcgaggaa     1440
gtcgtggaca agggtgcatc cgcgcagagc ttcattgagc ggatgaccaa ttttgataag     1500
aaccttccga tgaaaaggt cctgccaaag cattcgctgc tctacgagta tttcaccgtg     1560
tataacgaac tgactaaggt caagtacgtg acggagggaa tgcggaagcc agccttcctc     1620 tcagggaac aaaagaaggc tatcgtcgat ttgcttttta agaccaatcg taaagtgact     1680
gttaagcagc tgaaggagga ttatttcaag aagattgaat gtttcgactc cgtcgagatc     1740
agcggcgtgg aagatcgctt taacgcttcc ctcggtacct accacgacct gctcaagatc     1800
attaaggaca aggatttcct cgataacgag gaaaatgagg acatcttgga agatattgtc     1860
ctcacgttga cactttttga ggaccgcgaa atgatcgagg aacggctcaa gacatatgcc     1920
catttgttcg acgataaggt gatgaagcag ctgagcggc gtcgatacac cggatggggt     1980
cgccttagcc ggaagctgat caacggcatt cgagataagc aatctggtaa gactatcttg     2040
gatttcctta gtcggacggg cttcgccaac cgcaattttta tgcagcttat tcacgacgat     2100
tccctgacgt tcaaggagga catccagaag gcacaagtct caggacaagg ggattccctg     2160
```

-continued

```
cacgagcata tcgccaacct ggctggatcc ccggcgatca agaaggggat tcttcagacc    2220
gtcaaggttg tcgacgagct ggtcaaggtg atgggccgtc ataagccaga aaacatcgtg    2280
attgagatgg cccgagaaaa tcagaccact caaaagggtc agaagaacag ccgcgagcgg    2340
atgaagcgga tcgaggaagg cattaaggaa cttggttctc agatcctgaa ggagcaccct    2400
gttgaaaaca cacagctcca aaatgagaag ctgtatctct actatttgca aaatggacgc    2460
gacatgtacg tcgatcagga gctcgacatt aaccggttgt cggactacga tgttgacgct    2520
atcgtcccgc aatccttcct taaggacgat agcattgata acaaggtgct gactcgctca    2580
gataagaacc ggggcaagtc cgacaatgtt ccaagcgagg aagtggttaa gaagatgaag    2640
aactactggc gccaattgct taatgccaag ctcatcacac agcgcaagtt tgacaacttg    2700
accaaggccg agcggggagg gctgagtgaa ctcgataagg ctggcttcat caagcgtcaa    2760
ctcgtggaga cgcgacagat cacaaagcac gttgctcaga ttctggactc ccggatgaac    2820
acaaagtacg acgagaatga taagctcatc cgtgaagtta aggtcattac cctcaagtct    2880
aagttggtgt cggatttccg caaggacttc caattttata aggttcggga gatcaacaat    2940
tatcaccatg cacatgatgc gtacctcaac gcagtcgtgg gaactgcgct catcaagaag    3000
tatcccaagt tggagtccga attcgtctac ggggattata aggtttacga cgtccgcaag    3060
atgatcgcca agagtgagca ggaaattggc aaggccacgg ctaagtattt cttttactcc    3120
aacatcatga atttctttaa gacggagatc acactcgcca atggagaaat ccgtaagcga    3180
cctttgattg agaccaacgg cgagactggt gaaatcgttt gggataaggg cgcgacttc     3240 gctaccgtgc ggaaggttct gagcatgccg caagtcaata tcgtcaagaa aaccgaggtg    3300
cagacaggcg gtttctctaa ggaatcgatt cttccaaagc gtaactctga caagctgatc    3360
gctcgaaaga aggattggga ccccaagaag tatggagggt tcgattctcc tacagtggca    3420
tactcggttc tcgttgtcgc gaaggttgag aagggaaagt ctaagaagct gaagtcggtc    3480
aaggaactgc tcgggatcac cattatggag cgctccagct tcgaaaagaa tcccatcgac    3540
tttctcgagg ccaagggcta taaggaagtc aagaaggatc ttatcattaa gctgcctaag    3600
tactctttgt tcgagcttga aaacggtcga aagcgaatgc tcgcatcggc aggagagttg    3660 cagaaggggga atgaattggc acttccctca aagtacgtga acttcctgta tctcgcgtcc    3720
cactacgaga agctgaaggg tagccctgag gacaacgaac agaagcaact ttttgttgag    3780
caacacaagc attatctgga tgagatcatt gaacagattt cagagttcag taagcgcgtc    3840
atcctcgccg atgctaatct cgacaaggtg ttgtcggcct acaacaagca ccgtgacaag    3900
ccgatccgag agcaggctga aaatatcatt catctgttca ccctcactaa cttgggagca    3960
ccagcagcgt tcaagtattt tgatacgaca atcgaccgta agcgatacac gtccacaaag    4020
gaggtgcttg atgcgaccct gattcatcaa tccatcactg gctctatga aacccgtatc     4080 gaccttagtc aactgggggg cgacagcagg gctgacccca agaagaagag gaaggtgggt    4140
ggaggaggtt ctggaggtgg aggttctgca gagtatgtgc gggccctctt tgactttaat    4200
gggaatgatg aagaagacct tcccttttaag aaaggagaca tcctgagaat ccgggataag    4260
cctgaagagc agtggtggaa tgcagaggac agcgaaggaa agagggggat gattcctgtc    4320
ccttacgtgg agaagtattc cggagactat aaggaccacg acggagacta caaggatcat    4380
gatattgatt acaaagacga tgacgataag tctaggatga ccgacgctga gtacgtgaga    4440
atccatgaga agttggacat ctacacgttt aagaaacagt ttttcaacaa caaaaaatcc    4500
gtgtcgcata gatgctacgt tctctttgaa ttaaaacgac ggggtgaacg tagagcgtgt    4560
```

```
ttttggggct atgctgtgaa taaaccacag agcgggacag aacgtggcat tcacgccgaa    4620
atctttagca ttagaaaagt cgaagaatac ctgcgcgaca accccggaca attcacgata    4680
aattggtact catcctggag tccttgtgca gattgcgctg aaaaaatctt agaatggtat    4740
aaccaggagc tgcgggggaa cggccacact ttgaaaatct gggcttgcaa actctattac    4800
gagaaaaatg cgaggaatca aattgggctg tggaacctca gagataacgg ggttgggttg    4860
aatgtaatgg taagtgaaca ctaccaatgt tgcaggaaaa tattcatcca atcgtcgcac    4920
aatcaattga atgagaatag atggcttgag aagactttga agcgagctga aaaacgacgg    4980
agcgagttgt ccattatgat tcaggtaaaa atactccaca ccactaagag tcctgctgtt    5040
tctagaggct ccggaaccaa cctgtccgac atcatcgaga aggagaccgg caagcagctc    5100
gttatccagg agtccatcct gatgctgccc gaggaggtcg aggaggtcat cggcaacaag    5160
cccgagtccg acatcctggt ccacaccgcc tacgacgagt ccaccgacga gaacgtcatg    5220
ctgctgacct ccgacgcccc cgagtacaag ccctgggccc tggtcatcca ggactccaac    5280
ggcgagaaca agatcaagat gctgtccggc ggctccccca agaagaagcg caaggtctaa    5340
```

<210> SEQ ID NO 47
<211> LENGTH: 1779
<212> TYPE: PRT
<213> ORGANISM: Artificial Sequence
<220> FEATURE:
<223> OTHER INFORMATION: dCas9-AID-UGI_protein

<400> SEQUENCE: 47

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

-continued

```
Leu Ile Ala Gln Leu Pro Gly Glu Lys Lys Asn Gly Leu Phe Gly Asn
225             230             235             240

Leu Ile Ala Leu Ser Leu Gly Leu Thr Pro Asn Phe Lys Ser Asn Phe
            245             250             255

Asp Leu Ala Glu Asp Ala Lys Leu Gln Leu Ser Lys Asp Thr Tyr Asp
            260             265             270

Asp Asp Leu Asp Asn Leu Leu Ala Gln Ile Gly Asp Gln Tyr Ala Asp
            275             280             285

Leu Phe Leu Ala Ala Lys Asn Leu Ser Asp Ala Ile Leu Leu Ser Asp
    290             295             300

Ile Leu Arg Val Asn Thr Glu Ile Thr Lys Ala Pro Leu Ser Ala Ser
305             310             315             320

Met Ile Lys Arg Tyr Asp Glu His His Gln Asp Leu Thr Leu Leu Lys
            325             330             335

Ala Leu Val Arg Gln Gln Leu Pro Glu Lys Tyr Lys Glu Ile Phe Phe
            340             345             350

Asp Gln Ser Lys Asn Gly Tyr Ala Gly Tyr Ile Asp Gly Gly Ala Ser
            355             360             365

Gln Glu Glu Phe Tyr Lys Phe Ile Lys Pro Ile Leu Glu Lys Met Asp
    370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
    450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
    530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
    610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
```

-continued

```
                      645                   650                   655

Thr Gly Trp Gly Arg Leu Ser Arg Lys Leu Ile Asn Gly Ile Arg Asp
              660                   665                   670

Lys Gln Ser Gly Lys Thr Ile Leu Asp Phe Leu Lys Ser Asp Gly Phe
              675                   680                   685

Ala Asn Arg Asn Phe Met Gln Leu Ile His Asp Asp Ser Leu Thr Phe
          690                   695                   700

Lys Glu Asp Ile Gln Lys Ala Gln Val Ser Gly Gln Gly Asp Ser Leu
      705                   710                   715                   720

His Glu His Ile Ala Asn Leu Ala Gly Ser Pro Ala Ile Lys Lys Gly
                  725                   730                   735

Ile Leu Gln Thr Val Lys Val Val Asp Glu Leu Val Lys Val Met Gly
                  740                   745                   750

Arg His Lys Pro Glu Asn Ile Val Ile Glu Met Ala Arg Glu Asn Gln
                  755                   760                   765

Thr Thr Gln Lys Gly Gln Lys Asn Ser Arg Glu Arg Met Lys Arg Ile
          770                   775                   780

Glu Glu Gly Ile Lys Glu Leu Gly Ser Gln Ile Leu Lys Glu His Pro
      785                   790                   795                   800

Val Glu Asn Thr Gln Leu Gln Asn Glu Lys Leu Tyr Leu Tyr Tyr Leu
                  805                   810                   815

Gln Asn Gly Arg Asp Met Tyr Val Asp Gln Glu Leu Asp Ile Asn Arg
                  820                   825                   830

Leu Ser Asp Tyr Asp Val Asp Ala Ile Val Pro Gln Ser Phe Leu Lys
                  835                   840                   845

Asp Asp Ser Ile Asp Asn Lys Val Leu Thr Arg Ser Asp Lys Asn Arg
          850                   855                   860

Gly Lys Ser Asp Asn Val Pro Ser Glu Glu Val Val Lys Lys Met Lys
      865                   870                   875                   880

Asn Tyr Trp Arg Gln Leu Leu Asn Ala Lys Leu Ile Thr Gln Arg Lys
                  885                   890                   895

Phe Asp Asn Leu Thr Lys Ala Glu Arg Gly Gly Leu Ser Glu Leu Asp
                  900                   905                   910

Lys Ala Gly Phe Ile Lys Arg Gln Leu Val Glu Thr Arg Gln Ile Thr
                  915                   920                   925

Lys His Val Ala Gln Ile Leu Asp Ser Arg Met Asn Thr Lys Tyr Asp
          930                   935                   940

Glu Asn Asp Lys Leu Ile Arg Glu Val Lys Val Ile Thr Leu Lys Ser
      945                   950                   955                   960

Lys Leu Val Ser Asp Phe Arg Lys Asp Phe Gln Phe Tyr Lys Val Arg
                  965                   970                   975

Glu Ile Asn Asn Tyr His His Ala His Asp Ala Tyr Leu Asn Ala Val
                  980                   985                   990

Val Gly Thr Ala Leu Ile Lys Lys Tyr Pro Lys Leu Glu Ser Glu Phe
          995                   1000                  1005

Val Tyr Gly Asp Tyr Lys Val Tyr Asp Val Arg Lys Met Ile Ala
      1010                  1015                  1020

Lys Ser Glu Gln Glu Ile Gly Lys Ala Thr Ala Lys Tyr Phe Phe
      1025                  1030                  1035

Tyr Ser Asn Ile Met Asn Phe Phe Lys Thr Glu Ile Thr Leu Ala
      1040                  1045                  1050

Asn Gly Glu Ile Arg Lys Arg Pro Leu Ile Glu Thr Asn Gly Glu
      1055                  1060                  1065
```

-continued

```
Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

Ser Arg Ala Asp Pro Lys Lys Lys Arg Lys Val Gly Gly Gly Gly
    1370            1375            1380

Ser Gly Gly Gly Ser Ala Glu Tyr Val Arg Ala Leu Phe Asp
    1385            1390            1395

Phe Asn Gly Asn Asp Glu Glu Asp Leu Pro Phe Lys Lys Gly Asp
    1400            1405            1410

Ile Leu Arg Ile Arg Asp Lys Pro Glu Glu Gln Trp Trp Asn Ala
    1415            1420            1425

Glu Asp Ser Glu Gly Lys Arg Gly Met Ile Pro Val Pro Tyr Val
    1430            1435            1440

Glu Lys Tyr Ser Gly Asp Tyr Lys Asp His Asp Gly Asp Tyr Lys
    1445            1450            1455
```

-continued

```
Asp His  Asp Ile Asp Tyr Lys  Asp Asp Asp Lys  Ser Arg Met
    1460             1465             1470

Thr Asp  Ala Glu Tyr Val Arg  Ile His Glu Lys Leu  Asp Ile Tyr
    1475             1480             1485

Thr Phe  Lys Lys Gln Phe Phe  Asn Asn Lys Lys Ser  Val Ser His
    1490             1495             1500

Arg Cys  Tyr Val Leu Phe Glu  Leu Lys Arg Arg Gly  Glu Arg Arg
    1505             1510             1515

Ala Cys  Phe Trp Gly Tyr Ala  Val Asn Lys Pro Gln  Ser Gly Thr
    1520             1525             1530

Glu Arg  Gly Ile His Ala Glu  Ile Phe Ser Ile Arg  Lys Val Glu
    1535             1540             1545

Glu Tyr  Leu Arg Asp Asn Pro  Gly Gln Phe Thr Ile  Asn Trp Tyr
    1550             1555             1560

Ser Ser  Trp Ser Pro Cys Ala  Asp Cys Ala Glu Lys  Ile Leu Glu
    1565             1570             1575

Trp Tyr  Asn Gln Glu Leu Arg  Gly Asn Gly His Thr  Leu Lys Ile
    1580             1585             1590

Trp Ala  Cys Lys Leu Tyr Tyr  Glu Lys Asn Ala Arg  Asn Gln Ile
    1595             1600             1605

Gly Leu  Trp Asn Leu Arg Asp  Asn Gly Val Gly Leu  Asn Val Met
    1610             1615             1620

Val Ser  Glu His Tyr Gln Cys  Cys Arg Lys Ile Phe  Ile Gln Ser
    1625             1630             1635

Ser His  Asn Gln Leu Asn Glu  Asn Arg Trp Leu Glu  Lys Thr Leu
    1640             1645             1650

Lys Arg  Ala Glu Lys Arg Arg  Ser Glu Leu Ser Ile  Met Ile Gln
    1655             1660             1665

Val Lys  Ile Leu His Thr Thr  Lys Ser Pro Ala Val  Ser Arg Gly
    1670             1675             1680

Ser Gly  Thr Asn Leu Ser Asp  Ile Ile Glu Lys Glu  Thr Gly Lys
    1685             1690             1695

Gln Leu  Val Ile Gln Glu Ser  Ile Leu Met Leu Pro  Glu Glu Val
    1700             1705             1710

Glu Glu  Val Ile Gly Asn Lys  Pro Glu Ser Asp Ile  Leu Val His
    1715             1720             1725

Thr Ala  Tyr Asp Glu Ser Thr  Asp Glu Asn Val Met  Leu Leu Thr
    1730             1735             1740

Ser Asp  Ala Pro Glu Tyr Lys  Pro Trp Ala Leu Val  Ile Gln Asp
    1745             1750             1755

Ser Asn  Gly Glu Asn Lys Ile  Lys Met Leu Ser Gly  Gly Ser Pro
    1760             1765             1770

Lys Lys  Lys Arg Lys Val
    1775
```

<210> SEQ ID NO 48
<211> LENGTH: 20
<212> TYPE: DNA
<213> ORGANISM: Artificial Sequence
<220> FEATURE:
<223> OTHER INFORMATION: Primer pks_seq_r1

<400> SEQUENCE: 48
atttgcaaga gtggtttgtg                                          20

<210> SEQ ID NO 49
<211> LENGTH: 3792
<212> TYPE: DNA
<213> ORGANISM: Artificial Sequence
<220> FEATURE:
<223> OTHER INFORMATION: Mad7_coding

<400> SEQUENCE: 49

```
atgaacaacg gcacaaacaa cttccagaac ttcattggaa tctcgtcgtt gcagaagact      60
ttgcgcaacg ccctcatccc cacagaaact acccagcagt tcattgtgaa gaacggaatc     120
atcaaggaag atgaactccg aggcgagaac cgccagattt tgaaggacat catggatgat     180
tactaccgtg gtttcatctc ggaaacgctc tcctccattg acgacatcga ttggacttcg     240
ttgttcgaaa agatggaaat ccagctcaaa aacggcgata acaaggatac cttgatcaag     300
gagcagaccg agtatcggaa ggcgatccat aagaagttcg ccaacgatga tcggttcaag     360
aacatgttct cggccaagtt gatttccgac attctccccg aattcgtgat ccataacaac     420
aactactcgg cgtcggagaa ggaggagaag acgcaggtca tcaagttgtt ctcgaggttc     480
gccacatcgt tcaaagacta tttttaagaat cgtgcgaact gtttctcggc agatgatatc     540
tcctcgtcct cctgtcaccg cattgtgaac gacaacgcgg aaatcttctt ctcgaacgcg     600
ttggtgtata ggcgcatcgt gaagtccctc tccaacgatg acatcaacaa aatctcggga     660
gatatgaagg attcgctcaa ggagatgtcg ttggaggaaa tctactccta tgagaagtat     720
ggcgagttca ttacgcagga gggcatttcc ttctacaacg acatttgtgg taaagtcaac     780
tcgttcatga acctctactg tcagaaaaac aaggagaaca aaaacctcta taagctccag     840
aagttgcata agcagatcct ctgtatcgca gacacctcgt acgaggtccc ttacaagttc     900
gaatccgatg aggaggtcta ccagtccgtc aacggattct tggacaacat ctcctcgaaa     960
cacattgtcg agcggctccg aaagatcggc gataactaca acggctacaa cttggacaaa    1020
atctatatcg tctccaagtt ctatgagtcc gtctcgcaga aaacctatcg tgattgggag    1080
actatcaaca ctgcgctcga gattcactat aacaacatct gcctggtaa cggcaaatcg    1140 aaagccgaca aggtgaagaa ggccgtgaaa aacgatctcc agaagtcgat cacagaaatc    1200
aacgaactcg tctcgaacta caagctctgt tcggatgata catcaaggc ggaaacgtac    1260 atccatgaaa tctcgcatat cttgaacaac ttcgaggccc aggaactcaa atacaacccc    1320
gagatccact tggtcgagtc ggagctcaaa gcctcggagt tgaagaacgt cttggatgtc    1380
atcatgaacg cattccactg gtgttccgtg ttcatgaccg aggaactcgt cgataaagac    1440
aacaacttct acgcggaact cgaggaaatc tacgatgaaa tctatcccgt gatctccctc    1500
tacaacctcg tgcgaaacta cgtcactcag aagccctatt ccaccaagaa gatcaagctc    1560
aacttcggca tccccactct cgcagacggt tggtcgaagt cgaaggagta ctccaacaac    1620
gccattatcc tcatgcgaga caacctctac tacttgggta tcttcaacgc aaagaacaag    1680
ccggataaga agatcattga aggcaacact tcggaaaaca ggggagacta taagaagatg    1740
atctacaacc tcctccctgg acccaacaag atgattccta aagtgttcct ctcgtcgaag    1800
actggtgtgg aaacgtataa gccgtcggcc tacatcttgg agggctacaa acagaacaag    1860
catatcaagt cctcgaagga cttcgacatc actttctgtc acgacctcat cgactatttc    1920
aagaactgta ttgcaatcca tccggaatgg aagaacttcg gcttcgattt ctcggatact    1980
tcgacatacg aagatatctc gggattctac cgagaggtcg aattgcaggg ctataagatt    2040
gattggacct acatctcgga aaaggatatc gacttgctcc aggaaaaggg ccagctctac    2100
```

-continued

```
ctcttccaga tttacaacaa ggacttctcc aagaagtcga cgggtaacga caacttgcac      2160
acaatgtatc tcaaaaacct cttctcggag gagaacttga aggatatcgt gctcaaattg      2220
aacggagagg ccgaaatctt cttccgtaag tcctccatca agaacccgat catccataag      2280
aagggatcga tcttggtcaa ccggacttac gaagcagagg aaaaagatca gttcggaaac      2340
atccagattg tcaggaagaa catccctgaa aacatctatc aggagttgta taagtacttc      2400
aacgacaagt cggataagga gctctccgac gaagcagcca aactcaagaa cgtcgtcgga      2460
caccatgaag cagcaaccaa cattgtgaag gactaccggt acacttacga caagtacttc      2520
ttgcacatgc cgatcactat caacttcaaa gccaacaaga ccggattcat taacgacagg      2580
atcctccagt acattgccaa agaaaaggac ctccatgtca tcggtatcga caggggagaa      2640
cggaacctca tctacgtctc cgtgattgac acttgtggca acattgtcga acagaagtcg      2700
ttcaacatcg tcaacggtta cgattaccag attaagttga aacagcagga aggtgcgagg      2760
cagattgcgc gaaaggaatg gaaggagatt ggcaaaatca aggagattaa ggaaggctac      2820
ttgtcgttgg tcatccacga aatctcgaaa atggtgatca aatacaacgc catcatcgcc      2880
atggaagacc tctcgtacgg cttcaaaaag ggacggttca agtggagcg tcaggtgtac       2940 cagaagttcg aaacaatgtt gatcaacaag ttgaactact tggtgttcaa ggacatttcc      3000
attaccgaga acggaggatt gctcaagggt tatcagctca cgtacatccc cgacaagttg      3060
aaaaacgtgg gacaccagtg tggctgtatc ttctacgtgc ctgcagccta cacgtcgaaa      3120
atcgacccta caacaggatt cgtgaacatc ttcaagttca aggatctcac cgtcgacgcg      3180
aagcgggagt tcatcaaaaa gttcgactcc atccgctatg attcggagaa gaacttgttc      3240
tgtttcacat tcgactacaa caacttcatt actcagaaca ccgtgatgtc caaatcgtcg      3300
tggtccgtgt acacgtatgg tgtgcgcatc aaaaggcgct tcgtcaacgg tcgcttctcc      3360
aacgaatcgg acacgatcga tatcacgaaa gacatggaga aaacattgga aatgaccgac      3420
atcaactggc gtgacggcca tgacctcagg caggacatca tcgattacga gatcgtccag      3480
cacatcttcg aaatcttccg tctcaccgtg cagatgagga actccctctc cgagctcgaa      3540
gatcgggatt acgaccggct catttcccct gtgttgaacg agaacaacat cttctacgac      3600
tcggcaaaag cgggagatgc attgccgaag gacgccgatg cgaacggtgc atattgtatt      3660
gcactcaagg gtctctacga aatcaagcag atcaccgaaa actggaagga ggacggcaaa      3720
ttctcgaggg acaagttgaa gatttcgaac aaggattggt tcgatttcat ccagaacaag      3780
aggtacttgt aa                                                          3792
```

<210> SEQ ID NO 50
<211> LENGTH: 1263
<212> TYPE: PRT
<213> ORGANISM: Eubacterium rectale

<400> SEQUENCE: 50

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
```

-continued

```
65                   70                   75                   80

Leu Phe Glu Lys Met Glu Ile Gln Leu Lys Asn Gly Asp Asn Lys Asp
                85                   90                   95

Thr Leu Ile Lys Glu Gln Thr Glu Tyr Arg Lys Ala Ile His Lys Lys
                100                  105                  110

Phe Ala Asn Asp Asp Arg Phe Lys Asn Met Phe Ser Ala Lys Leu Ile
                115                  120                  125

Ser Asp Ile Leu Pro Glu Phe Val Ile His Asn Asn Asn Tyr Ser Ala
        130                  135                  140

Ser Glu Lys Glu Glu Lys Thr Gln Val Ile Lys Leu Phe Ser Arg Phe
145                  150                  155                  160

Ala Thr Ser Phe Lys Asp Tyr Phe Lys Asn Arg Ala Asn Cys Phe Ser
                165                  170                  175

Ala Asp Asp Ile Ser Ser Ser Ser Cys His Arg Ile Val Asn Asp Asn
                180                  185                  190

Ala Glu Ile Phe Phe Ser Asn Ala Leu Val Tyr Arg Arg Ile Val Lys
                195                  200                  205

Ser Leu Ser Asn Asp Asp Ile Asn Lys Ile Ser Gly Asp Met Lys Asp
        210                  215                  220

Ser Leu Lys Glu Met Ser Leu Glu Glu Ile Tyr Ser Tyr Glu Lys Tyr
225                  230                  235                  240

Gly Glu Phe Ile Thr Gln Glu Gly Ile Ser Phe Tyr Asn Asp Ile Cys
                245                  250                  255

Gly Lys Val Asn Ser Phe Met Asn Leu Tyr Cys Gln Lys Asn Lys Glu
                260                  265                  270

Asn Lys Asn Leu Tyr Lys Leu Gln Lys Leu His Lys Gln Ile Leu Cys
                275                  280                  285

Ile Ala Asp Thr Ser Tyr Glu Val Pro Tyr Lys Phe Glu Ser Asp Glu
        290                  295                  300

Glu Val Tyr Gln Ser Val Asn Gly Phe Leu Asp Asn Ile Ser Ser Lys
305                  310                  315                  320

His Ile Val Glu Arg Leu Arg Lys Ile Gly Asp Asn Tyr Asn Gly Tyr
                325                  330                  335

Asn Leu Asp Lys Ile Tyr Ile Val Ser Lys Phe Tyr Glu Ser Val Ser
                340                  345                  350

Gln Lys Thr Tyr Arg Asp Trp Glu Thr Ile Asn Thr Ala Leu Glu Ile
                355                  360                  365

His Tyr Asn Asn Ile Leu Pro Gly Asn Gly Lys Ser Lys Ala Asp Lys
        370                  375                  380

Val Lys Lys Ala Val Lys Asn Asp Leu Gln Lys Ser Ile Thr Glu Ile
385                  390                  395                  400

Asn Glu Leu Val Ser Asn Tyr Lys Leu Cys Ser Asp Asp Asn Ile Lys
                405                  410                  415

Ala Glu Thr Tyr Ile His Glu Ile Ser His Ile Leu Asn Asn Phe Glu
                420                  425                  430

Ala Gln Glu Leu Lys Tyr Asn Pro Glu Ile His Leu Val Glu Ser Glu
        435                  440                  445

Leu Lys Ala Ser Glu Leu Lys Asn Val Leu Asp Val Ile Met Asn Ala
        450                  455                  460

Phe His Trp Cys Ser Val Phe Met Thr Glu Glu Leu Val Asp Lys Asp
465                  470                  475                  480

Asn Asn Phe Tyr Ala Glu Leu Glu Glu Ile Tyr Asp Glu Ile Tyr Pro
                485                  490                  495
```

-continued

```
Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
                755                 760                 765

Thr Tyr Glu Ala Glu Glu Lys Asp Gln Phe Gly Asn Ile Gln Ile Val
            770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910
```

-continued

```
Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
        930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
                980                 985                 990

Tyr Leu Val Phe Lys Asp Ile Ser  Ile Thr Glu Asn Gly  Gly Leu Leu
        995                 1000                 1005

Lys Gly  Tyr Gln Leu Thr Tyr  Ile Pro Asp Lys Leu  Lys Asn Val
    1010                 1015                 1020

Gly His  Gln Cys Gly Cys Ile  Phe Tyr Val Pro Ala  Ala Tyr Thr
    1025                 1030                 1035

Ser Lys  Ile Asp Pro Thr Thr  Gly Phe Val Asn Ile  Phe Lys Phe
    1040                 1045                 1050

Lys Asp  Leu Thr Val Asp Ala  Lys Arg Glu Phe Ile  Lys Lys Phe
    1055                 1060                 1065

Asp Ser  Ile Arg Tyr Asp Ser  Glu Lys Asn Leu Phe  Cys Phe Thr
    1070                 1075                 1080

Phe Asp  Tyr Asn Asn Phe Ile  Thr Gln Asn Thr Val  Met Ser Lys
    1085                 1090                 1095

Ser Ser  Trp Ser Val Tyr Thr  Tyr Gly Val Arg Ile  Lys Arg Arg
    1100                 1105                 1110

Phe Val  Asn Gly Arg Phe Ser  Asn Glu Ser Asp Thr  Ile Asp Ile
    1115                 1120                 1125

Thr Lys  Asp Met Glu Lys Thr  Leu Glu Met Thr Asp  Ile Asn Trp
    1130                 1135                 1140

Arg Asp  Gly His Asp Leu Arg  Gln Asp Ile Ile Asp  Tyr Glu Ile
    1145                 1150                 1155

Val Gln  His Ile Phe Glu Ile  Phe Arg Leu Thr Val  Gln Met Arg
    1160                 1165                 1170

Asn Ser  Leu Ser Glu Leu Glu  Asp Arg Asp Tyr Asp  Arg Leu Ile
    1175                 1180                 1185

Ser Pro  Val Leu Asn Glu Asn  Asn Ile Phe Tyr Asp  Ser Ala Lys
    1190                 1195                 1200

Ala Gly  Asp Ala Leu Pro Lys  Asp Ala Asp Ala Asn  Gly Ala Tyr
    1205                 1210                 1215

Cys Ile  Ala Leu Lys Gly Leu  Tyr Glu Ile Lys Gln  Ile Thr Glu
    1220                 1225                 1230

Asn Trp  Lys Glu Asp Gly Lys  Phe Ser Arg Asp Lys  Leu Lys Ile
    1235                 1240                 1245

Ser Asn  Lys Asp Trp Phe Asp  Phe Ile Gln Asn Lys  Arg Tyr Leu
    1250                 1255                 1260
```

```
<210> SEQ ID NO 51
<211> LENGTH: 192
<212> TYPE: PRT
<213> ORGANISM: Artificial Sequence
<220> FEATURE:
<223> OTHER INFORMATION: LbCpf1_partial_protein

<400> SEQUENCE: 51
```

-continued

```
Ile Tyr Asn Lys Asp Phe Ser Asp Lys Ser His Gly Thr Pro Asn Leu
1               5                   10                  15

His Thr Met Tyr Phe Lys Leu Leu Phe Asp Glu Asn Asn His Gly Gln
            20                  25                  30

Ile Arg Leu Ser Gly Gly Ala Glu Leu Phe Met Arg Arg Ala Ser Leu
        35                  40                  45

Lys Lys Glu Glu Leu Val Val His Pro Ala Asn Ser Pro Ile Ala Asn
    50                  55                  60

Lys Asn Pro Asp Asn Pro Lys Lys Thr Thr Thr Leu Ser Tyr Asp Val
65                  70                  75                  80

Tyr Lys Asp Lys Arg Phe Ser Glu Asp Gln Tyr Glu Leu His Ile Pro
                85                  90                  95

Ile Ala Ile Asn Lys Cys Pro Lys Asn Ile Phe Lys Ile Asn Thr Glu
                100                 105                 110

Val Arg Val Leu Leu Lys His Asp Asp Asn Pro Tyr Val Ile Gly Ile
                115                 120                 125

Asp Arg Gly Glu Arg Asn Leu Leu Tyr Ile Val Val Val Asp Gly Lys
        130                 135                 140

Gly Asn Ile Val Glu Gln Tyr Ser Leu Asn Glu Ile Ile Asn Asn Phe
145                 150                 155                 160

Asn Gly Ile Arg Ile Lys Thr Asp Tyr His Ser Leu Leu Asp Lys Lys
                165                 170                 175

Glu Lys Glu Arg Phe Glu Ala Arg Gln Asn Trp Thr Ser Ile Glu Asn
                180                 185                 190
```

```
<210> SEQ ID NO 52
<211> LENGTH: 189
<212> TYPE: PRT
<213> ORGANISM: Artificial Sequence
<220> FEATURE:
<223> OTHER INFORMATION: FnCpf1_partial_protein

<400> SEQUENCE: 52
```

```
Ile Tyr Asn Lys Asp Phe Ser Ala Tyr Ser Lys Gly Arg Pro Asn Leu
1               5                   10                  15

His Thr Leu Tyr Trp Lys Ala Leu Phe Asp Glu Arg Asn Leu Gln Asp
            20                  25                  30

Val Val Tyr Lys Leu Asn Gly Glu Ala Glu Leu Phe Tyr Arg Lys Gln
        35                  40                  45

Ser Ile Pro Lys Lys Ile Thr His Pro Ala Lys Glu Ala Ile Ala Asn
    50                  55                  60

Lys Asn Lys Asp Asn Pro Lys Lys Glu Ser Val Phe Glu Tyr Asp Leu
65                  70                  75                  80

Ile Lys Asp Lys Arg Phe Thr Glu Asp Lys Phe Phe Phe His Cys Pro
                85                  90                  95

Ile Thr Ile Asn Phe Lys Ser Ser Gly Ala Asn Lys Phe Asn Asp Glu
                100                 105                 110

Ile Asn Leu Leu Leu Lys Glu Lys Ala Asn Asp Val His Ile Leu Ser
                115                 120                 125

Ile Asp Arg Gly Glu Arg His Leu Ala Tyr Tyr Thr Leu Val Asp Gly
        130                 135                 140

Lys Gly Asn Ile Ile Lys Gln Asp Thr Phe Asn Ile Ile Gly Asn Asp
145                 150                 155                 160

Arg Met Lys Thr Asn Tyr His Asp Lys Leu Ala Ala Ile Glu Lys Asp
                165                 170                 175
```

-continued

```
Arg Asp Ser Ala Arg Lys Asp Trp Lys Lys Ile Asn Asn
            180                 185

<210> SEQ ID NO 53
<211> LENGTH: 229
<212> TYPE: PRT
<213> ORGANISM: Artificial Sequence
<220> FEATURE:
<223> OTHER INFORMATION: Mad7_partial_protein

<400> SEQUENCE: 53

Ile Tyr Asn Lys Asp Phe Ser Lys Lys Ser Thr Gly Asn Asp Asn Leu
1               5                   10                  15

His Thr Met Tyr Leu Lys Asn Leu Phe Ser Glu Glu Asn Leu Lys Asp
            20                  25                  30

Ile Val Leu Lys Leu Asn Gly Glu Ala Glu Ile Phe Phe Arg Lys Ser
        35                  40                  45

Ser Ile Lys Asn Pro Ile Ile His Lys Lys Gly Ser Ile Leu Val Asn
    50                  55                  60

Arg Thr Tyr Glu Ala Glu Glu Lys Asp Gln Phe Gly Asn Ile Gln Ile
65                  70                  75                  80

Val Arg Lys Asn Ile Pro Glu Asn Ile Tyr Gln Glu Leu Tyr Lys Tyr
                85                  90                  95

Phe Asn Asp Lys Ser Asp Lys Glu Leu Ser Asp Glu Ala Ala Lys Leu
            100                 105                 110

Lys Asn Val Val Gly His His Glu Ala Ala Thr Asn Ile Val Lys Asp
            115                 120                 125

Tyr Arg Tyr Thr Tyr Asp Lys Tyr Phe Leu His Met Pro Ile Thr Ile
            130                 135                 140

Asn Phe Lys Ala Asn Lys Thr Gly Phe Ile Asn Asp Arg Ile Leu Gln
145                 150                 155                 160

Tyr Ile Ala Lys Glu Lys Asp Leu His Val Ile Gly Ile Asp Arg Gly
                165                 170                 175

Glu Arg Asn Leu Ile Tyr Val Ser Val Ile Asp Thr Cys Gly Asn Ile
            180                 185                 190

Val Glu Gln Lys Ser Phe Asn Ile Val Asn Gly Tyr Asp Tyr Gln Ile
            195                 200                 205

Lys Leu Lys Gln Gln Glu Gly Ala Arg Gln Ile Ala Arg Lys Glu Trp
    210                 215                 220

Lys Glu Ile Gly Lys
225

<210> SEQ ID NO 54
<211> LENGTH: 26
<212> TYPE: DNA
<213> ORGANISM: Artificial Sequence
<220> FEATURE:
<223> OTHER INFORMATION: Primer IF-Ptef-rev

<400> SEQUENCE: 54
ggtgaaggtt gtgttatgtt ttgtgg                                        26

<210> SEQ ID NO 55
<211> LENGTH: 21
<212> TYPE: DNA
<213> ORGANISM: Artificial Sequence
<220> FEATURE:
<223> OTHER INFORMATION: Primer IF-nls-fwd

<400> SEQUENCE: 55
```

-continued agcagggctg accccaagaa g                                                          21

<210> SEQ ID NO 56
<211> LENGTH: 36
<212> TYPE: DNA
<213> ORGANISM: Artificial Sequence
<220> FEATURE:
<223> OTHER INFORMATION: Primer IF-PtfMd7-fwd

<400> SEQUENCE: 56
aacacaacct tcaccatgaa caacggcaca aacaac                                          36

<210> SEQ ID NO 57
<211> LENGTH: 36
<212> TYPE: DNA
<213> ORGANISM: Artificial Sequence
<220> FEATURE:
<223> OTHER INFORMATION: Primer IF-nlsMd7-rev

<400> SEQUENCE: 57
ggggtcagcc ctgctaggca agtacctctt gttctg                                          36

<210> SEQ ID NO 58
<211> LENGTH: 88
<212> TYPE: DNA
<213> ORGANISM: Artificial Sequence
<220> FEATURE:
<223> OTHER INFORMATION: Primer sg-site_fwd

<400> SEQUENCE: 58
ttcgattcac ggatgatgca gtcaaaagac ctttttaatt tctactcttg tagatagatc              60
ttttttttgg ctcttgggtt cgaactgc                                                   88

<210> SEQ ID NO 59
<211> LENGTH: 130
<212> TYPE: DNA
<213> ORGANISM: Artificial Sequence
<220> FEATURE:
<223> OTHER INFORMATION: Primer sg-site_rev

<400> SEQUENCE: 59
tttggcttcg gaaagcacac gtgaagggta ggaacaaaga tggaatgatt ggcaggggtg              60
acccaaatgg tggggcataa aaaaaaagat gaccaaaaca tgggccttgg gcagttcgaa             120
cccaagagcc                                                                       130

<210> SEQ ID NO 60
<211> LENGTH: 35
<212> TYPE: DNA
<213> ORGANISM: Artificial Sequence
<220> FEATURE:
<223> OTHER INFORMATION: Mad7 sgRNA backbone

<400> SEQUENCE: 60
gtcaaaagac ctttttaatt tctactcttg tagat                                           35

<210> SEQ ID NO 61
<211> LENGTH: 5028
<212> TYPE: DNA
<213> ORGANISM: Artificial Sequence
<220> FEATURE:
<223> OTHER INFORMATION: Mad7d-AID-UGI_coding

<400> SEQUENCE: 61

-continued

```
atgaacaacg gcacaaacaa cttccagaac ttcattggaa tctcgtcgtt gcagaagact        60
ttgcgcaacg ccctcatccc cacagaaact acccagcagt tcattgtgaa gaacggaatc       120
atcaaggaag atgaactccg aggcgagaac cgccagattt tgaaggacat catggatgat       180
tactaccgtg gtttcatctc ggaaacgctc tcctccattg acgacatcga ttggacttcg       240
ttgttcgaaa agatggaaat ccagctcaaa aacggcgata acaaggatac cttgatcaag       300
gagcagaccg agtatcggaa ggcgatccat aagaagttcg ccaacgatga tcggttcaag       360
aacatgttct cggccaagtt gatttccgac attctccccg aattcgtgat ccataacaac       420
aactactcgg cgtcggagaa ggaggagaag acgcaggtca tcaagttgtt ctcgaggttc       480
gccacatcgt tcaaagacta tttttaagaat cgtgcgaact gtttctcggc agatgatatc       540
tcctcgtcct cctgtcaccg cattgtgaac gacaacgcgg aaatcttctt ctcgaacgcg       600
ttggtgtata ggcgcatcgt gaagtccctc tccaacgatg acatcaacaa aatctcggga       660
gatatgaagg attcgctcaa ggagatgtcg ttggaggaaa tctactccta tgagaagtat       720
ggcgagttca ttacgcagga gggcatttcc ttctacaacg acatttgtgg taaagtcaac       780
tcgttcatga acctctactg tcagaaaaac aaggagaaca aaaacctcta taagctccag       840
aagttgcata agcagatcct ctgtatcgca gacacctcgt acgaggtccc ttacaagttc       900
gaatccgatg aggaggtcta ccagtccgtc aacggattct tggacaacat ctcctcgaaa       960
cacattgtcg agcggctccg aaagatcggc gataactaca acggctacaa cttggacaaa      1020
atctatatcg tctccaagtt ctatgagtcc gtctcgcaga aaacctatcg tgattgggag      1080
actatcaaca ctgcgctcga gattcactat aacaacatct tgcctggtaa cggcaaatcg      1140
aaagccgaca aggtgaagaa ggccgtgaaa aacgatctcc agaagtcgat cacagaaatc      1200
aacgaactcg tctcgaacta caagctctgt tcggatgata acatcaaggc ggaaacgtac      1260
atccatgaaa tctcgcatat cttgaacaac ttcgaggccc aggaactcaa atacaacccc      1320
gagatccact tggtcgagtc ggagctcaaa gcctcggagt tgaagaacgt cttggatgtc      1380
atcatgaacg cattccactg gtgttccgtg ttcatgaccg aggaactcgt cgataaagac      1440
aacaacttct acgcggaact cgaggaaatc tacgatgaaa tctatcccgt gatctccctc      1500
tacaacctcg tgcgaaacta cgtcactcag aagccctatt ccaccaagaa gatcaagctc      1560
aacttcggca tccccactct cgcagacggt tggtcgaagt cgaaggagta ctccaacaac      1620
gccattatcc tcatgcgaga caacctctac tacttgggta tcttcaacgc aaagaacaag      1680
ccggataaga agatcattga aggcaacact tcggaaaaca agggagacta taagaagatg      1740
atctacaacc tcctccctgg acccaacaag atgattccta aagtgttcct ctcgtcgaag      1800
actggtgtgg aaacgtataa gccgtcggcc tacatcttgg agggctacaa acagaacaag      1860
catatcaagt cctcgaagga cttcgacatc actttctgtc acgacctcat cgactatttc      1920
aagaactgta ttgcaatcca tccggaatgg aagaacttcg gcttcgattt ctcggatact      1980
tcgacatacg aagatatctc gggattctac cgagaggtcg aattgcaggg ctataagatt      2040
gattggacct acatctcgga aaaggatatc gacttgctcc aggaaaaggg ccagctctac      2100
ctcttccaga tttacaacaa ggacttctcc aagaagtcga cgggtaacga caacttgcac      2160
acaatgtatc tcaaaaacct cttctcggag gagaacttga aggatatcgt gctcaaattg      2220
aacggagagg ccgaaatctt cttccgtaag tcctccatca agaacccgat catccataag      2280
aagggatcga tcttggtcaa ccggacttac gaagcagagg aaaaagatca gttcggaaac      2340
atccagattg tcaggaagaa catccctgaa aacatctatc aggagttgta taagtacttc      2400
```

-continued

```
aacgacaagt cggataagga gctctccgac gaagcagcca aactcaagaa cgtcgtcgga    2460
caccatgaag cagcaaccaa cattgtgaag gactaccggt acacttacga caagtacttc    2520
ttgcacatgc cgatcactat caacttcaaa gccaacaaga ccggattcat taacgacagg    2580
atcctccagt acattgccaa agaaaaggac ctccatgtca tcggtatcgc gaggggagaa    2640
cggaacctca tctacgtctc cgtgattgac acttgtggca acattgtcga acagaagtcg    2700
ttcaacatcg tcaacggtta cgattaccag attaagttga aacagcagga aggtgcgagg    2760
cagattgcgc gaaaggaatg gaaggagatt ggcaaaatca aggagattaa ggaaggctac    2820
ttgtcgttgg tcatccacga aatctcgaaa atggtgatca aatacaacgc catcatcgcc    2880
atggaagacc tctcgtacgg cttcaaaaag ggacggttca aagtggagcg tcaggtgtac    2940
cagaagttcg aaacaatgtt gatcaacaag ttgaactact tggtgttcaa ggacatttcc    3000
attaccgaga acggaggatt gctcaagggt tatcagctca cgtacatccc cgacaagttg    3060
aaaaacgtgg gacaccagtg tggctgtatc ttctacgtgc ctgcagccta cacgtcgaaa    3120
atcgacccta caacaggatt cgtgaacatc ttcaagttca aggatctcac cgtcgacgcg    3180
aagcgggagt tcatcaaaaa gttcgactcc atccgctatg attcggagaa gaacttgttc    3240
tgtttcacat tcgactacaa caacttcatt actcagaaca ccgtgatgtc caaatcgtcg    3300
tggtccgtgt acacgtatgg tgtgcgcatc aaaaggcgct tcgtcaacgg tcgcttctcc    3360
aacgaatcgg acacgatcga tatcacgaaa gacatggaga aaacattgga aatgaccgac    3420
atcaactggc gtgacggcca tgacctcagg caggacatca tcgattacga gatcgtccag    3480
cacatcttcg aaatcttccg tctcaccgtg cagatgagga actccctctc cgagctcgaa    3540
gatcgggatt acgaccggct catttccect gtgttgaacg agaacaacat cttctacgac    3600
tcggcaaaag cgggagatgc attgccgaag gacgccgatg cgaacggtgc atattgtatt    3660
gcactcaagg gtctctacga aatcaagcag atcaccgaaa actggaagga ggacggcaaa    3720
ttctcgaggg acaagttgaa gatttcgaac aaggattggt tcgatttcat ccagaacaag    3780
aggtacttgc ctagcagggc tgaccccaag aagaagagga aggtgggtgg aggaggttct    3840
ggaggtggag gttctgcaga gtatgtgcgg gccctctttg actttaatgg gaatgatgaa    3900
gaagaccttc cctttaagaa aggagacatc ctgagaatcc gggataagcc tgaagagcag    3960
tggtggaatg cagaggacag cgaaggaaag aggggggatga ttcctgtccc ttacgtggag    4020
aagtattccg gagactataa ggaccacgac ggagactaca aggatcatga tattgattac    4080
aaagacgatg acgataagtc taggatgacc gacgctgagt acgtgagaat ccatgagaag    4140
ttggacatct acacgtttaa gaaacagttt tccaacaaca aaaaatccgt gtcgcataga    4200
tgctacgttc tctttgaatt aaaacgacgg ggtgaacgta gagcgtgttt ttggggctat    4260
gctgtgaata aaccacagag cgggacagaa cgtggcattc acgccgaaat ctttagcatt    4320
agaaaagtcg aagaatacct gcgcgacaac cccggacaat tcacgataaa ttggtactca    4380
tcctggagtc cttgtgcaga ttgcgctgaa aaaatcttag aatggtataa ccaggagctg    4440 cggggggaacg gccacacttt gaaaatctgg gcttgcaaac tctattacga gaaaaatgcg    4500
aggaatcaaa ttgggctgtg gaacctcaga gataacgggg ttgggttgaa tgtaatggta    4560
agtgaacact accaatgttg caggaaaata ttcatccaat cgtcgcacaa tcaattgaat    4620
gagaatagat ggcttgagaa gactttgaag cgagctgaaa aacgacggag cgagttgtcc    4680
attatgattc aggtaaaaat actccacacc actaagagtc ctgctgtttc tagaggctcc    4740
```

-continued

```
ggaaccaacc tgtccgacat catcgagaag gagaccggca agcagctcgt tatccaggag        4800
tccatcctga tgctgcccga ggaggtcgag gaggtcatcg gcaacaagcc cgagtccgac        4860
atcctggtcc acaccgccta cgacgagtcc accgacgaga acgtcatgct gctgacctcc        4920
gacgcccccg agtacaagcc ctgggccctg gtcatccagg actccaacgg cgagaacaag        4980
atcaagatgc tgtccggcgg ctcccccaag aagaagcgca aggtctaa                     5028
```

<210> SEQ ID NO 62
<211> LENGTH: 1675
<212> TYPE: PRT
<213> ORGANISM: Artificial Sequence
<220> FEATURE:
<223> OTHER INFORMATION: Mad7d-AID-UGI_protein

<400> SEQUENCE: 62

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Asn Tyr Ser Ala
        130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
        210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320
```

-continued

```
His Ile Val Glu Arg Leu Arg Lys Ile Gly Asp Asn Tyr Asn Gly Tyr
            325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
            450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
            530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735
```

```
Val Leu Lys Leu Asn Gly Glu Ala Glu Ile Phe Phe Arg Lys Ser Ser
        740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Ala Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
        980                 985                 990

Tyr Leu Val Phe Lys Asp Ile Ser  Ile Thr Glu Asn Gly  Gly Leu Leu
        995                 1000                1005

Lys Gly  Tyr Gln Leu Thr Tyr  Ile Pro Asp Lys Leu  Lys Asn Val
    1010                1015                1020

Gly His  Gln Cys Gly Cys Ile  Phe Tyr Val Pro Ala  Ala Tyr Thr
    1025                1030                1035

Ser Lys  Ile Asp Pro Thr Thr  Gly Phe Val Asn Ile  Phe Lys Phe
    1040                1045                1050

Lys Asp  Leu Thr Val Asp Ala  Lys Arg Glu Phe Ile  Lys Lys Phe
    1055                1060                1065

Asp Ser  Ile Arg Tyr Asp Ser  Glu Lys Asn Leu Phe  Cys Phe Thr
    1070                1075                1080

Phe Asp  Tyr Asn Asn Phe Ile  Thr Gln Asn Thr Val  Met Ser Lys
    1085                1090                1095

Ser Ser  Trp Ser Val Tyr Thr  Tyr Gly Val Arg Ile  Lys Arg Arg
    1100                1105                1110

Phe Val  Asn Gly Arg Phe Ser  Asn Glu Ser Asp Thr  Ile Asp Ile
    1115                1120                1125

Thr Lys  Asp Met Glu Lys Thr  Leu Glu Met Thr Asp  Ile Asn Trp
    1130                1135                1140

Arg Asp  Gly His Asp Leu Arg  Gln Asp Ile Ile Asp  Tyr Glu Ile
```

```
            1145              1150              1155

Val Gln  His Ile Phe Glu Ile  Phe Arg Leu Thr Val  Gln Met Arg
    1160              1165              1170

Asn Ser  Leu Ser Glu Leu Glu  Asp Arg Asp Tyr Asp  Arg Leu Ile
    1175              1180              1185

Ser Pro  Val Leu Asn Glu Asn  Asn Ile Phe Tyr Asp  Ser Ala Lys
    1190              1195              1200

Ala Gly  Asp Ala Leu Pro Lys  Asp Ala Asp Ala Asn  Gly Ala Tyr
    1205              1210              1215

Cys Ile  Ala Leu Lys Gly Leu  Tyr Glu Ile Lys Gln  Ile Thr Glu
    1220              1225              1230

Asn Trp  Lys Glu Asp Gly Lys  Phe Ser Arg Asp Lys  Leu Lys Ile
    1235              1240              1245

Ser Asn  Lys Asp Trp Phe Asp  Phe Ile Gln Asn Lys  Arg Tyr Leu
    1250              1255              1260

Pro Ser  Arg Ala Asp Pro Lys  Lys Lys Arg Lys Val  Gly Gly Gly
    1265              1270              1275

Gly Ser  Gly Gly Gly Gly Ser  Ala Glu Tyr Val Arg  Ala Leu Phe
    1280              1285              1290

Asp Phe  Asn Gly Asn Asp Glu  Glu Asp Leu Pro Phe  Lys Lys Gly
    1295              1300              1305

Asp Ile  Leu Arg Ile Arg Asp  Lys Pro Glu Glu Gln  Trp Trp Asn
    1310              1315              1320

Ala Glu  Asp Ser Glu Gly Lys  Arg Gly Met Ile Pro  Val Pro Tyr
    1325              1330              1335

Val Glu  Lys Tyr Ser Gly Asp  Tyr Lys Asp His Asp  Gly Asp Tyr
    1340              1345              1350

Lys Asp  His Asp Ile Asp Tyr  Lys Asp Asp Asp Asp  Lys Ser Arg
    1355              1360              1365

Met Thr  Asp Ala Glu Tyr Val  Arg Ile His Glu Lys  Leu Asp Ile
    1370              1375              1380

Tyr Thr  Phe Lys Lys Gln Phe  Phe Asn Asn Lys Lys  Ser Val Ser
    1385              1390              1395

His Arg  Cys Tyr Val Leu Phe  Glu Leu Lys Arg Arg  Gly Glu Arg
    1400              1405              1410

Arg Ala  Cys Phe Trp Gly Tyr  Ala Val Asn Lys Pro  Gln Ser Gly
    1415              1420              1425

Thr Glu  Arg Gly Ile His Ala  Glu Ile Phe Ser Ile  Arg Lys Val
    1430              1435              1440

Glu Glu  Tyr Leu Arg Asp Asn  Pro Gly Gln Phe Thr  Ile Asn Trp
    1445              1450              1455

Tyr Ser  Ser Trp Ser Pro Cys  Ala Asp Cys Ala Glu  Lys Ile Leu
    1460              1465              1470

Glu Trp  Tyr Asn Gln Glu Leu  Arg Gly Asn Gly His  Thr Leu Lys
    1475              1480              1485

Ile Trp  Ala Cys Lys Leu Tyr  Tyr Glu Lys Asn Ala  Arg Asn Gln
    1490              1495              1500

Ile Gly  Leu Trp Asn Leu Arg  Asp Asn Gly Val Gly  Leu Asn Val
    1505              1510              1515

Met Val  Ser Glu His Tyr Gln  Cys Cys Arg Lys Ile  Phe Ile Gln
    1520              1525              1530

Ser Ser  His Asn Gln Leu Asn  Glu Asn Arg Trp Leu  Glu Lys Thr
    1535              1540              1545
```

-continued

```
Leu Lys  Arg Ala Glu Lys Arg  Arg Ser Glu Leu Ser  Ile Met Ile
    1550             1555          1560

Gln Val  Lys Ile Leu His Thr  Thr Lys Ser Pro Ala  Val Ser Arg
    1565             1570          1575

Gly Ser  Gly Thr Asn Leu Ser  Asp Ile Ile Glu Lys  Glu Thr Gly
    1580             1585          1590

Lys Gln  Leu Val Ile Gln Glu  Ser Ile Leu Met Leu  Pro Glu Glu
    1595             1600          1605

Val Glu  Glu Val Ile Gly Asn  Lys Pro Glu Ser Asp  Ile Leu Val
    1610             1615          1620

His Thr  Ala Tyr Asp Glu Ser  Thr Asp Glu Asn Val  Met Leu Leu
    1625             1630          1635

Thr Ser  Asp Ala Pro Glu Tyr  Lys Pro Trp Ala Leu  Val Ile Gln
    1640             1645          1650

Asp Ser  Asn Gly Glu Asn Lys  Ile Lys Met Leu Ser  Gly Gly Ser
    1655             1660          1665

Pro Lys  Lys Lys Arg Lys Val
    1670             1675

<210> SEQ ID NO 63
<211> LENGTH: 21
<212> TYPE: DNA
<213> ORGANISM: Artificial Sequence
<220> FEATURE:
<223> OTHER INFORMATION: Protospacer pTNA296 MdwA1

<400> SEQUENCE: 63
ttggagacca gaccagcgac a                                              21

<210> SEQ ID NO 64
<211> LENGTH: 21
<212> TYPE: DNA
<213> ORGANISM: Artificial Sequence
<220> FEATURE:
<223> OTHER INFORMATION: Protospacer pTNA297 MdwA2

<400> SEQUENCE: 64
gagaccagac cagcgacatc g                                              21

<210> SEQ ID NO 65
<211> LENGTH: 21
<212> TYPE: DNA
<213> ORGANISM: Artificial Sequence
<220> FEATURE:
<223> OTHER INFORMATION: Protospacer pTNA298 MdwA3

<400> SEQUENCE: 65
ttccagcaat gcttccatgc a                                              21

<210> SEQ ID NO 66
<211> LENGTH: 21
<212> TYPE: DNA
<213> ORGANISM: Artificial Sequence
<220> FEATURE:
<223> OTHER INFORMATION: Protospacer pTNA299 MdwA4

<400> SEQUENCE: 66
cagcaatgct tccatgcaat t                                              21

<210> SEQ ID NO 67
<211> LENGTH: 21
```

-continued

```
<212> TYPE: DNA
<213> ORGANISM: Artificial Sequence
<220> FEATURE:
<223> OTHER INFORMATION: Protospacer pTNA300 MdwA5

<400> SEQUENCE: 67
catgcaattc gtcaagagat c                                                    21

<210> SEQ ID NO 68
<211> LENGTH: 21
<212> TYPE: DNA
<213> ORGANISM: Artificial Sequence
<220> FEATURE:
<223> OTHER INFORMATION: Protospacer pTNA301 MdwA6

<400> SEQUENCE: 68
tcgagttcga gaactggtgg a                                                    21

<210> SEQ ID NO 69
<211> LENGTH: 21
<212> TYPE: DNA
<213> ORGANISM: Artificial Sequence
<220> FEATURE:
<223> OTHER INFORMATION: Protospacer pTNA302 MdwA7

<400> SEQUENCE: 69
cgatctcgag tagcgccact c                                                    21

<210> SEQ ID NO 70
<211> LENGTH: 21
<212> TYPE: DNA
<213> ORGANISM: Artificial Sequence
<220> FEATURE:
<223> OTHER INFORMATION: Protospacer pTNA303 MdwA8

<400> SEQUENCE: 70
atccctggcg gtaaccgagc a                                                    21

<210> SEQ ID NO 71
<211> LENGTH: 21
<212> TYPE: DNA
<213> ORGANISM: Artificial Sequence
<220> FEATURE:
<223> OTHER INFORMATION: Protospacer pTNA304 MdwA9

<400> SEQUENCE: 71
aggaaagcgg cgaactttcg t                                                    21

<210> SEQ ID NO 72
<211> LENGTH: 21
<212> TYPE: DNA
<213> ORGANISM: Artificial Sequence
<220> FEATURE:
<223> OTHER INFORMATION: Protospacer pTNA305 MdwA10

<400> SEQUENCE: 72
actgcatcgc aagaagccag g                                                    21

<210> SEQ ID NO 73
<211> LENGTH: 21
<212> TYPE: DNA
<213> ORGANISM: Artificial Sequence
<220> FEATURE:
<223> OTHER INFORMATION: Protospacer pTNA306 MdwA11

<400> SEQUENCE: 73
```
gccctgtcgt ggtacaagtg g                                          21

<210> SEQ ID NO 74
<211> LENGTH: 21
<212> TYPE: DNA
<213> ORGANISM: Artificial Sequence
<220> FEATURE:
<223> OTHER INFORMATION: Protospacer pTNA307 MdwA12

<400> SEQUENCE: 74
tggccggcgt gctcagttgc t                                          21

<210> SEQ ID NO 75
<211> LENGTH: 21
<212> TYPE: DNA
<213> ORGANISM: Artificial Sequence
<220> FEATURE:
<223> OTHER INFORMATION: Protospacer pTNA324 MdwA13

<400> SEQUENCE: 75
tacaggaggt tccagaagct c                                          21

<210> SEQ ID NO 76
<211> LENGTH: 21
<212> TYPE: DNA
<213> ORGANISM: Artificial Sequence
<220> FEATURE:
<223> OTHER INFORMATION: Protospacer pTNA325 MdwA14

<400> SEQUENCE: 76
tccagatcga attgcaagcc a                                          21

<210> SEQ ID NO 77
<211> LENGTH: 21
<212> TYPE: DNA
<213> ORGANISM: Artificial Sequence
<220> FEATURE:
<223> OTHER INFORMATION: Protospacer pTNA326 MdwA15

<400> SEQUENCE: 77
ctgaagctgg ccgattccag g                                          21

<210> SEQ ID NO 78
<211> LENGTH: 21
<212> TYPE: DNA
<213> ORGANISM: Artificial Sequence
<220> FEATURE:
<223> OTHER INFORMATION: Protospacer pTNA327 MdwA16

<400> SEQUENCE: 78
acacccagag cagtccagta a                                          21

<210> SEQ ID NO 79
<211> LENGTH: 21
<212> TYPE: DNA
<213> ORGANISM: Artificial Sequence
<220> FEATURE:
<223> OTHER INFORMATION: Protospacer pTNA328 MdwA17

<400> SEQUENCE: 79
gggccgagac actcccagtt a                                          21

<210> SEQ ID NO 80
<211> LENGTH: 21
<212> TYPE: DNA
<213> ORGANISM: Artificial Sequence -continued

```
<220> FEATURE:
<223> OTHER INFORMATION: Protospacer pTNA329 MdwA18

<400> SEQUENCE: 80
agatcccact tgtaggctgg g                                                       21

<210> SEQ ID NO 81
<211> LENGTH: 21
<212> TYPE: DNA
<213> ORGANISM: Artificial Sequence
<220> FEATURE:
<223> OTHER INFORMATION: Protospacer pTNA330 MdwA19

<400> SEQUENCE: 81
ttctccgccc aatccgctgt c                                                       21

<210> SEQ ID NO 82
<211> LENGTH: 61
<212> TYPE: DNA
<213> ORGANISM: Artificial Sequence
<220> FEATURE:
<223> OTHER INFORMATION: Primer 296-C9-sense

<400> SEQUENCE: 82
taatttctac tcttgtagat ttggagacca gaccagcgac attttttttgg ctcttgggtt           60 c                                                                            61

<210> SEQ ID NO 83
<211> LENGTH: 61
<212> TYPE: DNA
<213> ORGANISM: Artificial Sequence
<220> FEATURE:
<223> OTHER INFORMATION: Primer 296-C9-anti

<400> SEQUENCE: 83
gaacccaaga gccaaaaaaa tgtcgctggt ctggtctcca aatctacaag agtagaaatt           60
a                                                                            61

<210> SEQ ID NO 84
<211> LENGTH: 61
<212> TYPE: DNA
<213> ORGANISM: Artificial Sequence
<220> FEATURE:
<223> OTHER INFORMATION: Primer 297-C6-sense

<400> SEQUENCE: 84
taatttctac tcttgtagat gagaccagac cagcgacatc gttttttttgg ctcttgggtt           60 c                                                                            61

<210> SEQ ID NO 85
<211> LENGTH: 61
<212> TYPE: DNA
<213> ORGANISM: Artificial Sequence
<220> FEATURE:
<223> OTHER INFORMATION: Primer 297-C6-anti

<400> SEQUENCE: 85
gaacccaaga gccaaaaaaa cgatgtcgct ggtctggtct catctacaag agtagaaatt           60
a                                                                            61

<210> SEQ ID NO 86
<211> LENGTH: 61
<212> TYPE: DNA
```

-continued

```
<213> ORGANISM: Artificial Sequence
<220> FEATURE:
<223> OTHER INFORMATION: Primer 298-C4_7-sense

<400> SEQUENCE: 86
taatttctac tcttgtagat ttccagcaat gcttccatgc attttttttgg ctcttgggtt      60 c                                                                       61

<210> SEQ ID NO 87
<211> LENGTH: 61
<212> TYPE: DNA
<213> ORGANISM: Artificial Sequence
<220> FEATURE:
<223> OTHER INFORMATION: Primer 298-C4_7-anti

<400> SEQUENCE: 87
gaacccaaga gccaaaaaaa tgcatggaag cattgctgga aatctacaag agtagaaatt      60
a                                                                       61

<210> SEQ ID NO 88
<211> LENGTH: 61
<212> TYPE: DNA
<213> ORGANISM: Artificial Sequence
<220> FEATURE:
<223> OTHER INFORMATION: Primer 299-C1_4-sense

<400> SEQUENCE: 88
taatttctac tcttgtagat cagcaatgct tccatgcaat ttttttttgg ctcttgggtt      60
c                                                                       61

<210> SEQ ID NO 89
<211> LENGTH: 61
<212> TYPE: DNA
<213> ORGANISM: Artificial Sequence
<220> FEATURE:
<223> OTHER INFORMATION: Primer 299-C1_4-anti

<400> SEQUENCE: 89
gaacccaaga gccaaaaaaa aattgcatgg aagcattgct gatctacaag agtagaaatt      60
a                                                                       61

<210> SEQ ID NO 90
<211> LENGTH: 61
<212> TYPE: DNA
<213> ORGANISM: Artificial Sequence
<220> FEATURE:
<223> OTHER INFORMATION: Primer 300-C13-sense

<400> SEQUENCE: 90
taatttctac tcttgtagat catgcaattc gtcaagagat ctttttttgg ctcttgggtt      60
c                                                                       61

<210> SEQ ID NO 91
<211> LENGTH: 61
<212> TYPE: DNA
<213> ORGANISM: Artificial Sequence
<220> FEATURE:
<223> OTHER INFORMATION: Primer 300-C13-anti

<400> SEQUENCE: 91
gaacccaaga gccaaaaaaa gatctcttga cgaattgcat gatctacaag agtagaaatt      60
a                                                                       61
```

-continued

```
<210> SEQ ID NO 92
<211> LENGTH: 61
<212> TYPE: DNA
<213> ORGANISM: Artificial Sequence
<220> FEATURE:
<223> OTHER INFORMATION: Primer 301-C2_8-sense

<400> SEQUENCE: 92
taatttctac tcttgtagat tcgagttcga gaactggtgg atttttttgg ctcttgggtt     60
c                                                                      61

<210> SEQ ID NO 93
<211> LENGTH: 61
<212> TYPE: DNA
<213> ORGANISM: Artificial Sequence
<220> FEATURE:
<223> OTHER INFORMATION: Primer 301-C2_8-anti

<400> SEQUENCE: 93
gaacccaaga gccaaaaaaa tccaccagtt ctcgaactcg aatctacaag agtagaaatt     60
a                                                                      61

<210> SEQ ID NO 94
<211> LENGTH: 61
<212> TYPE: DNA
<213> ORGANISM: Artificial Sequence
<220> FEATURE:
<223> OTHER INFORMATION: Primer 302-C21-sense

<400> SEQUENCE: 94
taatttctac tcttgtagat cgatctcgag tagcgccact cttttttttgg ctcttgggtt    60 c                                                                      61

<210> SEQ ID NO 95
<211> LENGTH: 61
<212> TYPE: DNA
<213> ORGANISM: Artificial Sequence
<220> FEATURE:
<223> OTHER INFORMATION: Primer 302-C21-anti

<400> SEQUENCE: 95
gaacccaaga gccaaaaaaa gagtggcgct actcgagatc gatctacaag agtagaaatt     60
a                                                                      61

<210> SEQ ID NO 96
<211> LENGTH: 61
<212> TYPE: DNA
<213> ORGANISM: Artificial Sequence
<220> FEATURE:
<223> OTHER INFORMATION: Primer 303-C16-sense

<400> SEQUENCE: 96
taatttctac tcttgtagat atccctggcg gtaaccgagc attttttttgg ctcttgggtt    60 c                                                                      61

<210> SEQ ID NO 97
<211> LENGTH: 61
<212> TYPE: DNA
<213> ORGANISM: Artificial Sequence
<220> FEATURE:
<223> OTHER INFORMATION: Primer 303-C16-anti
```

```
<400> SEQUENCE: 97
gaacccaaga gccaaaaaaa tgctcggtta ccgccaggga tatctacaag agtagaaatt      60
a                                                                      61

<210> SEQ ID NO 98
<211> LENGTH: 61
<212> TYPE: DNA
<213> ORGANISM: Artificial Sequence
<220> FEATURE:
<223> OTHER INFORMATION: Primer 304-C11-sense

<400> SEQUENCE: 98
taatttctac tcttgtagat aggaaagcgg cgaactttcg ttttttttgg ctcttgggtt      60
c                                                                      61

<210> SEQ ID NO 99
<211> LENGTH: 61
<212> TYPE: DNA
<213> ORGANISM: Artificial Sequence
<220> FEATURE:
<223> OTHER INFORMATION: Primer 304-C11-anti

<400> SEQUENCE: 99
gaacccaaga gccaaaaaaa acgaaagttc gccgctttcc tatctacaag agtagaaatt      60
a                                                                      61

<210> SEQ ID NO 100
<211> LENGTH: 61
<212> TYPE: DNA
<213> ORGANISM: Artificial Sequence
<220> FEATURE:
<223> OTHER INFORMATION: Primer 305-C18-sense

<400> SEQUENCE: 100
taatttctac tcttgtagat actgcatcgc aagaagccag gttttttttgg ctcttgggtt     60 c                                                                      61

<210> SEQ ID NO 101
<211> LENGTH: 61
<212> TYPE: DNA
<213> ORGANISM: Artificial Sequence
<220> FEATURE:
<223> OTHER INFORMATION: Primer 305-C18-anti

<400> SEQUENCE: 101
gaacccaaga gccaaaaaaa cctggcttct tgcgatgcag tatctacaag agtagaaatt      60
a                                                                      61

<210> SEQ ID NO 102
<211> LENGTH: 61
<212> TYPE: DNA
<213> ORGANISM: Artificial Sequence
<220> FEATURE:
<223> OTHER INFORMATION: Primer 306-C15-sense

<400> SEQUENCE: 102
taatttctac tcttgtagat gccctgtcgt ggtacaagtg gttttttttgg ctcttgggtt     60 c                                                                      61

<210> SEQ ID NO 103
<211> LENGTH: 61
```

-continued

```
<212> TYPE: DNA
<213> ORGANISM: Artificial Sequence
<220> FEATURE:
<223> OTHER INFORMATION: Primer 306-C15-anti

<400> SEQUENCE: 103
gaacccaaga gccaaaaaaa ccacttgtac cacgacaggg catctacaag agtagaaatt        60
a                                                                        61

<210> SEQ ID NO 104
<211> LENGTH: 61
<212> TYPE: DNA
<213> ORGANISM: Artificial Sequence
<220> FEATURE:
<223> OTHER INFORMATION: Primer 307-C14-sense

<400> SEQUENCE: 104
taatttctac tcttgtagat tggccggcgt gctcagttgc ttttttttgg ctcttgggtt        60
c                                                                        61

<210> SEQ ID NO 105
<211> LENGTH: 61
<212> TYPE: DNA
<213> ORGANISM: Artificial Sequence
<220> FEATURE:
<223> OTHER INFORMATION: Primer 307-C14-anti

<400> SEQUENCE: 105
gaacccaaga gccaaaaaaa agcaactgag cacgccggcc aatctacaag agtagaaatt        60
a                                                                        61

<210> SEQ ID NO 106
<211> LENGTH: 61
<212> TYPE: DNA
<213> ORGANISM: Artificial Sequence
<220> FEATURE:
<223> OTHER INFORMATION: Primer 324-C12,13-sense

<400> SEQUENCE: 106
taatttctac tcttgtagat tacaggaggt tccagaagct ctttttttgg ctcttgggtt        60
c                                                                        61

<210> SEQ ID NO 107
<211> LENGTH: 61
<212> TYPE: DNA
<213> ORGANISM: Artificial Sequence
<220> FEATURE:
<223> OTHER INFORMATION: Primer 324-C12,13-anti

<400> SEQUENCE: 107
gaacccaaga gccaaaaaaa gagcttctgg aacctcctgt aatctacaag agtagaaatt        60
a                                                                        61

<210> SEQ ID NO 108
<211> LENGTH: 61
<212> TYPE: DNA
<213> ORGANISM: Artificial Sequence
<220> FEATURE:
<223> OTHER INFORMATION: Primer 325-C2,3-sense

<400> SEQUENCE: 108
taatttctac tcttgtagat tccagatcga attgcaagcc attttttttgg ctcttgggtt        60
```

-continued

```
c                                                                 61

<210> SEQ ID NO 109
<211> LENGTH: 61
<212> TYPE: DNA
<213> ORGANISM: Artificial Sequence
<220> FEATURE:
<223> OTHER INFORMATION: Primer 325-C2,3-anti

<400> SEQUENCE: 109
gaacccaaga gccaaaaaaa tggcttgcaa ttcgatctgg aatctacaag agtagaaatt    60
a                                                                 61

<210> SEQ ID NO 110
<211> LENGTH: 61
<212> TYPE: DNA
<213> ORGANISM: Artificial Sequence
<220> FEATURE:
<223> OTHER INFORMATION: Primer 326-C17,18-sense

<400> SEQUENCE: 110
taatttctac tcttgtagat ctgaagctgg ccgattccag gttttttttgg ctcttgggtt    60 c                                                                 61

<210> SEQ ID NO 111
<211> LENGTH: 61
<212> TYPE: DNA
<213> ORGANISM: Artificial Sequence
<220> FEATURE:
<223> OTHER INFORMATION: Primer 326-C17,18-anti

<400> SEQUENCE: 111
gaacccaaga gccaaaaaaa cctggaatcg gccagcttca gatctacaag agtagaaatt    60
a                                                                 61

<210> SEQ ID NO 112
<211> LENGTH: 61
<212> TYPE: DNA
<213> ORGANISM: Artificial Sequence
<220> FEATURE:
<223> OTHER INFORMATION: Primer 327-C15,16-sense

<400> SEQUENCE: 112
taatttctac tcttgtagat acacccagag cagtccagta attttttttgg ctcttgggtt    60 c                                                                 61

<210> SEQ ID NO 113
<211> LENGTH: 61
<212> TYPE: DNA
<213> ORGANISM: Artificial Sequence
<220> FEATURE:
<223> OTHER INFORMATION: Primer 327-C15,16-anti

<400> SEQUENCE: 113
gaacccaaga gccaaaaaaa ttactggact gctctgggtg tatctacaag agtagaaatt    60
a                                                                 61

<210> SEQ ID NO 114
<211> LENGTH: 61
<212> TYPE: DNA
<213> ORGANISM: Artificial Sequence
<220> FEATURE:
<223> OTHER INFORMATION: Primer 328-C15,16-2-sense
```

-continued

<400> SEQUENCE: 114
taatttctac tcttgtagat gggccgagac actcccagtt attttttttgg ctcttgggtt    60 c                                                                    61

<210> SEQ ID NO 115
<211> LENGTH: 61
<212> TYPE: DNA
<213> ORGANISM: Artificial Sequence
<220> FEATURE:
<223> OTHER INFORMATION: Primer 328-C15,16-2-anti

<400> SEQUENCE: 115
gaacccaaga gccaaaaaaa taactgggag tgtctcggcc catctacaag agtagaaatt    60
a                                                                    61

<210> SEQ ID NO 116
<211> LENGTH: 61
<212> TYPE: DNA
<213> ORGANISM: Artificial Sequence
<220> FEATURE:
<223> OTHER INFORMATION: Primer 329-C6,7-sense

<400> SEQUENCE: 116
taatttctac tcttgtagat agatcccact tgtaggctgg gttttttttgg ctcttgggtt    60 c                                                                    61

<210> SEQ ID NO 117
<211> LENGTH: 61
<212> TYPE: DNA
<213> ORGANISM: Artificial Sequence
<220> FEATURE:
<223> OTHER INFORMATION: Primer 329-C6,7-anti

<400> SEQUENCE: 117
gaacccaaga gccaaaaaaa cccagcctac aagtgggatc tatctacaag agtagaaatt    60
a                                                                    61

<210> SEQ ID NO 118
<211> LENGTH: 61
<212> TYPE: DNA
<213> ORGANISM: Artificial Sequence
<220> FEATURE:
<223> OTHER INFORMATION: Primer 330-C9,10-sense

<400> SEQUENCE: 118
taatttctac tcttgtagat ttctccgccc aatccgctgt cttttttttgg ctcttgggtt    60 c                                                                    61

<210> SEQ ID NO 119
<211> LENGTH: 61
<212> TYPE: DNA
<213> ORGANISM: Artificial Sequence
<220> FEATURE:
<223> OTHER INFORMATION: Primer 330-C9,10-anti

<400> SEQUENCE: 119
gaacccaaga gccaaaaaaa gacagcggat tgggcggaga aatctacaag agtagaaatt    60
a                                                                    61

<210> SEQ ID NO 120

-continued

```
<211> LENGTH: 21
<212> TYPE: DNA
<213> ORGANISM: Artificial Sequence
<220> FEATURE:
<223> OTHER INFORMATION: Primer pks_seq_f5

<400> SEQUENCE: 120
ttcttcaaca tgtcgcctcg g                                             21

<210> SEQ ID NO 121
<211> LENGTH: 19
<212> TYPE: DNA
<213> ORGANISM: Artificial Sequence
<220> FEATURE:
<223> OTHER INFORMATION: Primer Primer pks_seq_r6

<400> SEQUENCE: 121
gtgttacagt tgccagtgg                                                19

<210> SEQ ID NO 122
<211> LENGTH: 20
<212> TYPE: DNA
<213> ORGANISM: Artificial Sequence
<220> FEATURE:
<223> OTHER INFORMATION: Primer pks_seq_f4

<400> SEQUENCE: 122
ggtacttgat gaattcgtcg                                               20

<210> SEQ ID NO 123
<211> LENGTH: 22
<212> TYPE: DNA
<213> ORGANISM: Artificial Sequence
<220> FEATURE:
<223> OTHER INFORMATION: Primer MS-test-wA3

<400> SEQUENCE: 123
tgaattcaac tctttacaat cg                                            22

<210> SEQ ID NO 124
<211> LENGTH: 3792
<212> TYPE: DNA
<213> ORGANISM: Artificial Sequence
<220> FEATURE:
<223> OTHER INFORMATION: Mad7d coding sequence
<220> FEATURE:
<221> NAME/KEY: CDS
<222> LOCATION: (1)..(3792)

<400> SEQUENCE: 124 atg aac aac ggc aca aac aac ttc cag aac ttc att gga atc tcg tcg      48
Met Asn Asn Gly Thr Asn Asn Phe Gln Asn Phe Ile Gly Ile Ser Ser
1               5                   10                  15 ttg cag aag act ttg cgc aac gcc ctc atc ccc aca gaa act acc cag      96
Leu Gln Lys Thr Leu Arg Asn Ala Leu Ile Pro Thr Glu Thr Thr Gln
                20                  25                  30 cag ttc att gtg aag aac gga atc atc aag gaa gat gaa ctc cga ggc     144
Gln Phe Ile Val Lys Asn Gly Ile Ile Lys Glu Asp Glu Leu Arg Gly
            35                  40                  45 gag aac cgc cag att ttg aag gac atc atg gat gat tac tac cgt ggt     192
Glu Asn Arg Gln Ile Leu Lys Asp Ile Met Asp Asp Tyr Tyr Arg Gly
        50                  55                  60 ttc atc tcg gaa acg ctc tcc tcc att gac gac atc gat tgg act tcg     240
Phe Ile Ser Glu Thr Leu Ser Ser Ile Asp Asp Ile Asp Trp Thr Ser
65                  70                  75                  80
```

-continued

```
ttg ttc gaa aag atg gaa atc cag ctc aaa aac ggc gat aac aag gat        288
Leu Phe Glu Lys Met Glu Ile Gln Leu Lys Asn Gly Asp Asn Lys Asp
             85              90              95 acc ttg atc aag gag cag acc gag tat cgg aag gcg atc cat aag aag        336
Thr Leu Ile Lys Glu Gln Thr Glu Tyr Arg Lys Ala Ile His Lys Lys
            100             105             110 ttc gcc aac gat gat cgg ttc aag aac atg ttc tcg gcc aag ttg att        384
Phe Ala Asn Asp Asp Arg Phe Lys Asn Met Phe Ser Ala Lys Leu Ile
            115             120             125 tcc gac att ctc ccc gaa ttc gtg atc cat aac aac aac tac tcg gcg        432
Ser Asp Ile Leu Pro Glu Phe Val Ile His Asn Asn Asn Tyr Ser Ala
            130             135             140 tcg gag aag gag gag aag acg cag gtc atc aag ttg ttc tcg agg ttc        480
Ser Glu Lys Glu Glu Lys Thr Gln Val Ile Lys Leu Phe Ser Arg Phe
145             150             155             160 gcc aca tcg ttc aaa gag tat ttt aag aat cgt gcg aac tgt ttc tcg        528
Ala Thr Ser Phe Lys Glu Tyr Phe Lys Asn Arg Ala Asn Cys Phe Ser
                165             170             175 gca gat gat atc tcc tcg tcc tcc tgt cac cgc att gtg aac gac aac        576
Ala Asp Asp Ile Ser Ser Ser Ser Cys His Arg Ile Val Asn Asp Asn
            180             185             190 gcg gaa atc ttc ttc tcg aac gcg ttg gtg tat agg cgc atc gtg aag        624
Ala Glu Ile Phe Phe Ser Asn Ala Leu Val Tyr Arg Arg Ile Val Lys
            195             200             205 tcc ctc tcc aac gat gac atc aac aaa atc tcg gga gat atg aag gat        672
Ser Leu Ser Asn Asp Asp Ile Asn Lys Ile Ser Gly Asp Met Lys Asp
            210             215             220 tcg ctc aag gag atg tcg ttg gag gaa atc tac tcc tat gag aag tat        720
Ser Leu Lys Glu Met Ser Leu Glu Glu Ile Tyr Ser Tyr Glu Lys Tyr
225             230             235             240 ggc gag ttc att acg cag gag ggc att tcc ttc tac aac gac att tgt        768
Gly Glu Phe Ile Thr Gln Glu Gly Ile Ser Phe Tyr Asn Asp Ile Cys
                245             250             255 ggt aaa gtc aac tcg ttc atg aac ctc tac tgt cag aaa aac aag gag        816
Gly Lys Val Asn Ser Phe Met Asn Leu Tyr Cys Gln Lys Asn Lys Glu
            260             265             270 aac aaa aac ctc tat aag ctc cag aag ttg cat aag cag atc ctc tgt        864
Asn Lys Asn Leu Tyr Lys Leu Gln Lys Leu His Lys Gln Ile Leu Cys
            275             280             285 atc gca gac acc tcg tac gag gtc cct tac aag ttc gaa tcc gat gag        912
Ile Ala Asp Thr Ser Tyr Glu Val Pro Tyr Lys Phe Glu Ser Asp Glu
            290             295             300 gag gtc tac cag tcc gtc aac gga ttc ttg gac aac atc tcc tcg aaa        960
Glu Val Tyr Gln Ser Val Asn Gly Phe Leu Asp Asn Ile Ser Ser Lys
305             310             315             320 cac att gtc gag cgg ctc cga aag atc ggc gat aac tac aac ggc tac       1008
His Ile Val Glu Arg Leu Arg Lys Ile Gly Asp Asn Tyr Asn Gly Tyr
                325             330             335 aac ttg gac aaa atc tat atc gtc tcc aag ttc tat gag tcc gtc tcg       1056
Asn Leu Asp Lys Ile Tyr Ile Val Ser Lys Phe Tyr Glu Ser Val Ser
            340             345             350 cag aaa acc tat cgt gat tgg gag act atc aac act gcg ctc gag att       1104
Gln Lys Thr Tyr Arg Asp Trp Glu Thr Ile Asn Thr Ala Leu Glu Ile
            355             360             365 cac tat aac aac atc ttg cct ggt aac ggc aaa tcg aaa gcc gac aag       1152
His Tyr Asn Asn Ile Leu Pro Gly Asn Gly Lys Ser Lys Ala Asp Lys
            370             375             380 gtg aag aag gcc gtg aaa aac gat ctc cag aag tcg atc aca gaa atc       1200
Val Lys Lys Ala Val Lys Asn Asp Leu Gln Lys Ser Ile Thr Glu Ile
385             390             395             400
```

-continued

```
aac gaa ctc gtc tcg aac tac aag ctc tgt tcg gat gat aac atc aag      1248
Asn Glu Leu Val Ser Asn Tyr Lys Leu Cys Ser Asp Asp Asn Ile Lys
                405                 410                 415 gcg gaa acg tac atc cat gaa atc tcg cat atc ttg aac aac ttc gag      1296
Ala Glu Thr Tyr Ile His Glu Ile Ser His Ile Leu Asn Asn Phe Glu
                420                 425                 430 gcc cag gaa ctc aaa tac aac ccc gag atc cac ttg gtc gag tcg gag      1344
Ala Gln Glu Leu Lys Tyr Asn Pro Glu Ile His Leu Val Glu Ser Glu
                435                 440                 445 ctc aaa gcc tcg gag ttg aag aac gtc ttg gat gtc atc atg aac gca      1392
Leu Lys Ala Ser Glu Leu Lys Asn Val Leu Asp Val Ile Met Asn Ala
        450                 455                 460 ttc cac tgg tgt tcc gtg ttc atg acc gag gaa ctc gtc gat aaa gac      1440
Phe His Trp Cys Ser Val Phe Met Thr Glu Glu Leu Val Asp Lys Asp
465                 470                 475                 480 aac aac ttc tac gcg gaa ctc gag gaa atc tac gat gaa atc tat ccc      1488
Asn Asn Phe Tyr Ala Glu Leu Glu Glu Ile Tyr Asp Glu Ile Tyr Pro
                485                 490                 495 gtg atc tcc ctc tac aac ctc gtg cga aac tac gtc act cag aag ccc      1536
Val Ile Ser Leu Tyr Asn Leu Val Arg Asn Tyr Val Thr Gln Lys Pro
                500                 505                 510 tat tcc acc aag aag atc aag ctc aac ttc ggc atc ccc act ctc gca      1584
Tyr Ser Thr Lys Lys Ile Lys Leu Asn Phe Gly Ile Pro Thr Leu Ala
            515                 520                 525 gac ggt tgg tcg aag tcg aag gag tac tcc aac aac gcc att atc ctc      1632
Asp Gly Trp Ser Lys Ser Lys Glu Tyr Ser Asn Asn Ala Ile Ile Leu
        530                 535                 540 atg cga gac aac ctc tac tac ttg ggt atc ttc aac gca aag aac aag      1680
Met Arg Asp Asn Leu Tyr Tyr Leu Gly Ile Phe Asn Ala Lys Asn Lys
545                 550                 555                 560 ccg gat aag aag atc att gaa ggc aac act tcg gaa aac aag gga gac      1728
Pro Asp Lys Lys Ile Ile Glu Gly Asn Thr Ser Glu Asn Lys Gly Asp
                565                 570                 575 tat aag aag atg atc tac aac ctc ctc cct gga ccc aac aag atg att      1776
Tyr Lys Lys Met Ile Tyr Asn Leu Leu Pro Gly Pro Asn Lys Met Ile
            580                 585                 590 cct aaa gtg ttc ctc tcg tcg aag act ggt gtg gaa acg tat aag ccg      1824
Pro Lys Val Phe Leu Ser Ser Lys Thr Gly Val Glu Thr Tyr Lys Pro
            595                 600                 605 tcg gcc tac atc ttg gag ggc tac aaa cag aac aag cat atc aag tcc      1872
Ser Ala Tyr Ile Leu Glu Gly Tyr Lys Gln Asn Lys His Ile Lys Ser
        610                 615                 620 tcg aag gac ttc gac atc act ttc tgt cac gac ctc atc gac tat ttc      1920
Ser Lys Asp Phe Asp Ile Thr Phe Cys His Asp Leu Ile Asp Tyr Phe
625                 630                 635                 640 aag aac tgt att gca atc cat ccg gaa tgg aag aac ttc ggc ttc gat      1968
Lys Asn Cys Ile Ala Ile His Pro Glu Trp Lys Asn Phe Gly Phe Asp
                645                 650                 655 ttc tcg gat act tcg aca tac gaa gat atc tcg gga ttc tac cga gag      2016
Phe Ser Asp Thr Ser Thr Tyr Glu Asp Ile Ser Gly Phe Tyr Arg Glu
                660                 665                 670 gtc gaa ttg cag ggc tat aag att gat tgg acc tac atc tcg gaa aag      2064
Val Glu Leu Gln Gly Tyr Lys Ile Asp Trp Thr Tyr Ile Ser Glu Lys
            675                 680                 685 gat atc gac ttg ctc cag gaa aag ggc cag ctc tac ctc ttc cag att      2112
Asp Ile Asp Leu Leu Gln Glu Lys Gly Gln Leu Tyr Leu Phe Gln Ile
        690                 695                 700 tac aac aag gac ttc tcc aag aag tcg acg ggt aac gac aac ttg cac      2160
Tyr Asn Lys Asp Phe Ser Lys Lys Ser Thr Gly Asn Asp Asn Leu His
```

-continued

```
705                710                715                720 aca atg tat ctc aaa aac ctc ttc tcg gag gag aac ttg aag gat atc     2208
Thr Met Tyr Leu Lys Asn Leu Phe Ser Glu Glu Asn Leu Lys Asp Ile
            725                730                735 gtg ctc aaa ttg aac gga gag gcc gaa atc ttc ttc cgt aag tcc tcc     2256
Val Leu Lys Leu Asn Gly Glu Ala Glu Ile Phe Phe Arg Lys Ser Ser
            740                745                750 atc aag aac ccg atc atc cat aag aag gga tcg atc ttg gtc aac cgg     2304
Ile Lys Asn Pro Ile Ile His Lys Lys Gly Ser Ile Leu Val Asn Arg
            755                760                765 act tac gaa gca gag gaa aaa gat cag ttc gga aac atc cag att gtc     2352
Thr Tyr Glu Ala Glu Glu Lys Asp Gln Phe Gly Asn Ile Gln Ile Val
        770                775                780 agg aag aac atc cct gaa aac atc tat cag gag ttg tat aag tac ttc     2400
Arg Lys Asn Ile Pro Glu Asn Ile Tyr Gln Glu Leu Tyr Lys Tyr Phe
785                790                795                800 aac gac aag tcg gat aag gag ctc tcc gac gaa gca gcc aaa ctc aag     2448
Asn Asp Lys Ser Asp Lys Glu Leu Ser Asp Glu Ala Ala Lys Leu Lys
                805                810                815 aac gtc gtc gga cac cat gaa gca gca acc aac att gtg aag gac tac     2496
Asn Val Val Gly His His Glu Ala Ala Thr Asn Ile Val Lys Asp Tyr
            820                825                830 cgg tac act tac gac aag tac ttc ttg cac atg ccg atc act atc aac     2544
Arg Tyr Thr Tyr Asp Lys Tyr Phe Leu His Met Pro Ile Thr Ile Asn
            835                840                845 ttc aaa gcc aac aag acc gga ttc att aac gac agg atc ctc cag tac     2592
Phe Lys Ala Asn Lys Thr Gly Phe Ile Asn Asp Arg Ile Leu Gln Tyr
        850                855                860 att gcc aaa gaa aag gac ctc cat gtc atc ggt atc gcg agg gga gaa     2640
Ile Ala Lys Glu Lys Asp Leu His Val Ile Gly Ile Ala Arg Gly Glu
865                870                875                880 cgg aac ctc atc tac gtc tcc gtg att gac act tgt ggc aac att gtc     2688
Arg Asn Leu Ile Tyr Val Ser Val Ile Asp Thr Cys Gly Asn Ile Val
                885                890                895 gaa cag aag tcg ttc aac atc gtc aac ggt tac gat tac cag att aag     2736
Glu Gln Lys Ser Phe Asn Ile Val Asn Gly Tyr Asp Tyr Gln Ile Lys
            900                905                910 ttg aaa cag cag gaa ggt gcg agg cag att gcg cga aag gaa tgg aag     2784
Leu Lys Gln Gln Glu Gly Ala Arg Gln Ile Ala Arg Lys Glu Trp Lys
            915                920                925 gag att ggc aaa atc aag gag att aag gaa ggc tac ttg tcg ttg gtc     2832
Glu Ile Gly Lys Ile Lys Glu Ile Lys Glu Gly Tyr Leu Ser Leu Val
        930                935                940 atc cac gaa atc tcg aaa atg gtg atc aaa tac aac gcc atc atc gcc     2880
Ile His Glu Ile Ser Lys Met Val Ile Lys Tyr Asn Ala Ile Ile Ala
945                950                955                960 atg gaa gac ctc tcg tac ggc ttc aaa aag gga cgg ttc aaa gtg gag     2928
Met Glu Asp Leu Ser Tyr Gly Phe Lys Lys Gly Arg Phe Lys Val Glu
                965                970                975 cgt cag gtg tac cag aag ttc gaa aca atg ttg atc aac aag ttg aac     2976
Arg Gln Val Tyr Gln Lys Phe Glu Thr Met Leu Ile Asn Lys Leu Asn
            980                985                990 tac ttg gtg ttc aag gac att tcc  att acc gag aac gga  gga ttg ctc    3024
Tyr Leu Val Phe Lys Asp Ile Ser  Ile Thr Glu Asn Gly  Gly Leu Leu
            995                1000                1005 aag ggt  tat cag ctc acg tac  atc ccc gac aag ttg  aaa aac gtg       3069
Lys Gly  Tyr Gln Leu Thr Tyr  Ile Pro Asp Lys Leu  Lys Asn Val
    1010                1015                1020 gga cac  cag tgt ggc tgt atc  ttc tac gtg cct gca  gcc tac acg       3114
```

```
Gly His Gln Cys Gly Cys Ile Phe Tyr Val Pro Ala Ala Tyr Thr
    1025            1030            1035 tcg aaa atc gac cct aca aca gga ttc gtg aac atc ttc aag ttc        3159
Ser Lys Ile Asp Pro Thr Thr Gly Phe Val Asn Ile Phe Lys Phe
    1040            1045            1050 aag gat ctc acc gtc gac gcg aag cgg gag ttc atc aaa aag ttc        3204
Lys Asp Leu Thr Val Asp Ala Lys Arg Glu Phe Ile Lys Lys Phe
    1055            1060            1065 gac tcc atc cgc tat gat tcg gag aag aac ttg ttc tgt ttc aca        3249
Asp Ser Ile Arg Tyr Asp Ser Glu Lys Asn Leu Phe Cys Phe Thr
    1070            1075            1080 ttc gac tac aac aac ttc att act cag aac acc gtg atg tcc aaa        3294
Phe Asp Tyr Asn Asn Phe Ile Thr Gln Asn Thr Val Met Ser Lys
    1085            1090            1095 tcg tcg tgg tcc gtg tac acg tat ggt gtg cgc atc aaa agg cgc        3339
Ser Ser Trp Ser Val Tyr Thr Tyr Gly Val Arg Ile Lys Arg Arg
    1100            1105            1110 ttc gtc aac ggt cgc ttc tcc aac gaa tcg gac acg atc gat atc        3384
Phe Val Asn Gly Arg Phe Ser Asn Glu Ser Asp Thr Ile Asp Ile
    1115            1120            1125 acg aaa gac atg gag aaa aca ttg gaa atg acc gac atc aac tgg        3429
Thr Lys Asp Met Glu Lys Thr Leu Glu Met Thr Asp Ile Asn Trp
    1130            1135            1140 cgt gac ggc cat gac ctc agg cag gac atc atc gat tac gag atc        3474
Arg Asp Gly His Asp Leu Arg Gln Asp Ile Ile Asp Tyr Glu Ile
    1145            1150            1155 gtc cag cac atc ttc gaa atc ttc cgt ctc acc gtg cag atg agg        3519
Val Gln His Ile Phe Glu Ile Phe Arg Leu Thr Val Gln Met Arg
    1160            1165            1170 aac tcc ctc tcc gag ctc gaa gat cgg gat tac gac cgg ctc att        3564
Asn Ser Leu Ser Glu Leu Glu Asp Arg Asp Tyr Asp Arg Leu Ile
    1175            1180            1185 tcc cct gtg ttg aac gag aac aac atc ttc tac gac tcg gca aaa        3609
Ser Pro Val Leu Asn Glu Asn Asn Ile Phe Tyr Asp Ser Ala Lys
    1190            1195            1200 gcg gga gat gca ttg ccg aag gac gcc gat gcg aac ggt gca tat        3654
Ala Gly Asp Ala Leu Pro Lys Asp Ala Asp Ala Asn Gly Ala Tyr
    1205            1210            1215 tgt att gca ctc aag ggt ctc tac gaa atc aag cag atc acc gaa        3699
Cys Ile Ala Leu Lys Gly Leu Tyr Glu Ile Lys Gln Ile Thr Glu
    1220            1225            1230 aac tgg aag gag gac ggc aaa ttc tcg agg gac aag ttg aag att        3744
Asn Trp Lys Glu Asp Gly Lys Phe Ser Arg Asp Lys Leu Lys Ile
    1235            1240            1245 tcg aac aag gat tgg ttc gat ttc atc cag aac aag agg tac ttg        3789
Ser Asn Lys Asp Trp Phe Asp Phe Ile Gln Asn Lys Arg Tyr Leu
    1250            1255            1260 taa                                                                 3792
```

```
<210> SEQ ID NO 125
<211> LENGTH: 1263
<212> TYPE: PRT
<213> ORGANISM: Artificial Sequence
<220> FEATURE:
<223> OTHER INFORMATION: Synthetic Construct

<400> SEQUENCE: 125

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
```

```
            20                  25                  30
Gln Phe Ile Val Lys Asn Gly Ile Ile Lys Glu Asp Glu Leu Arg Gly
            35                  40                  45
Glu Asn Arg Gln Ile Leu Lys Asp Ile Met Asp Asp Tyr Tyr Arg Gly
            50                  55                  60
Phe Ile Ser Glu Thr Leu Ser Ser Ile Asp Asp Ile Asp Trp Thr Ser
65                  70                  75                  80
Leu Phe Glu Lys Met Glu Ile Gln Leu Lys Asn Gly Asp Asn Lys Asp
                85                  90                  95
Thr Leu Ile Lys Glu Gln Thr Glu Tyr Arg Lys Ala Ile His Lys Lys
                100                 105                 110
Phe Ala Asn Asp Asp Arg Phe Lys Asn Met Phe Ser Ala Lys Leu Ile
                115                 120                 125
Ser Asp Ile Leu Pro Glu Phe Val Ile His Asn Asn Asn Tyr Ser Ala
            130                 135                 140
Ser Glu Lys Glu Glu Lys Thr Gln Val Ile Lys Leu Phe Ser Arg Phe
145                 150                 155                 160
Ala Thr Ser Phe Lys Glu Tyr Phe Lys Asn Arg Ala Asn Cys Phe Ser
                165                 170                 175
Ala Asp Asp Ile Ser Ser Ser Ser Cys His Arg Ile Val Asn Asp Asn
                180                 185                 190
Ala Glu Ile Phe Phe Ser Asn Ala Leu Val Tyr Arg Arg Ile Val Lys
                195                 200                 205
Ser Leu Ser Asn Asp Asp Ile Asn Lys Ile Ser Gly Asp Met Lys Asp
            210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
                260                 265                 270
Asn Lys Asn Leu Tyr Lys Leu Gln Lys Leu His Lys Gln Ile Leu Cys
            275                 280                 285
Ile Ala Asp Thr Ser Tyr Glu Val Pro Tyr Lys Phe Glu Ser Asp Glu
            290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
            355                 360                 365
His Tyr Asn Asn Ile Leu Pro Gly Asn Gly Lys Ser Lys Ala Asp Lys
            370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
                420                 425                 430
Ala Gln Glu Leu Lys Tyr Asn Pro Glu Ile His Leu Val Glu Ser Glu
            435                 440                 445
```

```
Leu Lys Ala Ser Glu Leu Lys Asn Val Leu Asp Val Ile Met Asn Ala
    450             455             460

Phe His Trp Cys Ser Val Phe Met Thr Glu Glu Leu Val Asp Lys Asp
465             470             475             480

Asn Asn Phe Tyr Ala Glu Leu Glu Glu Ile Tyr Asp Glu Ile Tyr Pro
            485             490             495

Val Ile Ser Leu Tyr Asn Leu Val Arg Asn Tyr Val Thr Gln Lys Pro
            500             505             510

Tyr Ser Thr Lys Lys Ile Lys Leu Asn Phe Gly Ile Pro Thr Leu Ala
            515             520             525

Asp Gly Trp Ser Lys Ser Lys Glu Tyr Ser Asn Asn Ala Ile Ile Leu
    530             535             540

Met Arg Asp Asn Leu Tyr Tyr Leu Gly Ile Phe Asn Ala Lys Asn Lys
545             550             555             560

Pro Asp Lys Lys Ile Ile Glu Gly Asn Thr Ser Glu Asn Lys Gly Asp
            565             570             575

Tyr Lys Lys Met Ile Tyr Asn Leu Leu Pro Gly Pro Asn Lys Met Ile
            580             585             590

Pro Lys Val Phe Leu Ser Ser Lys Thr Gly Val Glu Thr Tyr Lys Pro
            595             600             605

Ser Ala Tyr Ile Leu Glu Gly Tyr Lys Gln Asn Lys His Ile Lys Ser
    610             615             620

Ser Lys Asp Phe Asp Ile Thr Phe Cys His Asp Leu Ile Asp Tyr Phe
625             630             635             640

Lys Asn Cys Ile Ala Ile His Pro Glu Trp Lys Asn Phe Gly Phe Asp
            645             650             655

Phe Ser Asp Thr Ser Thr Tyr Glu Asp Ile Ser Gly Phe Tyr Arg Glu
            660             665             670

Val Glu Leu Gln Gly Tyr Lys Ile Asp Trp Thr Tyr Ile Ser Glu Lys
    675             680             685

Asp Ile Asp Leu Leu Gln Glu Lys Gly Gln Leu Tyr Leu Phe Gln Ile
    690             695             700

Tyr Asn Lys Asp Phe Ser Lys Lys Ser Thr Gly Asn Asp Asn Leu His
705             710             715             720

Thr Met Tyr Leu Lys Asn Leu Phe Ser Glu Glu Asn Leu Lys Asp Ile
            725             730             735

Val Leu Lys Leu Asn Gly Glu Ala Glu Ile Phe Phe Arg Lys Ser Ser
            740             745             750

Ile Lys Asn Pro Ile Ile His Lys Lys Gly Ser Ile Leu Val Asn Arg
    755             760             765

Thr Tyr Glu Ala Glu Glu Lys Asp Gln Phe Gly Asn Ile Gln Ile Val
    770             775             780

Arg Lys Asn Ile Pro Glu Asn Ile Tyr Gln Glu Leu Tyr Lys Tyr Phe
785             790             795             800

Asn Asp Lys Ser Asp Lys Glu Leu Ser Asp Glu Ala Ala Lys Leu Lys
            805             810             815

Asn Val Val Gly His His Glu Ala Ala Thr Asn Ile Val Lys Asp Tyr
            820             825             830

Arg Tyr Thr Tyr Asp Lys Tyr Phe Leu His Met Pro Ile Thr Ile Asn
            835             840             845

Phe Lys Ala Asn Lys Thr Gly Phe Ile Asn Asp Arg Ile Leu Gln Tyr
    850             855             860
```

```
Ile Ala Lys Glu Lys Asp Leu His Val Ile Gly Ile Ala Arg Gly Glu
865             870             875             880

Arg Asn Leu Ile Tyr Val Ser Val Ile Asp Thr Cys Gly Asn Ile Val
                885             890             895

Glu Gln Lys Ser Phe Asn Ile Val Asn Gly Tyr Asp Tyr Gln Ile Lys
            900             905             910

Leu Lys Gln Gln Glu Gly Ala Arg Gln Ile Ala Arg Lys Glu Trp Lys
        915             920             925

Glu Ile Gly Lys Ile Lys Glu Ile Lys Glu Gly Tyr Leu Ser Leu Val
        930             935             940

Ile His Glu Ile Ser Lys Met Val Ile Lys Tyr Asn Ala Ile Ile Ala
945             950             955             960

Met Glu Asp Leu Ser Tyr Gly Phe Lys Lys Gly Arg Phe Lys Val Glu
                965             970             975

Arg Gln Val Tyr Gln Lys Phe Glu Thr Met Leu Ile Asn Lys Leu Asn
            980             985             990

Tyr Leu Val Phe Lys Asp Ile Ser  Ile Thr Glu Asn Gly  Gly Leu Leu
        995             1000             1005

Lys Gly  Tyr Gln Leu Thr Tyr  Ile Pro Asp Lys Leu  Lys Asn Val
    1010             1015             1020

Gly His  Gln Cys Gly Cys Ile  Phe Tyr Val Pro Ala  Ala Tyr Thr
    1025             1030             1035

Ser Lys  Ile Asp Pro Thr Thr  Gly Phe Val Asn Ile  Phe Lys Phe
    1040             1045             1050

Lys Asp  Leu Thr Val Asp Ala  Lys Arg Glu Phe Ile  Lys Lys Phe
    1055             1060             1065

Asp Ser  Ile Arg Tyr Asp Ser  Glu Lys Asn Leu Phe  Cys Phe Thr
    1070             1075             1080

Phe Asp  Tyr Asn Asn Phe Ile  Thr Gln Asn Thr Val  Met Ser Lys
    1085             1090             1095

Ser Ser  Trp Ser Val Tyr Thr  Tyr Gly Val Arg Ile  Lys Arg Arg
    1100             1105             1110

Phe Val  Asn Gly Arg Phe Ser  Asn Glu Ser Asp Thr  Ile Asp Ile
    1115             1120             1125

Thr Lys  Asp Met Glu Lys Thr  Leu Glu Met Thr Asp  Ile Asn Trp
    1130             1135             1140

Arg Asp  Gly His Asp Leu Arg  Gln Asp Ile Ile Asp  Tyr Glu Ile
    1145             1150             1155

Val Gln  His Ile Phe Glu Ile  Phe Arg Leu Thr Val  Gln Met Arg
    1160             1165             1170

Asn Ser  Leu Ser Glu Leu Glu  Asp Arg Asp Tyr Asp  Arg Leu Ile
    1175             1180             1185

Ser Pro  Val Leu Asn Glu Asn  Asn Ile Phe Tyr Asp  Ser Ala Lys
    1190             1195             1200

Ala Gly  Asp Ala Leu Pro Lys  Asp Ala Asp Ala Asn  Gly Ala Tyr
    1205             1210             1215

Cys Ile  Ala Leu Lys Gly Leu  Tyr Glu Ile Lys Gln  Ile Thr Glu
    1220             1225             1230

Asn Trp  Lys Glu Asp Gly Lys  Phe Ser Arg Asp Lys  Leu Lys Ile
    1235             1240             1245

Ser Asn  Lys Asp Trp Phe Asp  Phe Ile Gln Asn Lys  Arg Tyr Leu
    1250             1255             1260
```

-continued

```
<210> SEQ ID NO 126
<211> LENGTH: 1263
<212> TYPE: PRT
<213> ORGANISM: Artificial Sequence
<220> FEATURE:
<223> OTHER INFORMATION: Mad7d mature protein

<400> SEQUENCE: 126

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Asn Tyr Ser Ala
        130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Ser Leu Ser Asn Asp Asp Ile Asn Lys Ile Ser Gly Asp Met Lys Asp
        210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
            275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
```

183

184

```
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                    405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
        450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
        610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
        690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
        770                 775                 780

Arg Lys Asn Ile Pro Glu Asn Ile Tyr Gln Glu Leu Tyr Lys Tyr Phe
785                 790                 795                 800
```

-continued

```
Asn Asp Lys Ser Asp Lys Glu Leu Ser Asp Glu Ala Ala Lys Leu Lys
            805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Ala Arg Gly Glu
865                 870                 875                 880

Arg Asn Leu Ile Tyr Val Ser Val Ile Asp Thr Cys Gly Asn Ile Val
            885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
            980                 985                 990

Tyr Leu Val Phe Lys Asp Ile Ser  Ile Thr Glu Asn Gly  Gly Leu Leu
            995                 1000                1005

Lys Gly  Tyr Gln Leu Thr Tyr  Ile Pro Asp Lys Leu  Lys Asn Val
    1010                1015                1020

Gly His  Gln Cys Gly Cys Ile  Phe Tyr Val Pro Ala  Ala Tyr Thr
    1025                1030                1035

Ser Lys  Ile Asp Pro Thr Thr  Gly Phe Val Asn Ile  Phe Lys Phe
    1040                1045                1050

Lys Asp  Leu Thr Val Asp Ala  Lys Arg Glu Phe Ile  Lys Lys Phe
    1055                1060                1065

Asp Ser  Ile Arg Tyr Asp Ser  Glu Lys Asn Leu Phe  Cys Phe Thr
    1070                1075                1080

Phe Asp  Tyr Asn Asn Phe Ile  Thr Gln Asn Thr Val  Met Ser Lys
    1085                1090                1095

Ser Ser  Trp Ser Val Tyr Thr  Tyr Gly Val Arg Ile  Lys Arg Arg
    1100                1105                1110

Phe Val  Asn Gly Arg Phe Ser  Asn Glu Ser Asp Thr  Ile Asp Ile
    1115                1120                1125

Thr Lys  Asp Met Glu Lys Thr  Leu Glu Met Thr Asp  Ile Asn Trp
    1130                1135                1140

Arg Asp  Gly His Asp Leu Arg  Gln Asp Ile Ile Asp  Tyr Glu Ile
    1145                1150                1155

Val Gln  His Ile Phe Glu Ile  Phe Arg Leu Thr Val  Gln Met Arg
    1160                1165                1170

Asn Ser  Leu Ser Glu Leu Glu  Asp Arg Asp Tyr Asp  Arg Leu Ile
    1175                1180                1185

Ser Pro  Val Leu Asn Glu Asn  Asn Ile Phe Tyr Asp  Ser Ala Lys
    1190                1195                1200
```

-continued

```
Ala Gly  Asp Ala Leu Pro Lys  Asp Ala Asp Ala Asn  Gly Ala Tyr
    1205             1210              1215

Cys Ile  Ala Leu Lys Gly Leu  Tyr Glu Ile Lys Gln  Ile Thr Glu
    1220             1225              1230

Asn Trp  Lys Glu Asp Gly Lys  Phe Ser Arg Asp Lys  Leu Lys Ile
    1235             1240              1245

Ser Asn  Lys Asp Trp Phe Asp  Phe Ile Gln Asn Lys  Arg Tyr Leu
    1250             1255              1260
```

```
<210> SEQ ID NO 127
<211> LENGTH: 624
<212> TYPE: DNA
<213> ORGANISM: Artificial Sequence
<220> FEATURE:
<223> OTHER INFORMATION: PmCDA1 coding sequence

<400> SEQUENCE: 127
atgaccgacg ctgagtacgt gagaatccat gagaagttgg acatctacac gtttaagaaa      60
cagtttttca acaacaaaaa atccgtgtcg catagatgct acgttctctt tgaattaaaa     120
cgacggggtg aacgtagagc gtgtttttgg ggctatgctg tgaataaacc acagagcggg     180
acagaacgtg gcattcacgc cgaaatcttt agcattagaa aagtcgaaga atacctgcgc     240
gacaaccccg gacaattcac gataaattgg tactcatcct ggagtccttg tgcagattgc     300
gctgaaaaaa tcttagaatg gtataaccag gagctgcggg ggaacggcca cactttgaaa     360
atctgggctt gcaaactcta ttacgagaaa aatgcgagga tcaaattgg gctgtggaac      420 ctcagagata cggggttgg gttgaatgta atggtaagtg aacactacca atgttgcagg      480
aaaatattca tccaatcgtc gcacaatcaa ttgaatgaga atagatggct tgagaagact     540
ttgaagcgag ctgaaaaacg acggagcgag ttgtccatta tgattcaggt aaaaatactc     600
cacaccacta agagtcctgc tgtt                                            624
```

```
<210> SEQ ID NO 128
<211> LENGTH: 208
<212> TYPE: PRT
<213> ORGANISM: Artificial Sequence
<220> FEATURE:
<223> OTHER INFORMATION: PmCDA1 mature polypeptide

<400> SEQUENCE: 128

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
```

-continued

```
            130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205

<210> SEQ ID NO 129
<211> LENGTH: 315
<212> TYPE: DNA
<213> ORGANISM: Artificial Sequence
<220> FEATURE:
<223> OTHER INFORMATION: Linker coding sequence

<400> SEQUENCE: 129
cctagcaggg ctgaccccaa gaagaagagg aaggtgggtg gaggaggttc tggaggtgga        60
ggttctgcag agtatgtgcg ggccctcttt gactttaatg ggaatgatga agaagacctt       120
ccctttaaga aaggagacat cctgagaatc cgggataagc ctgaagagca gtggtggaat       180
gcagaggaca gcgaaggaaa gaggggggatg attcctgtcc cttacgtgga gaagtattcc      240
ggagactata aggaccacga cggagactac aaggatcatg atattgatta caaagacgat       300
gacgataagt ctagg                                                        315

<210> SEQ ID NO 130
<211> LENGTH: 105
<212> TYPE: PRT
<213> ORGANISM: Artificial Sequence
<220> FEATURE:
<223> OTHER INFORMATION: Linker mature polypeptide

<400> SEQUENCE: 130

Pro Ser Arg Ala Asp Pro Lys Lys Lys Arg Lys Val Gly Gly Gly Gly
1               5                   10                  15

Ser Gly Gly Gly Gly Ser Ala Glu Tyr Val Arg Ala Leu Phe Asp Phe
                20                  25                  30

Asn Gly Asn Asp Glu Glu Asp Leu Pro Phe Lys Lys Gly Asp Ile Leu
            35                  40                  45

Arg Ile Arg Asp Lys Pro Glu Glu Gln Trp Trp Asn Ala Glu Asp Ser
        50                  55                  60

Glu Gly Lys Arg Gly Met Ile Pro Val Pro Tyr Val Glu Lys Tyr Ser
65                  70                  75                  80

Gly Asp Tyr Lys Asp His Asp Gly Asp Tyr Lys Asp His Asp Ile Asp
                85                  90                  95

Tyr Lys Asp Asp Asp Asp Lys Ser Arg
            100                 105

<210> SEQ ID NO 131
<211> LENGTH: 297
<212> TYPE: DNA
<213> ORGANISM: Artificial Sequence
<220> FEATURE:
<223> OTHER INFORMATION: UGI coding sequence

<400> SEQUENCE: 131
tctagaggct ccggaaccaa cctgtccgac atcatcgaga aggagaccgg caagcagctc        60
```

-continued

```
gttatccagg agtccatcct gatgctgccc gaggaggtcg aggaggtcat cggcaacaag    120
cccgagtccg acatcctggt ccacaccgcc tacgacgagt ccaccgacga gaacgtcatg    180
ctgctgacct ccgacgcccc cgagtacaag ccctgggccc tggtcatcca ggactccaac    240
ggcgagaaca agatcaagat gctgtccggc ggctccccca agaagaagcg caaggtc       297
```

```
<210> SEQ ID NO 132
<211> LENGTH: 99
<212> TYPE: PRT
<213> ORGANISM: Artificial Sequence
<220> FEATURE:
<223> OTHER INFORMATION: UGI mature polypeptide

<400> SEQUENCE: 132

Ser Arg Gly Ser Gly Thr Asn Leu Ser Asp Ile Ile Glu Lys Glu Thr
1               5                   10                  15

Gly Lys Gln Leu Val Ile Gln Glu Ser Ile Leu Met Leu Pro Glu Glu
            20                  25                  30

Val Glu Glu Val Ile Gly Asn Lys Pro Glu Ser Asp Ile Leu Val His
        35                  40                  45

Thr Ala Tyr Asp Glu Ser Thr Asp Glu Asn Val Met Leu Leu Thr Ser
    50                  55                  60

Asp Ala Pro Glu Tyr Lys Pro Trp Ala Leu Val Ile Gln Asp Ser Asn
65                  70                  75                  80

Gly Glu Asn Lys Ile Lys Met Leu Ser Gly Gly Ser Pro Lys Lys Lys
                85                  90                  95

Arg Lys Val
```

```
<210> SEQ ID NO 133
<211> LENGTH: 17429
<212> TYPE: DNA
<213> ORGANISM: Artificial Sequence
<220> FEATURE:
<223> OTHER INFORMATION: pAT3530

<400> SEQUENCE: 133
accaatgctt aatcagtgag gcacctatct cagcgatctg tctatttcgt tcatccatag     60
ttgcctgact ccccgtcgtg tagataacta cgatacggga gggcttacca tctggcccca    120
gcgctgcgat gataccgcga gaaccacgct caccggctcc ggatttatca gcaataaacc    180
agccagccgg aagggccgag cgcagaagtg gtcctgcaac tttatccgcc tccatccagt    240
ctattaattg ttgccgggaa gctagagtaa gtagttcgcc agttaatagt ttgcgcaacg    300
ttgttgccat cgctacaggc atcgtggtgt cacgctcgtc gtttggtatg gcttcattca    360
gctccggttc ccaacgatca aggcgagtta catgatcccc catgttgtgc aaaaaagcgg    420
ttagctcctt cggtcctccg atcgttgtca gaagtaagtt ggccgcagtg ttatcactca    480
tggttatggc agcgctacat aattctctta ctgtcatgcc atccgtaaga tgcttttctg    540
tgactggtga gtactcaacc aagtcattct gagaatagtg tatgcggcga ccgagttgct    600
cttgcccggc gtcaatacgg gataataccg cgccacatag cagaacttta aaagtgctca    660
tcattggaaa acgttcttcg gggcgaaaac tctcaaggat cttaccgctg ttgagatcca    720
gttcgatgta acccactcgt gcacccaact gatcttcagc atcttttact ttcaccagcg    780
tttctgggtg agcaaaaaca ggaaggcaaa atgccgcaaa aaagggaata agggcgacac    840
ggaaatgttg aatactcata ttcttccttt ttcaatatta ttgaagcatt tatcagggtt    900
attgtctcat gagcggatac atatttgaat gtatttagaa aaataaacaa ataggggtca    960
```

-continued

```
gtgttacaac caattaacca attctgaaca ttatcgcgag cccatttata cctgaatatg      1020
gctcataaca cccccttgttt gcctggcggc agtagcgcgg tggtcccacc tgaccccatg      1080
ccgaactcag aagtgaaacg ccgtagcgcc gatggtagtg tggggactcc ccatgcgaga      1140
gtagggaact gccaggcatc aaataaaacg aaaggctcag tcgaaagact gggcctttcg      1200
cccgggctaa ttatggggtg tcgcccttat tcgactctat agtgaagttc ctattctcta      1260
gaaagtatag gaacttctga agtggggatt taaatgcggc cgcgctgagg gtttaatcga      1320
cgaagcagct gacggccagt gccaagctta acgcgtaccc gggcccagta tatgttccgc      1380
agatgactgg agctctgcca tacgtgccct ctcaagcacc atttgttcca tctacagaga      1440
ctagtcacca actagtctat caagactcac agggtacatt gctgagacca actgaccaga      1500
ggcagggtag cggattgacg gctccatctc cttcacttac aaggtctatt gaaagccctt      1560
tagcatcacc aagcggagaa tagattgtta agcttatttt ttgtatactg ttttgtgata      1620
gcacgaagtt tttccacggt atcttgtaaa aatatatatt tgtggcgggc ttacctacat      1680
caaattaata agagactaat tataaactaa acacacaagc aagctacttt agggtaaaag      1740
tttataaatg cttttgacgt ataaacgttg cttgtattta ttattacaat taaaggtgga      1800
tagaaaacct agagactagt tagaaactaa tctcaggttt gcgttaaact aaatcagagc      1860
ccgagaggtt aacagaacct agaaggggac tagatatccg ggtagggaaa caaaaaaaaa      1920
aaacaagaca gccacatatt agggagacta gttagaagct agttccagga ctaggaaaat      1980
aaaagacaat gataccacag tctagttgac aactagatag attctagatt gaggccaaag      2040
tctctgagat ccaggttagt tgcaactaat actagttagt atctagtctc ctataactct      2100
gaagctagaa taacttacta ctattatcct caccactgtt cagctgcgca aacggagtga      2160
ttgcaaggtg ttcagagact agttattgac tagtcagtga ctagcaataa ctaacaaggt      2220
attaacctac catgtctgcc atcaccctgc acttcctcgg gctcagcagc cttttcctcc      2280
tcattttcat gctcattttc cttgtttaag actgtgacta gtcaaagact agtccagaac      2340
cacaaaggag aaatgtctta ccactttctt cattgcttgt ctctttttgca ttatccatgt      2400 ctgcaactag ttagagtcta gttagtgact agtccgacga ggacttgctt gtctccggat      2460
tgttggagga actctccagg gcctcaagat ccacaacaga gccttctaga agactggtca      2520
ataactagtt ggtctttgtc tgagtctgac ttacgaggtt gcatactcgc tccctttgcc      2580
tcgtcaatcg atgagaaaaa gcgccaaaac tcgcaatatg gctttgaacc acacggtgct      2640
gagactagtt agaatctagt cccaaactag cttggatagc ttacctttgc cctttgcgtt      2700
gcgacaggtc ttgcagggta tggttccttt ctcaccagct gatttagctg ccttgctacc      2760
ctcacggcgg atctgccata aagagtggct agaggttata aattagcact gatcctaggt      2820
acggggctga atgtaacttg cctttccttt ctcatcgcgc ggcaagacag gcttgctcaa      2880
attcctacca gtcacagggg tatgcacggc gtacggacca cttgaactag tcacagatta      2940
gttagcaact agtctgcatt gaatggctgt acttacgggc cctcgccatt gtcctgatca      3000
tttccagctt caccctcgtt gctgcaaagt agttagtgac tagtcaagga ctagttgaaa      3060
tgggagaaga aactcacgaa ttctcgactc ccttagtatt gtggtccttg acttggtgc      3120 tgctatatat tagctaatac actagttaga ctcacagaaa cttacgcagc tcgcttgcgc      3180
ttcttggtag gagtcgggt tgggagaaca gtgccttcaa acaagccttc ataccatgct      3240
acttgactag tcagggacta gtcaccaagt aatctagata ggacttgcct ttggcctcca      3300
```

-continued

```
tcagttcctt catagtggga ggaccattgt gcaatgtaaa ctccatgccg tgggagttct    3360
tgtccttcaa gtgcttgacc aatatgtttc tgttggcaga gggaacctgt caactagtta    3420
ataactagtc agaaactatg atagcagtag actcactgta cgcttgaggc atcccttcac    3480
tcggcagtag acttcatatg gatggatatc aggcacgcca ttgtcgtcct gtggactagt    3540
cagtaactag gcttaaagct agtcgggtcg gcttactatc ttgaaatccg gcagcgtaag    3600
ctccccgtcc ttaactgcct cgagatagtg acagtactct ggggactttc ggagatcgtt    3660
atcgttatcg cgaatgctcg gcatactaac tgttgactag tcttggacta gtcccgagca    3720
aaaaggattg gaggaggagg aggaaggtga gagtgagaca aagagcgaaa taagagcttc    3780
aaaggctatc tctaagcagt atgaaggtta agtatctagt tcttgactag atttaaagag    3840
atttcgacta gttatgtacc tggagtttgg atataggaat gtgttgtggt aacgaaatgt    3900 aaggggggagg aaagaaaaag tcgtcaagag gtaactctaa gtcggccatt cctttttggg    3960
aggcgctaac cataaacggc atggtcgact tagagttagc tcaggggaatt tagggagtta    4020 tctgcgacca ccgaggaacg gcggaatgcc aaagaatccc gatggagctc tagctggcgg    4080
ttgacaaccc cacctttttgg cgtttctgcg gcgttgcagg cgggactgga tacttcgtag    4140
aaccagaaag gcaaggcaga acgcgctcag caagagtgtt ggaagtgata gcatgatgtg    4200
ccttgttaac taggtaccaa tctgcagtat gcttgatgtt atccaaagtg tgagagagga    4260
aggtccaaac atacacgatt gggagagggc ctaggtataa gagtttttga gtagaacgca    4320
tgtgagccca gccatctcga ggagattaaa cacgggccgg catttgatgg ctatgttagt    4380
accccaatgg aaacggtgag agtccagtgg tcgcagataa ctccctaaat tccctgagct    4440
aactctaagt cgaccatgcc gtttatggtt agcgcctccc aaaaaggaat ggccgactta    4500
gagttacctc ttgacgactt ttctcttcct cccccttaca tttcgttacc acaacacatt    4560
cctatatcca aactccaggt acataactag tcgaaatctc tttaaatcta gtcaagaact    4620
agatacttaa ccttcatact gcttagagat agcctttgaa gctcttattt cgctctttgt    4680
ctcactctca ccttcctcct cctcctccaa tccttttttgc tcgggactag tccaagacta    4740
gtcaacagtt agtatgccga gcattcgcga taacgataac gatctccgaa agtccccaga    4800
gtactgtcac tatctcgagg cagttaagga cggggagctt acgctgccgg atttcaagat    4860
agtaagccga cccgactagc tttaagccta gttactgact agtccacagg acgacaatgg    4920
cgtgcctgat atccatccat atgaagtcta ctgccgagtg aagggatgcc tcaagcgtac    4980
agtgagtcta ctgctatcat agtttctgac tagttattaa ctagttgaca ggttccctct    5040
gccaacagaa acatattggt caagcacttg aaggacaaga actcccacgg catggagttt    5100
acattgcaca atggtcctcc cactatgaag gaactgatgg aggccaaagg caagtcctat    5160
ctagattact tggtgactag tccctgacta gtcaagtagc atggtatgaa ggcttgtttg    5220
aaggcactgt tctcccaacc ccgactccta ccaagaagcg caagcgagct gcgtaagttt    5280
ctgtgagtct aactagtgta ttagctaata tatagcagca ccaagtccaa ggaccacaat    5340
actaagggag tcgagaattc gtgagtttct tctcccattt caactagtcc ttgactagtc    5400
actaactact ttgcagcaac gagggtgaag ctggaaatga tcaggacaat ggcgagggcc    5460
cgtaagtaca gccattcaat gcagactagt tgctaactaa tctgtgacta gttcaagtgg    5520
tccgtacgcc gtgcataccc ctgtgactgg taggaatttg agcaagcctg tcttgccgcg    5580
cgatgagaaa ggaaaggcaa gttacattca gccccgtacc taggatcagt gctaatttat    5640
aacctctagc cactctttat ggcagatccg ccgtgagggt agcaaggcag ctaaatcagc    5700
```

-continued

```
tggtgagaaa ggaaccatac cctgcaagac ctgtcgcaac gcaaagggca aaggtaagct   5760
atccaagcta gtttgggact agattctaac tagtctcagc accgtgtggt tcaaagccat   5820
attgcgagtt ttggcgcttt ttctcatcga ttgacgaggc aaagggagcg agtatgcaac   5880
ctcgtaagtc agactcagac aaagaccaac tagttattga ccagtcttct agaaggctct   5940
gttgtggatc ttgaggccct ggagagttcc tccaacaatc cggagacaag caagtcctcg   6000
tcggactagt cactaactag actctaacta gttgcagaca tggataatgc aaaagagaca   6060
agcaatgaag aaagtggtaa gacatttctc ctttgtggtt ctggactagt ctttgactag   6120
tcacagtctt aaacaaggaa aatgagcatg aaaatgagga ggaaaaggct gctgagcccg   6180
aggaagtgca gggtgatggc agacatggta ggttaatacc ttgttagtta ttgctagtca   6240
ctgactagtc aataactagt ctctgaacac cttgcaatca ctccgtttgc gcagctgaac   6300
agtggtgagg ataatagtag taagttattc tagcttcaga gttataggag actagatact   6360
aactagtatt agttgcaact aacctggatc tcagagactt tggcctcaat ctagaatcta   6420
tctagttgtc aactagactg tggtatcatt gtcttttatt ttcctagtcc tggaactagc   6480
ttctaactag tctccctaat atgtggctgt cttgtttttt tttttgttt ccctacccgg   6540 atatctagtc cccttctagg ttctgttaac ctctcgggct ctgatttagt ttaacgcaaa   6600
cctgagatta gtttctaact agtctctagg ttttctatcc acctttaatt gtaataataa   6660
atacaagcaa cgtttatacg tcaaaagcat ttataaactt ttaccctaaa gtagcttgct   6720
tgtgtgttta gtttataatt agtctcttat taatttgatg taggtaagcc cgccacaaat   6780
atatattttt acaagatacc gtggaaaaac ttcgtgctat cacaaaacag tatacaaaaa   6840
ataagcttaa caatctattc tccgcttggt gatgctaaag ggctttcaat agaccttgta   6900
agtgaaggag atggagccgt caatccgcta ccctgcctct ggtcagttgg tctcagcaat   6960
gtaccctgtg agtcttgata gactagttgg tgactagtct ctgtagatgg aacaaatggt   7020
gcttgagagg gcacgtatgg cagagctcca gtcatctgcg gaacatatac tgggcccggg   7080
aagatctcat ggtcatagct gtttccgtta attaatggtt cacttctctt tagaaatcaa   7140
ctgtgggttt tgcttttttgc ttcattctct ttgtcttctc catctttgat caaatcctgg   7200
actttctcaa tccccagcta attcaatcat agtcagtttt ctatttttat tatttctttt   7260
tcttttgaaa tgtgattaac aaccagtccg ttatatatct tgtacccaga ttacgcccaa   7320
ctcgtgctcc tcagccacaa agatactcaa ttgatagcca agatacatac ataccacaaa   7380
gtaaggactc catgcattga gtattactca tcgtattcta gactactcca aaactcagca   7440
catagacaaa caatacgaac ctcgtctagg ggtgattcag aggcggcaaa gcggggtttt   7500
cgcatttgat gttcctggca cttatgtaag cccacgcttc ccgctcaact aaaccatcag   7560
ccaatcagac tgctcagatt tatcttttga agggtaaata aatcattgta aagaagaaca   7620
agtggcttgc ttgtcaagca atggcatcat tggtctagtg gtagaattcg tcgttgccat   7680
cgacgaggcc cgtgttcgat tcacggatga tgcagtcaaa agaccttttt aatttctact   7740
cttgtagatg cgatcgcttt ttttttgagc atttatcagc ttgatataga ggtaggaatg   7800 tatgaggtg cagaatggct attttgttat tggagcgggt tcgaacgga gggcaggaga   7860 cttttttctaa atacgtcacg tgatatagag ctgctttaat taacgagaca gcagaatcac   7920
cgcccaagtt aagcctttgt gctgatcatg ctctcgaacg ggccaagttc gggaaaagca   7980
aaggagcgtt tagtgagggg caatttgact cacctcccag gcaacagatg aggggggcaa   8040
```

```
aaagaaagaa attttcgtga gtcaatatgg attccgagca tcattttctt gcggtctatc    8100
ttgctacgta tgttgatctt gacgctgtgg atcaagcaac gccactcgct cgctccatcg    8160
caggctggtc gcagacaaat taaaaggcgg caaactcgta cagccgcggg gttgtccgct    8220
gcaaagtaca gagtgataaa agccgccatg cgaccatcaa cgcgttgatg cccagctttt    8280
tcgatccgag aatccaccgt agaggcgata gcaagtaaag aaaagctaaa caaaaaaaaa    8340
tttctgcccc taagccatga aaacgagatg gggtggagca gaaccaagga aagagtcgcg    8400
ctgggctgcc gttccggaag gtgttgtaaa ggctcgacgc ccaaggtggg agtctaggag    8460
aagaatttgc atcgggagtg gggcgggtta cccctccata tccaatgaca gatatctacc    8520
agccaagggt ttgagcccgc ccgcttagtc gtcgtcctcg cttgcccctc cataaaagga    8580
tttcccctcc ccctcccaca aaattttctt tcccttcctc tccttgtccg cttcagtacg    8640
tatatcttcc cttccctcgc ttctctcctc catccttctt tcatccatct cctgctaact    8700
tctctgctca gcacctctac gcattactag ccgtagtatc tgagcacttc tcccttttat    8760
attccacaaa acataacaca accttcacca tgaacaacgg cacaaacaac ttccagaact    8820
tcattggaat ctcgtcgttg cagaagactt tgcgcaacgc cctcatcccc acagaaacta    8880
cccagcagtt cattgtgaag aacggaatca tcaaggaaga tgaactccga ggcgagaacc    8940
gccagatttt gaaggacatc atggatgatt actaccgtgg tttcatctcg gaaacgctct    9000
cctccattga cgacatcgat tggacttcgt tgttcgaaaa gatggaaatc cagctcaaaa    9060
acggcgataa caaggatacc ttgatcaagg agcagaccga gtatcggaag gcgatccata    9120
agaagttcgc caacgatgat cggttcaaga acatgttctc ggccaagttg atttccgaca    9180
ttctccccga attcgtgatc cataacaaca actactcggc gtcggagaag gaggagaaga    9240
cgcaggtcat caagttgttc tcgaggttcg ccacatcgtt caaagagtat tttaagaatc    9300
gtgcgaactg tttctcggca gatgatatct cctcgtcctc ctgtcaccgc attgtgaacg    9360
acaacgcgga aatcttcttc tcgaacgcgt tggtgtatag gcgcatcgtg aagtccctct    9420
ccaacgatga catcaacaaa atctcgggag atatgaagga ttcgctcaag gagatgtcgt    9480
tggaggaaat ctactcctat gagaagtatg gcgagttcat tacgcaggag ggcatttcct    9540
tctacaacga catttgtggt aaagtcaact cgttcatgaa cctctactgt cagaaaaaca    9600
aggagaacaa aaacctctat aagctccaga agttgcataa gcagatcctc tgtatcgcag    9660
acacctcgta cgaggtccct tacaagttcg aatccgatga ggaggtctac cagtccgtca    9720
acggattctt ggacaacatc tcctcgaaac acattgtcga gcggctccga aagatcggcg    9780
ataactacaa cggctacaac ttggacaaaa tctatatcgt ctccaagttc tatgagtccg    9840
tctcgcagaa aacctatcgt gattgggaga ctatcaacac tgcgctcgag attcactata    9900
acaacatctt gcctggtaac ggcaaatcga aagccgacaa ggtgaagaag gccgtgaaaa    9960
acgatctcca gaagtcgatc acagaaatca acgaactcgt ctcgaactac aagctctgtt   10020
cggatgataa catcaaggcg gaaacgtaca tccatgaaat ctcgcatatc ttgaacaact   10080
tcgaggccca ggaactcaaa tacaaccccg agatccactt ggtcgagtcg gagctcaaag   10140
cctcggagtt gaagaacgtc ttggatgtca tcatgaacgc attccactgg tgttccgtgt   10200
tcatgaccga ggaactcgtc gataaagaca acaacttcta cgcggaactc gaggaaatct   10260
acgatgaaat ctatcccgtg atctccctct acaacctcgt gcgaaactac gtcactcaga   10320
agccctattc caccaagaag atcaagctca acttcggcat ccccactctc gcagacggtt   10380
ggtcgaagtc gaaggagtac tccaacaacg ccattatcct catgcgagac aacctctact   10440
```

-continued

```
acttgggtat cttcaacgca aagaacaagc cggataagaa gatcattgaa ggcaacactt    10500
cggaaaacaa gggagactat aagaagatga tctacaacct cctccctgga cccaacaaga    10560
tgattcctaa agtgttcctc tcgtcgaaga ctggtgtgga aacgtataag ccgtcggcct    10620
acatcttgga gggctacaaa cagaacaagc atatcaagtc ctcgaaggac ttcgacatca    10680
ctttctgtca cgacctcatc gactatttca agaactgtat tgcaatccat ccggaatgga    10740
agaacttcgg cttcgatttc tcggatactt cgacatacga agatatctcg ggattctacc    10800
gagaggtcga attgcagggc tataagattg attggaccta catctcggaa aaggatatcg    10860
acttgctcca ggaaaagggc cagctctacc tcttccagat ttacaacaag gacttctcca    10920
agaagtcgac gggtaacgac aacttgcaca caatgtatct caaaaacctc ttctcggagg    10980
agaacttgaa ggatatcgtg ctcaaattga acggagaggc cgaaatcttc ttccgtaagt    11040
cctccatcaa gaacccgatc atccataaga agggatcgat cttggtcaac cggacttacg    11100
aagcagagga aaaagatcag ttcggaaaca tccagattgt caggaagaac atccctgaaa    11160
acatctatca ggagttgtat aagtacttca cgacaagtc ggataaggag ctctccgacg    11220
aagcagccaa actcaagaac gtcgtcggac accatgaagc agcaaccaac attgtgaagg    11280
actaccggta cacttacgac aagtacttct tgcacatgcc gatcactatc aacttcaaag    11340
ccaacaagac cggattcatt aacgacagga tcctccagta cattgccaaa gaaaaggacc    11400
tccatgtcat cggtatcgcg aggggagaac ggaacctcat ctacgtctcc gtgattgaca    11460
cttgtggcaa cattgtcgaa cagaagtcgt tcaacatcgt caacggttac gattaccaga    11520
ttaagttgaa acagcaggaa ggtgcgaggc agattgcgcg aaaggaatgg aaggagattg    11580
gcaaaatcaa ggagattaag gaaggctact tgtcgttggt catccacgaa atctcgaaaa    11640
tggtgatcaa atacaacgcc atcatcgcca tggaagacct ctcgtacggc ttcaaaaagg    11700
gacggttcaa agtggagcgt caggtgtacc agaagttcga aacaatgttg atcaacaagt    11760
tgaactactt ggtgttcaag gacatttcca ttaccgagaa cggaggattg ctcaagggtt    11820
atcagctcac gtacatcccc gacaagttga aaaacgtggg acaccagtgt ggctgtatct    11880
tctacgtgcc tgcagcctac acgtcgaaaa tcgaccctac aacaggattc gtgaacatct    11940
tcaagttcaa ggatctcacc gtcgacgcga agcgggagtt catcaaaaag ttcgactcca    12000
tccgctatga ttcggagaag aacttgttct gtttcacatt cgactacaac aacttcatta    12060
ctcagaacac cgtgatgtcc aaatcgtcgt ggtccgtgta cacgtatggt gtgcgcatca    12120
aaaggcgctt cgtcaacggt cgcttctcca acgaatcgga cacgatcgat atcacgaaag    12180
acatggagaa aacattggaa atgaccgaca tcaactggcg tgacggccat gacctcaggc    12240
aggacatcat cgattacgag atcgtccagc acatcttcga aatcttccgt ctcaccgtgc    12300
agatgaggaa ctccctctcc gagctcgaag atcgggatta cgaccggctc atttcccctg    12360
tgttgaacga gaacaacatc ttctacgact cggcaaaagc gggagatgca ttgccgaagg    12420
acgccgatgc gaacggtgca tattgtattg cactcaaggg tctctacgaa atcaagcaga    12480
tcaccgaaaa ctggaaggag gacggcaaat tctcgaggga caagttgaag atttcgaaca    12540
aggattggtt cgatttcatc cagaacaaga ggtacttgcc tagcagggct gaccccaaga    12600
agaagaggaa ggtgggtgga ggaggttctg gaggtggagg ttctgcagag tatgtgcggg    12660
ccctctttga ctttaatggg aatgatgaag aagaccttcc cttttaagaaa ggagacatcc    12720 tgagaatccg ggataagcct gaagagcagt ggtggaatgc agaggacagc gaaggaaaga    12780
```

```
gggggatgat tcctgtccct tacgtggaga agtattccgg agactataag gaccacgacg   12840
gagactacaa ggatcatgat attgattaca aagacgatga cgataagtct aggatgaccg   12900
acgctgagta cgtgagaatc catgagaagt tggacatcta cacgtttaag aaacagtttt   12960
tcaacaacaa aaaatccgtg tcgcatagat gctacgttct ctttgaatta aaacgacggg   13020
gtgaacgtag agcgtgtttt tggggctatg ctgtgaataa accacagagc gggacagaac   13080
gtggcattca cgccgaaatc tttagcatta gaaaagtcga agaataccctg cgcgacaacc   13140 ccggacaatt cacgataaat tggtactcat cctggagtcc ttgtgcagat tgcgctgaaa   13200
aaatcttaga atggtataac caggagctgc gggggaacgg ccacactttg aaaatctggg   13260
cttgcaaact ctattacgag aaaaatgcga ggaatcaaat tgggctgtgg aacctcagag   13320 ataacgggt tgggttgaat gtaatggtaa gtgaacacta ccaatgttgc aggaaaatat   13380
tcatccaatc gtcgcacaat caattgaatg agaatagatg gcttgagaag actttgaagc   13440
gagctgaaaa acgacggagc gagttgtcca ttatgattca ggtaaaaata ctccacacca   13500
ctaagagtcc tgctgtttct agaggctccg gaaccaacct gtccgacatc atcgagaagg   13560
agaccggcaa gcagctcgtt atccaggagt ccatcctgat gctgcccgag gaggtcgagg   13620
aggtcatcgg caacaagccc gagtccgaca tcctggtcca caccgcctac gacgagtcca   13680
ccgacgagaa cgtcatgctg ctgacctccg acgcccccga gtacaagccc tgggccctgg   13740
tcatccagga ctccaacggc gagaacaaga tcaagatgct gtccggcggc tcccccaaga   13800
agaagcgcaa ggtctaatgt acagcggaca ttcgatttat gccgttatga cttccttaaa   13860
aaagccttta cgaatgaaag aaatggaatt agacttgtta tgtagttgat tctacaatgg   13920
attatgattc ctgaacttca aatccgctgt tcattattaa tctcagctct tcccgtaaag   13980
ccaatgttga aactattcgt aaatgtacct cgttttgcgt gtaccttgct tatcacgtga   14040
tattacatga cctggacaga gttctgcgcg aaagtcataa cgtaaatccc gggcggtagg   14100
tgcgtcccgg gcggaaggta gttttctcgt ccaccccaac gcgttatca acctcaactt   14160 tcaacaacca tcatgccacc aaaagcgcgt aaaacaaagc gagatttgat tgagcaagag   14220
ggcaggatcc aatgcgcgat tcaagacatt aaaaatggaa aatttcaaaa aattgcgccc   14280
gcagcgcgtg catacaaaat tcatcccaat actcctcgtg tactgtgtaa gcgcccacta   14340
ggtaatatga catgattacg aattcgagct cggtacccgg ccggaactcc acgtctagag   14400
gatccaccag tgattgacca atgttttatc ttctacagtt ctgcctgtct accccattct   14460
agctgtacct gactacagag tagtttaatt gtggttgacc ccacagtcgg aggcggagga   14520
atacagcacc gatgtggcct gtctccatcc agattggcac gcaattttta cacgcggaaa   14580
agatcgagat agagtacgac tttaaattta gtccccggcg gcttctattt tagaatattt   14640
gagatttgat tctcaagcaa ttgatttggt tgggtcaccc tcaattggat aatataccctc  14700 attgctcggc tacttcaact catcaatcac cgtcataccc cgcatataac cctccattcc   14760
cacgatgtcg tccaagtcgc aattgactta cggtgctcga gccagcaagc accccaatcc   14820
tctggcaaag agacttttg agattgccga agcaaagaag acaaacgtta ccgtctctgc    14880
tgatgtgacg acaacccgag aactcctgga cctcgctgac cgtacggaag ctgttggatc   14940
caatacatat gccgtctagc aatggactaa tcaacttttg atgatacagg tctcggtccc   15000
tacatcgccg tcatcaagac acacatcgac atcctcaccg atttcagcgt cgacactatc   15060
aatggcctga atgtgctggc tcaaaagtac aacttttttga tcttcgagga ccgcaaattc   15120
atcgacatcg gcaataccgt ccagaagcaa taccacggcg gtgctctgag gatctccgaa   15180
```

```
tgggcccaca ttatcaactg cagcgttctc cctggcgagg gcatcgtcga ggctctggcc    15240
cagaccgcat ctgcgcaaga cttcccctat ggtcctgaga gaggactgtt ggtcctggca    15300
gagatgaccc ccaaaggatc gctggctacg ggcgagtata ccaaggcatc ggttgactac    15360
gctcgcaaat acaagaactt cgttatgggt ttcgtgtcga cgcgggccct gacggaagtg    15420
cagtcggatg tgtcttcagc ctcggaggat gaagatttcg tggtcttcac gacgggtgtg    15480
aacctctctt ccaaaggaga taagcttgga cagcaatacc agactcctgc atcggctatt    15540
ggacgcggtg ccgactttat catcgccggt cgaggcatct acgctgctcc cgacccggtt    15600
gaagctgcac agcggtacca gaaagaaggc tgggaagctt atatggccag agtatgcggc    15660
aagtcatgat ttcctcttgg agcaaaagtg tagtgccagt acgagtgttg tggaggaagg    15720
ctgcatacat tgtgcctgtc attaaacgat gagctcgtcc gtattggccc ctgtaatgcc    15780 atgtttttccg cccccaatcg tcaaggtttt ccctttgtta gattcctacc agtcatctag    15840
caaggcggcc gcagctagca caattgaggc atccccacta ccgcattaag acctcagcgc    15900
ggccgcaaat ttaaataaaa tgaagtgaag ttcctatact ttctagagaa taggaacttc    15960
tatagtgagt cgaataaggg cgacacaaaa tttattctaa atgcataata aatactgata    16020
acatcttata gtttgtatta tattttgtat tatcgttgac atgtataatt ttgatatcaa    16080
aaactgattt tcccttttatt attttcgaga tttattttct taattctctt taacaaacta    16140
gaaatattgt atatacaaaa aatcataaat aatagatgaa tagtttaatt ataggtgttc    16200
atcaatcgaa aaagcaacgt atcttattta aagtgcgttg cttttttctc atttataagg    16260
ttaaataatt ctcatatatc aagcaaagtg acaggcgccc ttaaatattc tgacaaatgc    16320
tctttcccta aactccccc ataaaaaaac ccgccgaagc gggttttttac gttatttgcg    16380 gattaacgat tactcgttat cagaaccgcc caggggcc gagcttaaga ctggccgtcg    16440
ttttacaaca cagaaagagt ttgtagaaac gcaaaaaggc catccgtcag gggccttctg    16500
cttagtttga tgcctggcag ttccctactc tcgccttccg cttcctcgct cactgactcg    16560
ctgcgctcgg tcgttcggct gcggcgagcg gtatcagctc actcaaaggc ggtaatacgg    16620
ttatccacag aatcaggggga taacgcagga agaacatgt gagcaaaagg ccagcaaaag    16680
gccaggaacc gtaaaaaggc cgcgttgctg gcgtttttcc ataggctccg ccccctgac    16740 gagcatcaca aaaatcgacg ctcaagtcag aggtggcgaa acccgacagg actataaaga    16800
taccaggcgt ttccccctgg aagctccctc gtgcgctctc ctgttccgac cctgccgctt    16860
accggatacc tgtccgcctt tctcccttcg ggaagcgtgg cgctttctca tagctcacgc    16920
tgtaggtatc tcagttcggt gtaggtcgtt cgctccaagc tgggctgtgt gcacgaaccc    16980
cccgttcagc ccgaccgctg cgccttatcc ggtaactatc gtcttgagtc caacccgta    17040 agacacgact tatcgccact ggcagcagcc actggtaaca ggattagcag agcgaggtat    17100
gtaggcggtg ctacagagtt cttgaagtgg tgggctaact acggctacac tagaagaaca    17160
gtatttggta tctgcgctct gctgaagcca gttaccttcg gaaaaagagt tggtagctct    17220
tgatccggca aacaaaccac cgctggtagc ggtggttttt ttgtttgcaa gcagcagatt    17280
acgcgcagaa aaaaggatc tcaagaagat cctttgatct tttctacggg gtctgacgct    17340
cagtggaacg acgcgcgcgt aactcacgtt aagggatttt ggtcatgagc ttgcgccgtc    17400
ccgtcaagtc agcgtaatgc tctgctttt                                      17429
```

<210> SEQ ID NO 134

<211> LENGTH: 6651
<212> TYPE: DNA
<213> ORGANISM: Aspergillus oryzae

<400> SEQUENCE: 134

```
atggaggggc cacgcggcgt ctatctcttc ggagaccaga caagtgattt cgacgccggc    60
ttacgtcgcc tcctacaagt aaagaataac acaattgttg catcgttctt ccagagatgc   120
tttcacgctt tgcgccaaga gatcgcgagg ctttcaccat ctgaacggaa gatcttcccc   180
cggtttacga gcatagtgga tctactggcg cgtcaccggg agtcagaccc taatccggct   240
ctggagagtg cgttgacctg tatctatcaa ttgggatgct ttataaagta cgtgtaactg   300
cagatcctga cccgtttgaa cgagcctaac ctgagatagc tactacggag accttggaaa   360
cgtgtaccca tctgcttcag actgccatat agttggcctg tgcgcgggtc ttcttagttc   420
tgcagctgta agctgttcga acaatgttgg agaattgctc cccgctgcgg ttgaagcggt   480
ggtggtagct ctccgacttg gtctatgcgt ccttaaagtt cgagagctgg tgagctctga   540
ccaagcgtcg tcaacaagct ggtcagtctt gatttcaggg attagcgaga aagatgcctc   600
gcagcttata ggagaattca ctgctgaacg ggtaagtcaa ttgatctgaa atagtttgca   660
ggacagaatg ttctaaccac tggataaagg caattcctcc ttcatccaaa ccgtatatca   720
gtgcggtggg atataacagt ataaccatca gcgcaccgcc taaggtcctt gatgatttaa   780
ttgattctag gctgtctaag agccataagc cggtgagggc gcaaatccat ggtccttacc   840
atgcagcaca tctgtactat ggccgagatg tcgacaggat catcgaaagc tgccataatg   900
aggtcgtttc aaactacaca ccccgtatcc ccgtactatc aagtactacg ggacagccga   960
tagaggccaa acacatgaaa gatctactta aggccgccct tgaagagatt ctactacgtc  1020
aactatgctg ggagaaagtg accgatgcct gctattccat attaaaaact gctcgtcatc  1080
aaccatgcaa gttgttccca atttcaagca ctgcgacaca aagcttgttt acagctctta  1140
cgaaagccgg gataaccgac atcgaagtgg aaaatgggct cggagatgtt cccacgaacc  1200
cgaaggacaa ccttaacatc agcggcaggg cggactgctc caagatagct atcattggca  1260
tgtctggacg attcccagaa gctgatggca cagagagttt ctgggacctt ctgtataatg  1320
gcctcgatgt acaccggaag gtgcctgcag agcgttggga tgttgatgcc cacgttgatc  1380
ctaccggaac aaaacggaac accagcaagg ttccatacgg atgctggata aacgaaccgg  1440
ggttatttga cccccgcttc ttcaatatgt cgccacgcga agccctccag gcagatcccg  1500
ctcaaagact tgcattgctc acggcctatg aagctcttga aatggccggc tttatccccg  1560
acagcacccc ttctacacag agggatcgag tcggcctctt ctatggaatg actagcgatg  1620
actatcggga gataaatagt ggtcaagata ttgatactta ctttatccct ggtgggaatc  1680
gtgctttcac acctggccgg ataaactact atttcaagtt cagtgggccc agcgtcagcg  1740
ttgatacagc ttgttcttca agtcttgcgg ctattcatat ggcttgcaat tcgatctgga  1800
gaaatgattg cgatgctgct attgctggag gtgtcaatat attgacaaac cctgataacc  1860
atgccggtct tgaccgtggc catttcctgt ccagaaccgg gaattgcaac acatttgacg  1920
atggtgctga tggctactgt agagcagatg gagtgggtac aatcattctc aagcggctgg  1980
aagacgctca ggcggacaac gatccaatcc tcggtgtgat caatggagcc tataccaatc  2040
attcggcaga agcagtctcg attacccgcc ctcatgttgg cgcacaagcg tttatctttta  2100 ataagctatt gaacgatgcc aatatcgacc ctaaggacgt cagctacgtt gaaatgcatg  2160
gaactggtac tcaagctggg gatgcggtgg aaatgcaatc ggtcttggat acgtttgctc  2220
```

```
ccgactaccg ccgtggacca ggacagtctc tccatcttgg ttccgccaaa gcaaatgttg     2280
ggcatggaga gtcagcatct ggtgtaactg cacttgtgaa agtgctgcta atgatgaaga     2340
agaataccat accccctcat tgtggtataa agactaagat caaccacaac ttccccacgg     2400
atctcgcgca acgaaatgtc cacattgcct ttcaacctac cccttggaac agaccggctt     2460
ccggaaagcg gcagtgcttc attaacaact tttcggcggc tggtggaaat accgctcttt     2520
tgatggaaga cgctccaatc gctgaggtta aggggcagga cactcgacct gttcacgttg     2580
tgtctgtatc ggcacgatcc cagagtgcgc tcaaaaacaa catcaactct ctcgtaaaat     2640
acatcgacga acaaggaagg tcattcaatg tgaacgaggc agactttatc ccaagcttgg     2700
catacaccac cacagcacgg cgtatccatc acccattccg tgtcacagct atcgggtcta     2760
gtttgcagga gctgcgtgac tcacttaaca acagctctcg tctggaaagc tttacccctg     2820
tccctgcgac ggcccctggc gtagggttcg tgttcgctgg ccaaggagct cagcacaccg     2880
gaatgggaag gcaactatac gaaaaatgct ctcaattccg ggcaacaatg cagcacttcg     2940
attgcattag tcaaaaccaa gggtttcctt cgatccttcc cttggttgac ggaagcgtgc     3000
ccgtggagga gctgggccct atcgtgacac agctcggcac cacatgtctt cagatggctt     3060
tggtcaacta ttggggttca ctaggtataa aacctgcgtt cgttcttggg catagtctcg     3120
gggagtttgc tgctttgaat accgcaggag tattatcgac ttccgatacc atctacctt    3180 gtggccgtcg ggctaccctc cttacagaat actgccaggt tgggacacac gccatgctgg    3240
ctgtcaaggc ttcctacccc caggtcaagc agttactgaa agaaggtgtg gatgaagttg     3300
cctgtgtcaa ctcacccagt gagacagtcg tcagtggcct caccgctgat attgatgact     3360
tggctcaaag gtgttccact gaaggttgga agtccactaa actaagggta ccgttcgctt     3420
tccattctgc ccaagttact ccaattcttg aacggtttca agaagaggcc cagggtgtca     3480
cgttccgtaa gccgtcgtta ccgtttgttt cctcactcct tggggaagtc atcaccgaat     3540
ctaattacga tgtcctggga gctcaatata tggtgaagca gtgccggaag tcggtgaact     3600
tccttggtgc tcttgaggcc accagatatg cgaaattgat gactgataag actgtctggc     3660
tggaagttgg tgcccatacc atttgctctg gtatgatcaa agcaacattc ggtccccagg     3720
ttaccactgt ggcatctctt cgccgagagg agaatgcatg gaaggtcctc tccaatagtc     3780
tatcggccct tcatttggct ggcattgata ttaattggaa agaatatcat caagacttca     3840
gctccagcca ccaggtgctc ccacttcctt cttacaagtg ggatctcaag aactactgga     3900
taccctacac taacaatttc tgccttacga agggtgctcc ccaaactgca attcaagctg     3960
caccacaaac tacattcctg accactgctg cgcaaaaggt tgttgagagt cgcgacgacg     4020
gtacaacagc gactgtcgtg gtgcaaaatg acatcgctga tcctgagttg aaccgtgtta     4080
tccaaggtca caaggtcaat ggagccgcac tttgcccatc ggtaagtatt gcatgcattg     4140
ccagactatc ttgtgttata attcggctac ttacgtattg cctagtcact ctacgcagat     4200
attgcccaga cacttggaga gtatcttatt gagaaataca aacccgagtt caaagatctt     4260
ggtctcgatg tgtgtgacat ggtcgtaccg aagccactca tcgcgaaggg aggagagcag     4320
ctctttagag tctctgctat tgctaattgg gctgagaaga aggcttcagt tcaagtatac     4380
gccgttaatg ctgacggcaa aaagaccgtg gatcatgcgt attgtacggt gaagttcttt     4440
gataccaatg cctccgagct cgagtggaag agaatctcgt acctggtcaa gagaagcatc     4500
gacagtcttc accagaatgc gggagacaggg gaggctcacc gtatccagcg aggaatggtc     4560
```

-continued

```
tataaacttt tcagcgcgtt ggtcgattat gatgaaaatt tcaagtcgat tcgcgaggtt     4620
atcctggaca gcgacaataa tgaggccacc gctcgtgtca aattccaagc accgccagga     4680
aatttccacc gaaacccatt ctggattgac agtttcggtc acttgtccgg attcattatg     4740
aatgcgagcg acgcgaccga ctctaagaac caagtatttg ttaaccatgg atgggattcg     4800
atgcgttgcc tgaagaagtt ctcgcctgat gtcacttatc gcacttatgt gaggatgcag     4860
ccatggcaaa acaacatttg ggctggagat gtttatatct ttgagggcga cgatattatt     4920
gctgtcttcg gaggtgtgaa ggtgggtacc tcactactga ttttggttcc tgcttactga     4980
catgataatt agttccaagc actggcacgc aagatacttg acactgttct tcccctgtt      5040 ggcggttcaa aggcaccaat tacagcgaaa tcaccacctc cagctcgcac tcagaaggcc     5100
aacaccggcg ccaagacccg tcctaaagca cctgttcctt ccaagtcgtt caccaaatct     5160
tctgggccga gtgttgtcgt acgcgcactc agcattctgg cctcagaagt tggcctggca     5220
gagtctgaaa tctcagacga catggtgttt gcggactacg gtgtagactc actcctctcc     5280
cttacagtta ctggcaggta tcgtgaagag ttgaacctcg atttggactc ctctgtgttt     5340
accgatcatc caactgtcaa cgacttcaag cggctcatcg cccaagtgag tccttcagag     5400
agccatgatg gttcctccag tgaacaagag tcgaatttct cttttcaacgg tggcgagtcc    5460 tcaagcgcaa gcacacctga cataacgtca ccgccgaatg agaaggtagc tcaagtcgag     5520
caaaacggca ccatgaagga aatccgtaac atcatggcgg aggagatcgg tgtacccgca     5580
gaagagatcg accctgacga gaacttggga gagatgggta tggactcgct tctctcccctt    5640 actgttcttg gaagaatacg ggagactttg gacatggacc tgccaggaga gttcttcatc     5700
gaaaaccaga ccctcaatga tatagaggtg gctttggacc taaaacccaa gactacctct     5760
gctccaattc ctatgccaga gccagtgaaa ttccctgaag ctatccacga cctccagcca     5820
aagcttgctc aacatcccaa ggccacatcc atcctgttac aaggaaaccc caggacagca     5880
acaaagacgt tattcttgtt tcctgacggc tctggctcag ctacatctta cgctaccatc     5940
cccggactct ctcctgacgt ctgcgtttac gggttgaatt gcccatatat gaagacacct     6000
gagaagctca aatgcagcct agatgaactc actgcgccct atgtagcaga gattcgtcgt     6060
cggcaaccca agggtcctta cagcttcggt ggctggtcag caggagggat ctgtgcatat     6120
gatgcggcac gccatctaat gtttgaggaa ggtgaacaag tcgaccgctt gcttctcctt     6180 gatacccct tccccatcgg cctcgagaag ctgccgcaga gattgtacgg cttcttcaac      6240
tctatcggtc tcttcggtga aggtaaaacg gcaccaccct cctggctcct accccacttc     6300 ctagcctta tcgacgctct cgacgcatac aaggccgcgc cccttccatt caaagacgag      6360
aaatgggcca agaaactgcc caagacttat atcatctggg ccaaggacgg tgtttgcggt      6420
aagccgggag atccccggcc tgatcccccg acagacggtt ccaaggatcc caaggagatg     6480
gtctggcttc ttaatgaccg gaccgatctg ggacctaaca agtgggatac attggttgga     6540
cctgagaata ttggtggaat cacagtaatg gaagatgcta atcatttttac gatgacgaag    6600 ggcgaaaaag cgaaagagtt gtctacattt atggctaacg ccatggctta a              6651
```

<210> SEQ ID NO 135
<211> LENGTH: 20
<212> TYPE: DNA
<213> ORGANISM: Artificial Sequence
<220> FEATURE:
<223> OTHER INFORMATION: pAT3532 protospacer

<400> SEQUENCE: 135

-continued acgctttgcg ccaagagatc                                                20

<210> SEQ ID NO 136
<211> LENGTH: 20
<212> TYPE: DNA
<213> ORGANISM: Artificial Sequence
<220> FEATURE:
<223> OTHER INFORMATION: pAT3533 protospacer

<400> SEQUENCE: 136
cgccaagaga tcgcgaggct                                                20

<210> SEQ ID NO 137
<211> LENGTH: 20
<212> TYPE: DNA
<213> ORGANISM: Artificial Sequence
<220> FEATURE:
<223> OTHER INFORMATION: pAT3534 protospacer

<400> SEQUENCE: 137
aagcactgcg acacaaagct                                                20

<210> SEQ ID NO 138
<211> LENGTH: 20
<212> TYPE: DNA
<213> ORGANISM: Artificial Sequence
<220> FEATURE:
<223> OTHER INFORMATION: pAT3535 protospacer

<400> SEQUENCE: 138
cattctgccc aagttactcc                                                20

<210> SEQ ID NO 139
<211> LENGTH: 20
<212> TYPE: DNA
<213> ORGANISM: Artificial Sequence
<220> FEATURE:
<223> OTHER INFORMATION: pAT3536 protospacer

<400> SEQUENCE: 139
cggaagccgg tctgttccaa                                                20

<210> SEQ ID NO 140
<211> LENGTH: 20
<212> TYPE: DNA
<213> ORGANISM: Artificial Sequence
<220> FEATURE:
<223> OTHER INFORMATION: pAT3537 protospacer

<400> SEQUENCE: 140
tacctagtga accccaatag                                                20

<210> SEQ ID NO 141
<211> LENGTH: 62
<212> TYPE: DNA
<213> ORGANISM: Artificial Sequence
<220> FEATURE:
<223> OTHER INFORMATION: Primer oAT3941

<400> SEQUENCE: 141
aatttctact cttgtagata cgctttgcgc caagagatct tttttttttga gcatttatca      60 gc                                                                   62

<210> SEQ ID NO 142

-continued

```
<211> LENGTH: 62
<212> TYPE: DNA
<213> ORGANISM: Artificial Sequence
<220> FEATURE:
<223> OTHER INFORMATION: Primer oAT3942

<400> SEQUENCE: 142
aatttctact cttgtagatc gccaagagat cgcgaggctt tttttttga gcatttatca      60 gc                                                                    62

<210> SEQ ID NO 143
<211> LENGTH: 62
<212> TYPE: DNA
<213> ORGANISM: Artificial Sequence
<220> FEATURE:
<223> OTHER INFORMATION: Primer oAT3943

<400> SEQUENCE: 143
aatttctact cttgtagata agcactgcga cacaaagctt tttttttga gcatttatca      60 gc                                                                    62

<210> SEQ ID NO 144
<211> LENGTH: 62
<212> TYPE: DNA
<213> ORGANISM: Artificial Sequence
<220> FEATURE:
<223> OTHER INFORMATION: Primer oAT3944

<400> SEQUENCE: 144
aatttctact cttgtagatc attctgccca agttactcct tttttttga gcatttatca      60 gc                                                                    62

<210> SEQ ID NO 145
<211> LENGTH: 62
<212> TYPE: DNA
<213> ORGANISM: Artificial Sequence
<220> FEATURE:
<223> OTHER INFORMATION: Primer oAT3945

<400> SEQUENCE: 145
aatttctact cttgtagatc ggaagccggt ctgttccaat tttttttga gcatttatca      60 gc                                                                    62

<210> SEQ ID NO 146
<211> LENGTH: 62
<212> TYPE: DNA
<213> ORGANISM: Artificial Sequence
<220> FEATURE:
<223> OTHER INFORMATION: Primer oAT3946

<400> SEQUENCE: 146
aatttctact cttgtagatt acctagtgaa ccccaatagt tttttttga gcatttatca      60 gc                                                                    62

<210> SEQ ID NO 147
<211> LENGTH: 18
<212> TYPE: DNA
<213> ORGANISM: Artificial Sequence
<220> FEATURE:
<223> OTHER INFORMATION: Primer oAT3912

<400> SEQUENCE: 147
tccaagttct ttgcatgc                                                   18
```

-continued

```
<210> SEQ ID NO 148
<211> LENGTH: 18
<212> TYPE: DNA
<213> ORGANISM: Artificial Sequence
<220> FEATURE:
<223> OTHER INFORMATION: Primer oAT3613

<400> SEQUENCE: 148
tatctcaggt taggctcg                                                 18

<210> SEQ ID NO 149
<211> LENGTH: 18
<212> TYPE: DNA
<213> ORGANISM: Artificial Sequence
<220> FEATURE:
<223> OTHER INFORMATION: Primer oJaL188

<400> SEQUENCE: 149
ccatggtcct taccatgc                                                 18

<210> SEQ ID NO 150
<211> LENGTH: 22
<212> TYPE: DNA
<213> ORGANISM: Artificial Sequence
<220> FEATURE:
<223> OTHER INFORMATION: Primer oAT3616

<400> SEQUENCE: 150
tatttatctc ccgatagtca tc                                            22

<210> SEQ ID NO 151
<211> LENGTH: 18
<212> TYPE: DNA
<213> ORGANISM: Artificial Sequence
<220> FEATURE:
<223> OTHER INFORMATION: Primer oAT919

<400> SEQUENCE: 151
ctggctgtca aggcttcc                                                 18

<210> SEQ ID NO 152
<211> LENGTH: 19
<212> TYPE: DNA
<213> ORGANISM: Artificial Sequence
<220> FEATURE:
<223> OTHER INFORMATION: Primer oAT1040

<400> SEQUENCE: 152
tttgtggtgc agcttgaat                                                19

<210> SEQ ID NO 153
<211> LENGTH: 17
<212> TYPE: DNA
<213> ORGANISM: Artificial Sequence
<220> FEATURE:
<223> OTHER INFORMATION: Primer oAT967

<400> SEQUENCE: 153
gcgaacacga accctac                                                  17

<210> SEQ ID NO 154
<211> LENGTH: 17
<212> TYPE: DNA
<213> ORGANISM: Artificial Sequence
<220> FEATURE:
```

-continued

<223> OTHER INFORMATION: Primer oAT3618

<400> SEQUENCE: 154
tcaaagcagc aaactcc                                                                17

<210> SEQ ID NO 155
<211> LENGTH: 1232
<212> TYPE: PRT
<213> ORGANISM: Sulfuricurvum sp. PC08-66

<400> SEQUENCE: 155

```
Met Leu His Ala Phe Thr Asn Gln Tyr Gln Leu Ser Lys Thr Leu Arg
1               5                   10                  15

Phe Gly Ala Thr Leu Lys Glu Asp Glu Lys Lys Cys Lys Ser His Glu
            20                  25                  30

Glu Leu Lys Gly Phe Val Asp Ile Ser Tyr Glu Asn Met Lys Ser Ser
        35                  40                  45

Ala Thr Ile Ala Glu Ser Leu Asn Glu Asn Glu Leu Val Lys Lys Cys
    50                  55                  60

Glu Arg Cys Tyr Ser Glu Ile Val Lys Phe His Asn Ala Trp Glu Lys
65                  70                  75                  80

Ile Tyr Tyr Arg Thr Asp Gln Ile Ala Val Tyr Lys Asp Phe Tyr Arg
                85                  90                  95

Gln Leu Ser Arg Lys Ala Arg Phe Asp Ala Gly Lys Gln Asn Ser Gln
            100                 105                 110

Leu Ile Thr Leu Ala Ser Leu Cys Gly Met Tyr Gln Gly Ala Lys Leu
        115                 120                 125

Ser Arg Tyr Ile Thr Asn Tyr Trp Lys Asp Asn Ile Thr Arg Gln Lys
    130                 135                 140

Ser Phe Leu Lys Asp Phe Ser Gln Gln Leu His Gln Tyr Thr Arg Ala
145                 150                 155                 160

Leu Glu Lys Ser Asp Lys Ala His Thr Lys Pro Asn Leu Ile Asn Phe
                165                 170                 175

Asn Lys Thr Phe Met Val Leu Ala Asn Leu Val Asn Glu Ile Val Ile
            180                 185                 190

Pro Leu Ser Asn Gly Ala Ile Ser Phe Pro Asn Ile Ser Lys Leu Glu
        195                 200                 205

Asp Gly Glu Glu Ser His Leu Ile Glu Phe Ala Leu Asn Asp Tyr Ser
    210                 215                 220

Gln Leu Ser Glu Leu Ile Gly Glu Leu Lys Asp Ala Ile Ala Thr Asn
225                 230                 235                 240

Gly Gly Tyr Thr Pro Phe Ala Lys Val Thr Leu Asn His Tyr Thr Ala
                245                 250                 255

Glu Gln Lys Pro His Val Phe Lys Asn Asp Ile Asp Ala Lys Ile Arg
            260                 265                 270

Glu Leu Lys Leu Ile Gly Leu Val Glu Thr Leu Lys Gly Lys Ser Ser
        275                 280                 285

Glu Gln Ile Glu Glu Tyr Phe Ser Asn Leu Asp Lys Phe Ser Thr Tyr
    290                 295                 300

Asn Asp Arg Asn Gln Ser Val Ile Val Arg Thr Gln Cys Phe Lys Tyr
305                 310                 315                 320

Lys Pro Ile Pro Phe Leu Val Lys His Gln Leu Ala Lys Tyr Ile Ser
                325                 330                 335

Glu Pro Asn Gly Trp Asp Glu Asp Ala Val Ala Lys Val Leu Asp Ala
            340                 345                 350
```

-continued

```
Val Gly Ala Ile Arg Ser Pro Ala His Asp Tyr Ala Asn Asn Gln Glu
    355             360             365

Gly Phe Asp Leu Asn His Tyr Pro Ile Lys Val Ala Phe Asp Tyr Ala
    370             375             380

Trp Glu Gln Leu Ala Asn Ser Leu Tyr Thr Thr Val Thr Phe Pro Gln
385             390             395             400

Glu Met Cys Glu Lys Tyr Leu Asn Ser Ile Tyr Gly Cys Glu Val Ser
            405             410             415

Lys Glu Pro Val Phe Lys Phe Tyr Ala Asp Leu Leu Tyr Ile Arg Lys
            420             425             430

Asn Leu Ala Val Leu Glu His Lys Asn Asn Leu Pro Ser Asn Gln Glu
    435             440             445

Glu Phe Ile Cys Lys Ile Asn Asn Thr Phe Glu Asn Ile Val Leu Pro
    450             455             460

Tyr Lys Ile Ser Gln Phe Glu Thr Tyr Lys Lys Asp Ile Leu Ala Trp
465             470             475             480

Ile Asn Asp Gly His Asp His Lys Lys Tyr Thr Asp Ala Lys Gln Gln
            485             490             495

Leu Gly Phe Ile Arg Gly Gly Leu Lys Gly Arg Ile Lys Ala Glu Glu
            500             505             510

Val Ser Gln Lys Asp Lys Tyr Gly Lys Ile Lys Ser Tyr Tyr Glu Asn
    515             520             525

Pro Tyr Thr Lys Leu Thr Asn Glu Phe Lys Gln Ile Ser Ser Thr Tyr
    530             535             540

Gly Lys Thr Phe Ala Glu Leu Arg Asp Lys Phe Lys Glu Lys Asn Glu
545             550             555             560

Ile Thr Lys Ile Thr His Phe Gly Ile Ile Ile Glu Asp Lys Asn Arg
            565             570             575

Asp Arg Tyr Leu Leu Ala Ser Glu Leu Lys His Glu Gln Ile Asn His
            580             585             590

Val Ser Thr Ile Leu Asn Lys Leu Asp Lys Ser Ser Glu Phe Ile Thr
    595             600             605

Tyr Gln Val Lys Ser Leu Thr Ser Lys Thr Leu Ile Lys Leu Ile Lys
    610             615             620

Asn His Thr Thr Lys Lys Gly Ala Ile Ser Pro Tyr Ala Asp Phe His
625             630             635             640

Thr Ser Lys Thr Gly Phe Asn Lys Asn Glu Ile Glu Lys Asn Trp Asp
            645             650             655

Asn Tyr Lys Arg Glu Gln Val Leu Val Glu Tyr Val Lys Asp Cys Leu
            660             665             670

Thr Asp Ser Thr Met Ala Lys Asn Gln Asn Trp Ala Glu Phe Gly Trp
            675             680             685

Asn Phe Glu Lys Cys Asn Ser Tyr Glu Asp Ile Glu His Glu Ile Asp
    690             695             700

Gln Lys Ser Tyr Leu Leu Gln Ser Asp Thr Ile Ser Lys Gln Ser Ile
705             710             715             720

Ala Ser Leu Val Glu Gly Gly Cys Leu Leu Leu Pro Ile Ile Asn Gln
            725             730             735

Asp Ile Thr Ser Lys Glu Arg Lys Asp Lys Asn Gln Phe Ser Lys Asp
            740             745             750

Trp Asn His Ile Phe Glu Gly Ser Lys Glu Phe Arg Leu His Pro Glu
    755             760             765
```

```
Phe Ala Val Ser Tyr Arg Thr Pro Ile Glu Gly Tyr Pro Val Gln Lys
    770             775             780

Arg Tyr Gly Arg Leu Gln Phe Val Cys Ala Phe Asn Ala His Ile Val
785             790             795             800

Pro Gln Asn Gly Glu Phe Ile Asn Leu Lys Lys Gln Ile Glu Asn Phe
            805             810             815

Asn Asp Glu Asp Val Gln Lys Arg Asn Val Thr Glu Phe Asn Lys Lys
            820             825             830

Val Asn His Ala Leu Ser Asp Lys Glu Tyr Val Val Ile Gly Ile Asp
            835             840             845

Arg Gly Leu Lys Gln Leu Ala Thr Leu Cys Val Leu Asp Lys Arg Gly
    850             855             860

Lys Ile Leu Gly Asp Phe Glu Ile Tyr Lys Lys Glu Phe Val Arg Ala
865             870             875             880

Glu Lys Arg Ser Glu Ser His Trp Glu His Thr Gln Ala Glu Thr Arg
            885             890             895

His Ile Leu Asp Leu Ser Asn Leu Arg Val Glu Thr Thr Ile Glu Gly
            900             905             910

Lys Lys Val Leu Val Asp Gln Ser Leu Thr Leu Val Lys Lys Asn Arg
            915             920             925

Asp Thr Pro Asp Glu Glu Ala Thr Glu Glu Asn Lys Gln Lys Ile Lys
    930             935             940

Leu Lys Gln Leu Ser Tyr Ile Arg Lys Leu Gln His Lys Met Gln Thr
945             950             955             960

Asn Glu Gln Asp Val Leu Asp Leu Ile Asn Asn Glu Pro Ser Asp Glu
            965             970             975

Glu Phe Lys Lys Arg Ile Glu Gly Leu Ile Ser Ser Phe Gly Glu Gly
            980             985             990

Gln Lys Tyr Ala Asp Leu Pro Ile  Asn Thr Met Arg Glu  Met Ile Ser
        995             1000                1005

Asp Leu  Gln Gly Val Ile Ala  Arg Gly Asn Asn Gln  Thr Glu Lys
    1010            1015            1020

Asn Lys  Ile Ile Glu Leu Asp  Ala Ala Asp Asn Leu  Lys Gln Gly
    1025            1030            1035

Ile Val  Ala Asn Met Ile Gly  Ile Val Asn Tyr Ile  Phe Ala Lys
    1040            1045            1050

Tyr Ser  Tyr Lys Ala Tyr Ile  Ser Leu Glu Asp Leu  Ser Arg Ala
    1055            1060            1065

Tyr Gly  Gly Ala Lys Ser Gly  Tyr Asp Gly Arg Tyr  Leu Pro Ser
    1070            1075            1080

Thr Ser  Gln Asp Glu Asp Val  Asp Phe Lys Glu Gln  Gln Asn Gln
    1085            1090            1095

Met Leu  Ala Gly Leu Gly Thr  Tyr Gln Phe Phe Glu  Met Gln Leu
    1100            1105            1110

Leu Lys  Lys Leu Gln Lys Ile  Gln Ser Asp Asn Thr  Val Leu Arg
    1115            1120            1125

Phe Val  Pro Ala Phe Arg Ser  Ala Asp Asn Tyr Arg  Asn Ile Leu
    1130            1135            1140

Arg Leu  Glu Glu Thr Lys Tyr  Lys Ser Lys Pro Phe  Gly Val Val
    1145            1150            1155

His Phe  Ile Asp Pro Lys Phe  Thr Ser Lys Lys Cys  Pro Val Cys
    1160            1165            1170

Ser Lys  Thr Asn Val Tyr Arg  Asp Lys Asp Asp Ile  Leu Val Cys
```

-continued

```
          1175                1180                1185

Lys Glu  Cys Gly Phe Arg Ser  Asp Ser Gln Leu Lys  Glu Arg Glu
     1190                1195                1200

Asn Asn  Ile His Tyr Ile His  Asn Gly Asp Asp Asn  Gly Ala Tyr
     1205                1210                1215

His Ile  Ala Leu Lys Ser Val  Glu Asn Leu Ile Gln  Met Lys
     1220                1225                1230

<210> SEQ ID NO 156
<211> LENGTH: 3699
<212> TYPE: DNA
<213> ORGANISM: Sulfuricurvum sp. PC08-66
<220> FEATURE:
<221> NAME/KEY: CDS
<222> LOCATION: (1)..(3699)

<400> SEQUENCE: 156 atg ctt cac gct ttc act aat cag tat caa ctt tct aaa aca ttg aga        48
Met Leu His Ala Phe Thr Asn Gln Tyr Gln Leu Ser Lys Thr Leu Arg
1                5                  10                  15 ttc gga gca act ctg aaa gaa gac gag aaa aaa tgc aag agt cat gag        96
Phe Gly Ala Thr Leu Lys Glu Asp Glu Lys Lys Cys Lys Ser His Glu
                20                  25                  30 gaa ctt aaa gga ttt gta gat att tca tat gaa aac atg aaa tct tcc       144
Glu Leu Lys Gly Phe Val Asp Ile Ser Tyr Glu Asn Met Lys Ser Ser
            35                  40                  45 gct aca atc gct gaa agt ttg aac gaa aat gaa ctt gtg aaa aaa tgc       192
Ala Thr Ile Ala Glu Ser Leu Asn Glu Asn Glu Leu Val Lys Lys Cys
        50                  55                  60 gaa agg tgt tat tct gag atc gtg aaa ttt cat aac gct tgg gag aaa       240
Glu Arg Cys Tyr Ser Glu Ile Val Lys Phe His Asn Ala Trp Glu Lys
65                  70                  75                  80 atc tac tac agg aca gat caa att gct gtc tat aaa gat ttc tat agg       288
Ile Tyr Tyr Arg Thr Asp Gln Ile Ala Val Tyr Lys Asp Phe Tyr Arg
                85                  90                  95 caa ctg tca aga aaa gct aga ttt gat gcc ggt aag caa aat tca caa       336
Gln Leu Ser Arg Lys Ala Arg Phe Asp Ala Gly Lys Gln Asn Ser Gln
            100                 105                 110 ctg ata acc tta gct tcc ctt tgc ggt atg tac caa gga gct aag tta       384
Leu Ile Thr Leu Ala Ser Leu Cys Gly Met Tyr Gln Gly Ala Lys Leu
        115                 120                 125 agt aga tac ata acc aat tat tgg aaa gat aac att act agg cag aaa       432
Ser Arg Tyr Ile Thr Asn Tyr Trp Lys Asp Asn Ile Thr Arg Gln Lys
        130                 135                 140 tca ttt ctt aaa gat ttt tcc caa cag tta cat caa tac act cgt gca       480
Ser Phe Leu Lys Asp Phe Ser Gln Gln Leu His Gln Tyr Thr Arg Ala
145                 150                 155                 160 ctg gaa aag tct gat aag gct cat aca aaa cct aat ctg atc aac ttc       528
Leu Glu Lys Ser Asp Lys Ala His Thr Lys Pro Asn Leu Ile Asn Phe
                165                 170                 175 aat aag acc ttt atg gtg ttg gcc aat ctc gtg aac gaa ata gtt att       576
Asn Lys Thr Phe Met Val Leu Ala Asn Leu Val Asn Glu Ile Val Ile
            180                 185                 190 cct ctt tct aat gga gcc atc tct ttt cca aac atc tct aag ctg gag       624
Pro Leu Ser Asn Gly Ala Ile Ser Phe Pro Asn Ile Ser Lys Leu Glu
        195                 200                 205 gac ggg gaa gag tcc cat ctt ata gaa ttt gca ctc aat gac tat tct       672
Asp Gly Glu Glu Ser His Leu Ile Glu Phe Ala Leu Asn Asp Tyr Ser
        210                 215                 220 cag ttg tct gaa tta att ggt gaa ttg aag gat gca ata gcc act aac       720
```

-continued

```
Gln Leu Ser Glu Leu Ile Gly Glu Leu Lys Asp Ala Ile Ala Thr Asn
225                 230                 235                 240 ggt ggt tac aca cca ttt gca aag gtg acc ctt aat cat tat aca gca      768
Gly Gly Tyr Thr Pro Phe Ala Lys Val Thr Leu Asn His Tyr Thr Ala
                    245                 250                 255 gaa cag aaa cca cac gta ttt aaa aat gat att gat gct aaa ata cgt      816
Glu Gln Lys Pro His Val Phe Lys Asn Asp Ile Asp Ala Lys Ile Arg
                260                 265                 270 gag ctt aag ttg att ggg ttg gtt gag acc ttg aaa gga aaa tcc agt      864
Glu Leu Lys Leu Ile Gly Leu Val Glu Thr Leu Lys Gly Lys Ser Ser
            275                 280                 285 gaa cag att gag gaa tac ttc tca aat tta gac aag ttt agc aca tac      912
Glu Gln Ile Glu Glu Tyr Phe Ser Asn Leu Asp Lys Phe Ser Thr Tyr
        290                 295                 300 aac gat agg aac caa tca gta atc gta aga act caa tgc ttt aag tat      960
Asn Asp Arg Asn Gln Ser Val Ile Val Arg Thr Gln Cys Phe Lys Tyr
305                 310                 315                 320 aaa ccc att cct ttt ttg gtt aag cat caa ctt gca aag tac att tca     1008
Lys Pro Ile Pro Phe Leu Val Lys His Gln Leu Ala Lys Tyr Ile Ser
                    325                 330                 335 gaa cca aac ggt tgg gat gaa gac gcc gta gct aag gtt ctg gat gct     1056
Glu Pro Asn Gly Trp Asp Glu Asp Ala Val Ala Lys Val Leu Asp Ala
                340                 345                 350 gtt gga gct att cgt tct cca gca cat gat tac gct aat aac caa gag     1104
Val Gly Ala Ile Arg Ser Pro Ala His Asp Tyr Ala Asn Asn Gln Glu
            355                 360                 365 ggg ttt gat tta aac cat tat cct att aaa gtc gct ttc gat tat gct     1152
Gly Phe Asp Leu Asn His Tyr Pro Ile Lys Val Ala Phe Asp Tyr Ala
        370                 375                 380 tgg gag cag ttg gct aat tct ttg tat acc acc gtg act ttt ccc caa     1200
Trp Glu Gln Leu Ala Asn Ser Leu Tyr Thr Thr Val Thr Phe Pro Gln
385                 390                 395                 400 gaa atg tgc gaa aaa tat tta aat agt atc tac ggt tgt gaa gtc tcc     1248
Glu Met Cys Glu Lys Tyr Leu Asn Ser Ile Tyr Gly Cys Glu Val Ser
                    405                 410                 415 aag gag cct gta ttt aaa ttc tat gct gat ctg ctt tat atc agg aag     1296
Lys Glu Pro Val Phe Lys Phe Tyr Ala Asp Leu Leu Tyr Ile Arg Lys
                420                 425                 430 aat ctg gct gta ctc gaa cat aag aac aat ctg ccc agt aat cag gaa     1344
Asn Leu Ala Val Leu Glu His Lys Asn Asn Leu Pro Ser Asn Gln Glu
            435                 440                 445 gag ttc ata tgt aag atc aac aac aca ttt gag aac atc gtg tta cca     1392
Glu Phe Ile Cys Lys Ile Asn Asn Thr Phe Glu Asn Ile Val Leu Pro
        450                 455                 460 tat aag att tct caa ttt gaa act tat aag aag gat ata ctt gcc tgg     1440
Tyr Lys Ile Ser Gln Phe Glu Thr Tyr Lys Lys Asp Ile Leu Ala Trp
465                 470                 475                 480 ata aac gat ggg cat gac cat aaa aaa tat act gat gca aaa cag caa     1488
Ile Asn Asp Gly His Asp His Lys Lys Tyr Thr Asp Ala Lys Gln Gln
                    485                 490                 495 tta ggt ttt att agg ggt gga ctc aag ggt agg att aag gca gaa gaa     1536
Leu Gly Phe Ile Arg Gly Gly Leu Lys Gly Arg Ile Lys Ala Glu Glu
                500                 505                 510 gtg tcc cag aaa gac aaa tat gga aaa atc aag tct tat tat gag aac     1584
Val Ser Gln Lys Asp Lys Tyr Gly Lys Ile Lys Ser Tyr Tyr Glu Asn
            515                 520                 525 cct tac act aaa ctc acc aac gaa ttt aag caa ata tcc tct act tat     1632
Pro Tyr Thr Lys Leu Thr Asn Glu Phe Lys Gln Ile Ser Ser Thr Tyr
        530                 535                 540
```

-continued

```
ggg aag acc ttc gct gag tta aga gac aaa ttt aaa gag aag aat gag    1680
Gly Lys Thr Phe Ala Glu Leu Arg Asp Lys Phe Lys Glu Lys Asn Glu
545             550             555             560 atc acc aaa att acc cac ttc ggt att ata ata gaa gat aaa aac aga    1728
Ile Thr Lys Ile Thr His Phe Gly Ile Ile Ile Glu Asp Lys Asn Arg
                565             570             575 gac aga tat tta ctt gca agc gag ttg aag cac gaa caa atc aac cac    1776
Asp Arg Tyr Leu Leu Ala Ser Glu Leu Lys His Glu Gln Ile Asn His
            580             585             590 gtc agt act atc ctt aac aag tta gat aaa tca tct gaa ttt att acc    1824
Val Ser Thr Ile Leu Asn Lys Leu Asp Lys Ser Ser Glu Phe Ile Thr
        595             600             605 tat caa gtt aag agc ctt aca agc aaa aca ttg att aaa ttg att aaa    1872
Tyr Gln Val Lys Ser Leu Thr Ser Lys Thr Leu Ile Lys Leu Ile Lys
    610             615             620 aat cac acc aca aag aag gga gcc att tca cca tat gct gat ttt cac    1920
Asn His Thr Thr Lys Lys Gly Ala Ile Ser Pro Tyr Ala Asp Phe His
625             630             635             640 acc agt aaa acc gga ttc aac aag aat gaa atc gaa aag aat tgg gat    1968
Thr Ser Lys Thr Gly Phe Asn Lys Asn Glu Ile Glu Lys Asn Trp Asp
                645             650             655 aat tat aag aga gaa cag gta ttg gtt gag tat gtc aaa gat tgt ctg    2016
Asn Tyr Lys Arg Glu Gln Val Leu Val Glu Tyr Val Lys Asp Cys Leu
            660             665             670 acc gat agt act atg gca aaa aac cag aac tgg gca gag ttc ggt tgg    2064
Thr Asp Ser Thr Met Ala Lys Asn Gln Asn Trp Ala Glu Phe Gly Trp
        675             680             685 aat ttt gag aaa tgc aac tcc tat gag gat atc gaa cac gaa atc gac    2112
Asn Phe Glu Lys Cys Asn Ser Tyr Glu Asp Ile Glu His Glu Ile Asp
690             695             700 caa aaa tca tat ttg ctg cag agc gat aca att agc aag cag agt att    2160
Gln Lys Ser Tyr Leu Leu Gln Ser Asp Thr Ile Ser Lys Gln Ser Ile
705             710             715             720 gct tcc ctc gtg gag ggg ggc tgt ctt ctc ctt cct ata att aac caa    2208
Ala Ser Leu Val Glu Gly Gly Cys Leu Leu Leu Pro Ile Ile Asn Gln
                725             730             735 gat ata aca agc aag gag agg aag gat aaa aat caa ttt tca aaa gat    2256
Asp Ile Thr Ser Lys Glu Arg Lys Asp Lys Asn Gln Phe Ser Lys Asp
            740             745             750 tgg aac cat att ttc gaa ggt tcc aaa gaa ttc cgt ctc cac cca gag    2304
Trp Asn His Ile Phe Glu Gly Ser Lys Glu Phe Arg Leu His Pro Glu
        755             760             765 ttc gca gtt agc tac agg aca cct att gaa ggg tat ccg gta cag aag    2352
Phe Ala Val Ser Tyr Arg Thr Pro Ile Glu Gly Tyr Pro Val Gln Lys
    770             775             780 agg tac ggg cgt ctg cag ttc gtt tgc gct ttt aat gca cac atc gtt    2400
Arg Tyr Gly Arg Leu Gln Phe Val Cys Ala Phe Asn Ala His Ile Val
785             790             795             800 cca caa aat ggt gag ttc atc aat ttg aaa aag cag atc gag aac ttt    2448
Pro Gln Asn Gly Glu Phe Ile Asn Leu Lys Lys Gln Ile Glu Asn Phe
                805             810             815 aac gat gaa gac gtt cag aaa cgt aat gtg act gaa ttc aat aaa aag    2496
Asn Asp Glu Asp Val Gln Lys Arg Asn Val Thr Glu Phe Asn Lys Lys
            820             825             830 gtg aat cat gca ctt tcc gac aaa gaa tac gtc gtt att ggt att gat    2544
Val Asn His Ala Leu Ser Asp Lys Glu Tyr Val Val Ile Gly Ile Asp
            835             840             845 aga ggc ctc aaa cag ctt gcc aca ctc tgt gtt tta gac aaa aga ggt    2592
Arg Gly Leu Lys Gln Leu Ala Thr Leu Cys Val Leu Asp Lys Arg Gly
    850             855             860
```

-continued

```
aaa att ctt gga gat ttt gag atc tac aaa aag gaa ttt gtg cgt gct      2640
Lys Ile Leu Gly Asp Phe Glu Ile Tyr Lys Lys Glu Phe Val Arg Ala
865             870             875             880 gaa aaa aga agc gag agt cat tgg gaa cac aca caa gca gaa acc aga      2688
Glu Lys Arg Ser Glu Ser His Trp Glu His Thr Gln Ala Glu Thr Arg
            885             890             895 cat atc ttg gat ctt tcc aat ttg cgt gtg gag aca aca ata gag ggt      2736
His Ile Leu Asp Leu Ser Asn Leu Arg Val Glu Thr Thr Ile Glu Gly
            900             905             910 aaa aag gtt ctc gtg gac cag agc ctc aca ctt gtg aaa aag aat cgt      2784
Lys Lys Val Leu Val Asp Gln Ser Leu Thr Leu Val Lys Lys Asn Arg
            915             920             925 gat aca cca gat gag gaa gct act gaa gaa aat aaa cag aaa atc aag      2832
Asp Thr Pro Asp Glu Glu Ala Thr Glu Glu Asn Lys Gln Lys Ile Lys
    930             935             940 ttg aag cag ctc agc tat att aga aaa ttg cag cat aag atg cag act      2880
Leu Lys Gln Leu Ser Tyr Ile Arg Lys Leu Gln His Lys Met Gln Thr
945             950             955             960 aac gaa cag gac gtt tta gat tta att aat aat gaa cca tca gat gaa      2928
Asn Glu Gln Asp Val Leu Asp Leu Ile Asn Asn Glu Pro Ser Asp Glu
            965             970             975 gaa ttt aag aaa aga atc gag ggg ctt att tcc agt ttt gga gaa gga      2976
Glu Phe Lys Lys Arg Ile Glu Gly Leu Ile Ser Ser Phe Gly Glu Gly
            980             985             990 cag aag tac gct gac ctt cca att  aat act atg aga gaa  atg atc tct     3024
Gln Lys Tyr Ala Asp Leu Pro Ile  Asn Thr Met Arg Glu  Met Ile Ser
        995             1000            1005 gat ctc  cag gga gtt atc gct  aga gga aac aac caa  aca gag aaa        3069
Asp Leu  Gln Gly Val Ile Ala  Arg Gly Asn Asn Gln  Thr Glu Lys
    1010            1015            1020 aat aaa  att att gaa tta gat  gct gca gac aac ctt  aaa caa ggt        3114
Asn Lys  Ile Ile Glu Leu Asp  Ala Ala Asp Asn Leu  Lys Gln Gly
    1025            1030            1035 att gta  gct aac atg atc gga  att gtt aat tac atc  ttc gct aag        3159
Ile Val  Ala Asn Met Ile Gly  Ile Val Asn Tyr Ile  Phe Ala Lys
    1040            1045            1050 tat tca  tac aag gct tac atc  tct ctt gag gat ttg  tca aga gcc        3204
Tyr Ser  Tyr Lys Ala Tyr Ile  Ser Leu Glu Asp Leu  Ser Arg Ala
    1055            1060            1065 tat gga  ggt gca aag tcc ggt  tat gac gga agg tat  ctg cca tca        3249
Tyr Gly  Gly Ala Lys Ser Gly  Tyr Asp Gly Arg Tyr  Leu Pro Ser
    1070            1075            1080 act tca  caa gac gag gat gta  gat ttc aag gaa cag  cag aat cag        3294
Thr Ser  Gln Asp Glu Asp Val  Asp Phe Lys Glu Gln  Gln Asn Gln
    1085            1090            1095 atg ctt  gca ggt ttg ggt acc  tac caa ttc ttc gag  atg cag ctt        3339
Met Leu  Ala Gly Leu Gly Thr  Tyr Gln Phe Phe Glu  Met Gln Leu
    1100            1105            1110 ctg aaa  aaa ctt caa aag att  cag agt gat aac acc  gtt ctg aga        3384
Leu Lys  Lys Leu Gln Lys Ile  Gln Ser Asp Asn Thr  Val Leu Arg
    1115            1120            1125 ttc gtg  ccc gct ttc aga tct  gca gat aac tat aga  aat att ttg        3429
Phe Val  Pro Ala Phe Arg Ser  Ala Asp Asn Tyr Arg  Asn Ile Leu
    1130            1135            1140 aga ctt  gag gaa act aaa tat  aag tct aag ccg ttc  ggc gtt gtt        3474
Arg Leu  Glu Glu Thr Lys Tyr  Lys Ser Lys Pro Phe  Gly Val Val
    1145            1150            1155 cat ttc  ata gat cca aag ttt  aca tca aag aaa tgc  ccc gtc tgt        3519
His Phe  Ile Asp Pro Lys Phe  Thr Ser Lys Lys Cys  Pro Val Cys
```

-continued

```
              1160                1165                1170 agc aaa  aca aat gta tac agg  gac aag gat gac atc  ttg gtt tgc     3564
Ser Lys  Thr Asn Val Tyr Arg  Asp Lys Asp Asp Ile  Leu Val Cys
    1175                1180                1185 aaa gag  tgc ggt ttt agg agc  gac tcc caa tta aaa  gaa aga gag     3609
Lys Glu  Cys Gly Phe Arg Ser  Asp Ser Gln Leu Lys  Glu Arg Glu
    1190                1195                1200 aat aac  att cat tat att cac  aac ggg gac gat aac  ggt gca tac     3654
Asn Asn  Ile His Tyr Ile His  Asn Gly Asp Asp Asn  Gly Ala Tyr
    1205                1210                1215 cac atc  gcc ctt aag agc gtt  gag aat ctt att cag  atg aag taa     3699
His Ile  Ala Leu Lys Ser Val  Glu Asn Leu Ile Gln  Met Lys
    1220                1225                1230

<210> SEQ ID NO 157
<211> LENGTH: 1232
<212> TYPE: PRT
<213> ORGANISM: Sulfuricurvum sp. PC08-66

<400> SEQUENCE: 157

Met Leu His Ala Phe Thr Asn Gln Tyr Gln Leu Ser Lys Thr Leu Arg
1               5                   10                  15

Phe Gly Ala Thr Leu Lys Glu Asp Glu Lys Lys Cys Lys Ser His Glu
                20                  25                  30

Glu Leu Lys Gly Phe Val Asp Ile Ser Tyr Glu Asn Met Lys Ser Ser
            35                  40                  45

Ala Thr Ile Ala Glu Ser Leu Asn Glu Asn Glu Leu Val Lys Lys Cys
        50                  55                  60

Glu Arg Cys Tyr Ser Glu Ile Val Lys Phe His Asn Ala Trp Glu Lys
65                  70                  75                  80

Ile Tyr Tyr Arg Thr Asp Gln Ile Ala Val Tyr Lys Asp Phe Tyr Arg
                85                  90                  95

Gln Leu Ser Arg Lys Ala Arg Phe Asp Ala Gly Lys Gln Asn Ser Gln
                100                 105                 110

Leu Ile Thr Leu Ala Ser Leu Cys Gly Met Tyr Gln Gly Ala Lys Leu
            115                 120                 125

Ser Arg Tyr Ile Thr Asn Tyr Trp Lys Asp Asn Ile Thr Arg Gln Lys
        130                 135                 140

Ser Phe Leu Lys Asp Phe Ser Gln Gln Leu His Gln Tyr Thr Arg Ala
145                 150                 155                 160

Leu Glu Lys Ser Asp Lys Ala His Thr Lys Pro Asn Leu Ile Asn Phe
                165                 170                 175

Asn Lys Thr Phe Met Val Leu Ala Asn Leu Val Asn Glu Ile Val Ile
            180                 185                 190

Pro Leu Ser Asn Gly Ala Ile Ser Phe Pro Asn Ile Ser Lys Leu Glu
            195                 200                 205

Asp Gly Glu Glu Ser His Leu Ile Glu Phe Ala Leu Asn Asp Tyr Ser
        210                 215                 220

Gln Leu Ser Glu Leu Ile Gly Glu Leu Lys Asp Ala Ile Ala Thr Asn
225                 230                 235                 240

Gly Gly Tyr Thr Pro Phe Ala Lys Val Thr Leu Asn His Tyr Thr Ala
                245                 250                 255

Glu Gln Lys Pro His Val Phe Lys Asn Asp Ile Asp Ala Lys Ile Arg
            260                 265                 270

Glu Leu Lys Leu Ile Gly Leu Val Glu Thr Leu Lys Gly Lys Ser Ser
        275                 280                 285
```

-continued

```
Glu Gln Ile Glu Glu Tyr Phe Ser Asn Leu Asp Lys Phe Ser Thr Tyr
    290                 295                 300

Asn Asp Arg Asn Gln Ser Val Ile Val Arg Thr Gln Cys Phe Lys Tyr
305                 310                 315                 320

Lys Pro Ile Pro Phe Leu Val Lys His Gln Leu Ala Lys Tyr Ile Ser
                325                 330                 335

Glu Pro Asn Gly Trp Asp Glu Asp Ala Val Ala Lys Val Leu Asp Ala
                340                 345                 350

Val Gly Ala Ile Arg Ser Pro Ala His Asp Tyr Ala Asn Asn Gln Glu
                355                 360                 365

Gly Phe Asp Leu Asn His Tyr Pro Ile Lys Val Ala Phe Asp Tyr Ala
    370                 375                 380

Trp Glu Gln Leu Ala Asn Ser Leu Tyr Thr Thr Val Thr Phe Pro Gln
385                 390                 395                 400

Glu Met Cys Glu Lys Tyr Leu Asn Ser Ile Tyr Gly Cys Glu Val Ser
                405                 410                 415

Lys Glu Pro Val Phe Lys Phe Tyr Ala Asp Leu Leu Tyr Ile Arg Lys
                420                 425                 430

Asn Leu Ala Val Leu Glu His Lys Asn Asn Leu Pro Ser Asn Gln Glu
                435                 440                 445

Glu Phe Ile Cys Lys Ile Asn Asn Thr Phe Glu Asn Ile Val Leu Pro
    450                 455                 460

Tyr Lys Ile Ser Gln Phe Glu Thr Tyr Lys Lys Asp Ile Leu Ala Trp
465                 470                 475                 480

Ile Asn Asp Gly His Asp His Lys Lys Tyr Thr Asp Ala Lys Gln Gln
                485                 490                 495

Leu Gly Phe Ile Arg Gly Gly Leu Lys Gly Arg Ile Lys Ala Glu Glu
                500                 505                 510

Val Ser Gln Lys Asp Lys Tyr Gly Lys Ile Lys Ser Tyr Tyr Glu Asn
                515                 520                 525

Pro Tyr Thr Lys Leu Thr Asn Glu Phe Lys Gln Ile Ser Ser Thr Tyr
    530                 535                 540

Gly Lys Thr Phe Ala Glu Leu Arg Asp Lys Phe Lys Glu Lys Asn Glu
545                 550                 555                 560

Ile Thr Lys Ile Thr His Phe Gly Ile Ile Glu Asp Lys Asn Arg
                565                 570                 575

Asp Arg Tyr Leu Leu Ala Ser Glu Leu Lys His Glu Gln Ile Asn His
                580                 585                 590

Val Ser Thr Ile Leu Asn Lys Leu Asp Lys Ser Ser Glu Phe Ile Thr
                595                 600                 605

Tyr Gln Val Lys Ser Leu Thr Ser Lys Thr Leu Ile Lys Leu Ile Lys
    610                 615                 620

Asn His Thr Thr Lys Lys Gly Ala Ile Ser Pro Tyr Ala Asp Phe His
625                 630                 635                 640

Thr Ser Lys Thr Gly Phe Asn Lys Asn Glu Ile Glu Lys Asn Trp Asp
                645                 650                 655

Asn Tyr Lys Arg Glu Gln Val Leu Val Glu Tyr Val Lys Asp Cys Leu
                660                 665                 670

Thr Asp Ser Thr Met Ala Lys Asn Gln Asn Trp Ala Glu Phe Gly Trp
                675                 680                 685

Asn Phe Glu Lys Cys Asn Ser Tyr Glu Asp Ile Glu His Glu Ile Asp
    690                 695                 700
```

```
Gln Lys Ser Tyr Leu Leu Gln Ser Asp Thr Ile Ser Lys Gln Ser Ile
705                 710                 715                 720

Ala Ser Leu Val Glu Gly Gly Cys Leu Leu Leu Pro Ile Ile Asn Gln
                725                 730                 735

Asp Ile Thr Ser Lys Glu Arg Lys Asp Lys Asn Gln Phe Ser Lys Asp
            740                 745                 750

Trp Asn His Ile Phe Glu Gly Ser Lys Glu Phe Arg Leu His Pro Glu
        755                 760                 765

Phe Ala Val Ser Tyr Arg Thr Pro Ile Glu Gly Tyr Pro Val Gln Lys
770                 775                 780

Arg Tyr Gly Arg Leu Gln Phe Val Cys Ala Phe Asn Ala His Ile Val
785                 790                 795                 800

Pro Gln Asn Gly Glu Phe Ile Asn Leu Lys Lys Gln Ile Glu Asn Phe
                805                 810                 815

Asn Asp Glu Asp Val Gln Lys Arg Asn Val Thr Glu Phe Asn Lys Lys
            820                 825                 830

Val Asn His Ala Leu Ser Asp Lys Glu Tyr Val Val Ile Gly Ile Asp
        835                 840                 845

Arg Gly Leu Lys Gln Leu Ala Thr Leu Cys Val Leu Asp Lys Arg Gly
    850                 855                 860

Lys Ile Leu Gly Asp Phe Glu Ile Tyr Lys Lys Glu Phe Val Arg Ala
865                 870                 875                 880

Glu Lys Arg Ser Glu Ser His Trp Glu His Thr Gln Ala Glu Thr Arg
                885                 890                 895

His Ile Leu Asp Leu Ser Asn Leu Arg Val Glu Thr Thr Ile Glu Gly
            900                 905                 910

Lys Lys Val Leu Val Asp Gln Ser Leu Thr Leu Val Lys Lys Asn Arg
        915                 920                 925

Asp Thr Pro Asp Glu Glu Ala Thr Glu Glu Asn Lys Gln Lys Ile Lys
    930                 935                 940

Leu Lys Gln Leu Ser Tyr Ile Arg Lys Leu Gln His Lys Met Gln Thr
945                 950                 955                 960

Asn Glu Gln Asp Val Leu Asp Leu Ile Asn Asn Glu Pro Ser Asp Glu
                965                 970                 975

Glu Phe Lys Lys Arg Ile Glu Gly Leu Ile Ser Ser Phe Gly Glu Gly
                980                 985                 990

Gln Lys Tyr Ala Asp Leu Pro Ile Asn Thr Met Arg Glu Met Ile Ser
        995                 1000                1005

Asp Leu Gln Gly Val Ile Ala Arg Gly Asn Asn Gln Thr Glu Lys
    1010                1015                1020

Asn Lys Ile Ile Glu Leu Asp Ala Ala Asp Asn Leu Lys Gln Gly
    1025                1030                1035

Ile Val Ala Asn Met Ile Gly Ile Val Asn Tyr Ile Phe Ala Lys
    1040                1045                1050

Tyr Ser Tyr Lys Ala Tyr Ile Ser Leu Glu Asp Leu Ser Arg Ala
    1055                1060                1065

Tyr Gly Gly Ala Lys Ser Gly Tyr Asp Gly Arg Tyr Leu Pro Ser
    1070                1075                1080

Thr Ser Gln Asp Glu Asp Val Asp Phe Lys Glu Gln Gln Asn Gln
    1085                1090                1095

Met Leu Ala Gly Leu Gly Thr Tyr Gln Phe Phe Glu Met Gln Leu
    1100                1105                1110

Leu Lys Lys Leu Gln Lys Ile Gln Ser Asp Asn Thr Val Leu Arg
```

```
     1115                 1120                 1125

Phe Val  Pro Ala Phe Arg Ser  Ala Asp Asn Tyr Arg  Asn Ile Leu
     1130                 1135                 1140

Arg Leu  Glu Glu Thr Lys Tyr  Lys Ser Lys Pro Phe  Gly Val Val
     1145                 1150                 1155

His Phe  Ile Asp Pro Lys Phe  Thr Ser Lys Lys Cys  Pro Val Cys
     1160                 1165                 1170

Ser Lys  Thr Asn Val Tyr Arg  Asp Lys Asp Asp Ile  Leu Val Cys
     1175                 1180                 1185

Lys Glu  Cys Gly Phe Arg Ser  Asp Ser Gln Leu Lys  Glu Arg Glu
     1190                 1195                 1200

Asn Asn  Ile His Tyr Ile His  Asn Gly Asp Asp Asn  Gly Ala Tyr
     1205                 1210                 1215

His Ile  Ala Leu Lys Ser Val  Glu Asn Leu Ile Gln  Met Lys
     1220                 1225                 1230
```

<210> SEQ ID NO 158
<211> LENGTH: 4995
<212> TYPE: DNA
<213> ORGANISM: Artificial Sequence
<220> FEATURE:
<223> OTHER INFORMATION: pMDT452: MAD7d-AID-UGI nucleotide sequence

<400> SEQUENCE: 158

```
atgaataatg gcacaaataa cttccagaac ttcattggca ttagcagcct gcaaaaaaca          60
ctgagaaatg cactgattcc gacagaaaca acacagcagt ttattgtcaa aaacggcatc         120
atcaaagagg atgaactgag aggcgaaaat cgccaaattc tgaaagatat catggacgac         180
tattaccgtg gctttatttc agaaacactg tccagcattg atgatatcga ttggacaagc         240
ctgttcgaga aaatggaaat ccaactgaaa aacggcgata caaagacac gctgattaaa         300 gaacaaacgg aatatcgcaa agcgatccac aaaaagtttg caaatgatga ccgctttaaa         360
aacatgttca gcgcgaaact gattagcgat attctgccgg aatttgtcat ccacaataat         420
aactatagcg cgagcgagaa agaagaaaaa acacaggtca ttaaactgtt tagccgcttt         480
gccacaagct tcaaagacta tttcaaaaat cgcgcaaact gctttagcgc agatgatatt         540
tcatcatcaa gctgccatcg gattgtcaat gataatgcgg aaatctttt tagcaacgca         600 ctggtctatc gcagaattgt taaatcattg agcaacgacg acatcaacaa aatctcaggc         660
gatatgaaag acagcctgaa agaaatgtca ctggaagaaa tctacagcta cgaaaaatac         720
ggcgaattta tcacacaaga aggcatcagc ttttacaacg atatttgcgg caaagtcaac         780
agctttatga atctgtattg ccagaaaaac aaagaaaaca aaacctgta taaactgcag         840 aaactgcaca gcagattct gtgcattgca gatacatcat atgaagtccc gtacaaattt         900
gagagcgacg aagaagttta tcaaagcgtt aatggctttc tggataacat cagcagcaaa         960
catattgttg aacgcctgag aaaaattggc gataactata tggctacaa cctggacaaa        1020 atctacatcg tcagcaaatt ttacgaaagc gtcagccaaa aacatatcg cgattgggaa        1080 acaattaata cagcgctgga aattcattat aacaacattc tgcctggcaa cggcaaaagc       1140
aaagcagata aagttaaaaa ggcggtcaaa aatgacctgc agaaaagcat tacagaaatc       1200
aatgaactgg tcagcaacta caaactgtgc tcagatgata tatcaaggc ggaaacgtac       1260 atccatgaaa ttagccatat cctgaacaac tttgaagcgc aagaactgaa atataacccg       1320
gaaatccatc tggttgaaag cgaactgaaa gcaagcgagc tgaaaaatgt tctggatgtc       1380
```

-continued

```
attatgaatg cgtttcattg gtgcagcgtc tttatgacag aagaactggt cgataaagat   1440
aacaactttt atgcggaact ggaagagatt tacgacgaaa tttatccggt catcagcctg   1500
tataatctgg ttcgcaatta tgtcacacag aaaccgtata gcacgaagaa aatcaaactg   1560
aactttggca ttccgacact ggcagatggc tggtcaaaat caaaagaata tagcaacaac   1620
gcgatcatcc tgatgcgcga taatctttat tatctgggca ttttcaacgc gaaaaacaag   1680
ccggacaaaa aaatcatcga aggcaatacg tcagagaaca aaggcgacta taaaaagatg   1740
atctataatc tgcttccggg accgaataaa atgatcccga aagttttct gtcaagcaaa    1800 acaggcgtcg aaacatataa accgtcagcg tatattctgg aaggctacaa acagaacaaa   1860
cacatcaaaa gcagcaagga ctttgacatc acattttgcc atgatctgat cgactacttt   1920
aagaactgca ttgcaattca tccggaatgg aaaaacttcg gctttgattt ttcagacacg   1980
agcacgtatg aagatatcag cggctttat agagaagttg aactgcaggg ctataaaatc    2040
gactggacat atatcagcga aaaggatatt gatctgctgc aagaaaaagg ccaactgtac   2100
ctgtttcaga tctacaacaa agacttcagc aaaaaaagc cggcaatga taacctgcat     2160 acgatgtacc tgaaaaacct ttttagcgaa gagaacctga agacattgt cctgaaactg     2220 aatggcgaag ccgaaatttt ctttcgcaaa tccagcatta aaaacccgat catccataaa   2280
aaaggcagca ttctggttaa ccgcacatat gaagcggaag aaaaagatca gtttggcaac   2340
attcagatcg tccgcaaaaa cattccggaa aacattatc aagaactgta caaatacttt      2400
aacgataaaa gcgataaaga actgtccgac gaagcagcga aacttaaaaa tgttgttggc   2460
catcatgaag cggcaacaaa cattgttaaa gactatcgct atacgtacga taaatacttt   2520
ctgcatatgc cgatcacgat caacttcaaa gcaaataaaa cgggctttat caacgatcgc   2580
attctgcagt atattgccaa agaaaaggat ctgcatgtca tcggcattgc tagaggcgaa   2640
cgcaatctga tttatgtcag cgttattgat acatgcggca acattgtcga acagaaaagc   2700
tttaacattg tcaacggcta tgactaccag atcaagctga aacagcaaga aggcgcaaga   2760
caaattgctc gcaaagaatg gaaagaaatc ggcaagatca agaaattaa agagggctat    2820 ctgagcctgg tcattcatga aatttctaaa atggtcatca aatataacgc gattatcgcc   2880
atggaagatc tgtcatatgg ctttaagaaa ggccgtttta aagtcgaaag acaggtctac   2940
cagaaattcg aaacaatgct gattaacaaa ctgaattatc tggtgtttaa agacatcagc   3000
atcacggaaa atggcggact gctgaaaggc tatcaactga catatattcc ggataagctt   3060
aaaaacgtcg gccatcaatg cggctgcatc ttttatgttc cggcagcgta tacatcaaaa   3120
attgatccga caacaggctt tgtcaacatc ttcaaattca aagatctgac ggtcgatgcg   3180
aaacgcgaat tcattaagaa atttgacagc atccgctacg acagcgagaa aaatctttc     3240 tgctttacgt tcgactacaa caactttatc acgcagaata cggttatgtc aaaaagcagc   3300
tggtcagtct atacatatgg cgttagaatt aaacgcagat ttgtgaacgg cagatttagc   3360
aatgaaagcg atacaatcga catcacgaaa gacatggaaa aaacgcttga aatgacggat   3420
attaactggc gtgatggaca tgatcttcgc caggatatta tcgattatga aatcgtccag   3480
cacatctttg aaaatcttag actgacagtc caaatgcgca attcactgtc agaacttgaa   3540
gatagagatt atgatcgcct gatttctccg gtcctgaatg aaaataacat cttttacgat   3600
agcgcaaaag caggcgacgc actgccgaaa gatgcggatg caaatggcgc atattgcatt   3660
gcactgaaag gcctgtatga aatcaaacaa atcaccgaga attggaaaga ggacggcaaa   3720
ttttcacggg ataaactgaa aatcagcaac aaggactggt ttgacttcat ccaaaataag   3780
```

-continued

```
cgctacctgc cgtcaagagc agatccgaag aaaaagagaa aagttggcgg aggcggatca    3840
ggcggaggtg gctcagcaga atatgttaga gcactgtttg attttaacgg caacgatgaa    3900
gaagatctgc cgttcaaaaa aggcgatatt ctgagaattc gcgacaaacc ggaagaacaa    3960
tggtggaatg cagaagatag cgaaggcaaa agaggcatga ttccggttcc gtatgttgaa    4020
aaatactcag gcgattacaa agatcatgac ggcgactata agaccatga catcgattat     4080 aaggacgacg atgataaaag cagaatgacg gatgcggaat atgttcgcat tcatgaaaaa    4140
ctggacatct acacgttcaa gaagcagttc ttcaacaaca aaaaaagcgt cagccataga    4200
tgctacgttc tgtttgaact gaaaagaaga ggcgaaagac gcgcatgctt ttggggctat    4260
gcagttaata aaccgcaatc aggcacagaa cgcggaattc atgcagaaat ctttagcatt    4320
cgcaaagtcg aagaatatct gagagataat ccgggacagt ttacgattaa ttggtattca    4380
tcatggtcac cgtgcgcaga ttgcgcagaa aaaattctgg aatggtataa ccaagaactg    4440
agaggcaatg gccatacact gaaaatttgg gcatgcaaac tgtactacga aaaaaatgca    4500
cgcaatcaaa ttggcctgtg gaatctgcgc gataatggcg ttggcctgaa tgttatggtt    4560
agcgaacatt atcaatgctg ccgcaaaatc tttattcaga gcagccataa tcagctgaat    4620
gaaaatagat ggctggaaaa aacactgaaa cgtgcggaaa aaagacgctc agaactgagc    4680
attatgatcc aggttaaaat cctgcataca acgaaatcac cggcagtttc aagaggctca    4740
ggcacaaatc tgagcgatat tatcgaaaaa gaaacgggca acagctggt cattcaagaa     4800 tcaattctga tgctgccgga agaagttgaa gaagtcattg caataaaacc ggaaagcgat    4860
atcctggttc atacagcata tgatgaaagc acagatgaaa atgtcatgct gctgacatca    4920
gatgcaccgg aatacaaacc gtgggcactt gttattcaag atagcaatgg cgagaacaag    4980
atcaaaatgc tgtaa                                                     4995
```

<210> SEQ ID NO 159
<211> LENGTH: 1664
<212> TYPE: PRT
<213> ORGANISM: Artificial Sequence
<220> FEATURE:
<223> OTHER INFORMATION: pMDT452: MAD7d-AID-UGI polypeptide sequence

<400> SEQUENCE: 159

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140
```

```
Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
                180                 185                 190

Ala Glu Ile Phe Phe Ser Asn Ala Leu Val Tyr Arg Arg Ile Val Lys
                195                 200                 205

Ser Leu Ser Asn Asp Asp Ile Asn Lys Ile Ser Gly Asp Met Lys Asp
        210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
        450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560
```

-continued

```
Pro Asp Lys Lys Ile Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Ile Lys Ser
            610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Ala Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
```

-continued

```
                        980               985                 990
Tyr Leu Val Phe Lys Asp Ile Ser  Ile Thr Glu Asn Gly  Gly Leu Leu
        995                1000                 1005

Lys Gly  Tyr Gln Leu Thr Tyr  Ile Pro Asp Lys Leu  Lys Asn Val
    1010                1015                1020

Gly His  Gln Cys Gly Cys Ile  Phe Tyr Val Pro Ala  Ala Tyr Thr
    1025                1030                1035

Ser Lys  Ile Asp Pro Thr Thr  Gly Phe Val Asn Ile  Phe Lys Phe
    1040                1045                1050

Lys Asp  Leu Thr Val Asp Ala  Lys Arg Glu Phe Ile  Lys Lys Phe
    1055                1060                1065

Asp Ser  Ile Arg Tyr Asp Ser  Glu Lys Asn Leu Phe  Cys Phe Thr
    1070                1075                1080

Phe Asp  Tyr Asn Asn Phe Ile  Thr Gln Asn Thr Val  Met Ser Lys
    1085                1090                1095

Ser Ser  Trp Ser Val Tyr Thr  Tyr Gly Val Arg Ile  Lys Arg Arg
    1100                1105                1110

Phe Val  Asn Gly Arg Phe Ser  Asn Glu Ser Asp Thr  Ile Asp Ile
    1115                1120                1125

Thr Lys  Asp Met Glu Lys Thr  Leu Glu Met Thr Asp  Ile Asn Trp
    1130                1135                1140

Arg Asp  Gly His Asp Leu Arg  Gln Asp Ile Ile Asp  Tyr Glu Ile
    1145                1150                1155

Val Gln  His Ile Phe Glu Ile  Phe Arg Leu Thr Val  Gln Met Arg
    1160                1165                1170

Asn Ser  Leu Ser Glu Leu Glu  Asp Arg Asp Tyr Asp  Arg Leu Ile
    1175                1180                1185

Ser Pro  Val Leu Asn Glu Asn  Asn Ile Phe Tyr Asp  Ser Ala Lys
    1190                1195                1200

Ala Gly  Asp Ala Leu Pro Lys  Asp Ala Asp Ala Asn  Gly Ala Tyr
    1205                1210                1215

Cys Ile  Ala Leu Lys Gly Leu  Tyr Glu Ile Lys Gln  Ile Thr Glu
    1220                1225                1230

Asn Trp  Lys Glu Asp Gly Lys  Phe Ser Arg Asp Lys  Leu Lys Ile
    1235                1240                1245

Ser Asn  Lys Asp Trp Phe Asp  Phe Ile Gln Asn Lys  Arg Tyr Leu
    1250                1255                1260

Pro Ser  Arg Ala Asp Pro Lys  Lys Lys Arg Lys Val  Gly Gly Gly
    1265                1270                1275

Gly Ser  Gly Gly Gly Gly Ser  Ala Glu Tyr Val Arg  Ala Leu Phe
    1280                1285                1290

Asp Phe  Asn Gly Asn Asp Glu  Glu Asp Leu Pro Phe  Lys Lys Gly
    1295                1300                1305

Asp Ile  Leu Arg Ile Arg Asp  Lys Pro Glu Glu Gln  Trp Trp Asn
    1310                1315                1320

Ala Glu  Asp Ser Glu Gly Lys  Arg Gly Met Ile Pro  Val Pro Tyr
    1325                1330                1335

Val Glu  Lys Tyr Ser Gly Asp  Tyr Lys Asp His Asp  Gly Asp Tyr
    1340                1345                1350

Lys Asp  His Asp Ile Asp Tyr  Lys Asp Asp Asp Asp  Lys Ser Arg
    1355                1360                1365

Met Thr  Asp Ala Glu Tyr Val  Arg Ile His Glu Lys  Leu Asp Ile
    1370                1375                1380
```

-continued

```
Tyr Thr  Phe Lys Lys Gln Phe  Phe Asn Asn Lys Lys  Ser Val Ser
    1385             1390             1395

His Arg  Cys Tyr Val Leu Phe  Glu Leu Lys Arg Arg  Gly Glu Arg
    1400             1405             1410

Arg Ala  Cys Phe Trp Gly Tyr  Ala Val Asn Lys Pro  Gln Ser Gly
    1415             1420             1425

Thr Glu  Arg Gly Ile His Ala  Glu Ile Phe Ser Ile  Arg Lys Val
    1430             1435             1440

Glu Glu  Tyr Leu Arg Asp Asn  Pro Gly Gln Phe Thr  Ile Asn Trp
    1445             1450             1455

Tyr Ser  Ser Trp Ser Pro Cys  Ala Asp Cys Ala Glu  Lys Ile Leu
    1460             1465             1470

Glu Trp  Tyr Asn Gln Glu Leu  Arg Gly Asn Gly His  Thr Leu Lys
    1475             1480             1485

Ile Trp  Ala Cys Lys Leu Tyr  Tyr Glu Lys Asn Ala  Arg Asn Gln
    1490             1495             1500

Ile Gly  Leu Trp Asn Leu Arg  Asp Asn Gly Val Gly  Leu Asn Val
    1505             1510             1515

Met Val  Ser Glu His Tyr Gln  Cys Cys Arg Lys Ile  Phe Ile Gln
    1520             1525             1530

Ser Ser  His Asn Gln Leu Asn  Glu Asn Arg Trp Leu  Glu Lys Thr
    1535             1540             1545

Leu Lys  Arg Ala Glu Lys Arg  Arg Ser Glu Leu Ser  Ile Met Ile
    1550             1555             1560

Gln Val  Lys Ile Leu His Thr  Thr Lys Ser Pro Ala  Val Ser Arg
    1565             1570             1575

Gly Ser  Gly Thr Asn Leu Ser  Asp Ile Ile Glu Lys  Glu Thr Gly
    1580             1585             1590

Lys Gln  Leu Val Ile Gln Glu  Ser Ile Leu Met Leu  Pro Glu Glu
    1595             1600             1605

Val Glu  Glu Val Ile Gly Asn  Lys Pro Glu Ser Asp  Ile Leu Val
    1610             1615             1620

His Thr  Ala Tyr Asp Glu Ser  Thr Asp Glu Asn Val  Met Leu Leu
    1625             1630             1635

Thr Ser  Asp Ala Pro Glu Tyr  Lys Pro Trp Ala Leu  Val Ile Gln
    1640             1645             1650

Asp Ser  Asn Gly Glu Asn Lys  Ile Lys Met Leu
    1655             1660
```

```
<210> SEQ ID NO 160
<211> LENGTH: 7682
<212> TYPE: DNA
<213> ORGANISM: Artificial Sequence
<220> FEATURE:
<223> OTHER INFORMATION: pMDT454 nucleotide sequence

<400> SEQUENCE: 160
aactaactca acgctagtag tggatttaat cccaaatgag ccaacagaac cagaaccaga      60
aacagaatca gaacaagtaa cattggattt agaaatggaa gaagaaaaaa gcaatgactt     120
cgtgtgaata atgcacgaaa tcgttgctta tttttttaa  aagcggtata ctagatataa     180
cgaaacaacg aactgaatag aaacgaaaaa agagccatga cacatttata aaatgtttga     240
cgacatttta taaatgcata gcccgataag attgccaaac caacgcttat cagttagtca     300
gatgaactct tccctcgtaa gaagttattt aattaacttt gtttgaagac ggtatataac     360
```

-continued

```
cgtactatca ttatataggg aaatcagaga gttttcaagt atctaagcta ctgaatttaa      420
gaattgttaa gcaatcaatc ggaaatcgtt tgattgcttt ttttgtattc atttatagaa      480
ggtggagttt gtatgaatca tgatgaatgt aaaacttata taaaaaatag tttattggag      540
ataagaaaat tagcaaatat ctatacacta gaaacgttta agaaagagtt agaaaagaga      600
aatatctact tagaaacaaa atcagataag tatttttctt cggaggggga agattatata      660
tataagttaa tagaaaataa caaaataatt tattcgatta gtggaaaaaa attgacttat      720
aaaggaaaaa aatctttttc aaaacatgca atattgaaac agttgaatga aaaagcaaac      780
caagttaatt aaacaaccta ttttataggra tttataggaa aggagaacag ctgaatgaat      840
atcccttttg ttgtagaaac tgtgcttcat gacggcttgt taaagtacaa atttaaaaat      900
agtaaaattc gctcaatcac taccaagcca ggtaaaagca aagggctat ttttgcgtat        960 cgctcaaaat caagcatgat tggcggtcgt ggtgttgttc tgacttccga ggaagcgatt     1020
caagaaaatc aagatacatt tacacattgg acacccaacg tttatcgtta tggaacgtat     1080
gcagacgaaa accgttcata cacgaaagga cattctgaaa acaatttaag acaaatcaat     1140
accttcttta ttgattttga tattcacacg gcaaaagaaa ctatttcagc aagcgatatt     1200
ttaacaaccg ctattgattt aggttttatg cctactatga ttatcaaatc tgataaaggt     1260
tatcaagcat attttgtttt agaaacgcca gtctatgtga cttcaaaatc agaatttaaa     1320
tctgtcaaag cagccaaaat aatttcgcaa aatatccgag aatattttgg aaagtctttg     1380
ccagttgatc taacgtgtaa tcattttggt attgctcgca taccaagaac ggacaatgta     1440
gaattttttg atcctaatta ccgttattct ttcaaagaat ggcaagattg gtctttcaaa     1500
caaacagata ataagggctt tactcgttca agtctaacgg ttttaagcgg tacagaaggc     1560
aaaaaacaag tagatgaacc ctggtttaat ctcttattgc acgaaacgaa attttcagga     1620
gaaaagggtt taatagggcg taataacgtc atgtttaccc tctctttagc ctactttagt     1680
tcaggctatt caatcgaaac gtgcgaatat aatatgtttg agtttaataa tcgattagat     1740
caacccttag aagaaaaaga agtaatcaaa attgttagaa gtgcctattc agaaaactat     1800
caaggggcta atagggaata cattaccatt ctttgcaaag cttgggtatc aagtgattta     1860
accagtaaag atttatttgt ccgtcaaggg tggtttaaat tcaagaaaaa aagaagcgaa     1920
cgtcaacgtg ttcatttgtc agaatggaaa gaagatttaa tggcttatat tagcgaaaaa     1980
agcgatgtat acaagcctta tttagtgacg accaaaaaag agattagaga agtgctaggc     2040
attcctgaac ggacattaga taaattgctg aaggtactga aggcgaatca ggaaattttc     2100
tttaagatta aaccaggaag aaatggtggc attcaacttg ctagtgttaa atcattgttg     2160
ctatcgatca ttaaagtaaa aaaagaagaa aaagaaagct atataaaggc gctgacaaat     2220
tcttttgact tagagcatac attcattcaa gagactttaa acaagctagc agaacgccct     2280
aaaacggaca cacaactcga tttgtttagc tatgatacag gctgaaaata aaacccgcac     2340
tatgccatta catttatatc tatgatacgt gtttgttttt tctttgctgt ttagcgaatg     2400
attagcagaa atatacagag taagattttta attaattatt aggggagaa ggagagagta      2460 gcccgaaaac ttttagttgg cttggactga acgaagtgag ggaaaggcta ctaaaacgtc     2520
gaggggcagt gagagcgaag cgaacacttg atttttttaat tttctatctt ttataggtca     2580
ttagagtata cttatttgtc ctataaacta tttagcagca aatagatttt attgaatagg     2640
tcatttaagt tgagcatatt agaggaggaa aatcttggag aaatatttga agaacccgat     2700
```

-continued

```
tacatggatt ggattagttc ttgtggttac gtggtttta actaaaagta gtgaattttt       2760 gattttggt gtgtgtgtct tgttgttagt atttgctagt caaagtgatt aaatagaatt       2820
catatccaat ttattttttt cttaacaagg gaggtgtttt ttaacatgac taaagtaggg      2880
tatgcacgtg tcagtagcaa agaacagaac ttagatagac aactgaaagc gttagagggc      2940
gtttctaagg tcttttcaga caaagcaagc ggtcaatcgg tcgaacgccc acaattacaa      3000
gctatgctta actatattcg tgaaggggat atagttgttg ttactgaatt agatcgatta      3060
ggacgaaata ataaagaatt aacagaattg atgaatcaaa ttcaaattaa gggggcaacc      3120
ctggaagtct taaatttacc ctcaatgaat ggtattgaag atgaaaattt aagacggctg      3180
attaataatt tagtgattga attgtataag taccaagcgg aatctgaacg caaacgaatt      3240
aaagaacgcc aagcccaagg aattgaaatt gctaagaaaa aaggaaaatt caaagggcga      3300
caactgaaat tcaaagaaaa tgatccacgt ttacaacacg ctttcgattt gtttttgaac      3360
ggtttatccg ataaagaagt tgaagaacaa actggaatta atcgccgaac gtttagaagg      3420
tatcgatcaa gatacaacgt gacagtcgat caaagaaaaa acaatgaaaa gagggatagt      3480
taatgagtac ggttatttta gctgaaaaac caagccaggc attagcctat gcaagtgctt      3540
taaaacaaag caccaaaaaa gacggttatt ttgagatcaa agacccaatc tttgcagatg      3600
aaacgtttat cacgtttggt tttgggcatt tagtcgagtt agcagaacca ggtcattatg      3660
acgaaaagtg gcaaaattgg aaacttgaat cattgccgat ttttcctgat cgatacgatt      3720
ttgaagtggc aacagataaa aaaaagcagt ttaaaattgt tgctgaactt ttaaaacaag      3780
caaatacaat cattgtcgca acagatagcg acagagaagg cgaaaacatt gcctggtcga      3840
tcattcataa agcaaatgcc ttttctaaag ataaaacgta taaaagacta tggatcaata      3900
gtttagaaaa agatgtgatc cgtagcggtt ttcaaaattt gcaaccagga atgaattact      3960 atcccttta tcaagaagcg caaacacgcc aaattgccga ttggttgatc ggcatgaatg      4020
caagcccttt gtatacgtta aatttacagc agaagggcgt acaaggtaca ttttcactag      4080
gacgtgttca aacgcccacc ttatatctta tttttcagcg ccaggaagcc atagaaaact      4140
ttagaaaaga acctttttc gaggtggaag ctagtataaa agtaaaccaa gggtcattta      4200
agggcgttat aagccccaca cagcgcttta aaacccaaga ggagctttta gcttttgttt      4260
cttctgaaca agctaaaata ggcaatcaag aggggataat tgctgatgtt caaaccaaag      4320
agaagaaaac gaatagtccg agtttgtttt ctttaagtag tttgcaatca aaagttaatc      4380
agctttataa agcgacagcg agccaaactt taaaagctat gcaaggactg tatgaagcaa      4440
aattattgag ttatccaaga acagatacac catttattac agagaacgaa tttgcttatt      4500
taaaagcgaa ttttggcaaa tatagcggtt ttttaggact tgatcttgaa atggttcaaa      4560
cagagcctag aaagcgttat gtggacggta gtaaggtaca ggaacaccac gccattatcc      4620
caacaaaaca agtacctacc gaatctgcat tagcgaaaat ggacgattta caacgaaaaa      4680
tatatgcttt agtcgttaaa acgaccgttg ccatgtttct acctgattat ttgtatgaag      4740
aaactaagat acaaaccaaa gtagccgact tacttttca atcaataggc aagacaccaa       4800
agcaagaagg ttggaaaatt cttttcaaac aacaaaccaa agaagaagaa gaggacgttc      4860
aaacgttacc cttggttatc attggagaac atgccgaggt tgacgttaag agtgccgaaa      4920
aagaaacaca accaccgaaa gcttttacag agggtacatt attaactgct atgaaaacgg      4980
cgaataaaac ggttgatgat gaagaagcaa tcaagatttt acaagaagtt gaggggattg      5040
gaacagaagc gacaagagca agcattattg aagccttgaa acaaaaagaa tatatccaag      5100
```

-continued

```
tgattaagaa taagcttgtt gtaactgaaa aaggaaaatt attgtgccag gcagttgaaa      5160
gtcagcacct tttaacgagt gctgaaatga cggctaaatg ggaaacgtat ttaaaaaaaa      5220
tcggtaaaag agaaggcaat caagagaact ttattacgaa tatcaaaaaa ttcattgttc      5280
atttactgga agctgtacct aacgatatag aaaaactaaa tttttctgat taccaggaac      5340
agaaagaaaa agaagcagaa aaaagtattg taggaaaatg tcctaagtgt ggcaacaata      5400
ttgtattaaa aaaatcgttt tatggttgtt caaattatcc tgaatgtaag tttactttag      5460
ctgaacattt tagaaagaaa aaactcacca aaacaaatgt aaaagaatta ctagagggaa      5520
aagaaaccct ggtaaaagga atcaaaacga aagatagaaa gtcctacaat gccgttgtaa      5580
aaatcggaga aaagggatat attgatttta tatctttctc aaaataaaca taaaagccct      5640
ttaaagaggg cttttatata ttaatcacaa atcacttatc acaaatcaca agtgatttgt      5700
gattgttgat gataaaataa gaataagaag aaatagaaag aagtgagtga ttgtgggaaa      5760
tttaggcgca caaaaagaaa aacgaaatga tacaccaatc agtgcaaaaa aagatataat      5820
gggagataag acggttcgtg ttcgtgctga cttgcaccat atcataaaaa tcgaaacagc      5880
aaagaatggc ggaaacgtaa aagaagttat ggaaataaga cttagaagca aacttaagag      5940
tgtgttgata gtgcagtatc ttaaaatttt gtataatagg aattgaagtt aaattagatg      6000
ctaaaaattt gtaattaaga aggagtgatt acatgaacaa aaatataaaa tattctcaaa      6060 acttttaac gagtgaaaaa gtactcaacc aaataataaa acaattgaat ttaaaagaaa      6120
ccgataccgt ttacgaaatt ggaacaggta aagggcattt aacgacgaaa ctggctaaaa      6180
taagtaaaca ggtaacgtct attgaattag acagtcatct attcaactta tcgtcagaaa      6240
aattaaaact gaatactcgt gtcactttaa ttcaccaaga tattctacag tttcaattcc      6300
ctaacaaaca gaggtataaa attgttggga gtattcctta ccatttaagc acacaaatta      6360
ttaaaaaagt ggtttttgaa agccatgcgt ctgacatcta tctgattgtt gaagaaggat      6420
tctacaagcg taccttggat attcaccgaa cactagggtt gctcttgcac actcaagtct      6480
cgattcagca attgcttaag ctgccagcgg aatgctttca tcctaaacca aaagtaaaca      6540
gtgtcttaat aaaacttacc cgccatacca cagatgttcc agataaatat tggaagctat      6600
atacgtactt tgtttcaaaa tgggtcaatc gagaatatcg tcaactgttt actaaaaatc      6660
agtttcatca agcaatgaaa cacgccaaag taaacaattt aagtaccgtt acttatgagc      6720
aagtattgtc tattttttaat agttatctat tatttaacgg gaggaaataa ttctatgagt      6780
cgcttttgta aatttggaaa gttacacgtt actaaaggga atgtagataa attattaggt      6840
atactactga cagcttccaa ggagctaaag agctggcgaa aggggatgt gctgcaaggc      6900 gattaagttg ggtaacgcca gggttttccc agtcacgacg ttgtaaaacg acggccagtg      6960
aattgatcaa gctttaaatg catgctagca acgcggccgc gttgctagca tgcatttaaa      7020
gcttgatcaa ttcgagctca ttattaatct gttcagcaat cgggcgcgat tgctgaataa      7080
aagatacgag agacctctct tgtatctttt ttattttgag tggttttgtc cgttacacta      7140
gaaaaccgaa agacaataaa aattttattc ttgctgagtc tggctttcgg taagctagac      7200
aaaacggaca aaataaaaat tggcaagggt ttaaggtgg agatttttttg agtgatcttc      7260 tcaaaaaata ctacctgtcc cttgctgatt tttaaacgag cacgagagca aaacccccct      7320
ttgctgaggg ggcagagggc aggtttttttt gtttctttt tctcgtaaaa aaaagaaagg      7380
tcttaaaggt tttatggttt tggtcggcac tgccgacagc ctcgcagagc acacacttta      7440
```

-continued

```
tgaatataaa gtatagtgtg ttatacttta cttggaagtg gttgccggaa agagcgaaaa      7500
tgcctcacat tgtcgacggt atcgataagc ttcccatact gaaactgcgg actatctaca      7560
agagtagaaa ttaaaaaggt cttttgacca tttttcttata caaattatat tatacatatc     7620
agtaaaataa tgtcaacccc cctttattcc tttttttac acagcggaca gtctggacag       7680
ca                                                                     7682

<210> SEQ ID NO 161
<211> LENGTH: 21
<212> TYPE: DNA
<213> ORGANISM: Artificial Sequence
<220> FEATURE:
<223> OTHER INFORMATION: PS1-AID protospacer pMDT454

<400> SEQUENCE: 161
agtccgcagt ttcagtatgg g                                                  21

<210> SEQ ID NO 162
<211> LENGTH: 21
<212> TYPE: DNA
<213> ORGANISM: Artificial Sequence
<220> FEATURE:
<223> OTHER INFORMATION: PS2-AID protospacer pMDT455

<400> SEQUENCE: 162
agatgtccca agcaaacggc a                                                  21

<210> SEQ ID NO 163
<211> LENGTH: 1743
<212> TYPE: DNA
<213> ORGANISM: Artificial Sequence
<220> FEATURE:
<223> OTHER INFORMATION: DsRed expression cassette

<400> SEQUENCE: 163
ataaatgagt agaaagcgcc atatcggcgc ttttcttttg aagaaaata tagggaaaat         60 ggtacttgtt aaaaattcgg aatatttata caatatcata tgtatcacat tgaaaggagg       120
ggcctgctgt ccagactgtc cgctgtgtaa aaaaaaggaa taaagggggg ttgacattat       180
tttactgata tgtataatat aatttgtata agaaaatgga ggggccctcg aaacgtaaga       240
tgaaacctta gataaaagtg cttttttttgt tgcaattgaa gaattattaa tgttaagctt      300
aattaaagat aatatctttg aattgtaacg cccctcaaaa gtaagaacta caaaaaaaga       360
atacgttata tagaaatatg tttgaacctt cttcagatta caaatatatt cggacggact       420
ctacctcaaa tgcttatcta actatagaat gacatacaag cacaaccttg aaaatttgaa       480
aatataacta ccaatgaact tgttcatgtg aattatcgct gtatttaatt ttctcaattc       540
aatatataat atgccaatac attgttacaa gtagaaatta agacaccctt gatagcctta       600
ctatacctaa catgatgtag tattaaatga atatgtaaat atatttatga taagaagcga       660
cttatttata atcattacat attttttctat tggaatgatt aagattccaa tagaatagtg      720
tataaattat ttatcttgaa aggagggatg cctaaaaacg aagaacatta aaaacatata       780
tttgcaccgt ctaatggatt tatgaaaaat cattttatca gtttgaaaat tatgtattat       840
ggagctctta taaaaatgag gagggaaccg aatggcttca actgaagacg taatcaaaga       900
gttcatgcgc ttcaaagtgc gaatggaagg aagtgtaaac gggcatgagt ttgaaattga       960
aggtgaaggt gaaggaaggc cttatgaagg aacgcaaact gcaaaactta aagtgacaaa       1020
aggaggaccg ctgccgtttg cttgggacat cttaagtccg cagtttcagt atgggtcaaa       1080
```

-continued

```
agtttatgta aagcatcctg ctgacattcc tgattacaaa aagttaagtt ttcctgaagg     1140
attcaagtgg gagcgcgtaa tgaactttga agatggaggt gtcgtaactg taacgcaaga     1200
ttcaagtctg caagacggtt gcttcattta caaagtaaag ttcattggcg tgaactttcc     1260
aagtgatggt cctgtaatgc agaaaaagac aatgggttgg gagccgtcaa ctgagaggct     1320
ttatccgcgt gatggtgtct tgaaaggtga aattcacaaa gccttaaagt tgaaagatgg     1380
agggcattat cttgttgagt tcaagagcat ttacatggcg aaaaagcctg tgcagcttcc     1440
tggctactac tatgttgatt caaaacttga cataactagt cacaacgaag actacacaat     1500
tgttgagcag tatgagcgaa ctgaaggaag gcatcatctt tttctttaag agaccagact     1560
tccaattgac actaaaggga tccagaagcg gcaacacgct aatcaataaa aaaacgctgt     1620
gcggttaaag ggcacagcgt tttttgtgta tgaatcgaaa aagaggagag atcgcactga     1680
taattgccaa cacaattaac atctcaatca aggtaaatgc tagcgcggcc gcgtcgacag     1740
gcc                                                                  1743
```

```
<210> SEQ ID NO 164
<211> LENGTH: 678
<212> TYPE: DNA
<213> ORGANISM: Artificial Sequence
<220> FEATURE:
<223> OTHER INFORMATION: DsRed coding region

<400> SEQUENCE: 164
atggcttcaa ctgaagacgt aatcaaagag ttcatgcgct tcaaagtgcg aatggaagga      60
agtgtaaacg ggcatgagtt tgaaattgaa ggtgaaggtg aaggaaggcc ttatgaagga     120
acgcaaactg caaaacttaa agtgacaaaa ggaggaccgc tgccgtttgc ttgggacatc     180
ttaagtccgc agtttcagta tgggtcaaaa gtttatgtaa agcatcctgc tgacattcct     240
gattacaaaa agttaagttt tcctgaagga ttcaagtggg agcgcgtaat gaactttgaa     300
gatggaggtg tcgtaactgt aacgcaagat tcaagtctgc aagacggttg cttcatttac     360
aaagtaaagt tcattggcgt gaactttcca agtgatggtc ctgtaatgca gaaaaagaca     420
atgggttggg agccgtcaac tgagaggctt tatccgcgtg atggtgtctt gaaaggtgaa     480
attcacaaag ccttaaagtt gaaagatgga gggcattatc ttgttgagtt caagagcatt     540
tacatggcga aaaagcctgt gcagcttcct ggctactact atgttgattc aaaacttgac     600
ataactagtc acaacgaaga ctacacaatt gttgagcagt atgagcgaac tgaaggaagg     660
catcatcttt ttctttaa                                                   678
```

```
<210> SEQ ID NO 165
<211> LENGTH: 16
<212> TYPE: DNA
<213> ORGANISM: Artificial Sequence
<220> FEATURE:
<223> OTHER INFORMATION: Primer ID 1202334

<400> SEQUENCE: 165
ttgcaccgtc taatgg                                                      16
```

```
<210> SEQ ID NO 166
<211> LENGTH: 20
<212> TYPE: DNA
<213> ORGANISM: Artificial Sequence
<220> FEATURE:
<223> OTHER INFORMATION: Primer ID 1228373
```

<400> SEQUENCE: 166
gatgatgcct tccttcagtt                                                            20

<210> SEQ ID NO 167
<211> LENGTH: 23
<212> TYPE: DNA
<213> ORGANISM: Artificial Sequence
<220> FEATURE:
<223> OTHER INFORMATION: wA target #2 WT

<400> SEQUENCE: 167
tccaacccac tccctggaat cgg                                                        23

<210> SEQ ID NO 168
<211> LENGTH: 23
<212> TYPE: DNA
<213> ORGANISM: Artificial Sequence
<220> FEATURE:
<223> OTHER INFORMATION: wA target #2 mut-1

<400> SEQUENCE: 168
tctaacccac tccctggaat cgg                                                        23

<210> SEQ ID NO 169
<211> LENGTH: 26
<212> TYPE: DNA
<213> ORGANISM: Artificial Sequence
<220> FEATURE:
<223> OTHER INFORMATION: wA target #3 WT

<400> SEQUENCE: 169
ccgccgattc cgagtcaaca tgctgg                                                     26

<210> SEQ ID NO 170
<211> LENGTH: 23
<212> TYPE: DNA
<213> ORGANISM: Artificial Sequence
<220> FEATURE:
<223> OTHER INFORMATION: wA target #1 WT

<400> SEQUENCE: 170
cagcagtcct ctgctctaga agg                                                        23

<210> SEQ ID NO 171
<211> LENGTH: 23
<212> TYPE: DNA
<213> ORGANISM: Artificial Sequence
<220> FEATURE:
<223> OTHER INFORMATION: wA target #1 mut-1/2/3

<400> SEQUENCE: 171
cagcagtcct ctgctctaga agg                                                        23

<210> SEQ ID NO 172
<211> LENGTH: 23
<212> TYPE: DNA
<213> ORGANISM: Artificial Sequence
<220> FEATURE:
<223> OTHER INFORMATION: wA target #2 mut-1/2/3

<400> SEQUENCE: 172
tttaacccac tccctggaat cgg                                                        23

<210> SEQ ID NO 173
<211> LENGTH: 23

-continued

```
<212> TYPE: DNA
<213> ORGANISM: Artificial Sequence
<220> FEATURE:
<223> OTHER INFORMATION: wA target #2 mut-4/5

<400> SEQUENCE: 173
tctaacccac tccctggaat cgg                                                    23

<210> SEQ ID NO 174
<211> LENGTH: 23
<212> TYPE: DNA
<213> ORGANISM: Artificial Sequence
<220> FEATURE:
<223> OTHER INFORMATION: wA target #3 WT

<400> SEQUENCE: 174
ccgattccga gtcaacatgc tgg                                                    23

<210> SEQ ID NO 175
<211> LENGTH: 23
<212> TYPE: DNA
<213> ORGANISM: Artificial Sequence
<220> FEATURE:
<223> OTHER INFORMATION: wA target #3 mut-1

<400> SEQUENCE: 175
ccgattccga gtcaacatac tag                                                    23

<210> SEQ ID NO 176
<211> LENGTH: 23
<212> TYPE: DNA
<213> ORGANISM: Artificial Sequence
<220> FEATURE:
<223> OTHER INFORMATION: wA target #3 mut-2/3/4

<400> SEQUENCE: 176
ccgattccga gtcaacatgc tag                                                    23

<210> SEQ ID NO 177
<211> LENGTH: 23
<212> TYPE: DNA
<213> ORGANISM: Artificial Sequence
<220> FEATURE:
<223> OTHER INFORMATION: wA target #4 WT

<400> SEQUENCE: 177
cctacgacga ctatgctggg aca                                                    23

<210> SEQ ID NO 178
<211> LENGTH: 23
<212> TYPE: DNA
<213> ORGANISM: Artificial Sequence
<220> FEATURE:
<223> OTHER INFORMATION: wA target #4 mut-1/2

<400> SEQUENCE: 178
cctacgacga ctatgctgaa aca                                                    23

<210> SEQ ID NO 179
<211> LENGTH: 23
<212> TYPE: DNA
<213> ORGANISM: Artificial Sequence
<220> FEATURE:
<223> OTHER INFORMATION: wA target #4 mut-3

<400> SEQUENCE: 179
```

-continued cctacgacga ctatgctgag aca                                          23

<210> SEQ ID NO 180
<211> LENGTH: 25
<212> TYPE: DNA
<213> ORGANISM: Artificial Sequence
<220> FEATURE:
<223> OTHER INFORMATION: MdwA8 WT

<400> SEQUENCE: 180
tttcatccct ggcggtaacc gagca                                        25

<210> SEQ ID NO 181
<211> LENGTH: 26
<212> TYPE: DNA
<213> ORGANISM: Artificial Sequence
<220> FEATURE:
<223> OTHER INFORMATION: MdwA8 mut-1

<400> SEQUENCE: 181
tttcatccct ggcggtaacc tgagca                                       26

<210> SEQ ID NO 182
<211> LENGTH: 25
<212> TYPE: DNA
<213> ORGANISM: Artificial Sequence
<220> FEATURE:
<223> OTHER INFORMATION: MdwA8 mut-2

<400> SEQUENCE: 182
tttcatccct ggcggtaacc aagca                                        25

<210> SEQ ID NO 183
<211> LENGTH: 25
<212> TYPE: DNA
<213> ORGANISM: Artificial Sequence
<220> FEATURE:
<223> OTHER INFORMATION: MdwA13 WT

<400> SEQUENCE: 183
gagcttctgg aacctcctgt acaaa                                        25

<210> SEQ ID NO 184
<211> LENGTH: 25
<212> TYPE: DNA
<213> ORGANISM: Artificial Sequence
<220> FEATURE:
<223> OTHER INFORMATION: MdwA13 mut-1

<400> SEQUENCE: 184
gagcttctag aacctcctgt acaaa                                        25

<210> SEQ ID NO 185
<211> LENGTH: 25
<212> TYPE: DNA
<213> ORGANISM: Artificial Sequence
<220> FEATURE:
<223> OTHER INFORMATION: MdwA8 mut-1/2

<400> SEQUENCE: 185
ttttattttt ggcggtaacc gagca                                        25

<210> SEQ ID NO 186
<211> LENGTH: 25
<212> TYPE: DNA
<213> ORGANISM: Artificial Sequence -continued

```
<220> FEATURE:
<223> OTHER INFORMATION: MdwA8 mut-3

<400> SEQUENCE: 186
tttcattttt ggcggtaacc gagca                                              25

<210> SEQ ID NO 187
<211> LENGTH: 25
<212> TYPE: DNA
<213> ORGANISM: Artificial Sequence
<220> FEATURE:
<223> OTHER INFORMATION: MdwA8 mut-4

<400> SEQUENCE: 187
tttcatcttt ggcggtaacc gagca                                              25

<210> SEQ ID NO 188
<211> LENGTH: 25
<212> TYPE: DNA
<213> ORGANISM: Artificial Sequence
<220> FEATURE:
<223> OTHER INFORMATION: MdwA8 mut-5

<400> SEQUENCE: 188
tttcatccct aacagtaacc gagca                                              25

<210> SEQ ID NO 189
<211> LENGTH: 25
<212> TYPE: DNA
<213> ORGANISM: Artificial Sequence
<220> FEATURE:
<223> OTHER INFORMATION: MdwA8 mut-6/7

<400> SEQUENCE: 189
tttcatccct ggcggtaact gagca                                              25

<210> SEQ ID NO 190
<211> LENGTH: 25
<212> TYPE: DNA
<213> ORGANISM: Artificial Sequence
<220> FEATURE:
<223> OTHER INFORMATION: MdwA8 mut-8/9

<400> SEQUENCE: 190
tttcatccct ggcggtaacc aagca                                              25

<210> SEQ ID NO 191
<211> LENGTH: 25
<212> TYPE: DNA
<213> ORGANISM: Artificial Sequence
<220> FEATURE:
<223> OTHER INFORMATION: MdwA8 mut-10

<400> SEQUENCE: 191
tttcatccct ggcggtaacc gagta                                              25

<210> SEQ ID NO 192
<211> LENGTH: 25
<212> TYPE: DNA
<213> ORGANISM: Artificial Sequence
<220> FEATURE:
<223> OTHER INFORMATION: MdwA2 WT

<400> SEQUENCE: 192
ctttttggag accagaccag cgaca                                              25
```

-continued

```
<210> SEQ ID NO 193
<211> LENGTH: 25
<212> TYPE: DNA
<213> ORGANISM: Artificial Sequence
<220> FEATURE:
<223> OTHER INFORMATION: MdwA2 mut-1/2/3

<400> SEQUENCE: 193
ctttttggag attagaccag cgaca                                                25

<210> SEQ ID NO 194
<211> LENGTH: 25
<212> TYPE: DNA
<213> ORGANISM: Artificial Sequence
<220> FEATURE:
<223> OTHER INFORMATION: MdwA2 mut-4/5/6

<400> SEQUENCE: 194
ctttttggag actagaccag cgaca                                                25

<210> SEQ ID NO 195
<211> LENGTH: 25
<212> TYPE: DNA
<213> ORGANISM: Artificial Sequence
<220> FEATURE:
<223> OTHER INFORMATION: MdwA2 mut-7

<400> SEQUENCE: 195
ctttttggag actagactag cgaca                                                25

<210> SEQ ID NO 196
<211> LENGTH: 25
<212> TYPE: DNA
<213> ORGANISM: Artificial Sequence
<220> FEATURE:
<223> OTHER INFORMATION: MdwA13 mut-2

<400> SEQUENCE: 196
gagcttctga aacctcctgt acaaa                                                25
```